United States Patent
Ahn et al.

(10) Patent No.: US 8,846,699 B2
(45) Date of Patent: Sep. 30, 2014

(54) QUINAZOLINE DERIVATIVES AS A MULTIPLEX INHIBITOR AND METHOD FOR THE PREPARATION THEREOF

(75) Inventors: Young-Gil Ahn, Seongnam-si (KR); Jong Woo Kim, Suwon-si (KR); Keuk Chan Bang, Incheon (KR); Bum Woo Park, Gwangmyeong-si (KR); Se Young Kim, Seongnam-si (KR); Kyungik Lee, Anyang-si (KR); Kyuhang Lee, Yongin-si (KR); Myoung-Sil Ko, Seoul (KR); Han Kyong Kim, Yongin-si (KR); Young Hoon Kim, Seoul (KR); Maeng Sup Kim, Seoul (KR); Gwan Sun Lee, Seoul (KR)

(73) Assignee: Hanmi Pharm. Co., Ltd. (KR)

( * ) Notice: Subject to any disclaimer, the term of this patent is extended or adjusted under 35 U.S.C. 154(b) by 546 days.

(21) Appl. No.: 12/093,108

(22) PCT Filed: Nov. 8, 2006

(86) PCT No.: PCT/KR2006/004670
§ 371 (c)(1),
(2), (4) Date: May 8, 2008

(87) PCT Pub. No.: WO2007/055514
PCT Pub. Date: May 18, 2007

(65) Prior Publication Data
US 2008/0318950 A1   Dec. 25, 2008

(30) Foreign Application Priority Data

Nov. 8, 2005 (KR) .......................... 10-2005-0106506
Nov. 6, 2006 (KR) .......................... 10-2006-0109137

(51) Int. Cl.
*A61K 31/517* (2006.01)
*C07D 239/94* (2006.01)
(52) U.S. Cl.
CPC .................................... *C07D 239/94* (2013.01)
USPC ....................... 514/266.2; 514/266.4; 544/293
(58) Field of Classification Search
USPC ........................................................ 544/293
See application file for complete search history.

(56) References Cited

U.S. PATENT DOCUMENTS

| | | | |
|---|---|---|---|
| 6,344,459 B1 | 2/2002 | Bridges et al. | |
| 6,602,863 B1 * | 8/2003 | Bridges et al. | ............... 514/183 |
| 6,972,288 B1 | 12/2005 | Himmelsbach et al. | |
| 2002/0082270 A1 | 6/2002 | Himmelsbach et al. | |
| 2002/0115675 A1 | 8/2002 | Himmelsbach et al. | |
| 2002/0169180 A1 | 11/2002 | Himmelsbach et al. | |
| 2002/0173509 A1 | 11/2002 | Himmelsbach et al. | |
| 2003/0149062 A1 | 8/2003 | Jung et al. | |
| 2003/0225079 A1 | 12/2003 | Singer et al. | |
| 2004/0158065 A1 | 8/2004 | Barth et al. | |
| 2005/0085495 A1 | 4/2005 | Soyka et al. | |
| 2005/0107358 A1 | 5/2005 | Himmelsbach et al. | |

FOREIGN PATENT DOCUMENTS

| | | |
|---|---|---|
| EP | 1510221 | 3/2005 |
| WO | 0031048 | 6/2000 |
| WO | 03068264 | 8/2003 |
| WO | 03089439 | 10/2003 |
| WO | 2005115145 | 12/2005 |

OTHER PUBLICATIONS

J.B. Smaill et al., "Tyrosine Kinase Inhibitors, 117, Irreversible Inhibitors of the Epidermal Growth Factor Receptor . . . ", Journal of Medicinal Chemistry, vol. 43, No. 7, Mar. 14, 2000, pp. 1380-1397.

* cited by examiner

*Primary Examiner* — Brian McDowell
(74) *Attorney, Agent, or Firm* — Baker & Hostetler LLP

(57) ABSTRACT

The present invention relates to a novel quinazoline derivative compound having the formula (1) as follows:

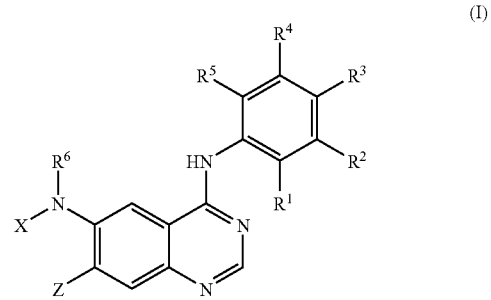

(I)

with the constituents defined in claim 1, and a pharmaceutically acceptable salt thereof as a multiplex inhibitor, a method for the preparation thereof, and a pharmaceutical composition and a therapeutic composition comprising same as an active ingredient. The inventive quinazoline derivative as a multiplex inhibitor can selectively and effectively inhibit diseases caused by the overactivity of a tyrosine kinase.

3 Claims, No Drawings

QUINAZOLINE DERIVATIVES AS A MULTIPLEX INHIBITOR AND METHOD FOR THE PREPARATION THEREOF

TECHNICAL FIELD

The present invention relates to a novel quinazoline derivative and a pharmaceutically acceptable salt thereof as a multiplex inhibitor which selectively and effectively inhibits diseases caused by the overactivity of a tyrosine kinase, a method for the preparation thereof, and a pharmaceutical composition and a therapeutic composition comprising same as an active ingredient.

BACKGROUND ART

Cancer is a fatal disease as a major cause of adult death, and the frequency of cancer is increasing. Most of the traditional drugs used for treating cancers, e.g., taxanes such as paclitaxel and doxetaxel; vinca alkaloids such as vincristine, vinblastine and vinorelbin; anthracyclines such as daunomycin and doxorubicin; camptothecins such as topotecan, irinotecan; actinomycin; and etopocid, are based on selective cytotoxicity, but such selectivity against cancer cells has been low thereby causing many side effects such as cytotoxicity to normal cells. Further, there are various problems that it is required for a patient to be hospitalized before his treatment, or the patient has to endure side effects such as those caused by excipients. Moreover, cancer cells frequently exhibit a resistance against an anticancer agent containing the above drugs.

To overcome such problems, many novel molecular-level targets have been identified by human genome sequencing, and they become available for treatment. Therefore, many studies are ongoing to develop an anticancer agent acting on specific targets in the cell not a cell itself, and to maximize the therapeutic effect of the anticancer agent without causing adverse side effects.

In cells, there are many signal transduction systems, which are functionally linked to each other to control the proliferation, growth, metastasis and death of cells. Protein tyrosine kinases play important roles in such cellular regulation, and their abnormal expression or mutation has been commonly observed in cancer cells. Protein tyrosine kinase is an enzyme which catalyzes the transportation of phosphate groups from ATP to tyrosines located on a protein substrate. Many growth factor receptor proteins function as tyrosine kinases to transport cellular signals. The interaction between growth factors and their receptors is necessary to control the normal cell growth, but abnormal signal transduction caused by the mutation or overexpression of any of the receptors may induce various diseases.

Further, protein tyrosine kinase receptors play important roles in a biochemical signal transduction passing through a cytoplasmic membrane. Transmembrane receptor molecules typically contain an inner cellular tyrosine kinase domain and an outer cellular ligand binding domain. The ligand binding of a receptor stimulates the phosphorylation of a tyrosine residue between the receptor and other inner cellular molecules, and the phosphorylation of the tyrosine residue induces signal transduction through various cellular reactions.

The comparison of homology of amino acid sequence discovers 19 subgroups of RTK (receptor tyrosine kinase) such as Flt (Fms-Like Tyrosine Kinase Receptor, Flt1 or VEGFR1), KDR (Kinase Insert Domain Containing Receptor, Flk-1 or VEGFR2), Flk4 (Fms-Like Tyrosine Kinase Receptor or VEGFR3), EGFR1 (Epidermal Growth Factor Receptor 1, Erb-B1 or HER-1), EGFR2 (Erb-B2 or HER-2), Erb-B3 and Erb-B4. Among theses, Flt and KDR are closely related to a vascular endothelial growth factor (VEGF) (see [De Vries et al., Science 255: 989-991, 1992; and Terman et al., Biochem. Biophys. Res. Comm. 187: 1579-1586, 1992]).

Protein tyrosine kinases have been classified into many families in terms of growth factors, and, specifically, VEGF-related VEGF receptor (VEGFR) tyrosine kinase has been intensely studied. The VEGFR tyrosine kinase is composed of a receptor and a tyrosine kinase, and delivers extracellular signals into the cell through the cellular membrane. The VEGFR tyrosine kinases are classified into VEGFR1, VEGFR2 and VEGFR3, and VEGFR2 (KDR) is a major VEGFR related to angiogenesis.

Unwanted pathological angiogenesis is related to diseases such as streaks of diabetes patient, psoriasis, cancer, rheumatoid arthritis, atheroma, Kaposi's sarcoma and angioma, (see [Fan et al., Trends Pharmacol. Sci. 16: 57-66, 1995; and Folkman, Nature Medicine 1: 27-31, 1995]). The change caused by metastasis of blood vessel accompanies biological reactions in both normal and abnormal cases (see [Cullinan-Bove et al., Endocrinology 133: 829-837, 1993; and Senger et al., Cancer and Metastasis Reviews 12: 303-324, 1993]), and polypeptides stimulating epithelial cell growth in vitro include Fibroblast Growth Factor (aFGF and bFGF) and VEGF. In contrast to FGFs, VEGFs are active only in specific epithelial cells due to the limited expression of their receptor.

Recently, it is reported that VEGF acts as an important stimulator to normal and pathological angiogenesis (see [Jakeman et al., Endocrinology 133: 848-859, 1993; and Kolch et al., Breast Cancer Research and Treatment 36: 139-155, 1995]) and metastasis of a blood vessel (see [Connolly et al., J. Biol. Chem. 264: 20017-20024, 1989]), antagonism of VEGF induced by removing of the VEGF by using antibodies can inhibit the proliferation of cancer cells (see [Kim et al., Nature 362: 841-844, 1993]).

International Patent Publications WO 2000/59509, WO 2002/90346 and WO 1998/35958 each discloses PTK787 (Novartis), which comprises a phthalazine framework, and selectively inhibits tyrosine receptors such as VEGFR1, VEGFR2 and VEGFR3.

International Patent Publications WO 2001/45689, WO 2001/37820, WO 2001/60814, WO 1999/61422 and WO 1998/50356 each discloses SU11248 (Sutent, Pfizer), which comprises an indolidone framework, and inhibits tyrosine receptors such as VEGFR1, VEGFR2, VEGFR3 and PDGFR.

International Patent Publications WO 2001/32651, WO 2004/14383 and WO 2004/14426, and U.S. Pat. No. 3,039,551 each discloses ZD6474 (Zactima, AstraZeneca), which comprises a quinazoline framework, and inhibits tyrosine receptors such as VEGFR2 and EGFR1.

International Patent Publications WO 2000/47212, WO 2001/74360, WO 2002/12228, WO 2002/12227, WO 2000/21955 and WO 2000/47212 each discloses AZD2171 (AstraZeneca), which comprises a quinazoline framework, and selectively inhibits a tyrosine receptor, VEGFR2.

International Patent Publications WO 2001/10859, WO 2001/23375, WO 2003/68223, WO 2003/68228 and WO 2003/68229 each discloses Bay-439006 (sorafenib, Bayer), which comprises an urea framework, and inhibits tyrosine kinase receptors such as VEGFR2, VEGFR3 and Raf-1.

International Patent Publications WO 1997/2266, WO 1997/27199, WO 1998/7726 and WO 2003/13541 each discloses AEE788 (Novartis), which comprises a pyrrolopyrimidine framework, and inhibits tyrosine kinase receptors such as HER-1 (EGFR1), HER-2 and VEGFR2.

International Patent Publications WO 02059110 discloses Pazopanib (GlaxoSmithKline), which comprises a pyrimidine framework, and inhibits tyrosine kinase receptors such as PDGF, c-Kit, VEGFR1, VEGFR2 and VEGFR3.

Further, as another protein tyrosine kinase growth factor, EGF-related EGF receptor (EGFR) tyrosine kinase also has been intensely studied. A EGFR tyrosine kinase is composed of a receptor and a tyrosine kinase, and delivers extracellular signals to the cell nuclear through the cellular membrane. The EGFR tyrosine kinases are classified by their structural differences into EGFR1 (Erb-B1 or HER-1), Erb-B2 (HER-2), Erb-B3 and Erb-B4, and all of the above members can form a homodimer- or heterodimer-signal delivery complex. This shows that overexpression of more than one members in a malignant disease can induce synergistic modification. These overexpressions of more than one members are often observed in human malignant tumor.

Therefore, the inhibition of mutated or overexpressed EGFR tyrosine kinases has been considered to be useful for treating tumors, and many drugs have been developed therefor, e.g., Gefitinib, Erlotinib, Carnertinib, Lapatinib. These are low molecular compounds, and inhibit the growth of tumor by inhibiting the role of EGFR tyrosine kinase to prolong the life time of patients or to provide therapeutic advantages.

International Patent Publications WO 1996/33981, WO 1996/33979, WO 1997/38994 and WO 1996/33980 each discloses a quinazoline derivative substituted with an alkoxyalkylamino or alkylaminoalkoxy group; International Patent Publications WO 1997/30034 and WO 1996/16960 each discloses a quinazoline derivative substituted with aryl or heteroaryl group; and International Patent Publications WO 2003/40109 and WO 2003/40108 each discloses compounds having various aminoalkoxy substituents at position 5 of quinazoline (the quinazoline is named in accordance with a reference [J. A. Joule, Chapman & Hall, *Heterocyclic chemistry*, 3rd Ed., 189]).

International Patent Publication WO 1995/19970 and U.S. Pat. Nos. 5,654,307 and 5,679,683 each discloses various tricyclic heteroaryl compound. International Patent Publications WO 1999/6396, WO 1999/6378, WO 1997/38983 and WO 2000/31048 each discloses quinazoline compounds that inhibit the tyrosine kinase irreversibly. Further, European Patent 0787722, and WO 1998/50038, WO 1999/24037 and WO 2000/6555 each also discloses quinazoline compounds that inhibit the tyrosine kinase irreversibly; U.S. Pat. No. 6,225,318, European Patents 0387063 and 01292591, and International Patent Publications WO 2001/98277, WO 2003/45939 and WO 2003/49740 each discloses compounds having various alkenyl or alkynyl substituents at position 6 of quinazoline; and International Patent Publications WO 1998/43960, WO 2000/18761, WO 2001/47892, WO 2001/72711, WO 2003/50090, WO 1999/9016, WO 2000/18740 and WO 2000/66583 each discloses 3-cyanoquinoline compounds.

International Patent Publications WO 1998/2434, WO 1998/2437, WO 1999/35132, WO 1999/35146, WO 2001/4111 and WO 2002/2552 each discloses various quinazoline compounds substituted with furan having various sulfonealkylamino substituents; and International Patent Publications WO 2003/53466 and WO 2001/94353 each discloses thienopyrimidine compounds. Further, International Patent Publications WO 2001/12227, WO 2004/14386, WO 2004/35057 and WO 2001/76586 disclose various methods for effectively treating tumors in combination with drugs having different mechanism with the tyrosine kinase or radiation therapy.

However, the above mentioned conventional quinazoline derivatives have to be taken in large dose for intended treatments, which causes such side effects such as diarrhea and skin eruption. Accordingly, there has continued to exist a need to develop an effective drug in a small dosage that gives no adverse side effect.

DISCLOSURE

Technical Problem

Accordingly, it is an object of the present invention to provide a novel quinazoline derivative as a multiplex inhibitor which selectively and effectively inhibits diseases caused by the overactivity of a tyrosine kinase such as a vascular endothelial growth factor receptor (VEGFR) and an epithelial growth factor receptor (EGFR) without any side effects, a method for the preparation thereof, and a pharmaceutical composition and a therapeutic composition comprising same as an active ingredient.

Technical Solution

In accordance with one aspect of the present invention, there is provided a quinazoline derivative of formula (I) or a pharmaceutically acceptable salt thereof:

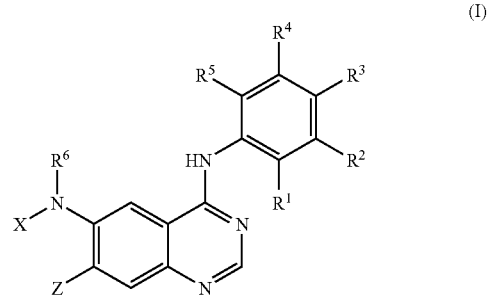

wherein
$R^1$, $R^2$, $R^3$, $R^4$ and $R^5$ are each independently hydrogen, hydroxy, halogen, trifluoromethyl, $C_1$-$C_6$alkyl, $C_1$-$C_6$alkoxy, $C_3$-$C_7$cycloalkyl, hydroxy$C_1$-$C_5$alkyl, $C_1$-$C_6$alkoxy$C_1$-$C_6$alkyl, amino, amino$C_1$-$C_4$alkyl, $C_1$-$C_6$alkylamino, $C_1$-$C_6$alkoxycarbonyl, $C_1$-$C_6$alkoxyaminocarbonyl, aryl$C_1$-$C_6$alkoxy, heteroaryl$C_1$-$C_6$alkoxy or aryl;

$R^6$ is hydrogen, $C_1$-$C_6$alkyl or di$C_1$-$C_6$alkylamino$C_1$-$C_6$alkyl;

X is $C_2$-$C_6$alkenylcarbonyl or $C_2$-$C_6$alkynylcarbonyl optionally substituted with $R^{11}$, $R^{11}$ being halogen, hydroxy, amino, thiol, carbamoyl, trifluoromethyl, cyano, $C_1$-$C_6$alkyl, $C_3$-$C_7$cycloalkyl, $C_1$-$C_6$alkoxy, $C_1$-$C_6$alkylamine, di$C_1$-$C_6$alkylamine, $C_1$-$C_6$alkylcarboamine, $C_2$-$C_6$alkenylcarboamine, $C_2$-$C_6$alkynylcarboamine, di$C_1$-$C_6$alkylcarboamine, $C_1$-$C_6$alkylthio, $C_1$-$C_6$alkylsulfonyl, $C_1$-$C_6$alkylsulfonylcarboamine, $C_1$-$C_6$alkoxycarbonyl or heterocyclo; and Z is $C_1$-$C_6$alkoxy, $C_1$-$C_6$alkenyloxy, aryloxy, heterocloooxy or heterocyclo$C_1$-$C_6$alkoxy optionally substituted with $R^{12}$, $R^{12}$ being halogen, hydroxy, amino, thiol, carbamoyl, trifluoromethyl, $C_1$-$C_6$alkyl, $C_3$-$C_7$cycloalkyl, $C_1$-$C_6$alkoxy, $C_1$-$C_6$alkylamine, di$C_1$-$C_6$alkylamine, $C_1$-$C_6$alkylcarboamine, $C_2$-$C_6$alkenylcarboamine, $C_2$-$C_6$alkynylcarboamine, $C_1$-$C_6$alkylamino$C_1$-$C_6$alkylcarboamine, di$C_1$-$C_6$alkylamino$C_1$-

C₆alkylcarboamine, C₁-C₆alkylaminoC₂-C₆alkenylcarboamine, diC₁-C₆alkylaminoC₂-C₆alkenylcarboamine, C₁-C₆alkoxyC₁-C₆alkylcarboamine, hydroxyC₁-C₆alkylcarboamine, C₁-C₆alkylthioC₁-C₆alkylcarboamine, C₁-C₆alkylsulfonylC₁-C₆alkylcarboamine, C₁-C₆alkylthio, C₁-C₆alkylsulfonyl, C₁-C₆alkylsulfonylamine, C₁-C₆alkoxycarbonyl, aminoC₁-C₆alkylcarboamine, C₁-C₆alkylurea, C₁-C₆alkylaminocarbonyl, C₁-C₆alkylthiourea, C₁-C₆alkenylurea, C₁-C₆alkenylthiourea, C₁-C₆alkylcarbonylC₁-C₆alkylamino, aminoC₁-C₆alkylcarboamine, C₁-C₆alkoxycarboamine, aryl, heteroaryl, heterocyclo, oxoheterocyclo, heterocyclocarboamine, heterocycloC₁-C₆alkylcarboamine, C₁-C₆alkylheterocycloC₁-C₆alkylcarboamine, diC₁-C₆alkylheterocycloC₁-C₆alkylcarboamine, C₁-C₆alkylcarboheterocycloC₁-C₆alkylcarboamine or C₁-C₆alkylcarboheterocyclocarboamine.

In accordance with another aspect of the present invention, there is provided a method for the preparation of the quinazoline derivative of formula (I) or the pharmaceutically acceptable salt thereof.

In accordance with further aspect of the present invention, there is provided a pharmaceutical composition for inhibiting the activity of a tyrosine kinase comprising the quinazoline derivative of formula (I) or the pharmaceutically acceptable salt thereof as an active ingredient.

In accordance with further aspect of the present invention, there is provided a therapeutic composition for treating diseases caused by the overactivity of a tyrosine kinase comprising the quinazoline derivative of formula (I) or the pharmaceutically acceptable salt thereof as an active ingredient.

In accordance with further aspect of the present invention, there is provided a use of the quinazoline derivative of formula (I) or the pharmaceutically acceptable salt thereof in the manufacture of a medicament for inhibiting the activity of a tyrosine kinase or for treating diseases caused by the overactivity of a tyrosine kinase.

Mode for Invention

In the quinazoline derivative of formula (I) of the present invention, $R^1$, $R^2$, $R^3$, $R^4$ and $R^5$ are preferably each independently hydrogen, hydroxy, halogen, $C_1$-$C_6$alkyl, $C_1$-$C_6$alkoxy, pyridin-2-yl-$C_1$-$C_6$alkoxy or $C_1$-$C_6$alkoxyaminocarbonyl;

$R^6$ is preferably hydrogen or $C_1$-$C_6$alkyl;

X is preferably ethenecarbonyl, 2-methyl-ethenecarbonyl or ethynecarbonyl; and

Z is preferably (N-acetyl-piperidin-4-yl)-methoxy, (N-trifluoroacetyl-piperidin-4-yl)-methoxy, (N-methanesulfonylmethylcarbonyl-piperidin-4-yl)-methoxy, (N-aminocarbonyl-piperidin-4-yl)-methoxy, (N-ethenecarbonyl-piperidin-4-yl)-methoxy, pyridin-4-yl-methoxy, (N-propaneaminocarbonyl-piperidin-4-yl)-methoxy, (N-dimethylaminomethylcarbonyl-piperidin-4-yl)-methoxy, (N-t-butylaminocarbonyl-piperidin-4-yl)-methoxy, (N-methyl-piperidin-4-yl)-methoxy, (N-ethylcarbonyl-piperidin-4-yl)-methoxy, (N-dimethylaminomethylcarbonyl-amino)-propoxy, (N-acetylamino)-propoxy, (N-trifluorocarbonyl-amino)-propoxy, (N-methanesulfonylcarbonyl-amino)-propoxy, (N-ethylaminocarbonyl-amino)-propoxy, (N-dimethyl-amino)-propoxy, (N-acetylamino)-ethoxy, (N-dimethyl-amino)-ethoxy, (N-acetylamino)-butoxy, (N-cyclopropane-carbonylamino)-ethoxy, (N-difluoro-carbonylamino)-ethoxy, (N-ethylaminocarbonyl-amino)-ethoxy, (N-aminocarbonyl-amino)-ethoxy, (N-dimethylamino-carbonylamino)-ethoxy, (N-ethenecarbonyl-amino)-ethoxy, (N-ethylcarbonyl-amino)-ethoxy, (N-trifluorocarbonyl-amino)-ethoxy, 2-amino-ethoxy, 2-methylamino-ethoxy, but-3-enyloxy, 2-methoxy-ethoxy, 2-methanesulfonylamino-ethoxy, 2-(3-propyl-ureido)-ethoxy, 2-(3-methyl-thioureido)-ethoxy, 2-(3-ethyl-thioureido)-ethoxy, 2-(3-isopropyl-ureido)-ethoxy, 2-(3-sec-butyl-ureido)-ethoxy, 2-(3-vinyl-ureido)-ethoxy, 2-(3-allyl-ureido)-ethoxy, 2-(acetyl-N-methyl-amino)-ethoxy, 2-acetylamino-ethylsulfanyl, 2-(2-methoxy-acetylamino)-ethoxy, 2-(2-hydroxy-acetylamino)-ethoxy, 2-(2-methylsulfanyl-acetylamino)-ethoxy, 2-(2-methanesulfonyl-acetylamino)-ethoxy, 2-isobutyrylamino-ethoxy, 2-(2-methyl-acrylamide)-ethoxy, 2-(but-2-enoylamide)-ethoxy, 2-butylamide-ethoxy, 2-(pent-2-enoylamide)-ethoxy, 2-(4-dimethylamino-but-2-enoylamide)-ethoxy, 2-(2-oxo-propylamino)-ethoxy, 2-[2-(N-ethyl-N'-methyl-amino)-acetylamino]-ethoxy, 2-(2-amino-acetylamino)-ethoxy, (R)-2-(2-dimethylamino-propionylamino)-ethoxy, 2-(3-diethylamino-propionylamino)-ethoxy, 2-(2-methylamino-acetylamino)-ethoxy, 2-(3-dimethylamino-propionylamino)-ethoxy, 2-(3-amino-propionylamino)-ethoxy, 2-(methyl-carbamyl)-ethoxy, 2-(3-methoxy-propionylamino)-ethoxy, (2-diethylamino-ethylcarbamoyl)-methoxy, 2-(4-dimethylamino-butyrylamino)-ethoxy, 2-(3-hydroxy-propionylamino)-ethoxy, 2-(2-(dimethylamino)-acetamido)-ethoxy, 2-(3-ethoxy-3-oxo-propionylamino)-ethoxy, 2-(3-hydroxy-3-oxo-propionylamino)-ethoxy, 2-(ethyl-oxalamyl)-ethoxy, 2-oxalamyl-ethoxy, 2-(methoxy-iminoacetylamino)-ethoxy, 2-(3-dimethylamino-2-methyl-propionylamino)-ethoxy, 2-(3-dimethylamino-butylamide)-ethoxy, 2-(dimethyl-acetylamino)-ethoxy, 2-acetylamino-1-methyl-ethoxy, 2-acetylamino-propoxy, (R)-2-acetylamino-propoxy, (S)-2-acetylamino-propoxy, 2-(propionylamino)-propoxy, 2-(3-propyl-ureido)-propoxy, 2-acetylamino-butoxy, 3-propionylamino-propoxy, 1-acetyl-pyrrolidin-3-yloxy, 1-acetyl-piperidin-3-yloxy, 2-(thiazol-2-ylamino)-ethoxy, 2-oxo-oxazolidin-5-ylmethoxy, 2-(thiophen-2-carbonylamino)-ethoxy, 2-(morpholine-N-carbonylamino)-ethoxy, 2-(piperazine-1-carbonylamino)-ethoxy, 2-(4-acetyl-piperazine-1-carbonylamino)-ethoxy, 2-(4-methyl-piperazine-1-carbonylamino)-ethoxy, (R)-2-(pyrrolidine-2-carbonylamino)-ethoxy, (R)-2-(1-methyl-pyrrolidine-2-carbonylamino)-ethoxy, 2-(1H-pyrrole-2-carbonylamino)-ethoxy, (S)-2-(1-methyl-pyrrolidine-2-carbonylamino)-ethoxy, 2-(2-piperidin-1-yl-acetylamino)-ethoxy, 2-[2-(4-methyl-piperazin-1-yl)-acetylamino]-ethoxy, 2-(2-morpholin-4-yl-acetylamino)-ethoxy, 2-(3-piperidin-1-yl-propionylamino)-ethoxy, 2-(1-acetyl-pyrrolidine-2-carbonylamino)-ethoxy, 2-(1-propionyl-pyrrolidine-2-carbonylamino)-ethoxy, 2-(2-pyrrolidin-1-yl-acetylamino)-ethoxy, 2-(2-2,5-dihydro-pyrrol-1-yl-acetylamino)-ethoxy, 4,5-dihydro-oxazol-2-ylmethoxy, 2-(2-azetidin-1-yl-acetylamino)-ethoxy, 2-(3-diethylamino-propionylamino)-propoxy, 2-(2-dimethylamino-acetylamino)-2-methyl-propoxy, 2-(2-dimethylamino-acetylamino)-3-methyl-buthoxy, 2-(2-dimethylamino-acetylamino)-propoxy, (R)-2-(2-dimethylamino-acetylamino)-propoxy, (S)-2-(2-dimethylamino-acetylamino)-propoxy, 2-(2-dimethylamino-acetylamino)-butoxy, 2-(2-dimethylamino-3-methoxy-propionylamino)-ethoxy, 2-(2-dimethylamino-3-hydroxy-propionylamino)-ethoxy, 2-(2-diethylamino-acetylamino)-ethoxy, 2-(3-t-butyl-ureido)-ethoxy or (N-ethylaminocarbonyl-piperidin-4-yl)-methoxy.

In the present invention, the term "heterocycle" refers to a 5 to 13-membered heteroaromatic or non-aromatic compound containing 1 to 3 of the elements selected from the group consisting of N, O, S, SO and $SO_2$, optionally substituted with one or more substituents selected from the group consisting of halogen, hydroxy, amino, nitro, trifluoromethyl, cyano, $C_1$-$C_6$alkyl, $C_1$-$C_6$alkoxy, amino$C_1$-$C_6$alkyl, $C_1$-$C_6$alkylamino, $C_3$-$C_7$cycloalkyl, $C_1$-$C_6$alkylcarbonyl, $C_2$-$C_6$alkenylcarbonyl, $C_2$-$C_6$alkynylcarbonyl, $C_1$-$C_6$alkylaminocarbonyl, $C_1$-$C_6$dialkylaminocarbonyl, $C_1$-$C_6$alkylsulfonylaminocarbonyl, $C_1$-$C_6$alkoxycarbonyl, arylaminocarbonyl and $C_3$-$C_7$cycloalkylaminocarbonyl.

In the present invention, the term "halogen" refers to fluoro, chloro, bromo or iodo, unless otherwise indicated.

In the present invention, the term "alkyl" refers to a monovalent saturated hydrocarbon radical having linear, circular or branched residue, unless otherwise indicated. The "alkyl" may contain any carbon-carbon double bond or triple bond when the alkyl is composed of 2 or more carbon atoms, and should have 3 or more carbon atoms to form circular residue.

In the present invention, the term "alkoxy" refers to an oxygen derivative of the said alkyl, unless otherwise indicated.

In the present invention, the term "aryl" refers to a $C_5$-$C_{12}$ cyclic or bicyclic aromatic hydrocarbon, e.g., phenyl or naphthyl, unless otherwise indicated.

Examples of more preferred compounds of formula (I) according to the present invention are:

N-[7-(1-acetyl-piperidin-4-ylmethoxy)-4-(4-bromo-2-fluoro-phenylamino)-quinazolin-6-yl]-acrylamide;
N-{4-(4-bromo-2-fluoro-phenylamino)-7-[1-(2,2,2-trifluoro-acetyl)-piperidin-4-ylmethoxy]-quinazolin-6-yl}-acrylamide;
N-{4-(4-bromo-2-fluoro-phenylamino)-7-[1-(2-methanesulfonyl-acetyl)-piperidin-4-ylmethoxy]-quinazolin-6-yl}-acrylamide;
4-[6-acryloylamino-4-(4-bromo-2-fluoro-phenylamino)-quinazolin-7-yloxymethyl]-piperidin-1-carboxylic acid amide;
N-[7-(1-acryloyl-piperidin-4-ylmethoxy)-4-(4-bromo-2-fluoro-phenylamino)-quinazolin-6-yl]-acrylamide;
N-[4-(4-bromo-2-fluoro-phenylamino)-7-(pyridin-4-ylmethoxy)-quinazolin-6-yl]-acrylamide;
N-[7-(1-acetyl-piperidin-4-ylmethoxy)-4-(2,3,4-trifluoro-phenylamino)-quinazolin-6-yl]-acrylamide;
N-[7-(1-acetyl-piperidin-4-ylmethoxy)-4-(4-bromo-2,6-difluoro-phenylamino)-quinazolin-6-yl]-acrylamide;
4-[6-acryloylamino-4-(4-bromo-2-fluoro-phenylamino)-quinazolin-7-yloxymethyl]-piperidin-1-carboxylic acid propylamide;
N-{4-(4-bromo-2-fluoro-phenylamino)-7-[1-(2-dimethylamino-acetyl)-piperidin-4-ylmethoxy]-quinazolin-6-yl}-acrylamide;
4-[6-acryloylamino-4-(4-bromo-2-fluoro-phenylamino)-quinazolin-7-yloxymethyl]-piperidin-1-carboxylic acid t-butylamide;
N-{4-(4-bromo-2-fluoro-phenylamino)-7-[3-(2-dimethylamino-acetylamino)-propoxy]-quinazolin-6-yl}-acrylamide;
N-[7-(3-acetylamino-propoxy)-4-(4-bromo-2-fluoro-phenylamino)-quinazolin-6-yl]-acrylamide;
N-{4-(4-bromo-2-fluoro-phenylamino)-7-[3-(2,2,2-trifluoro-acetylamino)-propoxy]-quinazolin-6-yl}-acrylamide;
N-{4-(4-bromo-2-fluoro-phenylamino)-7-[3-(2-methanesulfonyl-acetylamino)-propoxy]-quinazolin-6-yl}-acrylamide;
N-{4-(4-bromo-2-fluoro-phenylamino)-7-[3-(3-ethyl-ureido)-propoxy]-quinazolin-6-yl}-acrylamide;
N-[4-(4-bromo-2-fluoro-phenylamino)-7-(3-methylamino-propoxy)-quinazolin-6-yl]-acrylamide;
N-[7-(2-acetylamino-ethoxy)-4-(4-bromo-2-fluoro-phenylamino)-quinazolin-6-yl]-acrylamide;
N-[4-(4-bromo-2-fluoro-phenylamino)-7-(2-dimethylamino-ethoxy)-quinazolin-6-yl]-acrylamide;
N-[7-(4-acetylamino-butoxy)-4-(4-bromo-2-fluoro-phenylamino)-quinazolin-6-yl]-acrylamide;
Cyclopropane carboxylic acid {2-[6-acrylamino-4-(4-bromo-2-fluoro-phenylamino)-quinazolin-7-yloxy]-ethyl}-amide;
N-{4-(4-bromo-2-fluoro-phenylamino)-7-[2-(2,2-difluoro-acetylamino)-ethoxy]-quinazolin-6-yl}-acrylamide;
N-{4-(4-bromo-2-fluoro-phenylamino)-7-[2-(3-ethyl-ureido)-ethoxy]-quinazolin-6-yl}-acrylamide;
N-[4-(4-bromo-2-fluoro-phenylamino)-7-(2-ureido-ethoxy)-quinazolin-6-yl]-acrylamide,
N-[4-(4-bromo-2-fluoro-phenylamino)-7-[2-(2-dimethylamino-acetylamino)-ethoxy]-quinazolin-6-yl]-acrylamide;
N-{2-[6-acryloylamino-4-(4-bromo-2-fluoro-phenylamino)-quinazolin-7-yloxy]-ethyl}-acrylamide;
N-[4-(4-bromo-2-fluoro-phenylamino)-7-(2-propionylamino-ethoxy)-quinazolin-6-yl]-acrylamide;
N-[4-(4-bromo-2-fluoro-phenylamino)-7-[2-(2,2,2-trifluoro-acetylamino)-ethoxy]-quinazolin-6-yl]-acrylamide;
N-[7-(2-amino-ethoxy)-4-(4-bromo-2-fluoro-phenylamino)-quinazolin-6-yl]-acrylamide;
N-[4-(4-bromo-2-fluoro-phenylamino)-7-(2-methylamino-ethoxy)-quinazolin-6-yl]-acrylamide;
N-[4-(4-bromo-2-fluoro-phenylamino)-7-but-3-enyloxy-quinazolin-6-yl]-acrylamide;
N-[4-(4-bromo-2-fluoro-phenylamino)-7-(2-methoxy-ethoxy)-quinazolin-6-yl]-acrylamide;
N-[4-(4-bromo-2-fluoro-phenylamino)-7-(2-methanesulfonylamino-ethoxy)-quinazolin-6-yl]-acrylamide;
N-{4-(4-bromo-2-fluoro-phenylamino)-7-[2-(3-propyl-ureido)-ethoxy]-quinazolin-6-yl}-acrylamide;
N-{4-(4-bromo-2-fluoro-phenylamino)-7-[2-(3-methyl-thioureido)-ethoxy]-quinazolin-6-yl}-acrylamide;
N-{4-(4-bromo-2-fluoro-phenylamino)-7-[2-(3-ethyl-thioureido)-ethoxy]-quinazolin-6-yl}-acrylamide;
N-{4-(4-bromo-2-fluoro-phenylamino)-7-[2-(3-isopropyl-ureido)-ethoxy]-quinazolin-6-yl}-acrylamide;
N-{4-(4-bromo-2-fluoro-phenylamino)-7-[2-(3-sec-butyl-ureido)-ethoxy]-quinazolin-6-yl}-acrylamide;
N-{4-(4-bromo-2-fluoro-phenylamino)-7-[2-(3-vinyl-ureido)-ethoxy]-quinazolin-6-yl}-acrylamide;
N-[7-[2-(3-allyl-ureido)-ethoxy]-4-(4-bromo-2-fluoro-phenylamino)-quinazolin-6-yl]-acrylamide;
Morpholine-4-carboxylic acid {2-[6-acryloylamino-4-(4-bromo-3-chloro-2-fluoro-phenylamino)-quinazolin-7-yloxy]-ethyl}-amide;
N-[7-[2-(acetyl-methyl-amino)-ethoxy]-4-(4-bromo-2-fluoro-phenylamino)-quinazolin-6-yl]-acrylamide;
N-[7-(2-acetylamino-ethylsulfanyl)-4-(4-bromo-2-fluoro-phenylamino)-quinazolin-6-yl]-acrylamide;
N-{4-(4-bromo-2-fluoro-phenylamino)-7-[2-(2-methoxy-acetylamino)-ethoxy]-quinazolin-6-yl}-acrylamide;
N-{4-(4-bromo-2-fluoro-phenylamino)-7-[2-(2-hydroxy-acetylamino)-ethoxy]-quinazolin-6-yl}-acrylamide;
N-{4-(4-bromo-2-fluoro-phenylamino)-7-[2-(2-methylsulfanyl-acetylamino)-ethoxy]-quinazolin-6-yl}-acrylamide;
N-{4-(4-bromo-2-fluoro-phenylamino)-7-[2-(2-methanesulfonyl-acetylamino)-ethoxy]-quinazolin-6-yl}-acrylamide;

N-[4-(4-bromo-2-fluoro-phenylamino)-7-(2-isobutyrylamino-ethoxy)-quinazolin-6-yl]-acrylamide;
N-{2-[6-acryloylamino-4-(4-bromo-2-fluoro-phenylamino)-quinazolin-7-yloxy]-ethyl}-2-methyl-acrylamide;
But-2-enoic acid {2-[6-acryloylamino-4-(4-bromo-2-fluoro-phenylamino)-quinazolin-7-yloxy]-ethyl}-amide;
N-{2-[6-acryloylamino-4-(4-bromo-2-fluoro-phenylamino)-quinazolin-7-yloxy]-ethyl}-butylamide;
Pent-2-enoic acid {2-[6-acryloylamino-4-(4-bromo-2-fluoro-phenylamino)-quinazolin-7-yloxy]-ethyl}-amide;
4-dimethylamino-but-2-enoic acid {2-[6-acryloylamino-4-(4-bromo-2-fluoro-phenylamino)-quinazolin-7-yloxy]-ethyl}-amide;
N-{4-(4-bromo-3-chloro-2-fluoro-phenylamino)-7-[2-(3-t-butyl-ureido)-ethoxy]-quinazolin-6-yl}-acrylamide;
N-{4-(4-bromo-2-fluoro-phenylamino)-7-[2-(2-oxo-propylamino)-ethoxy]-quinazolin-6-yl}-acrylamide;
N-(4-(4-bromo-2-fluoro-phenylamino)-7-{2-[2-(ethyl-methyl-amino)-acetylamino]-ethoxy}-quinazolin-6-yl)-acrylamide;
N-[7-[2-(2-amino-acetylamino)-ethoxy]-4-(4-bromo-2-fluoro-phenylamino)-quinazolin-6-yl]-acrylamide;
N-{4-(4-bromo-2-fluoro-phenylamino)-7-[2-(2-dimethylamino-propionylamino)-ethoxy]-quinazolin-6-yl}-acrylamide;
N-{4-(4-bromo-2-fluoro-phenylamino)-7-[2-(3-diethylamino-propionylamino)-ethoxy]-quinazolin-6-yl}-acrylamide;
N-{4-(4-bromo-2-fluoro-phenylamino)-7-[2-(2-methylamino-acetylamino)-ethoxy]-quinazolin-6-yl}-acrylamide;
N-{4-(4-bromo-2-fluoro-phenylamino)-7-[2-(3-dimethylamino-propionylamino)-ethoxy]-quinazolin-6-yl}-acrylamide;
N-[7-[2-(3-amino-propionylamino)-ethoxy]-4-(4-bromo-2-fluoro-phenylamino)-quinazolin-6-yl]-acrylamide;
{2-[6-acryloylamino-4-(4-bromo-2-fluoro-phenylamino)-quinazolin-7-yloxy]-ethyl}-carbamic acid methylester;
N-{4-(4-bromo-2-fluoro-phenylamino)-7-[2-(3-methoxy-propionylamino)-ethoxy]-quinazolin-6-yl}-acrylamide;
N-{4-(4-bromo-2-fluoro-phenylamino)-7-[(2-diethylamino-ethylcarbamoyl)-methoxy]-quinazolin-6-yl}-acrylamide;
N-{2-[6-acryloylamino-4-(4-bromo-2-fluoro-phenylamino)-quinazolin-7-yloxy]-ethyl}-4-dimethylamino-butylamide;
N-{4-(4-bromo-2-fluoro-phenylamino)-7-[2-(3-hydroxy-propionylamino)-ethoxy]-quinazolin-6-yl}-acrylamide;
N-[4-(2,4-difluorophenylamino)-7-{2-[2-(dimethylamino)-acetylamino]-ethoxy}-quinazolin-6-yl]-acrylamide;
N-{2-[6-acryloylamino-4-(4-bromo-2-fluoro-phenylamino)-quinazolin-7-yloxy]-ethyl}-malonic acid ethylester;
N-{2-[6-acryloylamino-4-(4-bromo-2-fluoro-phenylamino)-quinazolin-7-yloxy]-ethyl}-malonic acid;
{2-[6-acryloylamino-4-(4-bromo-2-fluoro-phenylamino)-quinazolin-7-yloxy]-ethyl}-oxalamic acid ethylester;
{2-[6-acryloylamino-4-(4-bromo-2-fluoro-phenylamino)-quinazolin-7-yloxy]-ethyl}-oxalamic acid;
N-{4-(4-bromo-2-fluoro-phenylamino)-7-[2-(2-methoxy-imino-acetylamino)-ethoxy]-quinazolin-6-yl}-acrylamide;
N-{4-(4-bromo-2-fluoro-phenylamino)-7-[2-(3-dimethylamino-2-methyl-propionylamino)-ethoxy]-quinazolin-6-yl}-acrylamide;
N-{2-[6-acryloylamino-4-(4-bromo-2-fluoro-phenylamino)-quinazolin-7-yloxy]-ethyl}-3-dimethylamino-butylamide;
N-[7-(2-acetylamino-ethoxy)-4-(4-bromo-2-fluoro-phenylamino)-quinazolin-6-yl]-2-methyl-acrylamide;
Propionic acid [7-(2-acetylamino-ethoxy)-4-(4-bromo-2-fluoro-phenylamino)-quinazolin-6-yl]-amide;
N-[7-(2-acetylamino-ethoxy)-4-(4-bromo-2-fluoro-phenylamino)-quinazolin-6-yl]-N-methyl-acrylamide;
N-4-(4-bromo-3-fluoro-phenylamino)-7-[2-(2-dimethylamino-acetylamino)-ethoxy]-quinazolin-6-yl-acrylamide;
N-[7-(2-acetylamino-1-methyl-ethoxy)-4-(4-bromo-2-fluoro-phenylamino)-quinazolin-6-yl]-acrylamide;
N-[7-(2-acetylamino-propoxy)-4-(4-bromo-2-fluoro-phenylamino)-quinazolin-6-yl]-acrylamide;
(R)—N-[7-(2-acetylamino-propoxy)-4-(4-bromo-2-fluoro-phenylamino)-quinazolin-6-yl]-acrylamide;
(S)—N-[7-(2-acetylamino-propoxy)-4-(4-bromo-2-fluoro-phenylamino)-quinazolin-6-yl]-acrylamide;
N-[4-(4-bromo-2-fluoro-phenylamino)-7-(2-propionylamino-propoxy)-quinazolin-6-yl]-acrylamide;
N-{4-(4-bromo-2-fluoro-phenylamino)-7-[2-(3-propyl-ureido)-propoxy]-quinazolin-6-yl}-acrylamide;
N-[7-(2-acetylamino-butoxy)-4-(4-bromo-2-fluoro-phenylamino)-quinazolin-6-yl]-acrylamide;
N-[4-(4-bromo-2-fluoro-phenylamino)-7-(3-propionylamino-propoxy)-quinazolin-6-yl]-acrylamide;
N-[7-(1-acetyl-pyrrolidin-3-yloxy)-4-(4-bromo-2-fluoro-phenylamino)-quinazolin-6-yl]-acrylamide;
N-[7-(1-acetyl-piperidin-3-yloxy)-4-(4-bromo-2-fluoro-phenylamino)-quinazolin-6-yl]-acrylamide;
N-{4-(4-bromo-2-fluoro-phenylamino)-7-[2-(thiazol-2-ylamino)-ethoxy]-quinazolin-6-yl}-acrylamide;
N-[4-(4-bromo-2-fluoro-phenylamino)-7-(2-oxo-oxazolidin-5-ylmethoxy)-quinazolin-6-yl]-acrylamide;
Thiophene-2-carboxylic acid {2-[6-acryloylamino-4-(4-bromo-2-fluoro-phenylamino)-quinazolin-7-yloxy]-ethyl}-amide;
Morpholine-4-carboxylic acid {2-[6-acryloylamino-4-(4-bromo-2-fluoro-phenylamino)-quinazolin-7-yloxy]-ethyl}-amide;
Piperazine-1-carboxylic acid {2-[6-acryloylamino-4-(4-bromo-2-fluoro-phenylamino)-quinazolin-7-yloxy]-ethyl}-amide;
4-acetyl-piperazine-1-carboxylic acid {2-[6-acryloylamino-4-(4-bromo-2-fluoro-phenylamino)-quinazolin-7-yloxy]-ethyl}-amide;
4-methyl-piperazine-1-carboxylic acid {2-[6-acryloylamino-4-(4-bromo-2-fluoro-phenylamino)-quinazolin-7-yloxy]-ethyl}-amide;
Pyrrolidine-2-carboxylic acid {2-[6-acryloylamino-4-(4-bromo-2-fluoro-phenylamino)-quinazolin-7-yloxy]-ethyl}-amide;
1-methyl-pyrrolidine-2-carboxylic acid {2-[6-acryloylamino-4-(4-bromo-2-fluoro-phenylamino)-quinazolin-7-yloxy]-ethyl}-amide;
1H-pyrrole-2-carboxylic acid {2-[6-acryloylamino-4-(4-bromo-2-fluoro-phenylamino)-quinazolin-7-yloxy]-ethyl}-amide;
1-methyl-pyrrolidine-2-carboxylic acid {2-[6-acryloylamino-4-(4-bromo-2-fluoro-phenylamino)-quinazolin-7-yloxy]-ethyl}-amide;
N-{4-(4-bromo-2-fluoro-phenylamino)-7-[2-(2-piperidin-1-yl-acetylamino)-ethoxy]-quinazolin-6-yl}-acrylamide;

N-(4-(4-bromo-2-fluoro-phenylamino)-7-{2-[2-(4-methyl-piperazin-1-yl)-acetylamino]-ethoxy}-quinazolin-6-yl)-acrylamide;

N-{4-(4-bromo-2-fluoro-phenylamino)-7-[2-(2-morpholin-4-yl-acetylamino)-ethoxy]-quinazolin-6-yl}-acrylamide;

N-{4-(4-bromo-2-fluoro-phenylamino)-7-[2-(3-piperidin-1-yl-propionylamino)-ethoxy]-quinazolin-6-yl}-acrylamide;

1-acetyl-pyrrolidine-2-carboxylic acid {2-[6-acryloylamino-4-(4-bromo-2-fluoro-phenylamino)-quinazolin-7-yloxy]-ethyl}-amide;

1-propionyl-pyrrolidine-2-carboxylic acid {2-[6-acryloylamino-4-(4-bromo-2-fluoro-phenylamino)-quinazolin-7-yloxy]-ethyl}-amide;

N-{4-(4-bromo-2-fluoro-phenylamino)-7-[2-(2-pyrrolidin-1-yl-acetylamino)-ethoxy]-quinazolin-6-yl}-acrylamide;

N-{4-(4-bromo-2-fluoro-phenylamino)-7-[2-(2-2,5-dihydro-pyrrol-1-yl-acetylamino)-ethoxy]-quinazolin-6-yl}-acrylamide;

N-[4-(4-bromo-2-fluoro-phenylamino)-7-(4,5-dihydro-oxazol-2-ylmethoxy)-quinazolin-6-yl]-acrylamide;

N-[7-[2-(2-azetidin-1-yl-acetylamino)-ethoxy]-4-(4-bromo-2-fluoro-phenylamino)-quinazolin-6-yl]-acrylamide;

N-[7-(2-acetylamino-ethoxy)-4-(3-chloro-4-fluoro-phenylamino)-quinazolin-6-yl]-acrylamide;

N-[7-(2-acetylamino-ethoxy)-4-(4-chloro-2-fluoro-phenylamino)-quinazolin-6-yl]-acrylamide;

N-[7-(2-acetylamino-ethoxy)-4-(4-chloro-2-chloro-phenylamino)-quinazolin-6-yl]-acrylamide;

N-[7-(2-acetylamino-ethoxy)-4-(4-bromo-2-trifluoromethyl-phenylamino)-quinazolin-6-yl]-acrylamide;

N-[7-(2-acetylamino-ethoxy)-4-(4-bromo-2-chloro-phenylamino)-quinazolin-6-yl]-acrylamide;

N-{4-(4-chloro-2-fluoro-phenylamino)-7-[2-(2-dimethylamino-acetylamino)-ethoxy]-quinazolin-6-yl}-acrylamide;

N-[4-(3-chloro-2-fluoro-phenylamino)-7-{2-[2-(dimethylamino)-acetamido]-ethoxy}quinazolin-6-yl]-acrylamide;

N-[7-(2-acetylamino-ethoxy)-4-(2,3,4-trifluoro-phenylamino)-quinazolin-6-yl]-acrylamide;

N-[7-(2-acetylamino-ethoxy)-4-(4-bromo-2,5-difluoro-phenylamino)-quinazolin-6-yl]-acrylamide;

N-[7-(2-acetylamino-ethoxy)-4-(4-bromo-2,6-difluoro-phenylamino)-quinazolin-6-yl]-acrylamide;

N-[7-(2-acetylamino-ethoxy)-4-(4,5-dichloro-2-fluoro-phenylamino)-quinazolin-6-yl]-acrylamide;

N-[7-(2-acetylamino-ethoxy)-4-(2,4,5-trichloro-phenylamino)-quinazolin-6-yl]-acrylamide;

N-[4-(4-bromo-2,6-difluorophenylamino)-7-{2-[2-(dimethylamino)-acetamido]-ethoxy}-quinazolin-6-yl]-acrylamide;

N-{4-(4-bromo-2,3-difluoro-phenylamino)-7-[2-(2-dimethylamino-acetylamino)-ethoxy]-quinazolin-6-yl}-acrylamide;

N-{4-(4-bromo-2,3-difluoro-phenylamino)-7-[2-(3-diethylamino-propionylamino)-ethoxy]-quinazolin-6-yl}-acrylamide;

N-{4-(4-bromo-2,3-difluoro-phenylamino)-7-[2-(3-piperidin-1-yl-propionylamino)-ethoxy]-quinazolin-6-yl}-acrylamide;

N-{2-[6-acryloylamino-4-(4-bromo-2,3-difluoro-phenylamino)-quinazolin-7-oxy]-ethyl}-4-dimethylamino-butylamide;

N-[7-(2-acetylamino-ethoxy)-4-(6-chloro-pyridin-3-ylamino)-quinazolin-6-yl]-acrylamide;

N-[7-(2-acetylamino-ethoxy)-4-(4-chloro-2-fluoro-5-methoxy-phenylamino)-quinazolin-6-yl]-acrylamide;

N-{7-(2-acetylamino-ethoxy)-4-[3-chloro-4-(pyridin-3-ylmethoxy)-phenylamino]-quinazolin-6-yl}-acrylamide;

5-[7-(2-acetylamino-ethoxy)-6-acryloylamino-quinazolin-4-ylamino]-2-bromo-4-fluoro-N-methoxy-benzamide;

N-[7-(2-acetylamino-ethoxy)-4-(2,4-dichloro-5-methoxy-phenylamino)-quinazolin-6-yl]-acrylamide;

N-[7-(2-acetylamino-ethoxy)-4-(4-bromo-5-chloro-2-fluoro-phenylamino)-quinazolin-6-yl]-acrylamide;

N-[4-(4-bromo-5-chloro-2-fluoro-phenylamino)-7-(2-propionylamino-ethoxy)-quinazolin-6-yl]-acrylamide;

N-{4-(4-bromo-5-chloro-2-fluoro-phenylamino)-7-[2-(2-dimethylamino-acetylamino)-ethoxy]-quinazolin-6-yl}-acrylamide;

N-[4-(4,5-dichloro-2-fluoro-phenylamino)-7-(2-dimethylamino-ethoxy)-quinazolin-6-yl]-acrylamide;

N-[4-(4,5-dichloro-2-fluoro-phenylamino)-7-(2-propionylamino-ethoxy)-quinazolin-6-yl]-acrylamide;

N-{4-(4,5-dichloro-2-fluoro-phenylamino)-7-[2-(2-methoxy-acetylamino)-ethoxy]-quinazolin-6-yl}-acrylamide;

N-{4-(4,5-dichloro-2-fluoro-phenylamino)-7-[2-(2-methanesulfonyl-acetylamino)-ethoxy]-quinazolin-6-yl}-acrylamide;

N-{4-(4,5-dichloro-2-fluoro-phenylamino)-7-[2-(2-dimethylamino-acetylamino)-ethoxy]-quinazolin-6-yl}-acrylamide;

N-[7-(2-acetylamino-ethoxy)-4-(4-bromo-3-chloro-2-fluoro-phenylamino)-quinazolin-6-yl]-acrylamide;

N-[4-(4-bromo-3-chloro-2-fluoro-phenylamino)-7-(2-propionylamino-ethoxy)-quinazolin-6-yl]-acrylamide;

N-{4-(4-bromo-3-chloro-2-fluoro-phenylamino)-7-[2-(2-dimethylamino-acetylamino)-ethoxy]-quinazolin-6-yl}-acrylamide;

N-{4-(4-bromo-3-chloro-2-fluoro-phenylamino)-7-[2-(3-diethylamino-propionylamino)-ethoxy]-quinazolin-6-yl}-acrylamide;

N-{4-(4-bromo-3-chloro-2-fluoro-phenylamino)-7-[2-(3-hydroxy-propionylamino)-ethoxy]-quinazolin-6-yl}-acrylamide;

N-{4-(4-bromo-3-chloro-2-fluoro-phenylamino)-7-[2-(2-methoxy-acetylamino)-ethoxy]-quinazolin-6-yl}-acrylamide;

N-{4-(4-bromo-3-chloro-2-fluoro-phenylamino)-7-[2-(3-piperidin-1-yl-propionylamino)-ethoxy]-quinazolin-6-yl}-acrylamide;

N-{2-[6-acryloylamino-4-(4-bromo-3-chloro-2-fluoro-phenylamino)-quinazolin-7-yloxy]-ethyl}-4-dimethylamino-butylamide;

N-{4-(4-bromo-3-chloro-2-fluoro-phenylamino)-7-[2-(2-hydroxy-acetylamino)-ethoxy]-quinazolin-6-yl}-acrylamide;

N-{4-(4-bromo-3-chloro-2-fluoro-phenylamino)-7-[2-(3-methoxy-propionylamino)-ethoxy]-quinazolin-6-yl}-acrylamide;

N-{4-(4-bromo-3-chloro-2-fluoro-phenylamino)-7-[2-(2-diethylamino-acetylamino)-ethoxy]-quinazolin-6-yl}-acrylamide;

N-{4-(4-bromo-3-chloro-phenylamino)-7-[2-(2-dimethylamino-acetylamino)-ethoxy]-quinazolin-6-yl}-acrylamide;

N-{4-(4-bromo-2-fluoro-phenylamino)-7-[2-(2-dimethylamino-acetylamino-propoxy]-quinazolin-6-yl}-acrylamide;

N-{4-(4-bromo-2-fluoro-phenylamino)-7-[2-(2-dimethylamino-acetylamino)-2-methyl-propoxy]-quinazolin-6-yl}-acrylamide;

N-{4-(4-bromo-2-fluoro-phenylamino)-7-[2-(3-diethylamino-propionylamino)-propoxy]-quinazolin-6-yl}-acrylamide;

N-{4-(4-bromo-2-fluoro-phenylamino)-7-[2-(2-dimethylamino-acetylamino)-3-methyl-buthoxy]-quinazolin-6-yl}-acrylamide;

N-{4-(4-bromo-3-chloro-2-fluoro-phenylamino)-7-[2-(2-dimethylamino-acetylamino)-propoxy]-quinazolin-6-yl-acrylamide;

(S)—N-4-(4-bromo-3-chloro-2-fluoro-phenylamino)-7-[2-(2-dimethylamino-acetylamino)-propoxy]-quinazolin-6-yl-acrylamide;

(R)—N-{4-(4-bromo-3-chloro-2-fluoro-phenylamino)-7-[2-(2-dimethylamino-acetylamino)-propoxy]-quinazolin-6-yl-acrylamide;

N-{4-(4-bromo-2-fluoro-phenylamino)-7-[2-(2-dimethylamino-acetylamino)-butoxy]-quinazolin-6-yl}-acrylamide;

N-{4-(4-bromo-2-fluoro-phenylamino)-7-[2-(2-dimethylamino-3-methoxy-propionylamino)-ethoxy]-quinazolin-6-yl}-acrylamide;

N-{4-(4-bromo-2-fluoro-phenylamino)-7-[2-(2-dimethylamino-3-hydroxy-propionylamino)-ethoxy]-quinazolin-6-yl}-acrylamide;

(S)—N-4-(4-bromo-3-chloro-2-fluoro-phenylamino)-7-[2-(2-dimethylamino-acetylamino)-propoxy]-quinazolin-6-yl-acrylamide;

(R)—N-4-(4-bromo-3-chloro-2-fluoro-phenylamino)-7-[2-(2-dimethylamino-acetylamino)-propoxy]-quinazolin-6-yl-acrylamide;

{2-[6-acryloylamino-4-(4-bromo-3-chloro-2-fluoro-phenylamino)-quinazolin-7-yloxy]-ethyl}-carbamic acid methylester;

N-{4-(4-chloro-2,5-dimethoxy-phenylamino)-7-[2-(2-dimethylamino-acetylamino)-ethoxy]-quinazolin-6-yl}-acrylamide;

N-{4-(4-bromo-2-fluoro-phenylamino)-7-[2-(2-diethylamino-acetylamino)-ethoxy]-quinazolin-6-yl}-acrylamide;

N-{4-(4-bromo-3-chloro-2-fluoro-phenylamino)-7-[2-(3-ethyl-ureido)-ethoxy]-quinazolin-6-yl}-acrylamide;

N-{4-(4-bromo-3-chloro-2-fluoro-phenylamino)-7-[2-(3-propyl-ureido)-ethoxy]-quinazolin-6-yl}-acrylamide;

N-{4-(4-bromo-3-chloro-2-fluoro-phenylamino)-7-[2-(3-ethyl-thioureido)-ethoxy]-quinazolin-6-yl}-acrylamide;

4-[6-acryloylamino-4-(4-bromo-2-fluoro-phenylamino)-quinazolin-7-yloxymethyl]-piperidine-1-carboxylic acid ethylamide;

N-[7-(2-acetylamino-ethoxy)-4-(4-chloro-2,5-dimethoxy-phenylamino)-quinazolin-6-yl]-acrylamide; and N-[7-[2-(2-amino-propionylamino)-ethoxy]-4-(4-bromo-2-fluoro-phenylamino)-quinazolin-6-yl]-acrylamide.

The compound of formula (I) of the present invention may be prepared by the procedure shown in Reaction Scheme 1.

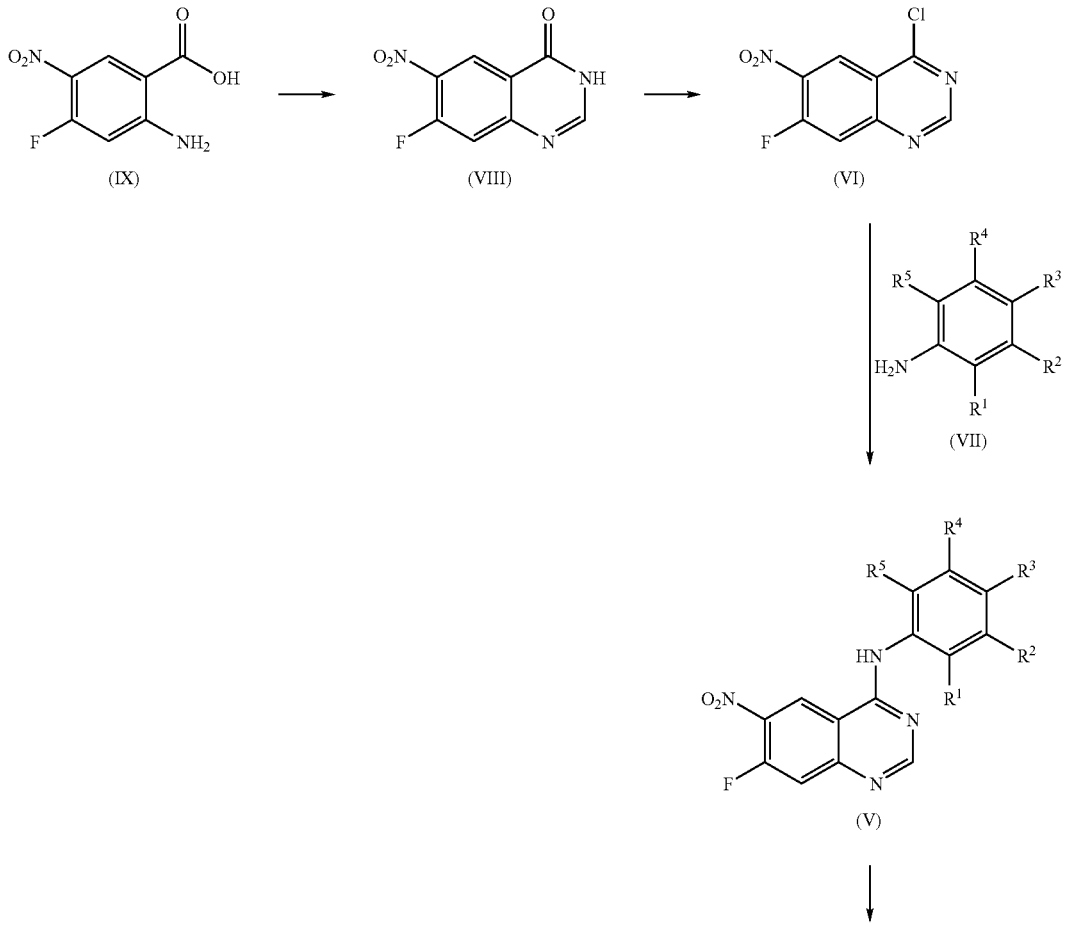

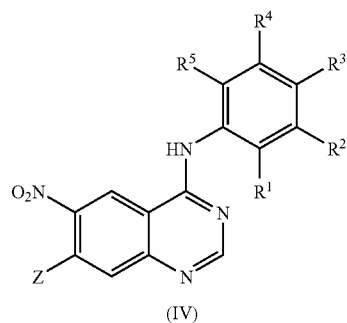

(IV)

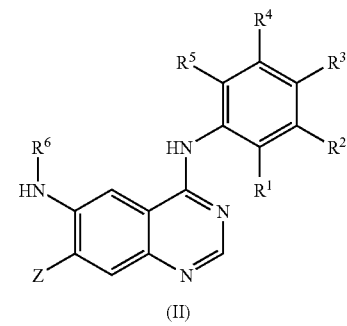

(II)

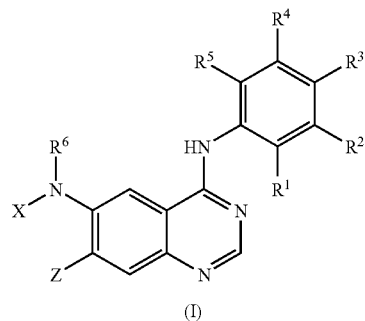

(I)

wherein

R$^1$, R$^2$, R$^3$, R$^4$, R$^5$, R$^6$, X and Z have the same meanings as defined above.

Specifically, the process for preparing of the compound of formula (I) of the present invention when X of formula (I) is C$_2$-C$_6$alkenyl or C$_1$-C$_6$alkynyl (i.e., the compound of formula (Ia) according to the Reaction Scheme 1 comprises the steps of 1) substituting Cl of a compound of formula (VI) with amine of a compound of formula (VII) to obtain a compound of formula (V);

2) subjecting the compound of formula (V) and an alcohol compound containing Z group (ZH) to a substitution reaction to obtain a compound of formula (IV);

3) reducing the compound of formula (IV) to obtain a compound of formula (II); and 4) subjecting the compound of formula (II) and a compound of formula (III) to a condensation reaction to obtain the compound of formula (Ia).

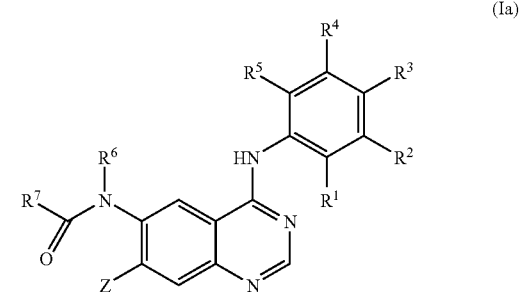

(Ia)

-continued

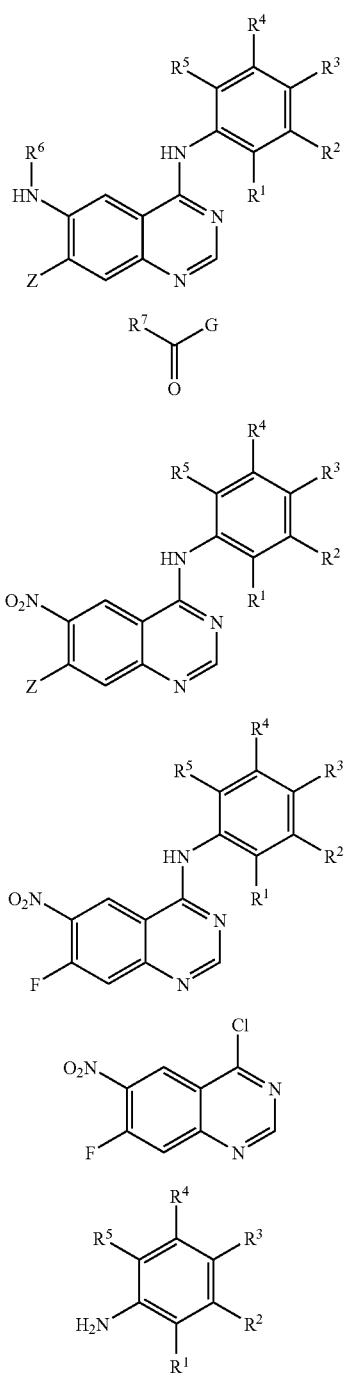

wherein
$R^1$, $R^2$, $R^3$, $R^4$, $R^5$, $R^6$ and Z have the same meanings as defined above;
$R^7$ is $C_2$-$C_6$alkenyl or $C_1$-$C_6$alkynyl optionally substituted with $R^{13}$, $R^{13}$ being halogen, hydroxy, amino, thiol, carbamoyl, trifluoromethyl, cyano, $C_1$-$C_6$alkyl, $C_3$-$C_7$cycloalkyl, $C_1$-$C_6$alkoxy, $C_1$-$C_6$alkylamine, di$C_1$-$C_6$alkylamine, $C_1$-$C_6$alkylcarboamine, $C_2$-$C_6$alkenylcarboamine, $C_2$-$C_6$alkynylcarboamine, di$C_1$-$C_6$alkylcarboamine, $C_1$-$C_6$alkylthio, $C_1$-$C_6$alkylsulfonyl, $C_1$-$C_6$alkylsulfonylcarboamine, $C_1$-$C_6$alkoxycarbonyl or heterocyclo; and
G is halogen, hydroxy or $C_1$-$C_6$alkanoyloxy.

Each step of the procedure of Reaction Scheme 1 is as follows.

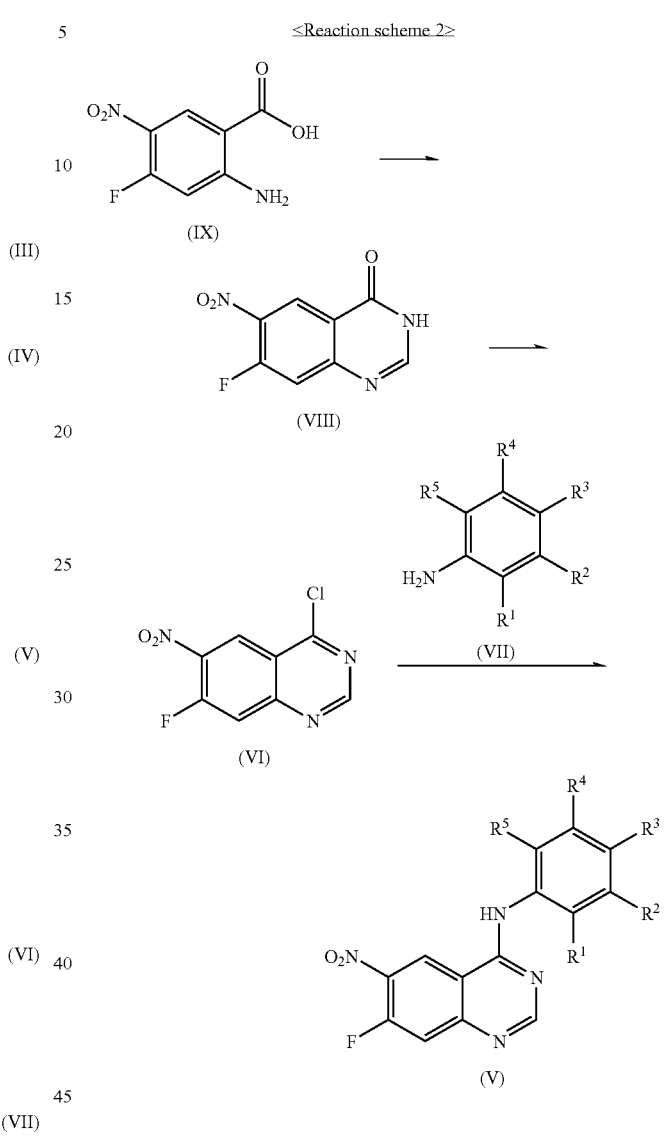

wherein
$R^1$, $R^2$, $R^3$, $R^4$ and $R^5$ have the same meanings as defined above.

In Reaction Scheme 2, Cl of the compound of formula (VI) is substituted with amine of the compound of formula (VII) to obtain the compound of formula (V). In this substitution reaction, a base selected from the group consisting of triethylamine, potassium carbonate, sodium carbonate, N,N-dimethylaniline and diisopropylethylamine may be added. The reaction can be carried out in a solvent such as isopropanol, acetonitrile, dimethylformamide and dimethylsulfoxide at a temperature ranging from 0° C. to 150° C., preferably from room temperature to 100° C.

The compound of formula (VI) can be prepared from a compound of formula (IX) through a compound of formula (VIII) in accordance with the method described in [Alexander J. Bridges et al., *Journal of Medicinal Chemistry* 39: 267, 1996], and the compound of formula (VII) is commercially available.

<Reaction Scheme 3>

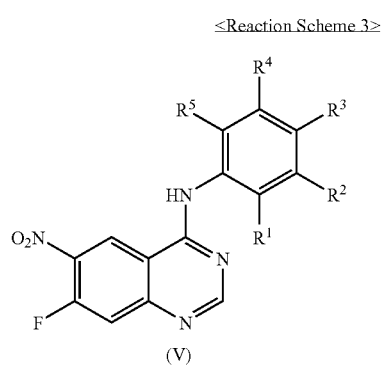

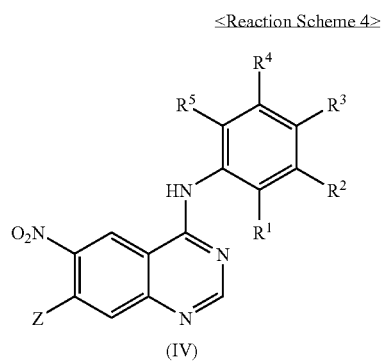

wherein
R¹, R², R³, R⁴, R⁵ and Z have the same meanings as defined above.

In Reaction Scheme 3, F of the compound of formula (V) prepared in Reaction Scheme 2 is substituted with Z of an alcohol compound (ZH) to obtain the compound of formula (IV), and the alcohol compound may be used in an amount of 1 to 10 equivalents, preferably 1 to 5 equivalents based on the compound of formula (V). In the substitution reaction, an inorganic base such as potassium carbonate, sodium carbonate, sodium hydroxide, sodium hydride, potassium-trimethylsilanoate, potassium t-butoxide or a base such as triethylamine, 1,8-diazabicyclo[5.4.0]undec-7-ene (DBU), N,N-diisopropylethylamine may be used in an amount of 1 to 5 equivalents based on the compound of formula (VI). The solvent used in this reaction may be dimethylformamide, dimethylsulfoxide, toluene or dimethylglycol, and the reaction can be carried out at a temperature ranging from 0° C. to the boiling point of the solvent used, preferably 0 to 100° C.

<Reaction Scheme 4>

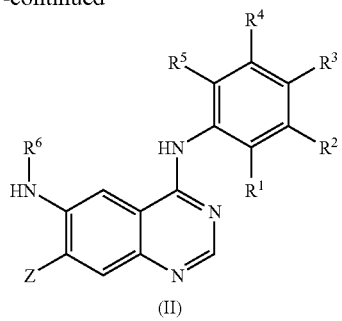

wherein
R¹, R², R³, R⁴, R⁵, R⁶ and Z have the same meanings as defined above.

In Reaction Scheme 4, the compound of formula (IV) prepared in Reaction Scheme 3 is subjected to a reduction reaction to obtain the compound of formula (II). The reductive agent which may be used in this reaction may be selected from the group consisting of indium, palladium, platinum, iron, tartar, and oxide or chloride thereof, and employed in an amount of 1 to 5 equivalents based on the compound of formula (IV). The reduction reaction can be carried out in the presence of hydrogen gas, and cyclohexene or cyclohexadien, or inorganic or organic acid such as acetic acid and hydrochloric acid can be added thereto. The solvent used in this reaction may be selected form the group consisting of THF, 1,4-dioxane, ethylacetate, $C_1$-$C_6$alcohol, methylene chloride, chloroform, water, hexane, toluene and a mixture thereof.

<Reaction Scheme 5>

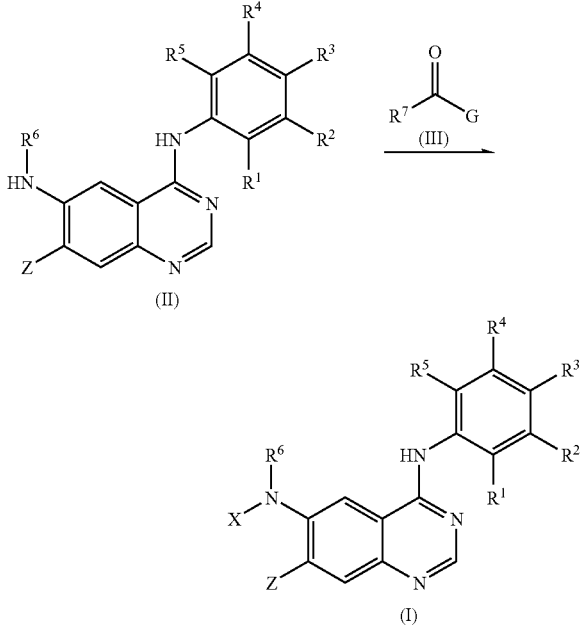

wherein
R¹, R², R³, R⁴, R⁵, R⁶, R⁷, X, Z and G have the same meanings as defined above.

In Reaction Scheme 5, the compound of formula (II) prepared in Reaction Scheme 4 is subjected to a condensation reaction with a compound of formula (III) to obtain the compound of formula (I). The compound of formula (III) may be employed in an amount of 1 to 10 equivalents, preferably 1 to 5 equivalents based on the compound of formula (II).

In case that the G of the compound of formula (III) is halogen or alkanoyloxy, the condensation reaction may be carried out by using just a solvent without a condensation reagent, and in case that the G is hydroxy, the condensation reaction may be carried out by using a condensation reagent such as 1-(3-dimethylaminopropyl)-3-ethylcarbodiimide, N,N-dicyclohexyldiimide, $C_1$-$C_6$alkyl chloroformate and O-(1H-benzotriazol-1-yl)-N,N,N',N'-tetramethyluronium tetrafluoroborate in an amount of 1 to 10 equivalents, preferably 1 to 5 equivalents based on the compound of formula (II).

Further, in the condensation reaction, a catalyst such as N,N-dimethylaminopyridine, N,N-hydroxysuccinimide and N-hydroxybenzotriazole may be used in an amount of 0.05 to 1 equivalent based on the compound of formula (II), and a base such as triethylamine, N,N-diisopropylethylamine, pyridine and N-methylmorpholine may be used in an amount of 1 to 5 equivalents based on the compound of formula (II). The solvent used in the reaction may be selected from the group consisting of methylene chloride, chloroform, N,N-dimethylformamide, tetrahydrofuran, 1,4-dioxane, acetonitrile and a mixture thereof, and the reaction can be carried out at a temperature ranging from −20° C. to the boiling point of the solvent used, preferably 0 to 40° C.

The compound of formula (I) of the present invention can also be used in the form of a pharmaceutically acceptable salt derived from an inorganic or organic acid, such as hydrochloric acid, sulfuric acid, phosphoric acid, nitric acid, malonic acid, succinic acid, citric acid, glutaric acid, acetic acid, maloic acid, formic acid, fumaric acid, tartaric acid, maleic acid, benzoic acid, methanesulfonic acid, benzenesulfonic acid and toluenesulfonic acid.

The inventive compound or the pharmaceutically acceptable salt thereof selectively and effectively inhibits the activity of a tyrosine kinase, preferably a vascular endothelial growth factor receptor (VEGFR) and an epithelial growth factor receptor (EGFR) as well as diseases caused by the overactivity of the tyrosine kinases, and provides enhanced therapeutic effects when combined with other anticancer agents or medicaments. For example, the inventive compound or the pharmaceutically acceptable salt thereof is useful for enhancing the effects of medicaments for treating cancer or other diseases selected from the group consisting of cell signal transduction inhibitors, mitosis inhibitors, alkylating agents, antimetabolites, antibiotics, growth factor inhibitors, cell cycle inhibitors, topoisomerase inhibitors, p-glycoprotein inhibitors, biological reaction modifiers, antihormonal agents and antiandrogen.

Specifically, the inventive quinazoline derivatives exhibit excellent inhibitory effects against VEGFR2 (KDR) tyrosine kinase as well as EGFR1 (Erb-B1 or HER-1) and EGFR2 (Erb-B2 or HER-2) tyrosine kinase. The compounds, which are equally effective on VEGFR and EGFR tyrosine kinases, can effectively treat cancers related to VEGF and EGF, preferably solid cancer, more preferably breast cancer, ovarian cancer, lung cancer, colon cancer and prostate cancer, and can be used for the treatment of VEGF-related diseases, preferably diabetes, psoriasis, rheumatoid arthritis, Kaposi's sarcoma, angioma, acute and chronic nephropathy, arterial restenosis, auto-immune disease, acute infection, eye disease caused by vein abruption. Unlike the quinazoline derivatives available in the market, since the compounds can effectively treat the diseases in an small amount without side effects such as diarrhea and skin rash, the inventive quinazoline derivative and the pharmaceutically acceptable salt thereof can be used in the manufacture of medicaments for inhibiting the activity of a tyrosine kinase or for treating the diseases caused by the overactivity of a tyrosine kinase.

Therefore, the present invention provides a pharmaceutical composition for inhibiting the activity of a tyrosine kinase and a therapeutic composition for treating diseases caused by the overactivity of a tyrosine kinase comprising the compound of formula (I) or a pharmaceutically acceptable salt thereof as an active ingredient together with the pharmaceutically acceptable carrier.

The inventive pharmaceutical or therapeutic composition may be formulated in accordance with any of the conventional methods in the form of tablet, granule, powder, capsule, syrup, emulsion or microemulsion for oral administration, and intramuscular, intravenous or subcutaneous for parenteral administration.

The inventive pharmaceutical or therapeutic composition for oral administration may be prepared by mixing the active ingredient with a carrier or excipient such as cellulose, calcium silicate, corn starch, lactose, sucrose, dextrose, calcium phosphate, sodium phosphate, stearic acid, magnesium stearate, calcium stearate, gelatin, talc, surfactant, suspension agent, emulsifier and diluent. Example of the carrier employed in the injectable composition of the present invention is a water, saline solution, glucose solution, glucose-like solution, alcohol, glycol ether (e.g., polyethylene glycol 400), oil, fatty acid, fatty acid ester, glyceride, surfactant, suspension agent and emulsifier.

The inventive compound or the pharmaceutically acceptable salt thereof may be administered orally or parenterally to a mammal including a human being to inhibit the activity of a tyrosine kinase. The dosage of the active ingredient may be adjusted in light of various relevant factors such as the condition of the subject to be treated, type and seriousness of illness, administration rate, and opinion of doctor. The inventive compound of formula (I) can be administered orally or parenterally in an effective amount ranging from about 0.01 to 100 mg/kg (body weight), preferably 0.2 to 50 mg/kg (body weight) per day in case of a mammal including a human being in a single dose or in divided doses. In certain cases, an amount less than the above dosage may be suitable. An amount greater than the above dosage may be used unless it causes deleterious side effects, and such amount can be administered in divided doses per day.

The following Examples are intended to further illustrate the present invention without limiting its scope.

Example 1

Preparation of N-[7-(1-acetyl-piperidin-4-yl-methoxy)-4-(4-bromo-2-fluoro-phenylamino)-quinazolin-6-yl]-acrylamide <1-1> 4-hydroxymethyl-piperidine-1-carboxylic acid t-butylester Di-t-butyl dicarbonate (17 g, 78 mmol) was added to a mixture of 4-hydroxymethylpiperidine (10 g, 87 mmol) and tetrahydrofuran (THF) 100 ml. The resulting solution was stirred at room temperature for 2 hours, distilled under a reduced pressure to remove the solvent, washed with salt solution and distilled water and extracted with diethylether 100 ml twice. The extract was dried over magnesium sulfate and distilled to obtain the title compound 16.2 g (yield: 86%).

$^1$H NMR (CDCl$_3$) δ: 1.21-1.12 (m, 2H), 1.46 (s, 9H), 1.73-1.65 (m, 3H), 2.70 (t, 2H), 3.50 (t, 2H), 4.13 (d, 2H).

<1-2> 7-fluoro-3H-quinazolin-4-one

A catalytic amount (1 ml) of N,N-dimethylamide was added to 2-amino-4-fluorobenzoic acid (50 g, 322 mmol) and formamide (77 ml, 1934 mmol), and the resulting solution was stirred. The solution was heated to 180° C. and stirred for 14 hours. The temperature of the solution was cooled to room temperature, and 300 ml of distilled water was added thereto. The resulting solid was stirred about 30 min, and filtered to obtain the title compound 41.3 g (yield: 78%).

$^1$H NMR (DMSO-$d_6$) δ: 7.47-7.35 (m, 2H), 8.20-8.13 (m, 2H), 11.85 (bs, 1H).

<1-3> 7-fluoro-6-nitro-3H-quinazolin-4-one

The compound of <1-2> (25 g, 152 mmol) was slowly added to a mixture of concentrated sulfuric acid (50 ml) and fuming nitric acid (51 ml) at 0° C. The resulting solution was stirred at room temperature for 1 hour, heated to 110° C. and stirred for 2 hours. The temperature of the solution was cooled to room temperature, and 300 ml of ice water was added thereto. The resulting solid was stirred about 30 min, and filtered to obtain the title compound 25 g (yield: 79%).

$^1$H NMR (CDCl$_3$) δ: 7.79 (d, 1H), 8.32 (s, 1H), 8.72 (d, 1H), 12.83 (bs, 1H).

<1-4> 4-chloro-7-fluoro-6-nitro-quinazoline

The compound of <1-3> (20 g, 96 mmol), thionyl chloride (170 ml), phosphorousoxy chloride (30 ml) and N,N-dimethylformamide (1 ml) were added into a reaction bottle and stirred. The resulting solution was heated to 100° C. until the mixture was melted transparently, and then stirred for 2 hours. The reaction temperature was cooled to room temperature, and the solution was distilled under a reduced pressure to remove the solvent. The resulting residue was distilled again after adding 300 ml of toluene thereto, and the procedure was repeated three times to obtain the title compound 21 g (yield: 99%).

$^1$H NMR (CDCl$_3$) δ: 7.73 (d, 1H), 8.30 (s, 1H), 8.72 (d, 1H).

<1-5> (4-bromo-2-fluoro-phenyl)-(7-fluoro-6-nitro-quinazolin-4-yl)-amine

The compound of <1-4> (15 g, 66 mmol) was stirred with 4-bromo-2-fluoro-aniline (13 g, 66 mmol) in the presence of isopropyl alcohol (90 ml). The resulting solution was heated to 80° C. and stirred for 4 hours. The temperature of the solution was cooled to room temperature, and the solution was stirred for 10 min after diluting the solution with 100 ml of acetone. The resulting solid was filtered, 100 ml of methanol was added thereto, and 7 N of ammonia diluted with methanol was added thereto until the solution became basic. The solution was distilled under a reduced pressure to remove methanol, 100 ml of water was added thereto, and the solid was filtered to obtain the title compound 25 g (yield: 99%).

$^1$H NMR (CDCl$_3$) δ: 7.39 (s, 2H), 7.59 (d, 1H), 7.73 (d, 1H), 8.48 (s, 1H), 9.41 (d, 1H), 10.35 (bs, 1H).

<1-6> 4-[4-(4-bromo-2-fluoro-phenylamino)-6-nitro-quinazolin-7-yloxymethyl]-piperidin-1-carboxylic acid t-butylester A mixture of sodium hydride (2.5 g, 105 mmol) and N,N-dimethyl-formamide (200 ml) was stirred at 0° C. The compound of <1-1> (17 g, 78.7 mmol) dissolved in 100 ml of N,N-dimethyl-formamide was slowly added to the mixture, and the resulting solution was stirred for 30 min. The compound of <1-5> (20 g, 52.5 mmol) dissolved in 200 ml of N,N-dimethyl-formamide was added thereto for 20 min. The resulting solution was slowly heated to room temperature, and stirred for 4 hours. 500 ml of saturated sodium bicarbonate solution was added thereto, and the resulting solution was extracted with 500 ml of ethylacetate twice and the separated organic layer was washed with 500 ml of distilled water. The organic layer was dried over magnesium sulfate and distilled under a reduced pressure to remove the solution. The resulting residue was subjected to column chromatography to obtain the title compound 15 g (yield: 50%).

$^1$H NMR (DMSO-$d_6$) δ: 1.42-1.27 (m, 2H), 1.48 (s, 9H), 1.88 (d, 2H), 2.11 (m, 1H), 2.78 (t, 2H), 4.08 (d, 2H), 4.21 (d, 2H), 7.42-7.39 (m, 3H), 7.65 (s, 1H), 8.37 (t, 1H), 8.50 (s, 1H), 8.78 (s, 1H).

<1-7> 4-[6-amino-4-(4-bromo-2-fluoro-phenylamino)-quinazolin-7-yloxymethyl]-piperidine-1-carboxylic acid t-butylester Iron (3.35 g, 60 mmol) was added to 20 ml of 5% acetic acid and heated to 100° C. The compound of <1-6> (3.46 g, 6 mmol) dissolved in 20 ml of acetic acid and 20 ml of dichloromethane was slowly added thereto. The resulting mixture was stirred for 4 hours, and cooled to room temperature. The resulting solution was filtered with celite and washed with 100 ml of dichloromethane. 100 ml of saturated sodium bicarbonate solution was added thereto, the solution was extracted with 100 ml of chloroform twice, the resulting organic layer was dried over magnesium sulfate, and distilled under a reduced pressure to obtain the title compound 3.1 g (yield: 95%).

$^1$H NMR (DMSO-$d_6$) δ: 1.28-1.17 (m, 2H), 1.41 (s, 9H), 1.86 (d, 2H), 2.04 (m, 1H), 2.77 (m, 2H), 4.04-4.02 (m, 4H), 5.36 (s, 2H), 7.06 (s, 1H), 7.29 (s, 1H), 7.52-7.44 (m, 1H), 7.62-7.55 (m, 2H), 8.22 (s, 1H), 9.17 (s, 1H).

<1-8> 4-[6-acryloylamino-4-(4-bromo-2-fluoro-phenylamino)-quinazolin-7-yloxymethyl]-piperidine-1-carboxylic acid t-butylester The compound of <1-7> (1 g, 1.83 mmol) and 20 ml of dichloromethane were mixed and stirred. The mixture was cooled to 0° C., and acryloyl chloride (166 mg, 1.83 mmol) diluted with dichloromethane was slowly added thereto. The solution was slowly heated to room temperature and stirred for 2 hours. The reacted solution was washed with 30 ml of saturated sodium bicarbonate solution and extracted with 30 ml of dichloromethane. The resulting organic layer was dried over magnesium sulfate, distilled under a reduced pressure and subjected to column chromatography to obtain the title compound 355 mg (yield: 31%).

$^1$H NMR (CDCl$_3$) δ: 1.36-1.21 (m, 2H), 1.43 (s, 9H), 1.79 (d, 2H), 2.08 (m, 1H), 2.74 (m, 2H), 4.02 (d, 2H), 4.18 (m, 2H), 5.84-5.79 (m, 1H), 6.45-6.24 (m, 2H), 7.27-7.18 (m, 3H), 7.97 (s, 1H), 8.17-8.10 (m, 2H), 8.58 (s, 1H), 9.08 (s, 1H).

<1-9> N-[4-(4-bromo-2-fluoro-phenylamino)-7-(piperidin-4-ylmethoxy)-quinazolin-6-yl]-acrylamide The compound of <1-8> (258 mg, 0.43 mmol) was stirred in the presence of 5 ml of dichloromethane. 1 ml of trifluoroacetic acid was added thereto, and stirred at room temperature for 30 min. The resulting solution was distilled under a reduced pressure to remove the solvent, washed with 10 ml of saturated sodium bicarbonate solution, and extracted with 20 ml of dichloromethane. The resulting organic layer was dried over magnesium sulfate and distilled under a reduced pressure to obtain the title compound 206 mg (yield: 96%).

¹H NMR (CDCl₃) δ: 1.68-1.51 (m, 2H), 2.04-1.94 (m, 2H), 2.16 (m, 1H), 2.95-2.75 (m, 2H), 3.44 (d, 2H), 4.14 (d, 2H), 5.84 (t, 1H), 6.49 (d, 2H), 7.34-7.24 (m, 3H), 7.61 (s, 1H), 8.27 (s, 1H), 8.32 (t, 1H), 8.66 (s, 1H), 9.16 (s, 1H).

<1-10> N-[7-(1-acetyl-piperidin-4-ylmethoxy)-4-(4-bromo-2-fluoro-phenylamino)-quinazolin-6-yl]-acrylamide The compound of <1-9> (220 mg, 0.44 mmol) and 7 ml of dichloromethane was mixed and stirred. The reaction temperature was cooled to 0° C., and acetyl chloride (38 mg, 0.48 mmol) diluted with 3 ml of dichloromethane was slowly added thereto. The solution was slowly heated to room temperature and stirred for 2 hours. The resulting solution was washed with 10 ml of saturated sodium bicarbonate solution, and extracted with 20 ml of dichloromethane. The resulting organic layer was dried over magnesium sulfate, distilled under a reduced pressure and subjected to column chromatography to obtain the title compound 13 mg (yield: 24%).

¹H NMR (CDCl₃) δ: 1.42-1.33 (m, 2H), 1.92 (d, 2H), 2.12 (s, 3H), 2.25-2.22 (m, 1H), 2.66-2.59 (m, 1H), 3.14 (t, 1H), 3.92 (d, 1H), 5.90-5.86 (m, 1H), 6.37-6.29-8 (m, 1H), 6.52-6.46 (m, 1H), 7.36-7.31 (m, 2H), 7.66 (bs, 1H), 8.01 (s, 1H), 8.08 (s, 1H), 8.32 (t, 1H), 8.66 (s, 1H), 9.15 (s, 1H).

Example 2

Preparation of N-{4-(4-bromo-2-fluoro-phenylamino)-7-[1-(2,2,2-trifluoro-acetyl)-piperidin-4-ylmethoxy]-quinazolin-6-yl}-acrylamide The compound of Example <1-9> (200 mg, 0.4 mmol) was added to 10 ml of THF and stirred. 1-(3-dimethylaminopropyl)-3-ethylcarbodiimide hydrochloride (383 mg, 2.0 mmol), trifluoroacetic acid (182 mg, 1.6 mmol) and pyridine (126 mg, 1.6 mmol) were added thereto at room temperature, and stirred for 6 hours. The reacted solution was washed with 10 ml of saturated sodium bicarbonate solution, and extracted with 20 ml of dichloromethane. The resulting organic layer was dried over magnesium sulfate, distilled under a reduced pressure and subjected to column chromatography to obtain the title compound 13 mg (yield: 5%).

¹H NMR (CDCl₃) δ: 1.79-1.68 (m, 2H), 2.56 (m, 1H), 3.11-3.07 (m, 2H), 3.48 (t, 1H), 4.40 (d, 4H), 4.91 (d, 1H), 6.16-6.12 (m, 1H), 6.77-6.52 (m, 2H), 7.63-7.56 (m, 2H), 7.92 (bs, 1H), 8.29 (s, 1H), 8.56 (t, 1H), 8.92 (s, 1H), 9.40 (s, 1H).

Example 3

Preparation of N-{4-(4-bromo-2-fluoro-phenylamino)-7-[1-(2-methanesulfonyl-acetyl)-piperidin-4-ylmethoxy]-quinazolin-6-yl}-acrylamide The procedure of Example 2 was repeated except for using the compound of Example <1-9> (100 mg, 0.2 mmol) and methanesulfonyl acetic acid (110 mg, 0.8 mmol) to obtain the title compound 26 mg (yield: 21%).

¹H NMR (CDCl₃) δ: 1.55-1.47 (m, 2H), 1.94-1.92 (m, 2H), 2.26 (m, 1H), 2.74 (t, 1H), 3.15 (s, 3H), 3.26 (s, 2H), 4.27-4.04 (m, 4H), 4.76 (d, 2H), 5.87 (d, 1H), 6.53-6.34 (m, 2H), 7.36-7.27 (m, 3H), 7.62 (s, 1H), 8.06 (s, 1H), 8.34 (t, 1H), 8.67 (s, 1H), 9.17 (s, 1H).

Example 4

Preparation of 4-[6-acryloylamino-4-(4-bromo-2-fluoro-phenylamino)-quinazolin-7-yloxymethyl]-piperidin-1-carboxylic acid amide The compound of Example <1-9> (150 mg, 0.3 mmol) and dichloromethanol were mixed and stirred. Then, trimethylsilyl isocyanate (155 mg, 1.35 mmol) was slowly added thereto. The resulting solution was stirred at room temperature for 4 hours, washed with 10 ml of saturated sodium bicarbonate solution, and extracted with 20 ml of dichloromethane. The resulting organic layer was dried over magnesium sulfate, distilled under a reduced pressure and subjected to column chromatography to obtain the title compound 33 mg (yield: 20%).

¹H-NMR (CD₃OD) δ: 1.38-1.29 (m, 2H), 1.93 (d, 2H), 2.23 (m, 1H), 2.90 (t, 2H), 4.15-4.04 (m, 4H), 5.89-5.85 (m, 1H), 6.48-6.42 (m, 1H), 667-6.58 (m, 1H), 7.24 (s, 1H), 7.48-7.38 (m, 2H), 7.60 (t, 1H), 8.39 (s, 1H), 8.85 (s, 1H).

Example 5

Preparation of N-[7-(1-acryloyl-piperidin-4-ylmethoxy)-4-(4-bromo-2-fluoro-phenylamino)-quinazolin-6-yl]-acrylamide The procedure of Example <1-8> was repeated except for using the compound of Example <1-9> (100 mg, 0.1998 mmol) to obtain the title compound 25 mg (yield: 22%).

¹H NMR (CDCl₃) δ: 9.14 (s, 1H), 8.66 (s, 1H), 8.39 (t, 1H), 8.05 (s, 1H), 7.46 (s, 1H), 7.35-7.31 (m, 3H), 6.63-6.50 (m, 2H), 6.33-6.25 (m, 2H), 8.86 (d, 1H), 5.69 (d, 1H), 4.1 (d, 2H), 3.13 (br, 1H), 2.73 (br, 1H), 2.25 (br, 1H), 1.99-1.50 (m, 4H), 1.56-1.45 (m, 2H).

Example 6

Preparation of N-[4-(4-bromo-2-fluoro-phenylamino)-7-(pyridin-4-ylmethoxy)-quinazolin-6-yl]-acrylamide <6-1> N⁴-(4-bromo-2-fluoro-phenyl)-7-fluoro-quinazoline-4,6-diamine The procedure of Example <1-7> was repeated except for using the compound of Example <1-5> (550 mg, 1.4430 mmol) to obtain the title compound 410 mg (yield: 77%).

¹H NMR (CDCl₃) δ: 8.95 (s, 1H), 7.71 (s, 1H), 7.52-7.32 (m, 3H), 7.12 (s, 1H).

<6-2> N-[4-(4-bromo-2-fluoro-phenylamino)-7-fluoro-quinazolin-6-yl]-acrylamide

The procedure of Example <1-8> was repeated except for using the compound of <6-1> (410 mg, 1.1153 mmol) to obtain the title compound 100 mg (yield: 22%).

¹H NMR (CDCl₃) δ: 9.22 (d, 1H), 8.72 (s, 1H), 8.33 (t, 1H), 7.80 (br, NH), 7.64-7.51 (m, 2H), 7.38-7.34 (m, 2H), 6.56 (d, 1H), 6.36 (dd, 1H), 5.93 (d, 1H).

<6-3> N-[4-(4-bromo-2-fluoro-phenylamino)-7-(pyridin-4-ylmethoxy)-quinazolin-6-yl]-acrylamide The procedure of Example <1-6> was repeated except for using the compound of <6-2> (500 mg, 1.2339 mmol) and pyridin-4-yl-methanol (269 mg, 2.4679 mmol) to obtain the title compound 152 mg (yield: 25%).

¹H NMR (DMSO-d₆) δ: 9.80 (d, 2H), 8.85 (s, 1H), 8.59 (d, 2H), 8.36 (s, 1H), 7.63-7.47 (m, 4H), 7.44 (s, 1H), 7.28 (s, 1H), 6.73 (dd, 1H), 6.32 (d, 1H), 5.82 (d, 1H), 5.49 (s, 1H).

Example 7

Preparation of N-[7-(1-acetyl-piperidin-4-yl-methoxy)-4-(2,3,4-trifluoro-phenylamino)-quinazolin-6-yl]-acrylamide <7-1> (7-fluoro-6-nitro-quinazolin-4-yl)-(2,3,4-trifluoro-phenyl)-amine The procedure of Example <1-5> was repeated except for using the compound of Example <1-4> (5 g, 0.0189 mol) and 2,3,4-trifluoro-phenylamine (2.78 g, 0.0189 mol) to obtain the title compound 5.8 g (yield: 92%).

¹H NMR (dMSO-d₆) δ: 10.69 (s, 1H), 9.52 (d, 1H), 8.63 (s, 1H), 7.89 (d, 1H), 7.41-7.26 (m, 2H).

<7-2> 4-[6-nitro-4-(2,3,4-trifluoro-phenylamino)-quinazolin-7-yloxymethyl]-piperidine-1-carboxylic acid t-butylester The procedure of Example <1-6> was repeated except for using the compound of <7-1> (700 mg, 2.0696 mmol) to obtain the title compound 500 mg (yield: 45%).

¹H NMR (dMSO-d₆) δ: 9.25 (s, 1H), 8.53 (s, 1H), 7.45-7.12 (m, 3H), 4.25 (d, 2H), 2.53 (d, 2H), 2.32 (s, 3H), 1.68 (t, 2H), 1.45 (s, 9H), 1.81-1.73 (m, 3H).

<7-3> 4-[6-amino-4-(2,3,4-trifluoro-phenylamino)-quinazolin-7-yloxymethyl]-piperidine-1-carboxylic acid t-butylester The procedure of Example <1-7> was repeated except for using the compound of <7-2> (1 g, 1.8744 mmol) to obtain the title compound 660 mg (yield: 70%).

¹H NMR (CDCl₃) δ: 8.58 (s, 1H), 8.35 (t, 1H), 7.17 (s, 1H), 7.05-6.99 (m, 2H), 6.93 (s, 1H), 4.31 (s, 2H), 4.21 (br, 2H), 4.05 (d, 2H), 2.77 (t, 2H), 2.10 (br, 1H), 1.85 (d, 2H), 1.47 (s, 9H), 1.43-1.35 (m, 2H).

<7-4> 4-[6-acryloylamino-4-(2,3,4-trifluoro-phenylamino)-quinazolin-7-yloxymethyl]-piperidine-1-carboxylic acid t-butylester The procedure of Example <1-8> was repeated except for using the compound of <7-3> (500 mg, 0.9930 mmol) to obtain the title compound 162 mg (yield: 29%).

¹H NMR (CDCl₃) δ: 9.18 (s, 1H), 8.66 (s, 1H), 8.12 (s, 1H), 8.00 (t, 1H), 7.49 (s, 1H), 7.09-7.01 (m, 2H), 6.51 (d, 1H), 6.39-6.30 (m, 1H), 5.89 (d, 1H), 4.22 (br, 2H), 4.13 (d, 2H), 2.84 (t, 2H), 2.06 (br, 1H), 1.86 (d, 2H), 1.49 (s, 9H), 1.44-1.37 (m, 2H).

<7-5> N-[7-(piperidin-4-ylmethoxy)-4-(2,3,4-trifluoro-phenylamino)-quinazolin-6-yl]-acrylamide The procedure of Example <1-9> was repeated except for using the compound of <7-4> (170 mg, 0.3048 mmol) to obtain the title compound 120 mg (yield: 86%).

¹H NMR (DMSO-d₆) δ: 9.10 (s, 1H), 8.58 (s, 1H), 8.10-8.05 (m, 2H), 7.45 (br, 1H), 6.99-6.93 (m, 1H), 6.42-6.33 (m, 2H), 5.86-5.72 (m, 1H), 4.09 (br, 2H), 4.04 (d, 2H), 2.66 (t, 2H), 2.10-1.93 (m, 3H), 1.37-1.27 (m, 2H).

<7-6> N-[7-(1-acetyl-piperidin-4-ylmethoxy)-4-(2,3,4-trifluoro-phenylamino)-quinazolin-6-yl]-acrylamide The procedure of Example <1-10> was repeated except for using the compound of <7-5> (120 mg, 0.2623 mmol) to obtain the title compound 19 mg (yield: 15%).

¹H NMR (dMSO-d₆) δ: 9.92 (s, 1H), 9.54 (s, 1H), 8.83 (s, 1H), 8.42 (s, 1H), 7.36-7.32 (m, 3H), 6.70 (dd, 1H), 6.30 (d, 1H), 5.70 (d, 1H), 4.39 (d, 1H), 4.09 (d, 2H), 3.84 (d, 1H), 3.04 (t, 2H), 2.16 (br, 1H), 1.98 (s, 3H), 1.85 (d, 2H), 1.34-1.22 (m, 2H).

Example 8

Preparation of N-[7-(1-acetyl-piperidin-4-yl-methoxy)-4-(4-bromo-2,6-difluoro-phenylamino)-quinazolin-6-yl]-acrylamide <8-1> (4-bromo-2,6-difluoro-phenyl)-(7-fluoro-6-nitro-quinazolin-4-yl)-amine The procedure of Example <1-5> was repeated except for using the compound of Example <1-4> (1.04 g, 4.56 mmol) and 4-bromo-2,5-difluoroaniline (950 mg, 4.56 mmol) to obtain the title compound 540 mg (yield: 29%).

¹H NMR (DMSO-d₆) δ: 10.58 (s, 1H), 9.54 (s, 1H), 8.60 (s, 1H), 7.87 (m, 1H), 7.64 (m, 2H).

<8-2> 4-[4-(4-bromo-2,6-difluoro-phenylamino)-6-nitro-quinazolin-7-yloxymethyl]-piperidine-1-carboxylic acid t-butylester The procedure of Example <1-6> was repeated except for using the compound of <8-1> (540 mg, 1.35 mmol) to obtain the title compound 510 mg (yield: 64%).

¹H NMR (DMSO-d₆) δ: 8.67 (s, 1H), 8.64 (s, 1H), 7.49 (s, 1H), 7.38 (s, 1H), 7.23 (s, 1H), 4.18 (d, 2H), 4.07 (d, 2H), 2.99-2.65 (m, 2H), 2.09 (m, 1H), 1.84 (d, 2H), 1.45 (s, 9H), 1.40-1.25 (m, 2H).

<8-3> N⁴-(4-bromo-2,6-difluoro-phenyl)-7-(piperidin-4-ylmethoxy)-quinazoline-4,6-diamine The procedure of Example <1-9> was repeated except for using the compound of <8-2> (510 mg, 0.86 mmol) to obtain the title compound 400 mg (yield: 99%).

¹H NMR (CDCl₃) δ: 8.91 (s, 1H), 8.58 (s, 1H), 7.34-7.28 (m, 2H), 7.16 (d, 2H), 3.97 (d, 2H), 3.16 (d, 2H), 2.66 (d, 2H), 2.04 (m, 1H), 1.85 (d, 2H), 1.39-1.26 (m, 2H).

<8-4> 1-{4-[4-(4-bromo-2,6-difluoro-phenylamino)-6-nitro-quinazolin-7-yloxymethyl]-piperidin-1-yl}-ethanone The procedure of Example <1-10> was repeated except for using the compound of <8-3> (395 mg, 0.8 mmol) to obtain the title compound 294 mg (yield: 68%).

¹H NMR (CDCl₃) δ: 9.71 (bs, 1H), 9.03 (s, 1H), 8.59 (s, 1H), 7.28-7.26 (s, 1H), 7.18-7.14 (m, 2H), 4.65 (d, 1H), 4.08-3.91 (m, 2H), 3.89 (d, 1H), 3.11 (t, 1H), 2.58 (t, 1H), 2.08 (s, 3H), 1.94 (d, 1H), 1.81 (d, 1H), 1.49-1.25 (m, 2H).

<8-5> 1-{4-[6-amino-4-(4-bromo-2,6-difluoro-phenylamino)-quinazolin-7-yloxymethyl]-piperidin-1-yl}-ethanone The procedure of Example <1-7> was repeated except for using the compound of <8-4> (294 mg, 0.55 mmol) to obtain the title compound 276 mg (yield: >99%).
$^1$H NMR (CDCl$_3$) δ: 8.79 (s, 1H), 7.76 (bs, 2H), 7.37 (s, 1H), 7.27 (s, 1H), 7.19 (s, 1H), 7.10-7.07 (m, 2H0, 4.59 (d, 1H), 3.89-3.77 (m, 3H), 3.02 (t, 1H), 2.52 (t, 1H), 2.14 (s, 3H), 1.78 (t, 2H), 1.26-1.15 (m, 3H).

<8-6> N-[7-(1-acetyl-piperidin-4-ylmethoxy)-4-(4-bromo-2,6-difluoro-phenylamino)-quinazolin-6-yl]-acrylamide The procedure of Example <1-8> was repeated except for using the compound of <8-5> (290 mg, 0.57 mmol) to obtain the title compound 58 mg (yield: 18%).
$^1$H NMR (CDCl$_3$) δ: 9.17 (s, 1H), 8.57 (s, 1H), 8.09 (s, 1H), 7.26 (s, 1H), 7.20-7.16 (m, 2H), 6.49-6.43 (m, 1H), 3.36-6.27 (m, 1H), 5.88-5.85 (m, 1H), 4.73 (d, 1H), 4.10 (d, 2H), 3.91 (d, 1H), 3.13 (t, 1H), 2.61 (t, 1H), 2.28 (m, 1H), 2.16 (s, 3H), 1.90 (d, 2H), 1.43-1.32 (m, 2H).

Example 9

Preparation of 4-[6-acryloylamino-4-(4-bromo-2-fluoro-phenylamino)-quinazolin-7-yloxymethyl]-piperidin-1-carboxylic acid propylamide The procedure of Example 4 was repeated except for using the compound of Example <1-9> (100 mg, 0.1998 mmol) and propyl isocyanate (19 μl, 0.1998 mmol) to obtain the title compound 98 mg (yield: 84%).
$^1$H NMR (DMSO-d$_6$) δ: 9.72 (s, 1H), 9.52 (s, 1H), 8.82 (s, 1H), 8.38 (s, 1H), 7.61 (d, 1H), 7.56-7.44 (m, 2H), 7.26 (s, 1H), 6.69 (dd, 1H), 6.39 (br, 1H), 6.29 (d, 1H), 5.79 (d, 1H), 4.07 (d, 2H), 3.99 (d, 2H), 2.96 (d, 2H), 2.66 (t, 2H), 2.05 (br, 1H), 1.79 (d, 2H), 1.39 (q, 2H), 1.21-1.16 (m, 2H), 0.81 (t, 3H).

Example 10

Preparation of N-{4-(4-bromo-2-fluoro-phenylamino)-7-[1-(2-dimethylamino-acetyl)-piperidin-4-ylmethoxy]-quinazolin-6-yl}-acrylamide The procedure of Example 2 was repeated except for using the compound of Example <1-9> (200 mg, 0.4 mmol) and ethyl dimethylamino-acetic acid (165 mg, 1.6 mmol) to obtain the title compound 45 mg (yield: 38%).
$^1$H-NMR (CDCl$_3$) δ: 9.13 (s, 1H), 8.65 (s, 1H), 8.31 (t, 1H), 8.07 (s, 1H), 7.65 (s, 1H), 7.35-7.23 (m, 3H), 6.50-6.26 (m, 2H), 5.87-5.84 (m, 1H), 4.69 (d, 1H), 4.23 (d, 1H), 4.09 (d, 2H), 3.16-3.03 (m, 4H), 2.62 (t, 1H), 2.27 (s, 6H), 1.88 (m, 2H), 1.41-1.32 (m, 2H).

Example 11

Preparation of 4-[6-acryloylamino-4-(4-bromo-2-fluoro-phenylamino)-quinazolin-7-yloxymethyl]-piperidin-1-carboxylic acid t-butylamide The procedure of Example 5 was repeated except for using the compound of Example <1-9> (100 mg, 0.1998 mmol) and t-butyl isocyanate (22 μl, 0.1998 mmol) to obtain the title compound 77 mg (yield: 65%).
$^1$H NMR (DMSO-d$_6$) δ: 9.72 (s, 1H), 9.53 (s, 1H), 8.79 (s, 1H), 8.36 (s, 1H), 7.62 (d, 1H), 7.51-7.42 (m, 2H), 7.28 (s, 1H), 6.71 (dd, 1H), 6.30 (dd, 1H), 5.80 (dd, 1H), 5.68 (s, 1H), 4.09 (d, 2H), 3.98 (d, 2H), 2.63 (t, 2H), 2.05 (br, 1H), 1.78 (d, 2H), 1.25 (s, 9H), 1.23-1.14 (m, 2H).

Example 12

Preparation of N-{4-(4-bromo-2-fluoro-phenylamino)-7-[3-(2-dimethylamino-acetylamino)-propoxy]-quinazolin-6-yl}-acrylamide <12-1> 3-{3-[4-(4-bromo-2-fluoro-phenylamino)-6-nitro-quinazolin-7-yloxy]-propyl}-1,1-dimethyl-urea The procedure of Example 2 was repeated except for using the compound of Example <13-3> (300 mg, 0.69 mmol) and N,N-dimethyl glycine (85 mg, 0.83 mmol) to obtain the title compound 180 mg (yield: 50%).
$^1$H NMR (CDCl$_3$) δ: 8.78 (s, 1H), 8.50 (s, 1H), 8.39 (t, 1H), 7.60 (s, 1H), 7.42-7.38 (m, 1H), 4.31 (t, 2H), 3.55 (q, 2H), 2.99 (s, 2H), 2.31 (s, 6H), 2.18 (q, 2H).

<12-2> 3-{3-[6-amino-4-(4-bromo-2-fluoro-phenylamino)-quinazolin-7-yloxy]-propyl}-1,1-dimethyl-urea The procedure of Example <1-7> was repeated except for using the compound of <12-1> (180 mg, 0.35 mmol) to obtain the title compound 170 mg (yield: 97%).
$^1$H NMR (CD$_3$OD) δ: 8.48 (s, 1H), 8.34 (s, 1H), 7.37 (s, 1H), 7.22 (d, 2H), 7.06 (s, 1H), 4.24 (s, 2H), 4.03-3.95 (m, 2H), 3.46 (t, 2H), 2.22 (s, 6H), 2.04 (t, 2H).

<12-3> N-{4-(4-bromo-2-fluoro-phenylamino)-7-[3-(2-dimethylamino-acetylamino)-propoxy]-quinazolin-6-yl}-acrylamide The procedure of Example <1-8> was repeated except for using the compound of <12-2> (170 mg, 0.35 mmol) to obtain the title compound 73 mg (yield: 39%).
$^1$H NMR (CDCl$_3$) δ: 9.07 (s, 1H), 8.93 (s, 1H), 8.57 (s, 1H), 8.14 (t, 1H), 7.76 (s, 1H), 7.37 (t, 1H), 7.27-7.21 (m, 2H), 7.16 (s, 1H), 6.68-6.59 (m, 1H), 6.45 (dd, 1H) 5.76 (dd, 1H), 4.19 (t, 2H), 3.51 (q, 2H), 2.92 (s, 2H), 2.23 (s, 6H), 2.09-2.01 (m, 2H).

Example 13

Preparation of N-[7-(3-acetylamino-propoxy)-4-(4-bromo-2-fluoro-phenylamino)-quinazolin-6-yl]-acrylamide <13-1> (3-hydroxy-propyl)-carbamic acid t-butylester The procedure of Example <1-1> was repeated except for using 3-amino-propyl-1-ol (10 g, 133 mmol) and di-t-butyl dicarbonate (34.9 g, 159 mmol) to obtain the title compound 18.6 g (yield: 80%).

¹H NMR (CDCl₃) δ: 4.86 (bs, 1H), 3.69 (m, 2H), 3.31 (q, 2H), 1.88 (bs, 1H), 1.69 (m, 2H), 1.47 (s, 9H).

<13-2> {3-[4-(4-bromo-2-fluoro-phenylamino)-6-nitro-quinazolin-7-yloxy]-propyl}-carbamic acid t-butylester The procedure of Example <1-6> was repeated except for using the compound of Example <1-5> (4.06 g, 10.6 mmol) and the compound of <13-1> (2.8 g, 15.9 mmol) to obtain the title compound 4 g (yield: 70%).
¹H NMR (CDCl₃) δ: 8.79 (s, 1H), 8.51 (s, 1H), 8.40 (t, 1H), 7.75 (bs, 1H), 7.43-7.39 (m, 3H), 4.96 (bs, 1H), 4.32 (t, 2H), 3.41 (q, 2H), 2.31 (p, 2H), 1.45 (s, 9H).

<13-3> [7-(3-amino-propoxy)-6-nitro-quinazolin-4-yl]-(4-bromo-2-fluoro-phenyl)-amine The procedure of Example <1-9> was repeated except for using the compound of <13-2> (3 g, 5.6 mmol) to obtain the title compound 2.4 g (yield: 98%).
¹H NMR (CDCl₃+CD₃OD) δ: 9.01 (s, 1H), 8.51 (s, 1H), 7.54 (t, 1H), 7.43-7.30 (m, 3H), 4.37 (t, 2H), 2.97 (t, 2H), 2.09 (p, 2H).

<13-4> N-{3-[4-(4-bromo-2-fluoro-phenylamino)-6-nitro-quinazolin-7-yloxy]-propyl}-acetamide The procedure of Example <1-10> was repeated except for using the compound of <13-3> (360 mg, 0.83 mmol) and acetyl chloride (65 mg, 0.83 mmol) to obtain the title compound 360 mg (yield: 91%).
¹H NMR (CDCl₃) δ: 9.00 (bs, 1H), 8.87 (s, 1H), 8.63 (s, 1H), 7.87 (t, 1H), 7.30-7.22 (m, 3H), 6.77 (t, 1H), 4.26 (t, 2H), 3.49 (q, 2H), 2.07 (p, 2H), 1.99 (s, 3H).

<13-5> N-{3-[6-amino-4-(4-bromo-2-fluoro-phenylamino)-quinazolin-7-yloxy]-propyl}-acetamide The procedure of Example <1-7> was repeated except for using the compound of <13-4> (360 mg, 0.75 mmol) to obtain the title compound 250 mg (yield: 74%).
¹H NMR (CDCl₃+CD₃OD) δ: 8.32 (s, 1H), 7.83 (s, 1H), 7.35-7.30 (m, 2H), 7.22 (s, 1H), 7.05 (s, 2H), 4.21 (t, 2H), 3.42 (t, 2H), 2.08 (p, 2H), 1.95 (s, 3H).

<13-6> N-[7-(3-acetylamino-propoxy)-4-(4-bromo-2-fluoro-phenylamino)-quinazolin-6-yl]-acrylamide The procedure of Example <1-8> was repeated except for using the compound of Example <13-5> (195 mg, 0.43 mmol) and acryloyl chloride (39 mg, 0.43 mmol) to obtain the title compound 34 mg (yield: 16%).
¹H NMR (CDCl₃) δ: 9.19 (s, 1H), 8.88 (s, 1H), 8.63 (s, 1H), 8.25 (t, 1H), 7.75 (bs, 1H), 7.35-7.30 (m, 2H), 7.22 (s, 1H), 6.71-6.63 (m, 1H), 6.53-6.47 (m, 1H), 5.88-5.81 (m, 1H), 4.24 (q, 2H), 3.54 (t, 2H), 2.08 (p, 2H), 2.02 (s, 3H).

Example 14

Preparation of N-{4-(4-bromo-2-fluoro-phenylamino)-7-[3-(2,2,2-trifluoro-acetylamino)-propoxy]-quinazolin-6-yl}-acrylamide <14-1> N-{3-[4-(4-bromo-2-fluoro-phenylamino)-6-nitro-quinazolin-7-yloxy]-propyl}-2,2,2-trifluoro-acetamide The procedure of Example 2 was repeated except for using the compound of Example <13-3> (300 mg, 0.69 mmol) and trifluoroacetic acid (315 mg, 2.76 mmol) to obtain the title compound 182 mg (yield: 50%).
¹H NMR (CDCl₃+CD₃OD) δ: 9.01 (s, 1H), 8.53 (s, 1H), 7.56 (t, 1H), 7.43-7.33 (m, 3H), 4.33 (t, 2H), 3.58 (t, 2H), 2.21-2.17 (m, 2H).

<14-2> N-{3-[6-amino-4-(4-bromo-2-fluoro-phenylamino)-quinazolin-7-yloxy]-propyl}-2,2,2-trifluoro-acetamide The procedure of Example <1-7> was repeated except for using the compound of Example <14-1> (180 mg, 0.34 mmol) to obtain the title compound 170 mg (yield: 99%).
¹H NMR (CDCl₃) δ: 8.46-8.39 (m, 2H), 8.02 (bs, 1H), 7.30-7.26 (m, 3H), 6.95 (s, 1H), 6.75 (s, 1H), 4.10-4.09 (m, 4H), 3.59 (, t, 2H), 2.15-2.11 (m, 2H).

<14-3> N-{4-(4-bromo-2-fluoro-phenylamino)-7-[3-(2,2,2-trifluoro-acetylamino)-propoxy]-quinazolin-6-yl}-acrylamide The procedure of Example <1-8> was repeated except for using the compound of Example <14-2> (170 mg, 0.34 mmol) and acryloyl chloride (31 mg, 0.34 mmol) to obtain the title compound 41 mg (yield: 22%).
¹H NMR (CDCl₃) δ: 8.97 (s, 1H), 8.52 (s, 1H), 8.33 (s, 1H), 8.19 (t, 1H), 7.57 (bs, 1H), 7.45-7.41 (m, 2H), 7.30-7.22 (m, 2H), 7.08 (s, 1H), 6.50-6.42 (m, 2H), 5.81-5.77 (m, 1H), 4.16 (t, 2H), 3.60 (q, 2H), 2.16 (p, 2H).

Example 15

Preparation of N-{4-(4-bromo-2-fluoro-phenylamino)-7-[3-(2-methanesulfonyl-acetylamino)-propoxy]-quinazolin-6-yl}-acrylamide <15-1> N-{3-[4-(4-bromo-2-fluoro-phenylamino)-6-nitro-quinazolin-7-yloxy]-propyl}-2-methanesulfonyl-acetamide The procedure of Example 2 was repeated except for using the compound of Example <13-3> (300 mg, 0.69 mmol) and methanesulfonyl-acetic acid (381 mg, 2.76 mmol) to obtain the title compound 200 mg (yield: 52%).
¹H NMR (CDCl₃) δ: 8.64 (s, 2H), 8.23 (bs, 1H), 8.04 (t, 1H), 7.69 (t, 1H), 7.35-7.31 (m, 3H), 4.30 (t, 2H), 4.01 (s, 2H), 3.59 (t, 2H), 3.11 (s, 3H), 2.13 (m, 2H).

<15-2> N-{3-[6-amino-4-(4-bromo-2-fluoro-phenylamino)-quinazolin-7-yloxy]-propyl}-2-methanesulfonyl-acetamide The procedure of Example <1-7> was repeated except for using the compound of <15-1> (200 mg, 0.36 mmol) to obtain the title compound 165 mg (yield: 87%).
¹H NMR (CDCl₃+CD₃OD) δ: 8.31 (s, 1H), 7.79 (t, 1H), 7.57 (s, 1H), 7.38-7.32 (m, 2H), 7.06 (s, 1H), 4.25 (t, 2H), 3.97 (d, 1H), 3.51 (t, 2H), 3.32 (s, 1H), 3.11 (s, 3H), 2.17-2.11 (m, 2H).

<15-3> N-{4-(4-bromo-2-fluoro-phenylamino)-7-[3-(2-methanesulfonyl-acetylamino)-propoxy]-quinazolin-6-yl}-acrylamide The procedure of Example <1-8> was repeated except for using the compound of <15-2> (165 mg, 0.31 mmol) and acryloyl chloride (28 mg, 0.31 mmol) to obtain the title compound 68 mg (yield: 38%).

¹H NMR (CDCl₃) δ: 8.89 (s, 1H), 8.49 (s, 1H), 8.29 (s, 1H), 8.18-8.12 (m, 2H), 7.35-7.30 (m, 2H), 7.16 (s, 1H), 6.39 (d, 2H), 5.78 (t, 1H), 4.23 (t, 2H), 3.98 (s, 2H), 3.59 (q, 2H), 3.08 (s, 3H), 2.10-2.04 (m, 2H).

Example 16

Preparation of N-{4-(4-bromo-2-fluoro-phenylamino)-7-[3-(3-ethyl-ureido)-propoxy]-quinazolin-6-yl}-acrylamide <16-1> 1-{3-[4-(4-bromo-2-fluoro-phenylamino)-6-nitro-quinazolin-7-yloxy]-propyl}-3-ethyl-urea The procedure of Example 4 was repeated except for using the compound of Example <13-3> (300 mg, 0.69 mmol) and ethylisocyanate (54 mg, 0.76 mmol) to obtain the title compound 120 mg (yield: 34%).
¹H NMR (DMSO-d₆) δ: 9.18 (s, 1H), 8.52 (s, 1H), 7.64 (m, 1H), 7.50-7.29 (m, 3H), 5.92 (m, 1H), 5.68 (m, 1H), 4.29 (t, 2H), 3.19 (q, 2H), 2.99 (t, 2H), 1.90-1.87 (m, 2H), 0.97 (t, 3H).

<16-2> 1-{3-[6-amino-4-(4-bromo-2-fluoro-phenylamino)-quinazolin-7-yloxy]-propyl}-3-ethyl-urea The procedure of Example <1-7> was repeated except for using the compound of <16-1> (120 mg, 0.24 mmol) to obtain the title compound 110 mg (yield: 96%).
¹H NMR (CDCl₃+CD₃OD) δ: 8.31 (s, 1H), 7.79 (t, 1H), 7.37-7.31 (m, 2H), 7.24 (s, 1H), 7.05 (s, 1H), 4.22 (t, 2H), 3.37 (q, 2H), 3.14 (q, 2H), 2.06 (p, 2H), 1.08 (t, 3H).

<16-3> N-{4-(4-bromo-2-fluoro-phenylamino)-7-[3-(3-ethyl-ureido)-propoxy]-quinazolin-6-yl}-acrylamide The procedure of Example <1-8> was repeated except for using the compound of <16-2> (110 mg, 0.23 mmol) and acryloyl chloride (21 mg, 0.23 mmol) to obtain the title compound 30 mg (yield: 25%).
¹H NMR (CDCl₃+CD₃OD) δ: 8.87 (s, 1H), 8.37 (s, 1H), 7.62 (t, 1H), 7.30 (t, 2H), 7.12 (s, 1H), 6.70-6.61 (m, 1H), 6.43-6.38 (m, 1H), 5.79-5.76 (m, 1H), 4.22 (t, 2H), 3.32 (t, 2H), 3.09 (q, 2H), 2.00 (p, 2H), 1.02 (t, 3H).

Example 17

Preparation of N-[4-(4-bromo-2-fluoro-phenylamino)-7-(3-methylamino-propoxy)-quinazolin-6-yl]-acrylamide <17-1> (4-bromo-2-fluoro-phenyl)-[7-(3-methylamino-propoxy)-6-nitro-quinazolin-4-yl]-amine The compound of Example <13-3> (300 mg, 0.69 mmol) was dissolved in a 1:1 mixture of tetrahydrofuran and methanol (3 ml each), formaldehyde (0.098 ml, 1.32 mmol) and sodium cyanoborohydride (0.064 g, 1.03 mmol) was added thereto, and stirred at room temperature for 1 hour. When the reaction was terminated, the reacted solution was distilled under a reduced pressure, dissolved in a small amount of methanol, recrystallized with diethylether, and filtered to obtain the title compound 190 mg (yield: 59%).
¹H NMR (CDCl₃) δ: 8.82 (s, 1H), 8.66 (s, 1H), 8.30 (t, 1H), 7.48-7.43 (m, 3H), 4.38 (q, 2H), 2.72-2.58 (m, 2H), 2.35 (s, 3H), 2.19-2.14 (m, 2H).

<17-2> N⁴-(4-bromo-2-fluoro-phenyl)-7-(3-methylamino-propoxy)-quinazoline-4,6-diamine The procedure of Example <1-7> was repeated except for using the compound of <17-1> (190 mg, 0.42 mmol) to obtain the title compound 136 mg (yield: 74%).
¹H NMR (CDCl₃) δ: 8.59-8.58 (m, 2H), 7.31-7.27 (m, 3H), 6.90 (s, 1H), 4.36 (bs, 2H), 4.19 (q, 2H), 2.57-2.48 (m, 2H), 2.27 (s, 3H), 2.04-2.01 (m, 2H).

<17-3> N-[4-(4-bromo-2-fluoro-phenylamino)-7-(3-methylamino-propoxy)-quinazolin-6-yl]-acrylamide The procedure of Example <1-8> was repeated except for using the compound of <17-2> (136 mg, 0.32 mmol) and acryloyl chloride (29 mg, 0.32 mmol) to obtain the title compound 66.3 mg (yield: 42%).
¹H NMR (CDCl₃) δ: 9.07 (s, 1H), 8.57 (s, 1H), 8.36 (bs, 1H), 8.19 (t, 1H), 7.67 (bs, 1H), 7.27-7.16 (m, 3H), 6.44-6.26 (m, 2H), 5.79-5.75 (m, 1H), 4.20 (q, 2H), 2.43 (q, 2H), 2.22 (s, 3H), 2.07-2.00 (m, 2H).

Example 18

Preparation of N-[7-(2-acetylamino-ethoxy)-4-(4-bromo-2-fluoro-phenylamino)-quinazolin-6-yl]-acrylamide <18-1> (2-hydroxy-ethyl)-carbamic acid t-butylester The procedure of Example <1-1> was repeated except for using 2-amino-ethanol (10 g, 160 mmol) to obtain the title compound 24 g (yield: 93%).
¹H NMR (CDCl₃) δ: 5.30 (bs, 1H), 3.72 (bs, 1H), 3.56 (t, 2H), 3.16 (t, 2H), 1.35 (s, 9H).

<18-2> {2-[4-(4-bromo-2-fluoro-phenylamino)-6-nitro-quinazolin-7-yloxy]-ethyl}-carbamic acid t-butylester The procedure of Example <1-6> was repeated except for using the compound of Example <1-5> (3 g, 7.87 mmol) and the compound of <18-1> (1.9 g, 11.8 mmol) to obtain the title compound 3.75 g (yield: 91%).
¹H NMR (DMSO-d₆) δ: 10.10 (bs, 1H), 9.06 (s, 1H), 8.44 (s, 1H), 7.59 (d, 1H), 7.47-7.38 (m, 3H), 6.88 (t, 1H), 4.23 (t, 2H), 3.28 (q, 2H), 1.29 (s, 9H).

<18-3> [7-(2-amino-ethoxy)-6-nitro-quinazolin-4-yl]-(4-bromo-2-fluoro-phenyl)-amine The procedure of Example <1-9> was repeated except for using the compound of <18-2> (3.7 g, 7.08 mmol) to obtain the title compound 2.91 g (yield: 97%).
¹H NMR (DMSO-d₆) δ: 9.05 (s, 1H), 8.40 (s, 1H), 7.59-7.55 (m, 1H), 7.45-7.36 (m, 3H), 4.17 (t, 2H), 2.86 (q, 2H).

<18-4> N-{2-[4-(4-bromo-2-fluoro-phenylamino)-6-nitro-quinazolin-7-yloxy]-ethyl}-acetamide The procedure of Example <1-10> was repeated except for using the compound of <18-3> (2.91 g, 6.89 mmol) to obtain the title compound 2.1 g (yield: 66%).
¹H NMR (DMSO-d₆) δ: 10.41 (bs, 1H), 9.36 (s, 1H), 8.73 (s, 1H), 8.27 (t, 1H), 7.88 (d, 1H), 7.73-7.67 (m, 3H), 4.53 (t, 2H), 3.88 (q, 2H), 2.03 (s, 3H).

<18-5> N-{2-[6-amino-4-(4-bromo-2-fluoro-phenylamino)-quinazolin-7-yloxy]-ethyl}-acetamide The procedure of Example <1-7> was repeated except for using the compound of <18-4> (2.1 g, 4.52 mmol) to obtain the title compound 1.4 g (yield: 71%).
$^1$H NMR (DMSO-$d_6$) δ: 9.16 (bs, 1H), 8.20 (m, 2H), 7.60-7.54 (m, 2H), 7.41 (d, 1H), 7.29 (s, 1H), 7.03 (s, 1H), 5.48 (bs, 2H), 4.10 (t, 2H), 3.53 (t, 2H), 1.86 (s, 3H).

<18-6> N-[7-(2-acetylamino-ethoxy)-4-(4-bromo-2-fluoro-phenylamino)-quinazolin-6-yl]-acrylamide The procedure of Example <1-8> was repeated except for using the compound of <18-5> (1.4 g, 3.22 mmol) to obtain the title compound 250 mg (yield: 16%).
$^1$H NMR (CDCl$_3$+CD$_3$OD) δ: 8.92 (s, 1H), 8.32 (s, 1H), 7.56 (t, 1H), 7.30-7.23 (m, 2H), 7.03 (s, 1H), 6.73-6.63 (m, 1H), 6.42-6.36 (m, 1H), 5.79-5.75 (m, 1H), 4.15 (t, 2H), 3.65 (t, 2H), 1.93 (s, 3H).

Example 19

Preparation of N-[4-(4-bromo-2-fluoro-phenylamino)-7-(2-dimethylamino-ethoxy)-quinazolin-6-yl]-acrylamide <19-1> (4-bromo-2-fluoro-phenyl)-[7-(2-dimethylamino-ethoxy)-6-nitro-quinazolin-4-yl]-amine The procedure of Example <17-1> was repeated except for using the compound of Example <18-3> (200 mg, 0.47 mmol) to obtain the title compound 71 mg (yield: 34%).
$^1$H NMR (CDCl$_3$) δ: (8.74 (s, 1H), 8.53 (s, 1H), 8.26 (t, 1H), 7.95 (bs, 1H), 7.39-7.34 (m, 3H), 4.32 (t, 2H), 2.86 (t, 2H), 2.36 (s, 6H).

<19-2> N$^4$-(4-bromo-2-fluoro-phenyl)-7-(2-dimethylamino-ethoxy)-quinazoline-4,6-diamine The procedure of Example <1-7> was repeated except for using the compound of <19-1> (71 mg, 0.16 mmol) to obtain the title compound 52 mg (yield: 68%).
$^1$H NMR (CDCl$_3$+CD$_3$OD) δ: 8.24 (s, 1H), 7.71 (t, 1H), 7.33-7.27 (m, 2H), 7.20 (s, 1H), 7.02 (s, 1H), 4.22 (t, 2H), 2.83 (t, 2H), 2.34 (s, 6H).

<19-3> N-[4-(4-bromo-2-fluoro-phenylamino)-7-(2-dimethylamino-ethoxy)-quinazolin-6-yl]-acrylamide The procedure of Example <1-8> was repeated except for using the compound of <19-2> (52 mg, 0.11 mmol) to obtain the title compound 18 mg (yield: 34%).
$^1$H NMR (CDCl$_3$) δ: 9.40 (bs, 1H), 9.19 (s, 1H), 8.67 (s, 1H), 8.31 (t, 1H), 7.71 (s, 1H), 7.40-7.25 (m, 3H), 6.52-6.46 (m, 2H), 5.83-5.54 (m, 1H), 4.30 (t, 2H), 2.84 (t, 2H), 2.38 (s, 6H).

Example 20

Preparation of N-[7-(4-acetylamino-butoxy)-4-(4-bromo-2-fluoro-phenylamino)-quinazolin-6-yl]-acrylamide <20-1> (4-hydroxy-butyl)-carbamic acid t-butylester The procedure of Example <1-1> was repeated except for using 4-amino-buthan-1-ol (3 g, 33.6 mmol) to obtain the title compound 6.17 g (yield: 97%).
$^1$H NMR (CDCl$_3$) δ: 4.61 (bs, 1H), 3.67-3.66 (m, 2H), 3.16-3.14 (m, 2H), 1.67-1.57 (m, 5H), 1.44 (s, 9H).

<20-2> {4-[4-(4-bromo-2-fluoro-phenylamino)-6-nitro-quinazolin-7-yloxy]-butyl}-carbamic acid t-butylester The procedure of Example <1-6> was repeated except for using the compound of Example <1-5> (1 g, 2.60 mmol) and the compound of <20-1> (1.99 g, 10.5 mmol) to obtain the title compound 300 mg (yield: 21%).
$^1$H NMR (CDCl$_3$) δ: 8.73 (s, 1H), 8.63 (s, 1H), 7.87 (t, 1H), 7.33-7.26 (m, 3H), 4.18 (t, 2H), 3.17-3.15 (m, 2H), 1.90-1.85 (m, 2H), 1.70-1.65 (m, 2H), 1.39 (s, 9H).

<20-3> [7-(4-amino-buthoxy)-6-nitro-quinazolin-4-yl]-(4-bromo-2-fluoro-phenyl)-amine The procedure of Example <1-9> was repeated except for using the compound of <20-2> (300 mg, 0.56 mmol) to obtain the title compound 157 mg (yield: 62%).
$^1$H NMR (CDCl$_3$) δ: 8.72 (s, 1H), 8.58 (s, 1H), 8.18 (t, 1H), 7.37-7.28 (m, 3H), 4.23 (t, 2H), 2.81 (m, 2H), 1.94-1.92 (m, 2H), 1.69 (m, 2H).

<20-4> N-{4-[4-(4-bromo-2-fluoro-phenylamino)-6-nitro-quinazolin-7-yloxy]-butyl}-acetamide The procedure of Example <1-10> was repeated except for using the compound of <20-3> (157 mg, 0.35 mmol) to obtain the title compound 117 mg (yield: 68%).
$^1$H NMR (CDCl$_3$) δ: 8.69 (s, 1H), 8.48 (s, 1H), 8.09 (t, 1H), 7.36-7.32 (m, 3H), 5.91 (bs, 1H), 4.22 (t, 2H), 3.33 (q, 2H), 1.98 (s, 3H), 1.94-1.88 (m, 2H), 1.79-1.67 (m, 2H).

<20-5> N-{4-[6-amino-4-(4-bromo-2-fluoro-phenylamino)-quinazolin-7-yloxy]-butyl}-acetamide The procedure of Example <1-7> was repeated except for using the compound of <20-4> (117 g, 0.24 mmol) to obtain the title compound 93 mg (yield: 75%).
$^1$H NMR (CDCl$_3$) δ: 8.44 (s, 1H), 8.12-8.15 (m, 1H), 7.34-7.32 (m, 3H), 7.14-7.03 (m, 1H), 4.18 (t, 2H), 3.29 (q, 2H), 1.96 (s, 3H), 1.91 (m, 2H), 1.73 (m, 2H).

<20-6> N-[7-(4-acetylamino-butoxy)-4-(4-bromo-2-fluoro-phenylamino)-quinazolin-6-yl]-acrylamide The procedure of Example <1-8> was repeated except for using the compound of <20-5> (93 mg, 0.18 mmol) to obtain the title compound 18 mg (yield: 19%).
$^1$H NMR (CDCl$_3$+CD$_3$OD) δ: 8.79 (s, 1H), 8.71 (s, 1H), 7.39 (t, 1H), 7.24-7.13 (m, 3H), 6.36-6.24 (m, 2H), 5.64-5.58 (m, 1H), 4.12 (t, 2H), 3.12-3.06 (m, 2H), 1.83-1.74 (m, 5H), 1.53-1.50 (m 2H).

Example 21

Preparation of cyclopropane carboxylic acid {2-[6-acrylamino-4-(4-bromo-2-fluoro-phenylamino)-quinazolin-7-yloxy]-ethyl}-amide <21-1> cyclopropane carboxylic acid {2-[4-(4-bromo-2-fluoro-phenylamino)-6-nitro-quinazolin-7-yloxy]-ethyl}-amide The procedure of Example 2 was repeated except for using the compound of Example <18-3> (250 mg, 0.59 mmol) and cyclopropane carboxylic acid (101 mg, 1.18 mmol) to obtain the title compound 99 mg (yield: 34%).

$^1$H NMR (CDCl$_3$+CD$_3$OD) δ: 8.98 (s, 1H), 8.49 (s, 1H), 7.52 (d, 1H), 7.39-7.31 (m, 3H), 4.31 (t, 2H), 3.70-3.65 (m, 2H), 1.56-1.49 (m, 1H), 0.90-0.87 (m, 2H), 0.77-0.71 (m, 2H).

<21-2> cyclopropane carboxylic acid {2-[6-amino-4-(4-bromo-2-fluoro-phenylamino)-quinazolin-7-yloxy]-ethyl}-amide The procedure of Example <1-7> was repeated except for using the compound of <21-1> (99 mg, 0.20 mmol) to obtain the title compound 81 mg (yield: 90%).

$^1$H NMR (CDCl$_3$+CD$_3$OD) δ: 8.31 (s, 1H), 7.79 (t, 1H), 7.37-7.27 (m, 2H), 7.24 (s, 1H), 7.03 (s, 1H), 4.20 (t, 2H), 3.73 (t, 2H), 1.56-1.52 (m, 1H), 0.92-0.88 (m, 2H), 0.78-0.71 (m, 2H).

<21-3> cyclopropane carboxylic acid {2-[6-acrylamino-4-(4-bromo-2-fluoro-phenylamino)-quinazolin-7-yloxy]-ethyl}-amide The procedure of Example <1-8> was repeated except for using the compound of <21-2> (81 mg, 0.18 mmol) to obtain the title compound 10 mg (yield: 11%).

$^1$H NMR (CDCl$_3$) δ: 9.15 (s, 1H), 8.94 (s, 1H), 8.58 (s, 1H), 8.25 (t, 1H), 7.55 (s, 1H), 7.29-7.25 (m, 2H), 7.05 (s, 1H), 6.77-6.68 (m, 1H), 6.49-6.44 (m, 1H), 6.25 (t, 1H), 5.79-5.75 (m, 1H), 4.13 (t, 2H), 3.67-3.63 (m, 2H), 1.39-1.35 (m, 1H), 0.95-0.93 (m, 2H), 0.76-0.69 (m, 2H).

Example 22

Preparation of N-{4-(4-bromo-2-fluoro-phenylamino)-7-[2-(2,2-difluoro-acetylamino)-ethoxy]-quinazolin-6-yl}-acrylamide <22-1> N-{2-[4-(4-bromo-2-fluoro-phenylamino)-6-nitro-quinazolin-7-yloxy]-ethyl}-2,2-difluoro-acetamide The procedure of Example 2 was repeated except for using the compound of Example <18-3> (300 mg, 0.71 mmol) to obtain the title compound 248 mg (yield: 69%).

$^1$H NMR (CDCl$_3$+CD$_3$OD) δ: 8.98 (s, 1H), 8.50 (s, 1H), 7.39-7.31 (m, 4H), 5.95 (t, 1H), 4.37 (t, 2H), 3.77 (t, 2H).

<22-2> N-{2-[6-amino-4-(4-bromo-2-fluoro-phenylamino)-quinazolin-7-yloxy]-ethyl}-2,2-difluoro-acetamide The procedure of Example <1-7> was repeated except for using the compound of <22-1> (248 mg, 0.49 mmol) and difluoroacetic acid (136 mg, 1.42 mmol) to obtain the title compound 170 mg (yield: 73%).

$^1$H NMR (DMSO-d$_6$) δ: 9.17 (s, 1H), 8.21 (s, 1H), 7.62-7.54 (m, 2H), 7.42 (d, 1H), 7.29 (s, 1H), 7.05 (s, 1H), 6.29 (t, 1H), 5.51 (s, 2H), 4.18 (t, 2H), 3.66 (q, 2H)

<22-3> N-{4-(4-bromo-2-fluoro-phenylamino)-7-[2-(2,2-difluoro-acetylamino)-ethoxy]-quinazolin-6-yl}-acrylamide The procedure of Example <1-8> was repeated except for using the compound of <22-2> (170 mg, 0.36 mmol) to obtain the title compound 24 mg (yield: 13%).

$^1$H NMR (CDCl$_3$+CD$_3$OD) δ: 9.03 (s, 1H), 8.41 (s, 1H), 7.64 (t, 1H), 7.39-7.32 (m, 2H), 7.12 (s, 1H), 6.75-6.69 (m, 1H), 6.49-6.17 (m, 1H), 5.99 (t, 1H), 5.85-5.81 (m, 1H), 4.28 (t, 2H), 3.83 (t, 2H).

Example 23

Preparation of N-{4-(4-bromo-2-fluoro-phenylamino)-7-[2-(3-ethyl-ureido)-ethoxy]-quinazolin-6-yl}-acrylamide <23-1> 1-{2-[4-(4-bromo-2-fluoro-phenylamino)-6-nitro-quinazolin-7-yloxy]-ethyl}-3-ethyl-urea The procedure of Example 4 was repeated except for using the compound of Example <18-3> (270 mg, 0.64 mmol) and ethylisocyanate (68 mg, 0.96 mmol) to obtain the title compound 263 mg (yield: 83%).

$^1$H NMR (DMSO-d$_6$) δ: 10.20 (bs, 1H), 9.13 (s, 1H), 8.62 (s, 1H), 7.64 (d, 1H), 7.47 (m, 2H), 6.01-5.96 (m, 2H), 4.24 (t, 2H), 3.40 (q, 2H), 3.04-2.94 (m, 2H), 0.96 (t, 3H).

<23-2> 1-{2-[6-amino-4-(4-bromo-2-fluoro-phenylamino)-quinazolin-7-yloxy]-ethyl}-3-ethyl-urea The procedure of Example <1-7> was repeated except for using the compound of <23-1> (263 mg, 0.53 mmol) to obtain the title compound 160 mg (yield: 64%).

$^1$H NMR (DMSO-d$_6$) δ: 9.14 (s, 1H), 8.19 (s, 1H), 7.59-7.53 (m, 2H), 7.41 (d, 1H), 7.27 (s, 1H), 7.02 (s, 1H), 6.19 (t, 1H), 5.92 (t, 1H), 5.46 (s, 2H), 4.06 (t, 2H), 3.46 (q, 2H), 3.02 (q, 2H), 0.98 (t, 3H).

<23-3> N-{4-(4-bromo-2-fluoro-phenylamino)-7-[2-(3-ethyl-ureido)-ethoxy]-quinazolin-6-yl}-acrylamide The procedure of Example <1-8> was repeated except for using the compound of <23-2> (160 mg, 0.34 mmol) and acryloyl chloride (31 mg, 0.34 mmol) to obtain the title compound 32 mg (yield: 18%).

$^1$H NMR (DMSO-d$_6$) δ: 9.37 (s, 1H), 9.59 (s, 1H), 9.12 (s, 1H), 8.35 (s, 1H), 7.60 (d, 1H), 7.49-7.40 (m, 2H), 7.20 (s, 1H), 6.98-6.88 (m, 1H), 6.36-6.30 (m, 1H), 6.21-6.19 (m, 1H), 6.10 (m, 1H), 5.85-5.81 (m, 1H), 4.15 (t, 2H), 3.50 (q, 2H), 3.02 (q, 2H), 0.96 (t, 3H).

Example 24

Preparation of N-[4-(4-bromo-2-fluoro-phenylamino)-7-(2-ureido-ethoxy)-quinazolin-6-yl]-acrylamide <24-1> {2-[6-amino-4-(4-bromo-2-fluoro-phenylamino)-quinazolin-7-yloxy]-ethyl}-carbamic acid t-butylester The procedure of Example <1-7> was repeated except for using the compound of Example <18-2> (600 mg, 1.15 mmol) to obtain the title compound 562 mg (yield: 99%).

$^1$H NMR (CDCl$_3$+CD$_3$OD) δ: 8.34 (s, 1H), 7.84 (t, 1H), 7.38-7.32 (m, 2H), 7.23 (s, 1H), 7.03 (s, 1H), 4.19 (t, 2H), 3.62 (q, 2H), 1.49 (s, 9H).

<24-2> {2-[6-acryloylamino-4-(4-bromo-2-fluoro-phenylamino)-quinazolin-7-yloxy]-ethyl}-carbamic acid t-butylester The procedure of Example <1-8> was repeated except for using the compound of <24-1> (562 mg, 1.14 mmol) and acryloyl chloride (103 mg, 1.14 mmol) to obtain the title compound 110 mg (yield: 18%).
$^1$H NMR (CDCl$_3$) δ: 9.22 (s, 1H), 9.11 (bs, 1H), 8.65 (s, 1H), 8.32 (t, 1H), 7.68 (s, 1H), 7.37-7.33 (m, 2H), 7.16 (s, 1H), 6.80-6.70 (m, 1H), 6.56-6.51 (m, 1H), 5.84-5.81 (m, 2H), 4.97 (m, 1H), 4.20 (t, 2H), 3.71-3.66 (m, 2H), 1.44 (s, 9H).

<24-3> N-[7-(2-amino-ethoxy-4-(4-bromo-2-fluoro-phenylamino)-quinazolin-6-yl]-acrylamide The procedure of Example <1-9> was repeated except for using the compound of <24-2> (100 mg, 0.18 mmol) to obtain the title compound 79 mg (yield: 97%).
$^1$H NMR (CDCl$_3$) δ: 9.03 (s, 1H), 8.77 (s, 1H), 8.56 (s, 1H), 8.41 (bs, 1H), 8.00 (t, 1H), 7.30-7.26 (m, 2H), 7.09 (s, 1H), 6.41-6.39 (m, 2H), 5.76-5.73 (m, 1H), 4.11 (t, 2H), 4.04-3.96 (m, 1H), 3.20 (m, 2H).

<24-4> N-[4-(4-bromo-2-fluoro-phenylamino)-7-(2-ureido-ethoxy)-quinazolin-6-yl]-acrylamide The procedure of Example 4 was repeated except for using the compound of <24-3> (50 mg, 0.11 mmol) and trimethylsilyl isocyanate (58 mg, 0.5 mmol) to obtain the title compound 44 mg (yield: 82%).
$^1$H NMR (CDCl$_3$+CD$_3$OD) δ: 9.00 (s, 1H), 8.42 (s, 1H), 7.68 (t, 1H), 7.37-7.30 (m, 2H), 7.09 (s, 1H), 6.80-6.71 (m, 1H), 6.48-6.42 (m, 1H), 5.84-5.80 (m, 1H), 4.17 (t, 2H), 3.66-3.63 (m, 2H).

Example 25

Preparation of N-[4-(4-bromo-2-fluoro-phenylamino)-7-[2-(2-dimethylamino-acetylamino)-ethoxy]-quinazolin-6-yl]-acrylamide <25-1> N-{2-[4-(4-bromo-2-fluoro-phenylamino)-6-nitro-quinazolin-7-yloxy]-ethyl}-2-dimethylamino-acetamide The procedure of Example <12-1> was repeated except for using the compound of Example <18-3> (300 mg, 0.71 mmol) to obtain the title compound 201 mg (yield: 56%).
$^1$H NMR (CDCl$_3$) δ: 8.79 (s, 1H), 8.67 (s, 1H), 8.26 (t, 1H), 8.07 (s, 1H), 7.81 (t, 1H), 7.43-7.39 (m, 3H), 4.37 (t, 2H), 3.84 (q, 2H), 3.01 (s, 2H), 2.34 (s, 6H).

<25-2> N-{2-[6-amino-4-(4-bromo-2-fluoro-phenylamino)-quinazolin-7-yloxy]-ethyl}-2-dimethylamino-acetamide The procedure of Example <1-7> was repeated except for using the compound of <25-1> (200 mg, 0.39 mmol) to obtain the title compound 113 mg (yield: 60%).
$^1$H NMR (CDCl$_3$) δ: 8.45 (s, 1H), 8.36 (t, 1H), 7.49 (t, 1H), 7.30 (bs, 1H), 7.20 (d, 1H), 7.17 (d, 1H), 7.00 (s, 1H), 6.85 (s, 1H), 4.39 (s, 2H), 4.10 (t, 2H), 3.70 (q, 2H), 2.89 (s, 2H).

<25-3> N-[4-(4-bromo-2-fluoro-phenylamino)-7-[2-(2-dimethylamino-acetylamino)-ethoxy]-quinazolin-6-yl]-acrylamide The procedure of Example <1-8> was repeated except for using the compound of <25-2> (113 mg, 0.24 mmol) and acryloyl chloride (23 mg, 0.28 mmol) to obtain the title compound 39 mg (yield: 31%).
$^1$H NMR (CDCl$_3$) δ: 9.17 (s, 1H), 8.93 (s, 1H), 8.60 (s, 1H), 8.20 (t, 1H), 7.79 (s, 1H), 7.67 (t, 1H), 7.30-7.26 (m, 2H), 7.11 (s, 1H), 6.86-6.80 (m, 1H), 6.50 (d, 1H), 4.19 (t, 2H), 3.83 (q, 2H), 3.00 (s, 2H), 2.50 (s, 1H), 2.25 (s, 6H).

Example 26

Preparation of N-{2-[6-acryloylamino-4-(4-bromo-2-fluoro-phenylamino)-quinazolin-7-yloxy]-ethyl}-acrylamide <26-1> N-{2-[4-(4-bromo-2-fluoro-phenylamino)-6-nitro-quinazolin-7-yloxy]-ethyl}-acrylamide The procedure of Example <1-8> was repeated except for using the compound of Example <18-3> (800 mg, 1.90 mmol) to obtain the title compound 220 mg (yield: 25%).
$^1$H NMR (CDCl$_3$) δ: 8.75 (d, 2H), 8.28 (s, 1H), 8.18 (t, 1H), 7.40 (d, 3H), 6.51 (br t, 1H), 6.36-6.16 (m, 2H), 5.71 (d, 1H), 4.38 (t, 2H), 3.90 (q, 2H).

<26-2> N-{2-[6-amino-4-(4-bromo-2-fluoro-phenylamino)-quinazolin-7-yloxy]-ethyl}-acrylamide The procedure of Example <1-7> was repeated except for using the compound of <26-1> (220 mg, 0.46 mmol) to obtain the title compound 86 mg (yield: 42%).
$^1$H NMR (CDCl$_3$+CD$_3$OD) δ: 8.39 (s, 1H), 7.98 (t, 1H), 7.38-7.34 (m, 2H), 7.20 (s, 1H), 7.06 (s, 1H), 6.33-6.17 (m, 2H), 5.68 (d, 1H), 4.28-4.19 (m, 2H), 3.82 (t, 2H).

<26-3> N-{2-[6-acryloylamino-4-(4-bromo-2-fluoro-phenylamino)-quinazolin-7-yloxy]-ethyl}-acrylamide The procedure of Example <1-8> was repeated except for using the compound of <26-2> (86 mg, 0.19 mmol) and acryloyl chloride (19 mg, 0.23 mmol) to obtain the title compound 8.8 mg (yield: 10%).
$^1$H NMR (CDCl$_3$+CD$_3$OD) δ: 9.01 (s, 1H), 8.47 (s, 1H), 7.83 (t, 1H), 7.81-7.26 (m, 2H), 7.05 (s, 1H), 6.83-6.17 (m, 2H), 6.49 (d, 1H), 6.25-6.15 (m, 2H), 5.82 (d, 1H), 5.63 (d, 1H), 4.19 (t, 2H), 3.80 (d, 2H).

Example 27

Preparation of N-[4-(4-bromo-2-fluoro-phenylamino)-7-(2-propionylamino-ethoxy)-quinazolin-6-yl]-acrylamide <27-1> N-{2-[4-(4-bromo-2-fluoro-phenylamino)-6-nitro-quinazolin-7-yloxy]-ethyl}-propionylamide The procedure of Example <1-8> was repeated except for using the compound of Example <18-3> (250 mg, 0.59 mmol) to obtain the title compound 227 mg (yield: 80%).
$^1$H NMR (DMSO-d$_6$) δ: 10.17 (s, 1H), 9.14 (s, 1H), 8.52 (s, 1H), 7.95 (br t, 1H), 7.67 (d, 1H), 7.49-7.46 (m, 3H), 4.32 (t, 2H), 3.51-3.40 (m, 2H), 2.08 (q, 2H), 0.98 (t, 3H).

<27-2> N-{2-[6-amino-4-(4-bromo-2-fluoro-phenylamino)-quinazolin-7-yloxy]-ethyl}-propionylamide The procedure of Example <1-7> was repeated except for using the compound of <27-1> (227 mg, 0.47 mmol) to obtain the title compound 200 mg (yield: 94%).

¹H NMR (CDCl₃+CD₃OD) δ: 8.37 (s, 1H), 7.93 (t, 1H), 7.36-7.31 (m, 2H), 7.20 (s, 1H), 7.03 (s, 1H), 4.22 (t, 2H), 3.36 (t, 2H), 2.26 (q, 2H), 1.19-1.14 (m, 3H).

<27-3> N-[4-(4-bromo-2-fluoro-phenylamino)-7-(2-propionylamino-ethoxy)-quinazolin-6-yl]-acrylamide The procedure of Example <1-8> was repeated except for using the compound of <27-2> (200 mg, 0.45 mmol) and acryloyl chloride (43 mg, 0.54 mmol) to obtain the title compound 10.8 mg (yield: 5%).
¹H NMR (CDCl₃) δ: 9.20 (s, 1H), 8.98 (s, 1H), 8.63 (s, 1H), 8.43 (t, 1H), 7.72 (s, 1H), 7.70-7.29 (m, 2H), 7.10 (s, 1H), 6.94-6.86 (m, 1H), 6.53 (d, 1H), 6.08 (t, 1H), 5.84 (d, 1H), 4.18 (t, 2H), 3.81 (q, 2H), 2.33-2.24 (m, 2H), 2.02 (s, 3H), 1.16 (t, 3H).

Example 28

Preparation of N-[4-(4-bromo-2-fluoro-phenylamino)-7-[2-(2,2,2-trifluoro-acetylamino)-ethoxy]-quinazolin-6-yl]-acrylamide <28-1> N-{2-[4-(4-bromo-2-fluoro-phenylamino)-6-nitro-quinazolin-7-yloxy]-ethyl}-2,2,2-trifluoro-acetamide The procedure of Example 2 was repeated except for using the compound of Example <18-3> (250 mg, 0.59 mmol) to obtain the title compound 190 mg (yield: 62%).
¹H NMR (DMSO-d₆) δ: 10.18 (s, 1H), 9.55 (br t, 1H), 9.15 (s, 1H), 8.54 (s, 1H), 7.67 (d, 1H), 7.53-7.46 (m, 3H), 4.45 (t, 2H), 3.64 (q, 2H).

<28-2> N-{2-[6-amino-4-(4-bromo-2-fluoro-phenylamino)-quinazolin-7-yloxy]-ethyl}-2,2,2-trifluoro-acetamide The procedure of Example <1-7> was repeated except for using the compound of <28-1> (190 mg, 0.37 mmol) to obtain the title compound 140 mg (yield: 78%).
¹H NMR (CD₃OD) δ: 8.21 (s, 1H), 7.67 (br t, 1H), 7.45-7.20 (m, 3H), 6.97 (s, 1H), 4.20 (d, 2H), 3.94-3.86 (m, 1H), 3.71 (s, 2H).

<28-3> N-[4-(4-bromo-2-fluoro-phenylamino)-7-[2-(2,2,2-trifluoro-acetylamino)-ethoxy]-quinazolin-6-yl}-acrylamide The procedure of Example <1-8> was repeated except for using the compound of <28-2> (140 mg, 0.29 mmol) and acryloyl chloride (31 mg, 0.34 mmol) to obtain the title compound 9.6 mg (yield: 6%).
¹H NMR (CDCl₃+CD₃OD) δ: 9.05 (s, 1H), 8.47 (s, 1H), 7.78-7.61 (m, 2H), 7.40-7.34 (m, 2H), 7.13 (s, 1H), 6.76-6.67 (s, 1H), 6.47 (dd, 1H), 5.84 (dd, 1H), 4.32-4.25 (m, 2H), 3.85 (t, 2H), 3.08 (s, 1H).

Example 29

Preparation of N-[7-(2-amino-ethoxy)-4-(4-bromo-2-fluoro-phenylamino)-quinazolin-6-yl]-acrylamide <29-1> (2-hydroxy-ethyl)-carbamic acid t-butylester The procedure of Example <1-1> was repeated except for using 2-amino-ethanol (10 g, 160 mmol) to obtain the title compound 24 g (yield: 91%).
¹H NMR (CDCl₃) δ: 5.30 (bs, 1H), 3.72 (bs, 1H), 3.56 (t, 2H), 3.16 (t, 2H), 1.35 (s, 9H).

<29-2> (4-bromo-2-fluoro-phenyl)-(7-fluoro-6-nitro-quinazolin-4-yl)-amine

The procedure of Example <1-5> was repeated except for using the compound of Example <1-4> (15 g, 66 mmol) and 4-bromo-2-fluoro-aniline (13 g, 66 mmol) to obtain the title compound 25 g (yield: 99%).
¹H NMR (CDCl₃) δ: 7.39 (s, 2H), 7.59 (d, 1H), 7.73 (d, 1H), 8.48 (s, 1H), 9.41 (d, 1H), 10.35 (bs, 1H).

<29-3> {2-[4-(4-bromo-2-fluoro-phenylamino)-6-nitro-quinazolin-7-yloxy]-ethyl}-carbamic acid t-butylester The procedure of Example <1-6> was repeated except for using the compound of <29-1> (17 g, 78.7 mmol) and the compound of <29-2> (20 g, 52.5 mmol) to obtain the title compound 15 g (yield: 50%).
¹H NMR (DMSO-d₆) δ: 10.10 (bs, 1H), 9.06 (s, 1H), 8.44 (s, 1H), 7.59 (d, 1H), 7.47-7.38 (m, 3H), 6.88 (t, 1H), 4.23 (t, 2H), 3.28 (q, 2H), 1.29 (s, 9H).

<29-4> {2-[6-amino-4-(4-bromo-2-fluoro-phenylamino)-quinazolin-7-yloxy]-ethyl}-carbamic acid t-butylester The procedure of Example <1-7> was repeated except for using the compound of <29-3> (3.46 g, 6 mmol) to obtain the title compound 3.1 g (yield: 95%).
¹H NMR (CDCl₃) δ: 8.65 (t, 1H), 8.62 (s, 1H), 7.37 (s, 1H), 7.33 (d, 1H), 7.22 (s, 1H), 7.17 (s, 1H), 6.93 (s, 1H), 4.94 (s, 2H), 4.23 (t, 2H), 3.69 (q, 2H), 1.48 (s, 9H).

<29-5> {2-[6-acryloylamino-4-(4-bromo-2-fluoro-phenylamino)-quinazolin-7-yloxy]-ethyl}-carbamic acid t-butylester 20 ml of distilled water and sodium bicarbonate (3.48 g, 41.43 mmol) was sequentially added to 200 ml of ethylacetate at room temperature. The compound of <29-4> (6.80 g, 13.81 mmol) was added thereto after stirring the solution for 10 min, the reaction temperature was cooled to 0° C., and acryloyl chloride (1.68 ml, 20.72 mmol) was added thereto. The solution was stirred for 40 min while slowly heating to room temperature, and distilled under a reduced pressure. Saturated sodium bicarbonate aqueous solution (100 ml) was added thereto, and extracted with chloroform (100 ml) twice. The separated organic layer was dried over magnesium sulfate, filtered and distilled under a reduced pressure, and resulting impure residue was subjected to column chromatography to obtain the title compound 2.8 g (yield: 37.1%).
¹H NMR (CDCl₃) δ: 9.26 (s, 1H), 9.13 (s, 1H), 8.69 (s, 1H), 8.40 (t, 1H), 7.54 (s, 1H), 7.38-7.35 (m, 2H), 7.18 (s, 1H), 6.77 (dd, 1H), 6.55 (ab, 1H), 5.84 (ab, 1H), 4.98 (t, 1H), 4.22 (t, 2H), 3.70 (q, 2H), 1.47 (s, 9H).

<29-6> N-[7-(2-amino-ethoxy)-4-(4-bromo-2-fluoro-phenylamino)-quinazolin-6-yl]-acrylamide The procedure of Example <1-9> was repeated except for using the compound of <29-5> (2.8 g, 5.2 mmol) to obtain the title compound 2.4 g (yield: 99%).

¹H NMR (CDCl₃) δ: 9.18 (s, 1H), 8.67 (s, 1H), 8.60 (s, 1H), 8.35 (t, 1H), 7.64 (s, 1H), 7.37-7.30 (m, 2H), 6.54-6.35 (m, 2H), 5.85 (dd, 1H), 4.26 (t, 2H), 3.26 (t, 2H).

Example 30

Preparation of N-[4-(4-bromo-2-fluoro-phenylamino)-7-(2-methylamino-ethoxy)-quinazolin-6-yl]-acrylamide <30-1> (2-hydroxy-ethyl)-methyl-carbamic acid t-butylester The procedure of Example <1-1> was repeated except for using 2-methylamino-ethanol (20 g, 266.2 mmol) to obtain the title compound 44.3 g (yield: 95%).
¹H NMR (CDCl₃) δ: 3.75 (q, 2H), 3.40 (t, 2H), 2.92 (s, 3H), 1.47 (s, 9H)

<30-2> {2-[4-(4-bromo-2-fluoro-phenylamino)-6-nitro-quinazolin-7-yloxy-ethyl}-methyl-carbamic acid t-butylester The procedure of Example <1-6> was repeated except for using the compound of Example <29-2> (570 mg, 1.49 mmol) and the compound of <30-1> (786 mg, 4.48 mmol) to obtain the title compound 218 mg (yield: 27%).
¹H NMR (CDCl₃) δ: 8.80 (s, 1H), 8.56-8.50 (m, 1H), 8.44-8.36 (m, 1H), 7.46-7.39 (m, 3H), 4.38-4.35 (m, 2H), 3.74 (t, 2H), 3.05 (s, 3H), 1.48 (s, 9H).

<30-3> {2-[6-amino-4-(4-bromo-2-fluoro-phenylamino)-quinazolin-7-yloxy]-ethyl}-methyl-carbamic acid t-butylester The procedure of Example <1-7> was repeated except for using the compound of <30-2> (218 mg, 0.4 mmol) to obtain the title compound 201 mg (yield: 99%).
¹H NMR (CDCl₃) δ: 8.67-8.61 (m, 2H), 7.35-7.31 (m, 2H), 7.20-7.16 (m, 2H), 6.90 (bs, 1H), 4.28 (t, 2H), 3.76 (m, 2H), 2.98 (s, 3H), 1.47 (s, 9H).

<30-4> {2-[6-acryloylamino-4-(4-bromo-2-fluoro-phenylamino)-quinazolin-7-yloxy]-ethyl}-methyl-carbamic acid t-butylester The procedure of Example <1-8> was repeated except for using the compound of <30-3> (201 mg, 0.4 mmol) to obtain the title compound 40 mg (yield: 18%).
¹H NMR (CDCl₃) δ: 9.22 (s, 1H), 9.11 (s, 1H), 8.67 (s, 1H), 8.34 (t, 1H), 7.61 (s, 1H), 7.36-7.32 (m, 2H), 7.18 (s, 1H), 6.76-6.70 (m, 1H), 6.56-6.50 (m, 1H), 5.84-5.81 (m, 1H), 4.26 (m, 2H), 3.80 (m, 2H), 2.99 (s, 3H), 1.47 (s, 9H).

<30-5> N-[4-(4-bromo-2-fluoro-phenylamino)-7-(2-methylamino-ethoxy)-quinazolin-6-yl]-acrylamide The procedure of Example <1-9> was repeated except for using the compound of <30-4> (38 mg, 0.07 mmol) to obtain the title compound 20 mg (yield: 64%).
¹H NMR (CDCl₃) δ: 9.11 (s, 1H), 8.88 (s, 1H), 8.63 (s, 1H), 8.25 (t, 1H), 7.34-7.31 (m, 3H), 7.21 (s, 1H), 6.51-6.37 (m, 2H), 5.81-5.78 (m, 1H), 4.28 (t, 2H), 3.13 (m, 2H), 2.55 (s, 3H).

Example 31

Preparation of N-[4-(4-bromo-2-fluoro-phenylamino)-7-but-3-enyloxy-quinazolin-6-yl]-acrylamide <31-1> (4-bromo-2-fluoro-phenyl)-(7-but-3-enyloxy-6-nitro-quinazolin-4-yl)-amine The procedure of Example <1-6> was repeated except for using the compound of Example <1-5> (1 g, 2.62 mmol) and but-3-en-1-ol (567 mg, 7.87 mmol) to obtain the title compound 386 mg (yield: 34%).
¹H NMR (CDCl₃)) δ: 8.80 (s, 1H), 8.46-8.40 (m, 2H), 7.52 (bs, 1H), 7.43-7.39 (m, 3H), 6.00-5.88 (m, 1H), 5.27-5.17 (m, 2H), 4.31 (t, 2H), 2.69 (q, 2H).

<31-2> N⁴-(4-bromo-2-fluoro-phenyl)-7-but-3-enyloxy-quinazoline-4,6-diamine

The procedure of Example <1-7> was repeated except for using the compound of <31-1> (386 mg 0.89 mmol) to obtain the title compound 350 mg (yield: 97%).
¹H NMR (CDCl₃) δ: 8.63-8.57 (m, 2H), 7.36-7.18 (m, 4H), 6.90 (s, 1H), 5.99-5.85 (m, 1H), 5.24-5.14 (m, 2H), 4.31 (bs, 2H), 4.21 (t, 2H), 2.65 (q, 2H).

<31-3> N-[4-(4-bromo-2-fluoro-phenylamino)-7-but-3-enyloxy-quinazolin-6-yl]-acrylamide The procedure of Example <29-5> was repeated except for using the compound of <31-2> (314 mg, 0.78 mmol) to obtain the title compound 62.8 mg (yield: 17%).
¹H NMR (CDCl₃) δ: 9.11 (s, 1H), 8.65 (s, 1H), 8.29 (t, 1H), 8.19 (s, 1H), 7.66 (s, 1H), 7.33-7.27 (m, 2H), 6.49-6.43 (m, 1H), 6.32-6.23 (m, 1H), 5.97-5.83 (m, 2H), 5.29-5.20 (m, 2H), 4.27 (t, 2H), 2.69 (q, 2H).

Example 32

Preparation of N-[4-(4-bromo-2-fluoro-phenylamino)-7-(2-methoxy-ethoxy)-quinazolin-6-yl]-acrylamide <32-1> (4-bromo-2-fluoro-phenyl)-[7-(2-methoxy-ethoxy)-6-nitro-quinazolin-4-yl]-amine The procedure of Example <1-6> was repeated except for using the compound of Example <1-5> (1 g, 2.62 mmol) and 2-methoxy-ethanol (598 mg, 7.87 mmol) to obtain the title compound 434 mg (yield: 38%).
¹H NMR (CDCl₃) δ: 8.80 (s, 1H), 8.48 (s, 1H), 8.42 (t, 1H), 7.54 (bs, 1H), 7.47 (s, 1H), 7.43-7.39 (m, 2H), 4.41 (t, 2H), 3.89 (t, 2H), 3.50 (s, 3H).

<32-2> N⁴-(4-bromo-2-fluoro-phenyl)-7-(2-methoxy-ethoxy)-quinazoline-4,6-diamine The procedure of Example <1-7> was repeated except for using the compound of <32-1> (434 mg 0.99 mmol) to obtain the title compound 380 mg (yield: 94%).

¹H NMR (CDCl₃) δ: 8.65-8.59 (m, 2H), 7.34-7.30 (m, 2H), 7.19 (s, 1H), 6.92 (s, 1H), 4.36 (bs, 2H), 4.32 (t, 2H), 3.87-3.84 (m, 2H), 3.46 (s, 3H).

<32-3> N-[4-(4-bromo-2-fluoro-phenylamino)-7-(2-methoxy-ethoxy)-quinazolin-6-yl]-acrylamide The procedure of Example <29-5> was repeated except for using the compound of <32-2> (380 mg, 0.93 mmol) to obtain the title compound 21 mg (yield: 5%).
¹H NMR (CDCl₃) δ: 9.17 (s, 1H), 8.67 (s, 1H), 8.39-8.30 (m, 2H), 7.64 (s, 1H), 7.36-7.30 (m, 3H), 6.52-6.47 (m, 1H), 6.40-6.31 (m, 1H), 5.87-5.84 (m, 1H), 4.38 (t, 2H), 3.86 (t, 2H), 3.48 (s, 3H).

Example 33

Preparation of N-[4-(4-bromo-2-fluoro-phenylamino)-7-(2-methanesulfonylamino-ethoxy)-quinazolin-6-yl]-acrylamide <33-1> N-{2-[4-(4-bromo-2-fluoro-phenylamino)-6-nitro-quinazolin-7-yloxy]-ethyl}-methane sulfonamide The procedure of Example <1-8> was repeated except for using the compound of Example <18-3> (250 mg, 0.59 mmol) and methanesulfonyl chloride (50 μl, 0.65 mmol) to obtain the title compound 286 mg (yield: 95%).
¹H NMR (DMSO-d₆) δ: 10.22 (d, 1H), 9.18 (s, 1H), 8.55 (s, 1H), 7.98 (s, 1H), 7.69 (d, 1H), 7.58-7.47 (m, 3H), 7.31 (t, 1H), 4.37 (t, 2H), 3.41 (q, 2H), 2.94 (s, 3H).

<33-2> N-{2-[6-amino-4-(4-bromo-2-fluoro-phenylamino)-quinazolin-7-yloxy]-ethyl}-methanesulfonamide The procedure of Example <1-7> was repeated except for using the compound of <33-1> (286 mg, 0.57 mmol) to obtain the title compound 80 mg (yield: 30%).
¹H NMR (DMSO-d₆) δ: 9.12 (s, 1H), 8.25 (s, 1H), 7.51 (t, 2H), 7.36 (d, 1H), 7.24 (s, 1H), 7.00 (s, 1H), 5.53 (s, 2H), 4.12 (t, 2H), 3.38 (q, 2H), 2.91 (s, 3H).

<33-3> N-[4-(4-bromo-2-fluoro-phenylamino)-7-(2-methanesulfonylamino-ethoxy)-quinazolin-6-yl]-acrylamide The procedure of Example <1-8> was repeated except for using the compound of <33-2> (70 mg, 0.15 mmol) to obtain the title compound 3 mg (yield: 3.8%).
¹H NMR (CDCl₃) δ: 9.21 (s, 1H), 9.06 (s, 1H), 8.71 (s, 1H), 8.35 (t, 1H), 7.81-7.64 (m, 1H), 7.46-7.43 (m, 3H), 7.10 (s, 1H), 6.65 (ab, 2H), 5.88 (dd, 1H), 4.11 (s, 2H), 3.80 (s, 2H), 3.21 (s, 3H).

Example 34

Preparation of N-{4-(4-bromo-2-fluoro-phenylamino)-7-[2-(3-propyl-ureido)-ethoxy]-quinazolin-6-yl}-acrylamide Propyl isocyanate (0.02 ml) was added to the compound of Example <29-6> (50 mg, 0.11 mmol) diluted with dichloromethane (5.0 ml), and stirred at room temperature for 1.5 hours. The reaction was terminated with 10 ml of saturated sodium bicarbonate solution, and the reacted solution was extracted with chloroform (50 ml of) twice. The separated organic layer was dried over magnesium sulfate, filtered and distilled under a reduced pressure. The resulting impure residue was subjected to column chromatography to obtain the title compound 28 mg (yield: 48%).
¹H NMR (CD₃OD) δ: 9.10 (s, 1H), 8.40 (s, 1H), 7.64 (t, 1H), 7.51-7.42 (m, 2H), 7.20 (s, 1H), 6.92 (ab, 1H), 6.50 (dd, 1H), 5.88 (dd, 1H), 4.26 (t, 2H), 3.71 (t, 2H), 3.13 (t, 2H), 1.49 (m, 2H), 0.90 (t, 3H).

Example 35

Preparation of N-{4-(4-bromo-2-fluoro-phenylamino)-7-[2-(3-methyl-thioureido)-ethoxy]-quinazolin-6-yl}-acrylamide The procedure of Example 44 was repeated except for using the compound of Example <29-6> (50 mg, 0.11 mmol) and methyl isothiocyanate (0.015 ml) to obtain the title compound 24 mg (yield: 41%).
¹H NMR (CDCl₃) δ: 9.10 (s, 1H), 8.87 (s, 1H), 8.50 (s, 1H), 8.28 (t, 1H), 7.38-7.30 (m, 3H), 7.00 (s, 1H), 6.84 (ab, 1H), 6.42 (dd, 1H), 5.80 (dd, 1H), 3.98 (s, 2H), 3.04 (s, 2H), 1.25 (s, 3H).

Example 36

Preparation of N-{4-(4-bromo-2-fluoro-phenylamino)-7-[2-(3-ethyl-thioureido)-ethoxy]-quinazolin-6-yl}-acrylamide The procedure of Example 34 was repeated except for using the compound of Example <29-6> (50 mg, 0.11 mmol) and ethyl isothiocyanate (0.020 ml) to obtain the title compound 24 mg (yield: 41%).
¹H NMR (CDCl₃) δ: 8.95 (s, 1H), 8.73 (s, 1H), 8.35 (s, 1H), 8.09 (t, 1H), 7.51 (br s, 1H), 7.23-7.14 (m, 4H), 6.83 (s, 1H), 6.69 (ab, 2H), 6.30 (dd, 1H), 5.45 (dd, 1H), 4.19 (s, 2H), 4.09 (s, 2H), 3.33 (s, 2H), 1.13 (t, 3H).

Example 37

Preparation of N-{4-(4-bromo-2-fluoro-phenylamino)-7-[2-(3-isopropyl-ureido)-ethoxy]-quinazolin-6-yl}-acrylamide The procedure of Example 34 was repeated except for using the compound of Example <29-6> (50 mg, 0.11 mmol) and isopropyl isocyanate (0.022 ml) to obtain the title compound 28 mg (yield: 47%).
¹H NMR (CDCl₃) δ: 9.37 (s, 1H), 9.26 (s, 1H), 8.66 (s, 1H), 8.35 (t, 1H), 7.38-7.33 (m, 2H), 7.15 (s, 1H), 6.92 (ab, 1H), 6.53 (dd, 1H), 5.82 (dd, 1H), 4.18 (t, 2H), 3.76 (q, 2H), 3.93 (m, 1H) 1.14 (d, 6H).

Example 38

Preparation of N-{4-(4-bromo-2-fluoro-phenylamino)-7-[2-(3-sec-butyl-ureido)-ethoxy]-quinazolin-6-yl}-acrylamide The procedure of Example 34 was repeated except for using the compound of Example <29-6> (50 mg, 0.11 mmol) and sec-butyl isocyanate (0.026 ml) to obtain the title compound 24 mg (yield: 38%).
¹H NMR (CDCl₃+CD₃OD) δ: 8.99 (s, 1H), 8.42 (s, 1H), 7.72 (t, 1H), 7.32-7.27 (m, 2H), 7.01 (s, 1H), 6.84 (ab, 1H), 6.43 (dd, 1H), 5.76 (dd, 1H), 4.14 (t, 2H), 3.59 (q, 2H), 1.32 (t, 2H), 0.98 (d, 3H), 0.77 (t, 3H).

Example 39

Preparation of N-{4-(4-bromo-2-fluoro-phenylamino)-7-[2-(3-vinyl-ureido)-ethoxy]-quinazolin-6-yl}-acrylamide The procedure of Example 34 was repeated except for using the compound of Example <29-6> (50 mg, 0.11 mmol) and vinyl isocyanate (0.026 ml) to obtain the title compound 27 mg (yield: 47%).

$^1$H NMR (CDCl$_3$+CD$_3$OD) δ: 8.99 (s, 1H), 8.43 (s, 1H), 7.72 (t, 1H), 7.33-7.27 (m, 3H), 7.03 (s, 1H), 6.76 (ab, 2H), 6.43 (dd, 1H), 5.79 (dd, 1H), 4.14-4.08 (m, 2H), 3.64 (s, 2H).

Example 40

Preparation of N-[7-[2-(3-allyl-ureido)-ethoxy]-4-(4-bromo-2-fluoro-phenylamino)-quinazolin-6-yl]-acrylamide The procedure of Example 44 was repeated except for using the compound of Example <29-6> (50 mg, 0.11 mmol) and allyl isocyanate (0.020 ml) to obtain the title compound 26 mg (yield: 44%).

$^1$H NMR (CDCl$_3$+CD$_3$OD) δ: 9.00 (s, 1H), 8.45 (s, 1H), 7.78 (t, 1H), 7.33-7.27 (m, 2H), 7.01 (s, 1H), 6.81 (ab, 1H), 6.43 (dd, 1H), 5.76 (dd, 2H), 4.97 (ab, 2H), 4.09 (t, 2H), 3.73 (d, 2H), 3.63 (q, 2H).

Example 41

Preparation of morpholine-4-carboxylic acid {2-[6-acryloylamino-4-(4-bromo-3-chloro-2-fluoro-phenylamino)-quinazolin-7-yloxy]-ethyl}-amide The procedure of Example 93 was repeated except for using the compound of Example <141-6> (80 mg, 0.166 mmol) to obtain the title compound 46 mg (yield: 46%).

$^1$H NMR (CD$_3$OD) δ: 9.91 (s, 1H), 9.63 (s, 1H), 9.16 (s, 1H), 8.41 (s, 1H), 7.68 (d, 1H), 7.48 (t, 1H), 7.24 (s, 1H), 6.83 (ab, 1H), 6.53 (dd, 1H), 5.79 (dd, 1H), 4.87 (t, 1H), 4.21 (t, 2H), 3.84 (q, 2H), 3.69 (t, 4H), 3.38 (t, 4H).

Example 42

Preparation of N-[7-[2-(acetyl-methyl-amino)-ethoxy]-4-(4-bromo-2-fluoro-phenylamino)-quinazolin-6-yl]-acrylamide <42-1> (4-bromo-2-fluoro-phenyl)-[7-(2-methylamino-ethoxy)-6-nitro-quinazolin-4-yl]-amine The procedure of Example <1-9> was repeated except for using the compound of Example <30-2> (80 mg, 0.15 mmol) to obtain the title compound 40 mg (yield: 61%).

$^1$H NMR (CDCl$_3$) δ: 8.75 (s, 1H), 8.56 (s, 1H), 8.28 (t, 1H), 7.40-7.34 (m, 3H), 4.34 (t, 2H), 3.10 (m, 2H), 2.56 (s, 3H).

<42-2> N-{2-[4-(4-bromo-2-fluoro-phenylamino)-6-nitro-quinazolin-7-yloxy]-ethyl}-N-methyl-acetamide The procedure of Example <1-8> was repeated except for using the compound of <42-1> (40 mg, 0.09 mmol) to obtain the title compound 40 mg (yield: 93%).

$^1$H NMR (CDCl$_3$+CD$_3$OD) δ: 8.99 (s, 1H), 8.50 (s, 1H), 7.54 (m, 1H), 7.40-7.31 (m, 3H), 4.39 (t, 2H), 3.84 (q, 2H), 3.21 (s, 3H), 2.11 (s, 3H).

<42-3> N-{2-[6-amino-4-(4-bromo-2-fluoro-phenylamino)-quinazolin-7-yloxy]-ethyl}-N-methyl-acetamide The procedure of Example <1-7> was repeated except for using the compound of <42-2> (40 mg, 0.084 mmol) to obtain the title compound 30 mg (yield: 80%).

$^1$H NMR (CDCl$_3$) δ: 8.59-8.51 (m, 2H), 7.33-7.29 (m, 3H), 7.12 (s, 1H), 6.89 (s, 1H), 4.28 (t, 2H), 3.88 (t, 2H), 3.13 (s, 3H), 2.13 (s, 3H).

<42-4> N-[7-[2-(acetyl-methyl-amino)-ethoxy]-4-(4-bromo-2-fluoro-phenylamino)-quinazolin-6-yl]-acrylamide The procedure of Example <29-5> was repeated except for using the compound of <42-3> (30 mg, 0.067 mmol) to obtain the title compound 5 mg (yield: 15%).

$^1$H NMR (CDCl$_3$) δ: 9.23 (s, 1H), 8.95 (s, 1H), 8.67 (s, 1H), 8.35 (t, 1H), 7.60 (s, 1H), 7.39-7.34 (m, 2H), 7.19 (s, 1H), 6.90-6.81 (m, 1H), 6.58-6.51 (m, 1H), 5.87-5.83 (m, 1H), 4.30 (t, 2H), 3.97 (q, 2H), 3.15 (s, 3H), 2.16 (s, 3H).

Example 43

Preparation of N-[7-(2-acetylamino-ethylsulfanyl)-4-(4-bromo-2-fluoro-phenylamino)-quinazolin-6-yl]-acrylamide <43-1> (2-mercapto-ethyl)-carbamic acid t-butylester The procedure of Example <1-1> was repeated except for using 2-amino-ethanethiol (5.0 g, 64.8 mmol) to obtain the title compound 9.8 g (85.3%).

$^1$H NMR (CDCl$_3$) δ: 5.01 (s, 1H), 3.30 (t, 2H), 2.63 (q, 2H), 1.43 (s, 9H).

<43-2> {2-[4-(4-bromo-2-fluoro-phenylamino)-6-nitro-quinazolin-7-ylsulfanyl]-ethyl}-carbamic acid t-butylester The procedure of Example <1-6> was repeated except for using the compound of Example <1-5> (698 mg, 3.94 mmol) and the compound of <43-1> (500 mg, 1.31 mmol) to obtain the title compound 540 mg (yield: 77%).

$^1$H NMR (DMSO) δ: 9.46 (s, 1H), 8.55 (s, 1H), 7.80-7.66 (m, 3H), 7.48 (s, 2H), 7.08 (s, 1H), 3.24 (br t, 2H), 1.34 (s, 9H).

<43-3> [7-(2-amino-ethylsulfanyl)-6-nitro-quinazolin-4-yl]-(4-bromo-2-fluoro-phenyl)-amine The procedure of Example <1-9> was repeated except for using the compound of <43-2> (540 mg, 1.0 mmol) to obtain the title compound 380 mg (yield: 87%).

$^1$H NMR (DMSO) δ: 9.42 (s, 1H), 8.49 (s, 1H), 7.74 (s, 1H), 7.66 (d, 1H), 7.47 (t, 2H), 3.20 (t, 2H), 2.91 (q, 2H).

<43-4> N-{2-[4-(4-bromo-2-fluoro-phenylamino)-6-nitro-quinazolin-7-ylsulfanyl]-ethyl}-acetamide The procedure of Example <1-10> was repeated except for using the compound of <43-3> (380 mg, 0.86 mmol) and acetyl chloride (0.07 ml, 0.95 mmol) to obtain the title compound 120 mg (yield: 29%).

¹H NMR (DMSO) δ: 9.50 (s, 1H), 8.58 (s, 1H), 8.19 (t, 1H), 7.85 (s, 1H), 7.70 (d, 1H), 7.55-7.47 (m, 2H), 3.25 (t, 2H), 1.80 (s, 3H).

<43-5> N-{2-[6-amino-4-(4-bromo-2-fluoro-phenylamino)-quinazolin-7-ylsulfanyl]-ethyl}-acetamide The procedure of Example <1-7> was repeated except for using the compound of <43-4> (120 mg, 0.25 mmol) to obtain the title compound 93 mg (yield: 83%).
¹H NMR (DMSO) δ: 9.39 (s, 1H), 8.23 (s, 1H), 8.14 (s, 1H), 7.67-7.37 (m, 5H), 3.09 (t, 2H), 1.80 (s, 3H).

<43-6> N-[7-(2-acetylamino-ethylsulfanyl)-4-(4-bromo-2-fluoro-phenylamino)-quinazolin-6-yl]-acrylamide The procedure of Example <29-5> was repeated except for using the compound of <43-5> (50 mg, 0.10 mmol) to obtain the title compound 1.2 mg (yield: 2%).
¹H NMR (DMSO-$d_6$) δ: 9.13 (s, 1H), 8.76-8.62 (m, 4H), 8.40 (t, 1H), 8.10 (s, 1H), 7.75 (s, 1H), 7.66 (d, 2H), 7.42-7.37 (m, 5H), 7.01 (s, 1H), 6.55-6.50 (m, 2H), 6.05 (s, 1H), 5.96 (d, 1H), 5.92 (s, 1H), 3.68 (q, 2H), 3.53 (q, 2H), 3.24 (t, 3H).

Example 44

Preparation of N-{4-(4-bromo-2-fluoro-phenylamino)-7-[2-(2-methoxy-acetylamino)-ethoxy]-quinazolin-6-yl}-acrylamide Pyridine (26 mg, 0.33 mmol) and 1-(3-dimethylaminopropyl)-3-ethylcarbodiimide hydrochloride (84 mg, 0.44 mmol) were sequentially added to a mixture of the compound of <29-6> (50 mg, 0.11 mmol) and methoxy acetic acid (30 mg, 0.33 mmol) diluted with THF (5 ml), and stirred for 6 hours. The reaction was terminated by adding water (30 ml), and the reacted solution was extracted with chloroform (30 ml of) twice. The separated organic layer was dried over magnesium sulfate, filtered and distilled under a reduced pressure. The resulting impure residue was subjected to column chromatography to obtain the title compound 20 mg (yield: 35%).
¹H NMR (CDCl$_3$) δ: 9.22 (s, 1H), 8.95 (bs, 1H), 8.65 (s, 1H), 8.30 (t, 1H), 7.65 (bs, 1H), 7.36-7.30 (m, 2H), 7.15 (s, 1H), 7.03 (t, 1H), 6.84-6.75 (m, 1H), 6.56-6.50 (m, 1H), 5.85-5.81 (m, 1H), 4.23 (t, 1H), 3.96 (s, 2H), 3.88 (q, 2H), 3.43 (s, 3H).

Example 45

Preparation of N-{4-(4-bromo-2-fluoro-phenylamino)-7-[2-(2-hydroxy-acetylamino)-ethoxy]-quinazolin-6-yl}-acrylamide The procedure of Example 44 was repeated except for using the compound of Example <29-6> (50 mg, 0.11 mmol) and hydroxy-acetic acid (25 mg, 0.33 mmol) to obtain the title compound 4 mg (yield: 7%).
¹H NMR (CDCl$_3$+CD$_3$OD) δ: 9.05 (s, 1H), 8.54 (s, 1H), 7.91 (t, 1H), 7.52-7.33 (m, 2H), 7.13 (s, 1H), 6.76-6.70 (m, 1H), 6.53-6.47 (m, 1H), 5.85-5.81 (m, 1H), 4.25 (t, 2H), 4.08 (s, 2H), 3.85 (q, 2H).

Example 46

Preparation of N-{4-(4-bromo-2-fluoro-phenylamino)-7-[2-(2-methylsulfanyl-acetylamino)-ethoxy]-quinazolin-6-yl}-acrylamide The procedure of Example 44 was repeated except for using the compound of Example <29-6> (50 mg, 0.11 mmol) and methylsulfanyl-acetic acid (35 mg, 0.33 mmol) to obtain the title compound 13 mg (yield: 22%).
¹H NMR (CDCl$_3$+CD$_3$OD) δ: 9.03 (s, 1H), 8.50 (s, 1H), 7.83 (t, 1H), 7.72 (t, 1H), 7.36-7.29 (m, 2H), 7.10 (s, 1H), 6.83-6.74 (m, 1H), 6.52-6.46 (m, 1H), 5.85-5.81 (m, 1H), 4.22 (t, 2H), 3.81 (q, 2H), 3.20 (s, 2H), 2.04 (s, 3H).

Example 47

Preparation of N-{4-(4-bromo-2-fluoro-phenylamino)-7-[2-(2-methanesulfonyl-acetylamino)-ethoxy]-quinazolin-6-yl}-acrylamide The procedure of Example 44 was repeated except for using the compound of Example <29-6> (50 mg, 0.11 mmol) and methylsulfonyl-acetic acid (45 mg, 0.33 mmol) to obtain the title compound 23 mg (yield: 37%).
¹H NMR (DMSO-$d_6$) δ: 9.77 (s, 1H), 9.26 (s, 1H), 9.05 (s, 1H), 8.71 (m, 1H), 8.37 (s, 1H), 7.63-7.60 (m, 1H), 7.46-7.44 (m, 2H), 7.27 (s, 1H), 6.79-6.71 (m, 1H), 6.35-6.30 (m, 1H), 5.85-5.83 (m, 1H), 4.25 (t, 2H), 4.14 (s, 2H), 3.66 (t, 2H), 3.11 (s, 3H).

Example 48

Preparation of N-[4-(4-bromo-2-fluoro-phenylamino)-7-(2-isobutyrylamino-ethoxy)-quinazolin-6-yl]-acrylamide The procedure of Example 44 was repeated except for using the compound of Example <29-6> (50 mg, 0.11 mmol) and isobutyryl chloride (0.013 ml, 0.12 mmol) to obtain the title compound 24 mg (yield: 42%).
¹H NMR (CDCl$_3$) δ: 9.26 (s, 1H), 9.01 (s, 1H), 8.66 (s, 1H), 8.35 (t, 1H), 7.55 (s, 1H), 7.37-7.34 (m 2H), 7.18 (s, 1H), 6.94 (ab, 1H), 6.55 (dd, 1H), 5.87 (t, 2H), 4.22 (t, 2H), 3.84 (q, 2H), 1.17 (d, 6H).

Example 49

Preparation of N-{2-[6-acryloylamino-4-(4-bromo-2-fluoro-phenylamino)-quinazolin-7-yloxy]-ethyl}-2-methyl-acrylamide The procedure of Example 44 was repeated except for using the compound of Example <29-6> (50 mg, 0.11 mmol) and metacryloy chloride (0.015 ml, 0.13 mmol) to obtain the title compound 14 mg (yield: 24%).
¹H NMR (DMSO-$d_6$) δ: 9.22 (s, 1H), 9.01 (s, 1H), 8.64 (s, 1H), 8.32 (t, 1H), 7.60 (s, 1H), 7.36-7.31 (m, 2H), 7.13 (s, 1H), 6.89 (dd, 1H), 6.53 (ab, 1H), 6.34 (t, 1H), 5.83 (ab, 1H), 5.75 (s, 1H), 5.40 (s, 1H), 4.24 (t, 2H), 3.94 (q, 2H), 1.96 (s, 3H).

Example 50

Preparation of but-2-enoic acid {2-[6-acryloylamino-4-(4-bromo-2-fluoro-phenylamino)-quinazolin-7-yloxy]-ethyl}-amide The procedure of Example 44 was repeated except for using the compound of Example <29-6> (50 mg, 0.11 mmol)

and but-2-enoyl chloride (45 mg, 0.33 mmol) to obtain the title compound 24 mg (yield: 42%).

$^1$H NMR (CDCl$_3$+CD$_3$OD) δ: 9.02 (s, 1H), 8.42 (s, 1H), 7.67 (t, 1H), 7.40-7.34 (m, 2H), 7.11 (s, 1H), 6.87-6.82 (m, 2H), 6.52-6.45 (m, 1H), 5.96-5.85 (m, 2H), 4.25 (t, 2H), 3.80 (t, 2H), 1.86-1.84 (m, 3H).

Example 51

Preparation of N-{2-[6-acryloylamino-4-(4-bromo-2-fluoro-phenylamino)-quinazolin-7-yloxy]-ethyl}-butylamide The procedure of Example 44 was repeated except for using the compound of Example <29-6> (50 mg, 0.11 mmol) and butyric acid (29 mg, 0.33 mmol) to obtain the title compound 11 mg (yield: 19%).

$^1$H NMR (CDCl$_3$+CD$_3$OD) δ: 8.85 (s, 1H), 8.31 (s, 1H), 7.65 (t, 1H), 7.16-7.06 (m, 3H), 6.88 (s, 1H), 6.96-6.60 (m, 1H), 6.32-6.27 (m, 1H), 5.65-5.62 (m, 1H), 3.98 (t, 2H), 3.54 (t, 2H), 1.99 (t, 2H), 1.57-1.37 (m, 2H), 0.66 (t, 3H).

Example 52

Preparation of pent-2-enoic acid {2-[6-acryloylamino-4-(4-bromo-2-fluoro-phenylamino)-quinazolin-7-yloxy]-ethyl}-amide The procedure of Example 44 was repeated except for using the compound of Example <29-6> (500 mg, 1.1 mmol) and trans-pent-2-enoylic acid (336 mg, 3.3 mmol) to obtain the title compound 327 mg (yield: 55%).

$^1$H NMR (DMSO-d$_6$) δ: 9.64 (s, 1H), 9.25 (s, 1H), 8.97 (s, 1H), 8.26 (s, 1H), 8.18 (t, 1H), 7.50 (d, 1H), 7.36-7.30 (m, 2H), 7.14 (s, 1H), 6.81-6.59 (m, 2H), 6.26-6.20 (m, 1H), 5.85-5.73 (m, 2H), 4.13 (t, 2H), 3.53 (q, 2H), 2.02 (q, 2H), 0.87 (t, 3H).

Example 53

Preparation of 4-dimethylamino-but-2-enoic acid {2-[6-acryloylamino-4-(4-bromo-2-fluoro-phenylamino)-quinazolin-7-yloxy]-ethyl}-amide <53-1> 4-bromo-but-2-enoic acid {2-[4-(4-bromo-2-fluoro-phenylamino)-6-nitro-quinazolin-7-yloxy]-ethyl}-amide Oxalylchloride (449 mg, 3.54 mmol) and 1 droplet of N,N-dimethylformamide was sequentially added to t-butyldimethylsilyl 4-bromo-2-butenoate (842 mg, 3.54 mmol) diluted with dichloromethane (5 ml). The solution was stirred at room temperature for 1 hour, and distilled under a reduced pressure. The obtained residue was dissolved in THF (10 ml), and diisopropylethyl amine (459 mg, 3.55 mmol) was added thereto. The compound of Example <18-3> (1 g, 2.36 mmol) diluted with THF (5 ml) was added thereto at 0° C., and the solution was stirred at room temperature for 3 hours. The reaction was terminated by adding saturated sodium bicarbonate aqueous solution (30 ml), and the reacted solution was extracted with a 3:1 mixture (30 ml) of chloroform and isopropyl alcohol twice and washed with salt solution (30 ml). The separated organic layer was dried over magnesium sulfate, filtered and distilled under a reduced pressure, and resulting impure residue was subjected to column chromatography to obtain the title compound 280 mg (yield: 22%).

$^1$H NMR (CDCl$_3$) δ: 8.81 (s, 1H), 8.56 (s, 1H), 8.40 (t, 1H), 7.64 (bs, 1H), 7.43-7.30 (m, 3H), 7.03-6.93 (m, 1H), 6.40 (bs, 1H), 4.38 (t, 2H), 4.20 (d, 1H), 4.04 (d, 1H), 3.92 (t, 2H).

<53-2> 4-dimethylamino-but-2-enoic acid {2-[4-(4-bromo-2-fluoro-phenylamino)-6-nitro-quinazoline]-ethyl}-amide 2N dimethylamine (5.2 ml, 10.5 mmol) was added to the compound of <53-1> (280 mg, 0.52 mmol) diluted with THF (5 ml), and the solution was stirred at room temperature for 2 hours. The reaction was terminated by adding saturated sodium bicarbonate aqueous solution (30 ml), and the reacted solution was extracted with a 3:1 mixture (30 ml) of chloroform and isopropyl alcohol twice and washed with salt solution (30 ml). The separated organic layer was dried over magnesium sulfate, filtered and distilled under a reduced pressure, and resulting impure residue was subjected to column chromatography to obtain the title compound 190 mg (yield: 67%).

$^1$H NMR (CDCl$_3$) δ: 8.92 (s, 1H), 8.64 (s, 1H), 8.45 (t, 1H), 7.75 (bs, 1H), 7.59-7.34 (m, 3H), 6.99-6.90 (m, 1H), 6.33 (bs, 1H), 6.12 (d, 1H), 4.44 (t, 2H), 3.97 (t, 2H), 3.16 (d, 2H), 2.35 (s, 6H).

<53-3> 4-dimethylamino-but-2-enoic acid {2-[6-amino-4-(4-bromo-2-fluoro-phenylamino)-quinazolin-7-yloxy]-ethyl}-amide The procedure of Example <1-7> was repeated except for using the compound of <53-2> (190 mg, 0.35 mmol) to obtain the title compound 120 mg (yield: 67%).

$^1$H NMR (CDCl$_3$+CD$_3$OD) δ: 8.80 (s, 1H), 8.62 (s, 1H), 8.35 (t, 1H), 7.52-7.49 (m, 3H), 6.80-6.78 (m, 1H), 6.23 (d, 1H), 4.38 (t, 2H), 3.85 (t, 2H), 3.12 (d, 2H), 2.33 (s, 6H).

<53-4> 4-dimethylamino-but-2-enoic acid {2-[6-acryloylamino-4-(4-bromo-2-fluoro-phenylamino)-quinazolin-7-yloxy]-ethyl}-amide The procedure of Example <1-8> was repeated except for using the compound of <53-3> (120 mg, 0.23 mmol) to obtain the title compound 36 mg (yield: 28%).

$^1$H NMR (CDCl$_3$) δ: 9.17 (s, 1H), 9.13 (s, 1H), 8.59 (s, 1H), 8.36 (t, 1H), 8.20 (t, 1H), 7.32-7.29 (m, 2H), 7.18 (s, 1H), 6.95-6.73 (m, 2H), 6.48-6.43 (m, 2H), 5.82-5.79 (m, 1H), 4.21 (t, 2H), 3.85 (s, 2H), 3.66 (q, 2H), 2.69 (s, 6H).

Example 54

Preparation of N-{4-(4-bromo-3-chloro-2-fluoro-phenylamino)-7-[2-(3-t-butyl-ureido)-ethoxy]-quinazolin-6-yl}-acrylamide The procedure of Example 11 was repeated except for using the compound of Example <141-6> (80 mg, 0.166 mmol) to obtain the title compound 22 mg (yield: 23%).

$^1$H NMR (CD$_3$OD) δ: 9.91 (s, 1H), 9.63 (s, 1H), 9.16 (s, 1H), 8.41 (s, 1H), 7.68 (d, 1H), 7.48 (t, 1H), 7.24 (s, 1H), 6.83 (ab, 1H), 6.53 (dd, 1H), 5.79 (dd, 1H), 4.21 (t, 2H), 3.84 (q, 2H), 1.25 (s, 9H).

Example 55

Preparation of N-{4-(4-bromo-2-fluoro-phenylamino)-7-[2-(2-oxo-propylamino)-ethoxy]-quinazolin-6-yl}-acrylamide 1-chloro-propan-2-one (24 mg, 0.26 mmol) was added to a mixture of the compound of Example <29-6> (100 mg, 0.22 mmol) and potassium carbonate (46 mg, 0.33 mmol) diluted with N,N-dimethylformamide (1 ml), and the solution was refluxed and stirred at 70° C. for 2 hours. The reaction was terminated by adding water, and the organic layer extracted with ethyl acetate was washed with water twice. The separated organic layer was dried over magnesium sulfate, filtered and distilled under a reduced pressure, and resulting impure residue was subjected to column chromatography to obtain the title compound 10 mg (yield: 9%).

$^1$H NMR (CDCl$_3$) δ: 8.80 (s, 1H), 8.45 (s, 1H), 7.99 (t, 1H), 7.36-7.31 (m, 2H), 6.79 (s, 1H), 6.73-6.64 (m, 1H), 6.43-6.38 (m, 1H), 5.80-5.77 (m, 1H), 4.23 (t, 2H), 4.23-4.21 (m, 2H), 3.63 (q, 2H), 2.15 (s, 3H).

Example 56

Preparation of N-(4-(4-bromo-2-fluoro-phenylamino)-7-{2-[2-(ethyl-methyl-amino)-acetylamino]-ethoxy}-quinazolin-6-yl)-acrylamide <56-1> 2-bromo-N-{2-[4-(4-bromo-2-fluoro-phenylamino)-6-nitro-quinazolin-7-yloxy]-ethyl}-acetamide The procedure of Example 44 was repeated except for using the compound of Example <29-6> (8.5 g, 20.13 mmol) and bromoacetic acid (3.4 g, 24.16 mmol) to obtain the title compound 7.1 g (yield: 64%).

$^1$H NMR (DMSO-d$_6$) δ: 10.29 (s, 1H), 9.19 (s, 1H), 8.54 (s, 2H), 7.71 (d, 1H), 7.53 (s, 3H), 4.38 (t, 2H), 3.94 (s, 2H), 3.21 (s, 2H).

<56-2> N-{2-[4-(4-bromo-2-fluoro-phenylamino)-6-nitro-quinazolin-7-yloxy]-ethyl}-2-(ethyl-methyl-amino)-acetamide The compound of <56-1> (350 mg, 0.64 mmol) was added to a mixture of N-ethylmethylamine (0.066 ml, 0.77 mmol) and potassium carbonate (133 mg, 0.96 mmol) diluted with N,N-dimethylformamide (10 ml), and the solution was refluxed and stirred at 90° C. for 3 hours and slowly cooled to room temperature. The reaction was terminated by adding saturated sodium bicarbonate aqueous solution (15 ml), and the reacted solution was extracted with ethylacetate (30 ml). The separated organic layer was washed with distilled water 4 times, dried over magnesium sulfate, filtered and distilled under a reduced pressure, and resulting impure residue was subjected to column chromatography to obtain the title compound 220 mg (yield: 66%).

$^1$H NMR (CDCl$_3$)) δ: 8.91 (s, 1H), 8.67 (s, 1H), 8.35 (t, 1H), 8.03 (br t, 1H), 7.82 (s, 1H), 7.42 (s, 2H), 7.27 (s, 1H), 4.25 (t, 2H), 3.83 (q, 2H), 3.03 (s, 2H), 2.51 (q, 2H), 2.29 (s, 3H), 1.06 (t, 3H).

<56-3> N-{2-[6-amino-4-(4-bromo-2-fluoro-phenylamino)-quinazolin-7-yloxy]-ethyl}-2-(ethyl-methyl-amino)-acetamide The procedure of Example <1-7> was repeated except for using the compound of <56-2> (220 mg, 0.42 mmol)) to obtain the title compound 210 mg (yield: 99%).

$^1$H NMR (CDCl$_3$) δ: 8.56 (s, 1H), 8.48 (t, 1H), 7.68 (t, 1H), 7.37 (s, 1H), 7.28 (t, 3H), 7.10 (s, 1H), 6.94 (s, 1H), 4.47 (s, 2H), 4.20 (t, 2H), 3.79 (q, 2H), 3.02 (s, 2H), 2.46 (q, 2H), 2.24 (s, 3H), 1.01 (t, 3H).

<56-4> N-(4-(4-bromo-2-fluoro-phenylamino)-7-{2-[2-(ethyl-methyl-amino)-acetylamino]-ethoxy}-quinazolin-6-yl)-acrylamide The procedure of Example <29-5> was repeated except for using the compound of <56-3> (210 mg, 0.43 mmol) to obtain the title compound 100 mg (yield: 43%).

$^1$H NMR (CDCl$_3$) δ: 9.25 (s, 1H), 9.00 (s, 1H), 8.67 (s, 1H), 8.37 (t, 1H), 7.76 (s, 1H), 7.50 (s, 1H), 7.34 (d, 2H), 7.17 (s, 1H), 6.86 (ab, 1H), 6.54 (dd, 1H), 5.84 (dd, 1H), 4.29 (t, 2H), 3.87 (q, 2H), 3.04 (s, 2H), 2.47 (q, 2H), 2.24 (s, 3H), 1.01 (t, 3H).

Example 57

Preparation of N-[7-[2-(2-amino-acetylamino)-ethoxy]-4-(4-bromo-2-fluoro-phenylamino)-quinazolin-6-yl]-acrylamide <57-1> ({2-[6-acryloylamino-4-(4-bromo-2-fluoro-phenylamino)-quinazolin-7-yloxy]-ethylcarbamoyl}-methyl)-carbamic acid t-butylester The procedure of Example 44 was repeated except for using the compound of Example <29-6> (50 mg, 0.11 mmol) and t-buthoxycarbonylamino-acetic acid (0.39 mg, 0.22 mmol) to obtain the title compound 70.4 mg (yield: 99%).

$^1$H NMR (CDCl$_3$+CD$_3$OD) δ: 8.96 (s, 1H), 8.45 (s, 1H), 7.84 (t, 1H), 7.42 (s, 1H), 7.25 (t, 2H), 7.19 (s, 1H), 7.01 (s, 1H), 6.68 (ab, 1H), 6.34 (dd, 1H), 5.75 (dd, 1H), 5.40 (s, 1H), 4.11 (s, 2H), 3.68 (s, 2H), 2.22 (s, 2H), 1.29 (s, 9H).

<57-2> N-[7-[2-(2-amino-acetylamino)-ethoxy]-4-(4-bromo-2-fluoro-phenylamino)-quinazolin-6-yl]-acrylamide The procedure of Example <1-9> was repeated except for using the compound of <57-1> (70.4 mg, 0.12 mmol) to obtain the title compound 39.2 mg (yield: 67%).

$^1$H NMR (CDCl$_3$+CD$_3$OD) δ: 8.95 (s, H), 8.42 (s, 1H), 7.72 (t, 1H), 7.30-7.25 (m, 2H), 7.03 (s, 1H), 6.72 (ab, 1H), 6.42 (dd, 1H), 5.77 (dd, 1H), 4.15 (t, 2H), 3.72 (t, 2H), 3.05 (s, 2H).

Example 58

Preparation of N-{4-(4-bromo-2-fluoro-phenylamino)-7-[2-(2-dimethylamino-propionylamino)-ethoxy]-quinazolin-6-yl}-acrylamide N-[7-[2-(2-amino-propionylamino)-ethoxy]-4-(4-bromo-2-fluoro-phenylamino)-quinazolin-6-yl]-acrylamide (30 mg, 0.06 mmol) and 37 weight % of formaldehyde (9 μl, 0.12 mmol) were diluted with THF (1 ml) and methanol (1 ml), and stirred at room temperature for 10 min. Sodium cyanoborohydride (11 mg, 0.17 mmol) was added thereto, and the solution was stirred for 4 hours. The resulting solution was distilled under a reduced pressure to remove the solvent, saturated sodium bicarbonate aqueous solution (20 ml) was added thereto, and extracted with chloroform (20 ml) twice. The separated organic layer was dried over magnesium sulfate, filtered and distilled under a reduced pressure, and resulting impure residue was subjected to column chromatography to obtain the title compound 23 mg (yield: 73%).

¹H NMR (CDCl₃+CD₃OD) δ: 9.46 (s, 1H), 8.52 (s, 1H), 7.84 (t, 1H), 7.37 (t, 3H), 7.18 (s, 1H), 6.83 (ab, 1H), 6.53 (dd, 1H), 5.88 (dd, 1H), 4.38 (s, 2H), 3.84 (s, 2H), 2.36 (s, 6H), 2.05 (s, 1H), 1.29 (s, 3H).

Example 59

Preparation of N-{4-(4-bromo-2-fluoro-phenylamino)-7-[2-(3-diethylamino-propionylamino)-ethoxy]-quinazolin-6-yl}-acrylamide The procedure of Example 44 was repeated except for using the compound of Example <29-6> (50 mg, 0.10 mmol) and 3-diethylaminopropionic acid hydrochloride (23 mg, 0.12 mmol) to obtain the title compound 26.8 mg (yield: 42%).
¹H NMR (CDCl₃)) δ: 9.25 (t, 1H), 9.23 (s, 1H), 9.05 (s, 1H), 8.65 (s, 1H), 8.33 (t, 1H), 7.57 (s, 1H), 7.35-7.31 (m, 2H), 7.14 (s, 1H), 6.87 (ab, 1H), 6.52 (dd, 1H), 5.81 (dd, 1H), 4.18 (t, 2H), 3.78 (q, 2H), 2.67 (t, 2H), 2.54 (q, 4H), 2.42 (t, 2H), 1.00 (t, 6H).

Example 60

Preparation of N-{4-(4-bromo-2-fluoro-phenylamino)-7-[2-(2-methylamino-acetylamino)-ethoxy]-quinazolin-6-yl}-acrylamide <60-1> N-{2-[4-(4-bromo-2-fluoro-phenylamino)-6-nitro-quinazolin-7-yloxy]-ethyl}-2-methylamino-acetamide The procedure of Example 44 was repeated except for using the compound of Example <18-3> (100 mg, 0.24 mmol) and sarcosine (25 mg, 0.28 mmol) to obtain the title compound 20 mg (yield: 17%).
¹H NMR (CDCl₃) δ: 8.79 (s, 1H), 8.69 (s, 1H), 8.19 (s, 2H), 7.96 (q, 1H), 7.33 (t, 3H), 6.48 (d, 2H), 4.23 (t, 1H), 3.74 (s, 1H), 3.29-3.20 (m, 2H), 2.33 (t, 1H), 2.22 (s, 3H), 1.72 (t, 1H).

<60-2> ({2-[4-(4-bromo-2-fluoro-phenylamino)-6-nitro-quinazolin-7-yloxy]-ethylcarbamoyl}-methyl)-methyl-carbamic acid t-butylester The procedure of Example <1-1> was repeated except for using the compound of <60-1> (20 mg, 0.04 mmol) to obtain the title compound 40 mg (yield: 99%).
¹H NMR (CDCl₃) δ: 8.69 (s, 1H), 8.44 (s, 1H), 8.28 (t, 1H), 7.52 (s, 1H), 7.32 (s, 2H), 7.17 (s, 1H), 5.01 (s, 1H), 4.21 (t, 2H), 3.56 (q, 2H), 1.53 (s, 2H), 1.36 (s, 9H), 1.17 (s, 3H).

<60-3> ({2-[6-amino-4-(4-bromo-2-fluoro-phenylamino)-quinazolin-7-yloxy]-ethylcarbamoyl}-methyl)-methyl-carbamic acid t-butylester The procedure of Example <1-7> was repeated except for using the compound of <60-2> (40 mg, 0.07 mmol) to obtain the title compound 38 mg (yield: 99%).
¹H NMR (CDCl₃) δ: 8.45 (s, 2H), 7.93 (s, 1H), 7.25-7.20 (m, 2H), 7.06 (s, 2H), 6.82 (s, 1H), 5.03 (s, 1H), 4.08 (t, 2H), 3.56 (q, 2H), 2.00 (d, 2H), 1.39 (s, 9H), 1.14 (s, 3H).

<60-4> ({2-[6-acryloylamino-4-(4-bromo-2-fluoro-phenylamino)-quinazolin-7-yloxy]-ethylcarbamoyl}-methyl)-methyl-carbamic acid t-butylester The procedure of Example <29-5> was repeated except for using the compound of <60-3> (38 mg, 0.07 mmol) to obtain the title compound 7 mg (yield: 16%).

¹H NMR (CDCl₃) δ: 9.23 (s, 1H), 9.11 (s, 1H), 8.66 (s, 1H), 8.37 (s, 1H), 7.59 (s, 1H), 7.37-7.33 (m, 2H), 7.17 (s, 1H), 6.74 (ab, 1H), 6.56 (dd, 1H), 5.82 (dd, 1H), 4.97 (s, 1H), 4.20 (t, 2H), 3.69 (q, 2H), 1.56 (s, 2H), 1.46 (s, 9H), 1.18 (s, 3H).

<60-5> N-{4-(4-bromo-2-fluoro-phenylamino)-7-[2-(2-methylamino-acetylamino)-ethoxy]-quinazolin-6-yl}-acrylamide The procedure of Example <1-9> was repeated except for using the compound of <60-4> (7 mg, 0.01 mmol) to obtain the title compound 3 mg (yield: 51%).
¹H NMR (CDCl₃) δ: 9.16 (s, 1H), 8.67 (s, 1H), 8.55 (s, 1H), 8.34 (t, 1H), 7.66 (s, 1H), 7.36-7.25 (m, 3H), 6.42 (ab, 2H), 5.84 (d, 1H), 5.01 (s, 1H), 4.26 (s, 2H), 3.27 (s, 2H), 2.02 (d, 2H), 1.25 (s, 9H), 0.86 (d, 3H).

Example 61

Preparation of N-{4-(4-bromo-2-fluoro-phenylamino)-7-[2-(3-dimethylamino-propionylamino)-ethoxy]-quinazolin-6-yl}-acrylamide The procedure of Example 44 was repeated except for using the compound of Example <29-6> (100 mg, 0.22 mmol) and 3-dimethylamino-propionic acid hydrochloride (103 mg, 0.67 mmol) to obtain the title compound 23 mg (yield: 19%).
¹H NMR (CDCl₃) δ: 9.22 (s, 1H), 9.05 (s, 1H), 8.98 (t, 1H), 8.64 (s, 1H), 8.31 (t, 1H), 7.62 (bs, 1H), 7.34-7.31 (m, 2H), 7.14 (s, 1H), 6.91-6.82 (m, 1H), 6.55-6.49 (m, 1H), 5.83-5.80 (m, 1H), 4.19 (t, 2H), 3.79 (q, 2H), 2.53 (t, 2H), 2.41 (t, 2H), 2.22 (s, 6H).

Example 62

Preparation of N-[7-[2-(3-amino-propionylamino)-ethoxy]-4-(4-bromo-2-fluoro-phenylamino)-quinazolin-6-yl]-acrylamide <62-1> (2-{2-[6-acryloylamino-4-(4-bromo-2-fluoro-phenylamino)-quinazolin-7-yloxy]-ethylcarbamoyl}-ethyl)-carbamic acid t-butylester The procedure of Example 44 was repeated except for using the compound of Example <29-6> (40 mg, 0.09 mmol) and 3-t-buthoxycarbonylamino-propionic acid (34 mg, 0.18 mmol) to obtain the title compound 42 mg (yield: 76%).
¹H NMR (CDCl₃) δ: 9.00 (s, 1H), 8.47 (s, 1H), 7.85 (t, 1H), 7.63 (s, 1H), 7.30-7.26 (m, 2H), 7.04 (s, 1H), 6.71 (dd, 1H), 6.45 (d, 1H), 5.79 (d, 1H), 5.31 (s, 1H), 4.14 (t, 2H), 3.69 (q, 2H), 3.32 (q, 2H), 2.98 (s, 3H), 2.39 (t, 2H), 1.31 (s, 9H).

<62-2> N-[7-[2-(3-amino-propionylamino)-ethoxy]-4-(4-bromo-2-fluoro-phenylamino)-quinazolin-6-yl]-acrylamide The procedure of Example <1-9> was repeated except for using the compound of <62-1> (40 mg, 0.06 mmol) to obtain the title compound 13 mg (yield: 39%).
¹H NMR (CDCl₃+CD₃OD) δ: 9.13 (s, 1H), 8.51 (s, 1H), 7.81 (t, 1H), 7.41-7.35 (m, 3H), 7.14 (s, 1H), 6.81 (dd, 1H), 6.53 (d, 1H), 5.88 (d, 1H), 4.24 (t, 2H), 3.69 (q, 2H), 2.98 (t, 2H), 2.39 (t, 2H).

Example 63

Preparation of {2-[6-acryloylamino-4-(4-bromo-2-fluoro-phenylamino)-quinazolin-7-yloxy]-ethyl}-carbamic acid methylester The procedure of Example <1-10> was repeated except for using the compound of Example <29-6> (100 mg, 0.22 mmol) and methylchloroformate (23 mg, 0.24 mmol) to obtain the title compound 25 mg (yield: 23%).

$^1$H NMR (DMSO-d$_6$) δ: 9.75 (s, 1H), 9.34 (s, 1H), 9.06 (s, 1H), 8.37 (s, 1H), 7.61 (d, 1H), 7.51-7.44 (m, 3H), 7.24 (s, 1H), 6.80-6.71 (m, 1H), 6.37-6.31 (m, 1H), 5.87-5.84 (m, 1H), 4.20 (t, 2H), 3.57 (s, 3H), 3.51 (q, 2H).

Example 64

Preparation of N-{4-(4-bromo-2-fluoro-phenylamino)-7-[2-(3-methoxy-propionylamino)-ethoxy]-quinazolin-6-yl}-acrylamide The procedure of Example 44 was repeated except for using the compound of Example <29-6> (100 mg, 0.22 mmol) and 3-methoxy propionic acid (25 µl, 0.27 mmol) to obtain the title compound 17.5 mg (yield: 15%).

$^1$H NMR (CDCl$_3$) δ: 9.25 (s, 1H), 8.95 (s, 1H), 8.66 (s, 1H), 8.37 (t, 1H), 7.56 (s, 1H), 7.37-7.31 (m, 2H), 7.17 (s, 1H), 6.85 (ab, 1H), 6.63 (s, 1H), 6.53 (dd, 1H), 5.84 (dd, 1H), 4.22 (t, 2H), 3.85 (q, 2H), 3.63 (t, 2H), 3.31 (s, 3H), 2.54 (t, 2H).

Example 65

Preparation of N-{4-(4-bromo-2-fluoro-phenylamino)-7-[(2-diethylamino-ethylcarbamoyl)-methoxy]-quinazolin-6-yl}-acrylamide <65-1> N'-benzyl-N,N-diethyl-ethane-1,2-diamine 2-(diethylamino)-ethyl chloride hydrochloride (1 g, 5.81 mmol) and benzylamine (1.3 ml, 11.62 mmol) were dissolved in t-butanol (40 ml), triethylamine (3.2 ml, 23.24 mmol) was added thereto, and the resulting solution was refluxed for 12 hours. The solution was cooled to room temperature, and distilled under a reduced pressure to remove the solvent. The resulting solid was removed by filtration under a reduced pressure, and the residual solution was extracted with ethylacetate The separated organic layer was washed with saturated sodium bicarbonate aqueous solution, dried over magnesium sulfate, filtered and distilled under a reduced pressure to obtain the title compound 560 mg (yield: 47%).

$^1$H NMR (CDCl$_3$) δ: 7.43 (s, 5H), 3.80 (s, 2H), 2.68 (t, 2H), 2.57 (t, 2H), 2.50 (q, 4H), 0.99 (t, 6H).

<65-2> 2-(diethylamino)-ethylamine

The compound of <65-1> (560 mg, 2.71 mmol) was dissolved in methyl alcohol (15 ml), 10 weight % of palladium/carbon (560 mg) was added thereto, and the solution was stirred for 48 hours in the presence of 1 atmosphere hydrogen gas. The resulting solution was filtered under a reduced pressure to remove the palladium/carbon and distilled under a reduced pressure to obtain the title compound 315 mg (yield: 99%).

$^1$H NMR (CDCl$_3$) δ: 3.18 (t, J=5.7 Hz, 2H), 2.47 (t, 2H), 2.39 (q, 4H), 0.87 (t, 6H).

<65-3> [4-(4-bromo-2-fluoro-phenylamino)-6-nitro-quinazolin-7-yloxy]-acetic acid 3N HCl aqueous solution (2 ml) was added to the compound of Example <109-2> (180 mg, 0.39 mmol) diluted with ethanol (2 ml), and the resulting solution was refluxed for 12 hours. The solution was concentrated under a reduced pressure, basified with 1N sodium hydroxide aqueous solution and extracted with ethylacetate. The separated water layer was acidified with 3N HCl and extracted with ethylacetate. The separated organic layer was washed with salt solution, dried over magnesium sulfate, filtered and distilled under a reduced pressure to obtain the title compound 46 mg (yield: 27%).

$^1$H NMR (DMSO-d$_6$, 300 MHz) δ: 8.76 (s, 1H), 8.38-8.25 (m, 1H), 8.08 (s, 1H), 7.55-7.49 (m, 1H), 7.31-7.24 (m, 1H), 7.16-7.08 (m, 1H), 7.01 (s, 1H), 3.35 (s, 2H).

<65-4> 2-[4-(4-bromo-2-fluoro-phenylamino)-6-nitro-quinazolin-7-yloxy]-N-(2-diethylamino-ethyl)-acetamide The procedure of Example 44 was repeated except for using the compound of <65-3> (46 mg, 0.11 mmol) and the compound of <65-2> (25 mg, 0.22 mmol) to obtain the title compound 17 mg (yield: 29%)

$^1$H NMR (MeOD, 300 MHz) δ: 9.02 (d, J=6.8 Hz, 1H), 8.20 (s, 1H), 7.49-7.30 (m, 3H), 7.02 (d, J=7.9 Hz, 1H), 4.55 (s, 2H), 3.86 (t, J=5.4 Hz, 2H), 3.53 (t, J=5.4 Hz, 2H), 2.75-2.50 (m, 4H), 1.02-0.85 (m, 6H).

<65-5> N-{4-(4-bromo-2-fluoro-phenylamino)-7-[(2-diethylamino-ethylcarbamoyl)-methoxy]-quinazolin-6-yl}-acrylamide The procedure of Example <1-7> was repeated except for using the compound of <65-4> (16 mg, 0.030 mmol) to obtain 2-[6-amino-4-(4-bromo-2-fluoro-phenylamino)-quinazolin-7-yloxy]-N-(2-diethylamino-ethyl)-acetamide 15 mg (yield: 80%), and then the procedure of Example <29-5> was repeated without any purification to obtain the title compound 2 mg (yield: 12%).

$^1$H NMR (DMSO-d$_6$, 300 MHz) δ: 9.02 (d, J=6.8 Hz, 1H), 8.20 (s, 1H), 7.49-7.30 (m, 3H), 7.02 (d, J=7.9 Hz, 1H), 6.85 (dd, J=10.2, 17.1 Hz, 1H), 6.35 (d, J=17.1 Hz, 1H), 5.86 (d, J=10.2 Hz, 1H), 4.55 (s, 2H), 3.86 (t, J=5.4 Hz, 2H), 3.53 (t, J=5.4 Hz, 2H), 2.75-2.50 (m, 4H), 1.02-0.85 (m, 6H).

Example 66

Preparation of N-{2-[6-acryloylamino-4-(4-bromo-2-fluoro-phenylamino)-quinazolin-7-yloxy]-ethyl}-4-dimethylamino-butylamide The procedure of Example 44 was repeated except for using the compound of Example <29-6> (100 mg, 0.22 mmol) and 3-(dimethylamino)butyric acid hydrochloride (23 mg, 0.13 mmol) to obtain the title compound 11 mg (yield: 18%).

$^1$H NMR (CDCl$_3$) δ: 9.20 (s, 1H), 9.06 (s, 1H), 8.61 (s, 1H), 8.25 (t, 1H), 77.3 (s, 1H), 7.65 (t, 1H), 7.34-7.29 (m, 2H), 7.12 (s, 1H), 6.84 (ab, 1H), 6.52 (dd, 1H), 5.80 (dd, 1H), 4.24 (t, 2H), 3.85 (q, 2H), 2.40 (t, 2H), 2.31 (t, 2H), 2.20 (s, 6H), 1.83 (q, 2H).

Example 67

Preparation of N-{4-(4-bromo-2-fluoro-phenylamino)-7-[2-(3-hydroxy-propionylamino)-ethoxy]-quinazolin-6-yl}-acrylamide <67-1> N-{2-[4-(4-bromo-2-fluoro-phenylamino)-6-nitro-quinazolin-7-yloxy]-ethyl}-3-methoxy-propionylamide The procedure of Example 44 was repeated except for using the compound of Example <18-3> (500 mg, 1.18 mmol) and 3-methoxypropionic acid (0.167 ml, 1.78 mmol) to obtain the title compound 500 mg (yield: 83%).
$^1$H NMR (300 MHz, DMSO-d$_6$) δ: 10.23 (s, 1H), 9.45 (s, 1H), 8.54 (s, 1H), 8.05 (t, 1H), 7.70 (d, 1H), 7.56-7.47 (m, 3H), 4.31 (t, 1H), 3.77-3.46 (m, 4H), 3.19 (s, 3H), 2.31 (t, 2H).

<67-2> N-{2-[4-(4-bromo-2-fluoro-phenylamino)-6-nitro-quinazolin-7-yloxy]-ethyl}-3-hydroxy-propionylamide The compound of <67-1> (500 mg, 0.984 mmol) was diluted with dichloromethane (10 ml), and the solution was cooled to 0° C. Boron tribromide (0.279 ml, 2.95 mmol) was slowly added thereto while keeping the solution temperature, and stirred for 3 hours. The solution was slowly heated to room temperature, and the reaction was terminated by adding saturated sodium bicarbonate. The resulting solution was distilled under a reduced pressure to remove the solvent and filtered under a reduced pressure to obtain the title compound 400 mg (yield: 82%).
$^1$H NMR (300 MHz, DMSO-d$_6$) δ: 9.15 (s, 1H), 8.60 (s, 1H), 8.04 (t, 1H), 7.72 (d, 1H), 7.55-7.43 (m, 3H), 4.33 (t, 2H), 3.60 (t, J=6.6 Hz, 2H), 3.50 (t, 2H), 2.26 (t, 2H).

<67-3> N-{2-[6-amino-4-(4-bromo-2-fluoro-phenylamino)-quinazolin-7-yloxy]-ethyl}-3-hydroxy-propionylamide The procedure of Example <1-7> was repeated except for using the compound of <67-2> (400 mg, 0.809 mmol) to obtain the title compound 290 mg (yield: 77%).
$^1$H NMR (300 MHz, DMSO-d$_6$) δ: 9.16 (s, 1H), 8.23-8.16 (m, 2H), 7.44-7.40 (m, 2H), 7.30 (s, 1H), 7.04 (s, 1H), 5.49 (br, 2H), 4.59 (t, 1H), 4.12 (t, 2H), 3.64 (q, 2H), 3.56 (q, 2H), 2.31 (t, 2H).

<67-4> N-{4-(4-bromo-2-fluoro-phenylamido)-7-[2-(3-hydroxy-propionylamino)-ethoxy]-quinazolin-6-yl}-acrylamide The procedure of Example <29-5> was repeated except for using the compound of <67-3> (100 mg, 0.215 mmol) to obtain the title compound 44 mg (yield: 51%)
$^1$H NMR (300 MHz, DMSO-d$_6$) δ: 9.05 (s, 1H), 8.41 (s, 1H), 7.88 (s, 1H), 7.48-7.39 (m, 2H), 7.23 (s, 1H), 6.68 (m, 1H), 6.50 (d, 1H), 5.88 (d, 1H), 4.40 (m, 1H), 4.28 (m, 2H), 3.88 (m, 2H), 3.64 (m, 2H), 3.47 (m, 2H).

Example 68

Preparation of N-[4-(2,4-difluorophenylamino)-7-{2-[2-(dimethylamino)-acetylamino]-ethoxy}-quinazolin-6-yl]-acrylamide <68-1> N-(2,4-difluorophenyl)-7-fluoro-6-nitro-quinazoline-4-amine The procedure of Example <1-5> was repeated except for using the compound of Example <1-4> (500 mg, 1.89 mmol) and 2,4-difluoroaniline (247 μl, 2.46 mmol) to obtain the title compound 442 mg (yield: 63%)
$^1$H NMR (300 MHz, DMSO-d$_6$) 9.86 (d, 1H), 8.86 (s, 1H), 8.01 (t, 1H), 7.63-7.44 (m, 2H), 7.26-7.20 (m, 1H).

<68-2> t-butyl 2-[4-(2,4-difluorophenylamino)-6-nitroquinazolin-7-yloxy]ethylcarbamate The procedure of Example <1-6> was repeated except for using the compound of <68-1> (394 mg, 1.06 mmol) to obtain the title compound 363 mg (yield: 74%).
$^1$H NMR (300 MHz, DMSO-d$_6$) 10.28 (s, 1H), 9.15 (s, 1H), 8.64 (s, 1H), 7.54-7.49 (m, 3H), 7.29 (t, 1H), 6.96 (brs, 1H), 4.30 (t, 2H), 3.34 (q, 2H), 1.36 (s, 9H).

<68-3> 7-(2-aminoethoxy)-N-(2,4-difluorophenyl)-6-nitroquinazoline-4-amine

The procedure of Example <1-9> was repeated except for using the compound of <68-2> (350 mg, 0.76 mmol) to obtain the title compound 240 mg (yield: 87%)
$^1$H NMR (300 MHz, DMSO-d$_6$) 9.15 (s, 1H), 8.49 (s, 1H), 7.57-7.51 (m, 1H), 7.45 (s, 1H), 7.38 (dd, J=3.0, 9.0 Hz, 1H), 7.15 (dd, 1H), 4.25 (t, 2H), 3.13 (brs, 1H), 2.95 (q, 2H).

<68-4> N-{2-[4-(2,4-difluorophenylamino)-6-nitro-quinazolin-7-yloxy]ethyl}-2-(dimethylamino)-acetamide The procedure of Example <25-1> was repeated except for using the compound of <68-3> (220 mg, 0.61 mmol) to obtain the title compound 143 mg (yield: 56%)
$^1$H NMR (CDCl$_3$) 8.74 (s, 1H), 8.68 (s, 1H), 8.20-8.10 (m, 1H), 8.03 (brs, 1H), 7.80 (brs, 1H), 7.40 (s, 1H), 7.03-6.97 (m, 2H), 4.35 (t, 2H), 3.82 (q, 2H), 2.99 (s, 2H), 2.32 (s, 6H).

<68-5> N-{2-[6-amino-4-(2,4-difluorophenylamino)-quinazolin-7-yloxy]ethyl}-2-(dimethylamino)-acetamide The procedure of Example <1-7> was repeated except for using the compound of <68-4> (120 mg, 0.27 mmol) to obtain the title compound 112 mg (yield: 99%).
$^1$H NMR (300 MHz, MeOD) 8.21 (brs, 1H), 7.61-7.59 (m, 1H), 7.31 (s, 1H), 7.10-7.01 (m, 3H), 4.26 (t, J=5.4 Hz, 2H), 3.77 (t, J=5.4 Hz, 2H), 3.45 (s, 2H), 1.97 (s, 6H).

<68-6> N-[4-(2,4-difluorophenylamino)-7-{2-[2-(dimethylamino)-acetamido]ethoxy}quinazolin-6-yl]acrylamide The procedure of Example <29-5> was repeated except for using the compound of <68-5> (100 mg, 0.24 mmol) to obtain the title compound 26 mg (yield: 23%).
$^1$H NMR (300 MHz, DMSO-d$_6$) 9.70 (s, 1H), 9.36 (s, 1H), 9.09 (s, 1H), 8.35 (s, 1H), 8.21 (brs, 1H), 7.51-7.49 (m, 1H), 7.36-7.31 (m, 1H), 7.25 (s, 1H), 7.12-7.11 (m, 3H), 6.85 (dd, J=10.2, 17.1 Hz, 1H), 6.35 (d, 1H), 5.86 (d, 1H), 4.24 (t, J2H), 3.63 (t, 2H), 2.92 (s, 2H), 2.16 (s, 6H).

Example 69

Preparation of N-{2-[6-acryloylamino-4-(4-bromo-2-fluoro-phenylamino)-quinazolin-7-yloxy]-ethyl}-malonic acid ethylester The procedure of Example 44 was repeated except for using the compound of Example <29-6> (150 mg, 0.336 mmol) and mono-ethylmalonate (47 μl, 0.402 mmol) to obtain the title compound 500 mg (yield: 64%).

$^1$H NMR (300 MHz, DMSO-$d_6$) δ: 9.76 (s, 1H), 9.29 (s, 1H), 9.11 (s, 1H), 8.55 (s, 1H), 8.38 (s, 1H), 7.64 (d, 1H), 7.48-7.44 (m, 2H), 7.25 (s, 1H), 6.79 (m, 1H), 6.37 (d, 1H), 5.81 (d, 1H), 4.22 (t, 2H), 4.00 (q, 2H), 3.63 (m, 3H), 2.71 (s, 2H), 1.11 (t, 3H).

Example 70

Preparation of N-{2-[6-acryloylamino-4-(4-bromo-2-fluoro-phenylamino)-quinazolin-7-yloxy]-ethyl}-malonic acid The compound of Example 69 (70 mg, 0.125 mmol) was diluted with THF (1 ml) and water (1 ml), and lithium hydroxide (10 mg, 0.375 mmol) was added thereto. After 1 hour, pH was adjusted to 4 by adding 2N HCl aqueous solution, and the resulting solid was filtered under a reduced pressure and washed with water to obtain the title compound 18 mg (yield: 278%).

$^1$H NMR (300 MHz, DMSO-$d_6$) δ: 9.55 (s, 1H), 9.30 (s, 1H), 8.77 (s, 1H), 8.55 (s, 1H), 7.77 (d, 1H), 7.56-7.47 (m, 2H), 7.33 (s, 1H), 6.93 (m, 1H), 6.39 (d, 1H), 5.89 (d, 1H), 4.27 (t, 2H), 3.66 (m, 3H), 3.25 (s, 2H).

Example 71

Preparation of {2-[6-acryloylamino-4-(4-bromo-2-fluoro-phenylamino)-quinazolin-7-yloxy]-ethyl}-oxalamic acid ethylester The compound of Example <29-6> (150 mg, 0.336 mmol) was diluted with dichloromethane (1 ml), and ethylchlorooxoacetate (45 μl, 0.402 ml) was added thereto. After stirring the solution for 1 hour, the solution was distilled under a reduced pressure to remove the solvent, and basified with saturated sodium bicarbonate. The resulting solid was filtered under a reduced pressure and washed with water to obtain the title compound 180 mg (yield: 98%).

$^1$H NMR (300 MHz, DMSO-$d_6$) δ: 9.77 (s, 1H), 9.27 (s, 1H), 9.09 (s, 1H), 8.38 (s, 1H), 7.64 (d, 1H), 7.48-7.42 (m, 2H), 7.28 (s, 1H), 6.82 (m, 1H), 6.37 (d, 1H), 5.83 (d, 1H), 4.27 (t, 2H), 4.22 (q, 2H), 3.69 (m, 2H), 1.26 (t, 3H).

Example 72

Preparation of {2-[6-acryloylamino-4-(4-bromo-2-fluoro-phenylamino)-quinazolin-7-yloxy]-ethyl}-oxalamic acid The procedure of Example 70 was repeated except for using the compound of Example 71 (100 mg, 0.183 mmol) to obtain the title compound 180 mg (yield: 98%).

$^1$H NMR (300 MHz, DMSO-$d_6$) δ: 9.77 (s, 1H), 9.27 (s, 1H), 9.09 (s, 1H), 8.38 (s, 1H), 7.64 (d, 1H), 7.48-7.42 (m, 2H), 7.28 (s, 1H), 6.82 (m, 1H), 6.37 (d, 1H), 5.83 (d, 1H), 4.27 (t, 2H), 4.22 (q, 2H), 3.69 (m, 2H), 1.26 (t, 3H).

Example 73

Preparation of N-{4-(4-bromo-2-fluoro-phenylamino)-7-[2-(2-methoxyimino-acetylamino)-ethoxy]-quinazolin-6-yl}-acrylamide The procedure of Example 44 was repeated except for using the compound of Example <29-6> (100 mg, 0.224 mmol) and methoxyimino-acetic acid (28 mg, 0.269 mmol) to obtain the title compound 77 mg (yield: 65%).

$^1$H NMR (300 MHz, DMSO-$d_6$) δ: 9.77 (s, 1H), 9.33 (s, 1H), 9.09 (s, 1H), 8.65 (s, 1H), 8.38 (s, 1H), 7.63 (d, 1H), 7.60 (s, 1H), 7.48-7.45 (m, 2H), 7.28 (s, 1H), 6.80 (m, 1H), 6.37 (d, 1H), 5.87 (d, 1H), 4.28 (t, 2H), 3.92 (s, 3H), 3.79 (m, 2H).

Example 74

Preparation of N-{4-(4-bromo-2-fluoro-phenylamino)-7-[2-(3-dimethylamino-2-methyl-propionylamino)-ethoxy]-quinazolin-6-yl}-acrylamide <74-1> (2-{2-[4-(4-bromo-2-fluoro-phenylamino)-6-nitro-quinazolin-7-yloxy]-ethylcarbamoyl}-propyl)-carbamic acid t-butylester The procedure of Example 44 was repeated except for using the compound of Example <18-3> (500 mg, 1.18 mmol) and 3-t-buthoxycarbonylamino-2-methyl-propionic acid (289 mg, 1.42 mmol) to obtain the title compound 680 mg (yield: 95%).

$^1$H NMR (CDCl$_3$) δ: 8.78 (s, 1H), 8.57 (s, 1H), 8.32 (t, 1H), 7.42-7.37 (m, 3H), 4.33 (t, 2H), 3.80 (m, 2H), 3.28 (t, 2H), 2.55 (m, 1H), 1.38 (m, 9H), 1.14 (d, 3H).

<74-2> 3-amino-N-{2-[4-(4-bromo-2-fluoro-phenylamino)-6-nitro-quinazolin-7-yloxy]-ethyl}-2-methyl-propionylamide The procedure of Example <1-9> was repeated except for using the compound of <74-1> (680 mg, 1.12 mmol) to obtain the title compound 520 mg (yield: 92%).

$^1$H NMR (300 MHz, CD$_3$OD) δ: 8.95 (s, 1H), 8.48 (s, 1H), 7.75-7.39 (m, 4H), 4.39 (t, 2H), 3.70 (m, 2H), 3.32 (t, 2H), 2.75 (m, 1H), 1.25 (d, 3H).

<74-3> N-{2-[4-(4-bromo-2-fluoro-phenylamino)-6-nitro-quinazolin-7-yloxy]-ethyl}-3-dimethylamino-2-methyl-propionylamide The compound of Example <74-2> (520 mg, 1.03 mmol) and 37 weight % formaldehyde (305 mg, 4.10 mmol) were diluted with ethanol (5 ml) and acetic acid (0.5 ml), and stirred for 1 hour. Sodium cyanoborohydride (386 mg, 6.15 mmol) was added thereto, and the solution was stirred for 1 hour and basified with saturated sodium bicarbonate. The separated organic layer extracted with ethylacetate was dried over magnesium sulfate, filtered and distilled under a reduced pressure, and resulting impure residue was subjected to column chromatography to obtain the title compound 280 mg (yield: 51%).

$^1$H NMR (CDCl$_3$) δ: 8.77 (s, 1H), 8.55 (s, 1H), 8.35 (t, 1H), 7.40-7.37 (m, 3H), 7.26 (m, 2H), 4.33 (t, 2H), 3.80 (m, 2H), 2.96 (m, 2H), 2.64 (m, 1H), 2.43 (s, 6H), 1.17 (d, 3H).

<74-4> N-{4-(4-bromo-2-fluoro-phenylamino)-7-[2-(3-dimethylamino-2-methyl-propionylamino)-ethoxy]-quinazolin-6-yl}-acrylamide The procedure of Example <65-5> was repeated except for using the compound of <74-3> (280 mg, 0.525 mmol) to obtain the title compound 25 mg (yield: 9%).

$^1$H NMR (CDCl$_3$) δ: 9.21 (s, 1H), 8.65 (s, 1H), 8.30 (t, 1H), 7.68 (br, 1H), 7.34-7.32 (m, 3H), 7.15 (s, 1H), 6.93 (m, 1H), 6.55 (m, 1H), 5.84 (m, 1H), 4.34 (t, 2H), 3.93 (m, 2H), 3.03 (m, 2H), 2.64 (m, 1H), 2.37 (s, 6H), 1.23 (d, 3H).

Example 75

Preparation of N-{2-[6-acryloylamino-4-(4-bromo-2-fluoro-phenylamino)-quinazolin-7-yloxy]-ethyl}-3-dimethylamino-butylamide <75-1> (2-{2-[4-(4-bromo-2-fluoro-phenylamino)-6-nitro-quinazolin-7-yloxy]-ethylcarbamoyl}-1-methyl-ethyl)-carbamic acid t-butylester The procedure of Example 44 was repeated except for using the compound of Example <29-6> (500 mg, 1.18 mmol) and 3-t-buthoxycarbonylaminobutyric acid (361 mg, 1.78 mmol) to obtain the title compound 680 mg (yield: 95%).
$^1$H NMR (300 MHz, DMSO-d$_6$) d: 9.17 (s, 1H), 8.54 (s, 1H), 8.32 (s, 1H), 8.07 (s, 1H), 7.70 (d, 1H), 7.50 (m, 3H), 4.32 (m, 2H), 3.80 (m, 2H), 3.48 (m, 2H), 2.27 (m, 1H), 1.17 (d, 3H).

<75-2> 3-amino-N-{2-[4-(4-bromo-2-fluoro-phenylamino)-6-nitro-quinazolin-7-yloxy]-ethyl}-butylamide The procedure of Example <1-9> was repeated except for using the compound of <75-1> (680 mg, 1.12 mmol) to obtain the title compound 540 mg (yield: 94%).
$^1$H NMR (300 MHz, CD$_3$OD) δ: 9.25 (s, 1H), 8.68 (s, 1H), 7.69 (d, 1H), 7.46-7.30 (m, 3H), 4.34 (m, 2H), 3.80 (m, 2H), 3.48 (m, 2H), 2.56 (m, 1H), 1.26 (d, 3H).

<75-3> N-{2-[4-(4-bromo-2-fluoro-phenylamino)-6-nitro-quinazolin-7-yloxy]-ethyl}-3-dimethylamino-butylamino The procedure of Example <74-3> was repeated except for using the compound of <75-2> (588 mg, 1.09 mmol) to obtain the title compound 85 mg (yield: 15%).
$^1$H NMR (CDCl$_3$) δ: 8.77 (s, 1H), 8.55 (s, 1H), 8.33 (m, 2H), 7.69 (d, 1H), 7.40-7.30 (m, 3H), 4.37 (m, 2H), 3.71 (m, 2H), 3.48 (m, 2H), 2.40 (s, 6H), 2.29 (m, 1H), 1.17 (d, 3H).

<75-4> N-{2-[6-acryloylamino-4-(4-bromo-2-fluoro-phenylamino)-quinazolin-7-yloxy]-ethyl}-3-dimethylamino-butylamide The procedure of Example <65-5> was repeated except for using the compound of <75-3> (60 mg, 0.118 mmol) to obtain the title compound 2 mg (yield: 1%).
$^1$H NMR (CDCl$_3$) δ: 9.23 (s, 1H), 8.98 (s, 1H), 8.65 (s, 1H), 8.31 (t, 2H), 7.65 (s, 1H), 7.36-7.23 (m, 2H), 7.17 (m, 1H), 6.87 (m, 1), 6.56 (d, 1H), 5.86 (m, 1H), 4.33 (m, 2H), 3.00 (m, 2H), 2.51 (m, 2H), 2.30 (s, 6H), 2.24 (m, 1H), 1.14 (d, 3H).

Example 76

Preparation of N-[7-(2-acetylamino-ethoxy)-4-(4-bromo-2-fluoro-phenylamino)-quinazolin-6-yl]-2-methyl-acrylamide The procedure of Example <1-10> was repeated except for using the compound of Example <18-5> (50 mg, 0.11 mmol) and 2-methyl-acryloylchloride (12 mg, 0.12 mmol) to obtain the title compound 15 mg (yield: 27%).
$^1$H NMR (CDCl$_3$) δ: 9.25 (s, 1H), 9.06 (s, 1H), 8.68 (s, 1H), 8.39 (t, 1H), 7.52 (bs, 1H), 7.36-7.32 (m, 2H), 7.27 (s, 1H), 6.17 (t, 1H), 4.33-4.27 (m, 2H), 3.86-3.79 (m, 2H), 2.04 (s, 3H), 1.63 (s, 3H).

Example 77

Preparation of propionic acid [7-(2-acetylamino-ethoxy)-4-(4-bromo-2-fluoro-phenylamino)-quinazolin-6-yl]-amide The procedure of Example <1-10> was repeated except for using the compound of Example <18-5> (50 mg, 0.11 mmol) and propionic acid (23 mg, 0.33 mmol) to obtain the title compound 13 mg (yield: 24%).
$^1$H NMR (CDCl$_3$) δ: 9.05 (s, 1H), 8.77 (bs, 1H), 8.62 (s, 1H), 8.33 (t, 1H), 7.52-7.49 (m, 1H), 7.32-7.29 (m, 3H), 7.09 (s, 1H), 6.03 (t, 1H), 4.15 (t, 2H), 3.78 (q, 2H), 2.01 (s, 3H).

Example 78

Preparation of N-[7-(2-acetylamino-ethoxy)-4-(4-bromo-2-fluoro-phenylamino)-quinazolin-6-yl]-N-methyl-acrylamide <78-1> {2-[4-(4-bromo-2-fluoro-phenylamino)-6-formylamino-quinazolin-7-yloxy]-ethyl}-carbamic acid t-butylester The procedure of Example 44 was repeated except for using the compound of Example <29-4> (500 mg, 1.02 mmol) and formic acid (140 mg, 3.06 mmol) to obtain the title compound 411 mg (yield: 77%).
$^1$H NMR (CDCl$_3$) δ: 9.08 (s, 2H), 8.69-8.62 (m, 2H), 8.38 (t, 1H), 7.49 (s, 1H), 7.39-7.35 (m, 2H), 7.20 (s, 1H), 4.99-4.86 (m, 1H), 4.23 (t, 2H), 3.72-3.68 (m, 2H), 1.49 (s, 9H).

<78-2> {2-[4-(4-bromo-2-fluoro-phenylamino)-6-methylamino-quinazolin-7-yloxy]-ethyl}-carbamic acid t-butylester Lithium aluminum hydride (150 mg, 3.95 mmol) was diluted with THF (5 ml) at 0° C., and the compound of <78-1> (411 mg, 0.79 mmol) diluted with THF (5 ml) was slowly added thereto. After stirred for 2 hours, the reaction was terminated by adding water (1 ml) and 1N NaOH (1.5 ml). After stirred for 10 min, the solution was filtered by using celite under a reduced pressure, and extracted with chloroform (30 ml). The separated organic layer was dried over magnesium sulfate, filtered and distilled under a reduced pressure, and resulting impure residue was subjected to column chromatography to obtain the title compound 125 mg (yield: 31%).
$^1$H NMR (CDCl$_3$) δ: 8.80-8.75 (m, 2H), 7.55-7.51 (m, 2H), 7.44 (m, 1H), 7.30 (s, 1H), 6.66 (s, 1H), 5.24 (bs, 1H), 5.08 (m, 1H), 4.39 (t, 2H), 3.85 (q, 2H), 3.20 (d, 3H), 1.66 (s, 9H).

<78-3> {2-[6-(acryloyl-methyl-amino)-4-(4-bromo-2-fluoro-phenylamino)-quinazolin-7-yloxy]-ethyl}-carbamic acid t-butylester The procedure of Example <29-5> was repeated except for using the compound of <78-2> (125 mg, 0.25 mmol) to obtain the title compound 66 mg (yield: 47%).
$^1$H NMR (CDCl$_3$) δ: 8.74 (s, 1H), 8.30 (t, 1H), 7.92 (bs, 1H), 7.86 (s, 1H), 7.43-7.32 (m, 3H), 7.18 (m, 1H), 6.45-6.40

(m, 1H), 6.05-5.96 (m, 1H), 5.57-5.53 (m, 1H), 4.15 (t, 2H), 3.55 (q, 2H), 3.33 (s, 3H), 1.42 (s, 9H).

<78-4> N-[7-(2-amino-ethoxy)-4-(4-bromo-2-fluoro-phenylamino)-quinazolin-6-yl]-N-methyl-acrylamide The procedure of Example <1-9> was repeated except for using the compound of <78-3> (66 mg, 0.12 mmol) to obtain the title compound 53 mg (yield: 92%).
$^1$H NMR (CDCl$_3$) δ: 8.67 (s, 1H), 8.19 (t, 1H), 8.02 (bs, 1H), 7.83 (s, 1H), 7.32-7.21 (m, 3H), 6.35-6.30 (m, 1H), 6.07-5.98 (m, 1H), 5.49-5.45 (m, 1H), 4.11-4.02 (m, 2H), 4.02-3.92 (m, 2H), 3.27 (s, 3H).

<78-5> N-[7-(2-acetylamino-ethoxy)-4-(4-bromo-2-fluoro-phenylamino)-quinazolin-6-yl]-N-methyl-acrylamide The procedure of Example <1-10> was repeated except for using the compound of <78-4> (53 mg, 0.11 mmol) to obtain N-[7-(2-acetylamino-ethoxy)-4-(4-bromo-2-fluoro-phenylamino)-quinazolin-6-yl]-N-methyl-acrylamide 18 mg (yield: 32%).
$^1$H NMR (CDCl$_3$+CD$_3$OD) δ: 8.50 (s, 1H), 8.26 (s, 1H), 7.62-7.56 (m, 1H), 7.41-7.34 (m, 2H), 7.25 (s, 1H), 6.36-6.30 (m, 1H), 6.09-6.00 (m, 1H), 5.59-5.56 (m, 1H), 4.26-4.18 (m, 2H), 3.59 (t, 2H), 3.33 (s, 3H), 1.93 (s, 3H).

Example 79

Preparation of N-4-(4-bromo-3-fluoro-phenylamino)-7-[2-(2-dimethylamino-acetylamino)-ethoxy]-quinazolin-6-yl-acrylamide

<79-1> (4-bromo-3-fluoro-phenyl)-(7-fluoro-6-nitro-quinazolin-4-yl)-amine

The procedure of Example <1-5> was repeated except for using the compound of Example <1-4> (3 g, 11.36 mmol) and 4-bromo-3-fluoro-phenylamine (2.16 g, 11.36 mmol) to obtain the title compound 4.0 g (yield: 93%).
$^1$H NMR (DMSO-d$_6$) δ: 9.49 (s, 1H), 8.63 (s, 1H), 7.66 (s, 1H), 7.66-7.60 (m, 1H), 7.37-7.31 (m, 1H).

<79-2> {3-[4-(4-bromo-3-fluoro-phenylamino)-6-nitro-quinazolin-7-yloxy]-ethyl}-carbamic acid t-butylester The procedure of Example <67-2> was repeated except for using the compound of <79-1> (4.0 g, 10.49 mmol) to obtain the title compound 4.0 g (yield: 73%).
$^1$H NMR (DMSO-d$_6$) δ: 9.11 (s, 1H), 8.54 (d, 1H), 7.97 (d, 1H), 7.63-7.60 (m, 1H), 7.51 (d, 1H), 7.36 (s, 1H), 6.95 (m, 1H), 4.28 (t, 2H), 2.56 (t, 2H), 1.38 (s, 9H).

<79-3> [7-(2-amino-ethoxy)-6-nitro-quinazolin-4-yl]-(4-bromo-3-fluoro-phenyl)-amine The procedure of Example <1-9> was repeated except for using the compound of <79-2> (4.0 g, 7.65 mmol) to obtain the title compound 1.96 g (yield: 61%).
$^1$H NMR (DMSO-d$_6$) δ: 9.47 (s, 1H), 8.69 (d, 1H), 8.08 (d, 1H), 7.72-7.65 (m, 1H), 7.63-7.59 (m, 1H), 7.47 (s, 1H), 4.26 (t, 2H), 2.95 (s, 2H).

<79-4> N-{2-[4-(4-bromo-3-fluoro-phenylamino)-6-nitro-quinazolin-7-oxy]-ethyl}-2-dimethylamino-acetamide The procedure of Example 44 was repeated except for using the compound of <79-3> (135 mg, 0.319 mmol) to obtain the title compound 146 mg (yield: 90%).
$^1$H NMR (DMSO-d$_6$) δ: 10.24 (s, 1H), 9.26 (s, 1H), 8.74 (s, 1H), 8.14 (d, 1H), 7.93 (d, 1H), 7.74-7.65 (m, 2H), 7.58 (s, 1H), 7.47 (s, 1H), 4.40 (t, 2H), 3.58 (m, 2H), 2.88 (s, 2H), 2.14 (s, 6H).

<79-5> N-{2-[6-amino-4-(4-bromo-3-fluoro-phenylamino)-quinazolin-7-oxy]-ethyl}-2-dimethylamino-acetamide The procedure of Example <1-7> was repeated except for using the compound of <79-4> (145 mg, 0.285 mmol) to obtain the title compound 65 mg (yield: 48%).
$^1$H NMR (DMSO-d$_6$) δ: 9.49 (s, 1H), 8.41 (s, 1H), 8.17 (d, 2H), 7.69-7.65 (m, 2H), 7.37 (s, 1H), 7.07 (s, 1H), 5.54 (bs, 2H), 4.14 (t, 2H), 3.59 (t, 2H), 2.90 (s, 2H), 2.21 (s, 6H).

<79-6> N-4-(4-bromo-3-fluoro-phenylamino)-7-[2-(2-dimethylamino-acetylamino)-ethoxy]-quinazolin-6-yl-acrylamide The procedure of Example <29-5> was repeated except for using the compound of <79-5> (65 mg, 0.136 mmol) to obtain the title compound 55 mg (yield: 75%).
$^1$H NMR (CD$_3$OD) δ: 8.87 (s, 1H), 8.49 (s, 1H), 7.94 (d, 1H), 7.52-7.50 (m, 2H), 7.12 (s, 1H), 6.92-6.83 (m, 1H), 6.53 (d, 2H), 6.19 (d, 1H), 5.92 (d, 1H), 5.66 (t, 1H), 4.30 (t, 2H), 3.84 (t, 2H), 3.40 (s, 2H), 2.71 (s, 6H).

Example 80

Preparation of N-[7-(2-acetylamino-1-methyl-ethoxy)-4-(4-bromo-2-fluoro-phenylamino)-quinazolin-6-yl]-acrylamide

<80-1> (2-hydroxy-propyl)-carbamic acid t-butylester

The procedure of Example <1-1> was repeated except for using 1-amino-propan-2-ol (1.9 g, 25.1 mmol) to obtain the title compound 3.2 g (yield: 73%).
$^1$H NMR (CDCl$_3$) δ: 4.64 (bs, 1H), 3.80-3.78 (m, 1H), 3.68-3.61 (m, 1H), 3.55-3.49 (m, 1H), 2.57 (bs, 1H), 1.45 (s, 9H), 1.15 (d, 3H).

<80-2> {2-[4-(4-bromo-2-fluoro-phenylamino)-6-nitro-quinazolin-7-yloxy]-propyl}-carbamic acid t-butylester The procedure of Example <1-6> was repeated except for using the compound of Example <1-5> (382 mg, 1.0 mmol) and the compound of <80-1> (500 mg, 2.9 mmol) to obtain the title compound 431 mg (yield: 80%).
$^1$H NMR (CDCl$_3$)) δ: 8.79 (s, 1H), 8.52 (s, 1H), 8.41 (t, 1H), 7.55 (bs, 1H), 7.41-7.38 (m, 3H), 4.87 (m, 1H), 4.22 (m, 2H), 1.45 (s, 9H), 1.14 (d, 3H).

<80-3> [7-(2-amino-1-methyl-ethoxy)-6-nitro-quinazolin-4-yl]-(4-bromo-2-fluoro-phenyl)-amine The procedure of Example <1-9> was repeated except for using the compound of <80-2> (431 mg, 0.80 mmol) to obtain the title compound 330 mg (yield: 95%).

¹H NMR (CDCl₃)) δ: 8.84 (s, 1H), 8.61 (s, 1H), 7.79 (t, 1H), 7.38-7.31 (m, 3H), 4.19-4.15 (m, 1H), 3.92 (t, 1H), 3.46-3.35 (m, 2H), 1.22 (d, 3H).

<80-4> N-{2-[4-(4-bromo-2-fluoro-phenylamino)-6-nitro-quinazolin-7-yloxy]-propyl}-acetamide The procedure of Example <1-10> was repeated except for using the compound of <80-3> (330 mg, 0.76 mmol) and acetyl chloride (65 mg, 0.83 mmol) to obtain the title compound 204 mg (yield: 56%).
¹H NMR (CDCl₃+CD₃OD) δ: 8.98 (s, 1H), 8.52 (s, 1H), 7.58-7.46 (m, 2H), 7.39-7.27 (m, 3H), 4.40 (m, 1H), 4.19-4.18 (d, 2H), 1.98 (s, 3H), 1.35 (d, 3H).

<80-5> N-{2-[6-amino-4-(4-bromo-2-fluoro-phenylamino)-quinazolin-7-yloxy]-propyl}-acetamide The procedure of Example <1-7> was repeated except for using the compound of <80-4> (204 mg, 0.43 mmol) to obtain the title compound 169 mg (yield: 88%).
¹H NMR (CDCl₃+CD₃OD) δ: 8.31 (s, 1H), 7.82 (t, 1H), 7.35-7.29 (m, 2H), 7.21 (s, 1H), 7.00 (s, 1H), 4.47-4.46 (m, 1H), 4.11-4.00 (m, 2H), 1.98 (s, 3H), 1.30 (d, 3H).

<80-6> N-[7-(2-acetylamino-1-methyl-ethoxy)-4-(4-bromo-2-fluoro-phenylamino)-quinazolin-6-yl]-acrylamide The procedure of Example <29-5> was repeated except for using the compound of <80-5> (169 mg, 0.38 mmol) to obtain the title compound 20 mg (yield: 11%).
¹H NMR (CDCl₃) δ: 9.20 (s, 1H), 8.95 (bs, 1H), 8.64 (s, 1H), 8.31 (t, 1H), 8.01 (s, 1H), 7.61 (bs, 1H), 7.35-7.31 (m, 2H), 7.10 (s, 1H), 6.90-6.81 (m, 1H), 6.55-6.49 (m, 1H), 5.85-5.77 (m, 1H), 4.68-4.65 (m, 1H), 4.21-4.16 (m, 1H), 3.83 (t, 1H), 2.06 (s, 3H), 1.31 (d, 3H).

Example 81

Preparation of N-[7-(2-acetylamino-propoxy)-4-(4-bromo-2-fluoro-phenylamino)-quinazolin-6-yl]-acrylamide <81-1> (2-hydroxy-1-methyl-ethyl)-carbamic acid t-butylester The procedure of Example <1-1> was repeated except for using 2-amino-propan-1-ol (3 g, 39.9 mmol) to obtain the title compound 6.4 g (yield: 91%).
¹H NMR (CDCl₃) δ: 4.89 (bs, 1H), 4.43 (m, 1H), 4.06 (m, 1H), 3.95 (m, 2H), 1.41 (s, 9H), 1.31 (d, 3H).

<81-2> {2-[4-(4-bromo-2-fluoro-phenylamino)-6-nitro-quinazolin-7-yloxy]-1-methyl-ethyl}-carbamic acid t-butylester The procedure of Example <1-6> was repeated except for using the compound of Example <1-5> (5 g, 13.1 mmol) and the compound of <81-1> (6.9 g, 39.3 mmol) to obtain the title compound 2.2 g (yield: 31%).
¹H NMR (CDCl₃) δ: 8.79 (s, 1H), 8.52 (s, 1H), 8.41 (t, 1H), 7.55 (bs, 1H), 7.41-7.38 (m, 3H), 4.85 (m, 1H), 4.22 (m, 2H), 1.45 (s, 9H), 1.38 (d, 3H).

<81-3> {2-[6-amino-4-(4-bromo-2-fluoro-phenylamino)-quinazolin-7-yloxy]-1-methyl-ethyl}-carbamic acid t-butylester The procedure of Example <1-7> was repeated except for using the compound of <81-2> (2.1 g, 3.9 mmol) to obtain the title compound 2 g (yield: 99%).
¹H NMR (CDCl₃) δ: 8.65-8.59 (m, 2H), 7.33-7.29 (m, 2H), 7.19 (bs, 1H), 7.12 (s, 1H), 6.88 (s, 1H), 4.63 (d, 1H), 4.41 (bs, 2H), 4.23 (m, 1H), 4.14-4.09 (m, 1H), 4.01-3.99 (m, 1H), 1.45 (s, 9H), 1.31 (d, 3H).

<81-4> {2-[6-acryloylamino-4-(4-bromo-2-fluoro-phenylamino)-quinazolin-7-yloxy]-1-methyl-ethyl}-carbamic acid t-butylester The procedure of Example <29-5> was repeated except for using the compound of <81-3> (2.0 g, 3.9 mmol) to obtain the title compound 200 mg (yield: 9%).
¹H NMR (CDCl₃) δ: 9.25 (s, 1H), 9.20 (bs, 1H), 8.67 (s, 1H), 8.38 (t, 1H), 7.51 (s, 1H), 7.37-7.28 (m, 3H), 7.15 (s, 1H), 6.78-6.73 (m, 1H), 6.56-6.51 (m, 1H), 5.84-5.81 (m, 1H), 4.64-4.62 (m, 1H), 4.33-4.31 (m, 1H), 4.15-4.11 (m, 1H), 3.94 (t, 1H), 1.44 (s, 9H), 1.31 (d, 3H).

<81-5> N-[7-(2-amino-propoxy)-4-(4-bromo-2-fluoro-phenylamino)-quinazolin-6-yl]-acrylamide The procedure of Example <1-9> was repeated except for using the compound of <81-4> (200 mg, 0.36 mmol) to obtain the title compound 165 mg (yield: 99%).
¹H NMR (CDCl₃) δ: 9.17 (s, 1H), 8.68 (s, 1H), 8.48 (bs, 1H), 8.38 (t, 1H), 7.58 (bs, 1H), 7.37-7.29 (m, 3H), 6.52-6.47 (m, 1H), 6.40-6.32 (m, 1H), 5.87-5.84 (m, 1H), 4.14-4.09 (m, 1H), 4.04-3.96 (m, 1H), 3.52-3.50 (m, 1H), 1.26 (d, 3H).

<81-6> N-[7-(2-acetylamino-propoxy)-4-(4-bromo-2-fluoro-phenylamino)-quinazolin-6-yl]-acrylamide The procedure of Example <1-10> was repeated except for using the compound of <81-5> (200 mg, 0.44 mmol) to obtain the title compound 161 mg (yield: 73%).
¹H NMR (DMSO-d₆) δ: 9.18 (bs, 1H), 8.21 (s, 1H), 8.04 (d, 2H), 7.61-7.54 (m, 2H), 7.42 (d, 1H), 7.29 (s, 1H), 7.04 (s, 1H), 5.46 (bs, 2H), 4.28 (m, 1H), 4.07-3.98 (m 2H), 1.85 (s, 3H), 1.22 (d, 3H).

Example 82

Preparation of (R)—N-[7-(2-acetylamino-propoxy)-4-(4-bromo-2-fluoro-phenylamino)-quinazolin-6-yl]-acrylamide <82-1> (R)-(2-hydroxy-1-methyl-ethyl)-carbamic acid t-butylester The procedure of Example <1-1> was repeated except for using (R)-2-amino-propan-1-ol (3 g, 39.9 mmol) to obtain the title compound 5.7 g (yield: 82%).
¹H NMR (CDCl₃) δ: 4.89 (bs, 1H), 3.90 (bs, 1H), 3.85 (m, 1H), 3.75 (m, 2H), 1.47 (s, 9H), 1.30 (d, 3H).

<82-2> (R)-{2-[4-(4-bromo-2-fluoro-phenylamino)-6-nitro-quinazolin-7-yloxy]-1-methyl-ethyl}-carbamic acid t-butylester The procedure of Example <1-6> was repeated except for using the compound of Example <1-5> (500 mg, 1.31 mmol) and the compound of <82-1> (690 mg, 3.93 mmol) to obtain the title compound 188 mg (yield: 35%).
$^1$H NMR (CDCl$_3$) δ: 8.71-8.60 (m, 2H), 8.15-8.10 (m 2H), 7.36-7.30 (m, 3H), 4.89 (d, 1H), 4.15-4.08 (m, 2H), 4.03 (s, 1H), 1.41 (s, 9H), 1.24 (d, 3H).

<82-3> (R)-[7-(2-amino-propoxy)-6-nitro-quinazolin-4-yl]-(4-bromo-2-fluoro-phenyl)-amine The procedure of Example <1-9> was repeated except for using the compound of <82-2> (188 mg, 0.35 mmol) to obtain the title compound 107 mg (yield: 71%).
$^1$H NMR (CDCl$_3$+CD$_3$OD) δ: 8.97 (s, 1H), 8.53 (s, 1H), 7.58 (t, 1H), 7.38-7.30 (m, 3H), 4.20-4.16 (m, 1H), 3.98-3.90 (m, 1H), 3.48-3.32 (m, 1H), 1.22 (d, 3H).

<82-4> (R)—N-{2-[4-(4-bromo-2-fluoro-phenylamino)-6-nitro-quinazolin-7-yloxy]-1-methyl-ethyl}-acetamide The procedure of Example <1-10> was repeated except for using the compound of <82-3> (107 mg, 0.25 mmol) to obtain the title compound 45 mg (yield: 36%).
$^1$H NMR (CDCl$_3$+CD$_3$OD) δ: 8.87 (s, 1H), 8.55 (s, 1H), 7.72-7.70 (m, 1H), 7.32-7.25 (m, 3H), 6.62 (m, 2H), 4.40 (m, 1H), 4.19 (m, 2H), 1.95 (s, 3H), 1.29 (d, 3H).

<82-5> (R)—N-{2-[6-amino-4-(4-bromo-2-fluoro-phenylamino)-quinazolin-7-yloxy]-1-methyl-ethyl}-acetamide The procedure of Example <1-7> was repeated except for using the compound of <82-4> (45 mg, 0.09 mmol) to obtain the title compound 40 mg (yield: 99%).
$^1$H NMR (CDCl$_3$+CD$_3$OD) δ: 8.30 (s, 1H), 7.78 (t, 1H), 7.37-7.23 (m, 2H), 7.21 (s, 1H), 6.98 (s, 1H), 4.49-4.45 (m, 1H), 4.13-4.01 (m, 2H), 2.04 (s, 3H), 1.31 (d, 3H).

<82-6> (R)—N-[7-(2-acetylamino-propoxy)-4-(4-bromo-2-fluoro-phenylamino)-quinazolin-6-yl]-acrylamide The procedure of Example <29-5> was repeated except for using the compound of <82-5> (40 mg, 0.09 mmol) to obtain the title compound 20 mg (yield: 44%).
$^1$H NMR (CDCl$_3$+CD$_3$OD) δ: 9.10-9.02 (m, 1H), 8.57-8.51 (m, 1H), 7.91-7.88 (m, 1H), 7.39-7.31 (m, 2H), 7.10 (s, 1H), 6.89-6.80 (m, 1H), 6.56-6.50 (m, 1H), 5.86 (d, 1H), 4.64 (bs, 1H), 4.21-4.11 (m, 2H), 3.90 (t, 1H), 2.06 (s, 3H), 1.32-1.29 (m, 3H).

Example 83

Preparation of (S)—N-[7-(2-acetylamino-propoxy)-4-(4-bromo-2-fluoro-phenylamino)-quinazolin-6-yl]-acrylamide <83-1> (S)-(2-hydroxy-1-methyl-ethyl)-carbamic acid t-butylester The procedure of Example <1-1> was repeated except for using (S)-2-amino-propan-1-ol (3 g, 39.9 mmol) to obtain the title compound 5.2 g (yield: 75%).
$^1$H NMR (CDCl$_3$) δ: 4.85 (bs, 1H), 3.99 (bs, 1H), 3.81 (m, 1H), 3.70 (m, 2H), 1.45 (s, 9H), 1.33 (d, 3H).

<83-2> (S)-{2-[4-(4-bromo-2-fluoro-phenylamino)-6-nitro-quinazolin-7-yloxy]-1-methyl-ethyl}-carbamic acid t-butylester The procedure of Example <1-6> was repeated except for using the compound of Example <1-5> (500 mg, 1.31 mmol) and the compound of <83-1> (690 mg, 3.93 mmol) to obtain the title compound 277 mg (yield: 40%).
$^1$H NMR (CDCl$_3$) δ: 8.78 (s, 1H), 8.53 (s, 1H), 8.39 (t, 1H), 7.58 (bs, 1H), 7.44-7.36 (m, 3H), 4.84 (bs, 1H), 4.25-4.21 (m, 1H), 1.57 (s, 2H), 1.45 (s, 9H), 1.37 (d, 2H).

<83-3> (S)-[7-(2-amino-propoxy)-6-nitro-quinazolin-4-yl]-(4-bromo-2-fluoro-phenyl)-amine The procedure of Example <1-9> was repeated except for using the compound of <83-2> (277 mg, 0.52 mmol) to obtain the title compound 192 mg (yield: 85%).
$^1$H NMR (DMSO-d$_6$) δ: 9.15 (s, 1H), 8.49 (s, 1H), 7.68-7.64 (m, 1H), 7.53-7.43 (m, 3H), 4.12-4.01 (m, 2H), 3.21 (q, 1H), 1.10 (d, 3H).

<83-4> (S)—N-{2-[4-(4-bromo-2-fluoro-phenylamino)-6-nitro-quinazolin-7-yloxy]-1-methyl-ethyl}-acetamide The procedure of Example <1-10> was repeated except for using the compound of <83-3> (38 mg, 0.48 mmol) to obtain the title compound 114 mg (yield: 54%).
$^1$H NMR (CDCl$_3$) δ: 8.82 (s, 1H), 8.68 (m, 2H), 8.03-7.97 (m, 1H), 7.34-7.24 (m, 3H), 6.20 (d, 1H), 4.51-4.47 (m, 1H), 4.26-4.15 (m, 2H), 2.00 (s, 3H), 1.35 (d, 3H).

<83-5> (S)—N-{2-[6-amino-4-(4-bromo-2-fluoro-phenylamino)-quinazolin-7-yloxy]-1-methyl-ethyl}-acetamide The procedure of Example <1-7> was repeated except for using the compound of <83-4> (114 mg, 0.24 mmol) to obtain the title compound 100 mg (yield: 91%).
$^1$H NMR (CDCl) δ: 8.47-8.39 (m, 2H), 7.37-7.19 (m, 3H), 6.95-6.85 (m, 2H), 6.34 (d, 1H), 4.48 (bs, 2H), 3.82-3.69 (m, 3H), 1.98 (s, 3H), 1.20 (d, 3H).

<83-6> (S)—N-[7-(2-acetylamino-propoxy)-4-(4-bromo-2-fluoro-phenylamino)-quinazolin-6-yl]-acrylamide The procedure of Example <29-5> was repeated except for using the compound of <83-5> (100 mg, 0.22 mmol) to obtain the title compound 38 mg (yield: 34%).
$^1$H NMR (CDCl$_3$) δ: 9.27 (s, 1H), 9.02 (s, 1H), 8.71 (s, 1H), 8.39 (t, 1H), 7.66 (bs, 1H), 7.45-7.39 (m, 2H), 7.18 (s, 1H), 6.98-6.89 (m, 1H), 6.63-6.57 (m, 1H), 5.93-5.89 (m, 1H), 5.75 (d, 1H), 4.78-4.71 (m, 1H), 4.28-4.24 (m, 1H), 3.91 (t, 1H), 2.14 (s, 3H), 1.40 (d, 3H)

Example 84

Preparation of N-[4-(4-bromo-2-fluoro-phenylamino)-7-(2-propionylamino-propoxy)-quinazolin-6-yl]-acrylamide The procedure of Example <1-10> was repeated except for using the compound of Example <81-5> (50 mg, 0.11 mmol)

and propionyl chloride (11 mg, 0.12 mmol) to obtain the title compound 23 mg (yield: 40%).

$^1$H NMR (CDCl$_3$+CD$_3$OD) δ: 9.07 (s, 1H), 9.03 (s, 1H), 8.53 (s, 1H), 7.93 (t, 1H), 7.36-7.30 (m, 2H), 7.06 (s, 1H), 6.93-6.84 (m, 1H), 6.52-6.47 (m, 1H), 6.25 (d, 1H), 5.83 (d, 1H), 4.67-4.62 (m, 1H), 4.19-4.15 (m, 1H), 3.85 (t, 1H), 2.33-2.15 (m, 2H), 1.28 (d, 3H), 1.12 (t, 3H).

Example 85

Preparation of N-{4-(4-bromo-2-fluoro-phenylamino)-7-[2-(3-propyl-ureido)-propoxy]-quinazolin-6-yl}-acrylamide The compound of Example <81-5> (50 mg, 0.11 mmol) and 1-isocyanato-propane (28 mg, 0.33 mmol) were diluted with dichloromethane (3 ml), and the solution was stirred for 3 hours. The reaction was terminated by adding water (30 ml), and extracted with dichloromethane (30 ml) twice. The separated organic layer was dried over magnesium sulfate, filtered and distilled under a reduced pressure, and resulting impure residue was subjected to column chromatography to obtain the title compound 25 mg (yield: 42%).

$^1$H NMR (CDCl$_3$+CD$_3$OD) δ: 9.11 (s, 1H), 8.54 (s, 1H), 7.88 (q, 1H), 7.40-7.33 (m, 2H), 7.07 (s, 1H), 7.02-6.93 (m, 1H), 6.55-6.49 (m, 1H), 5.84 (d, 1H), 4.45-4.43 (m, 1H), 4.18-4.14 (m, 1H), 3.83 (t, 1H), 3.13 (t, 2H), 1.46 (q, 2H), 1.26 (d, 3H), 0.88 (t, 3H).

Example 86

Preparation of N-[7-(2-acetylamino-butoxy)-4-(4-bromo-2-fluoro-phenylamino)-quinazolin-6-yl]-acrylamide <86-1> (1-hydroxymethyl-propyl)-carbamic acid t-butylester The procedure of Example <1-1> was repeated except for using 2-amino-buthan-1-ol (5 g, 56 mmol) to obtain the title compound 9 g (yield: 85%).

$^1$H NMR (CDCl$_3$) δ: 4.60 (bs, 1H), 3.68-3.61 (m, 1H), 3.57-3.51 (m, 2H), 2.43 (bs, 1H), 1.57-1.47 (m, 2H), 1.43 (s, 9H), 0.94 (t, 3H).

<86-2> {1-[4-(4-bromo-2-fluoro-phenylamino)-6-nitro-quinazolin-7-yloxymethyl]-propyl}-carbamic acid t-butylester The procedure of Example <1-6> was repeated except for using the compound of Example <1-5> (500 mg, 1.31 mmol) and the compound of <86-1> (745 mg, 3.93 mmol) to obtain the title compound 300 mg (yield: 42%).

$^1$H NMR (CDCl$_3$) δ: 9.09-9.06 (m, 1H), 8.75 (d, 1H), 7.77-7.76 (m, 2H), 7.45-7.41 (m, 2H), 4.77 (t, 1H), 4.64-4.56 (m, 1H), 4.34 (t, 1H), 1.97-1.85 (m, 2H), 1.03-0.98 (m, 3H).

<86-3> [7-(2-amino-buthoxy)-6-nitro-quinazolin-4-yl]-(4-bromo-2-fluoro-phenyl)-amine The procedure of Example <1-9> was repeated except for using the compound of <86-2> (350 mg, 0.63 mmol) to obtain the title compound 285 mg (yield: 99%).

$^1$H NMR (CDCl$_3$+CD$_3$OD) δ: 8.82 (s, 1H), 8.52 (s, 1H), 7.69-7.66 (m, 1H), 7.29-7.19 (m, 3H), 4.17-4.13 (m, 1H), 3.97-3.88 (m, 2H), 1.57-1.43 (m, 2H), 0.96 (t, 3H).

<86-4> N-{1-[4-(4-bromo-2-fluoro-phenylamino)-6-nitro-quinazolin-7-yloxymethyl]-propyl}-acetamide The procedure of Example <1-10> was repeated except for using the compound of <86-3> (285 mg, 0.63 mmol) to obtain the title compound 200 mg (yield: 65%).

$^1$H NMR (CDCl$_3$) δ: 8.91 (s, 1H), 8.63 (s, 1H), 7.79 (t, 1H), 7.40-7.31 (m, 3H), 6.59 (bs, 1H), 4.29-4.23 (m, 3H), 2.05 (s, 3H), 1.78-1.67 (m, 2H), 1.00 (t, 3H).

<86-5> N-{1-[6-amino-4-(4-bromo-2-fluoro-phenylamino)-quinazolin-7-yloxymethyl]-propyl}-acetamide The procedure of Example <1-7> was repeated except for using the compound of <86-4> (200 mg, 0.41 mmol) to obtain the title compound 185 mg (yield: 97%).

$^1$H NMR (CDCl+MeOD) δ: 8.40-8.25 (m, 2H), 7.26-7.23 (m, 3H), 6.91 (s, 1H), 4.24 (m, 1H), 3.98-3.89 (m, 2H), 2.13 (s, 3H), 1.60-1.46 (m, 2H), 0.93 (t, 3H).

<86-6> N-[7-(2-acetylamino-butoxy)-4-(4-bromo-2-fluoro-phenylamino)-quinazolin-6-yl]-acrylamide The procedure of Example <29-5> was repeated except for using the compound of <86-5> (185 mg, 0.4 mmol) to obtain the title compound 30 mg (yield: 14%).

$^1$H NMR (CDCl$_3$) δ: 8.91 (s, 1H), 8.45 (s, 1H), 7.75 (t, 1H), 7.32-7.26 (m, 3H), 7.01 (s, 1H), 6.81-6.72 (m, 1H), 6.47-6.42 (m, 1H), 5.81-5.78 (m, 1H), 4.33 (m, 1H), 4.18-4.14 (m, 1H), 3.88-3.81 (m, 1H), 1.97 (s, 3H), 1.67-1.46 (m, 2H), 1.00 (t, 3H).

Example 87

Preparation of N-[4-(4-bromo-2-fluoro-phenylamino)-7-(3-propionylamino-propoxy)-quinazolin-6-yl]-acrylamide <87-1> (3-hydroxy-propyl)-carbamic acid t-butylester The procedure of Example <1-1> was repeated except for using 3-amino-propan-1-ol (10 g, 133 mmol) to obtain the title compound 18.6 g (yield: 80%).

$^1$H-NMR (CDCl$_3$) δ: 4.86 (bs, 1H), 3.69 (m, 2H), 3.31 (q, 2H), 1.88 (bs, 1H), 1.69 (m, 2H), 1.47 (s, 9H).

<87-2> {3-[4-(4-bromo-2-fluoro-phenylamino)-6-nitro-quinazolin-7-yloxy]-propyl}-carbamic acid t-butylester The procedure of Example <1-6> was repeated except for using the compound of Example <1-5> (4.06 g, 10.6 mmol) and the compound of <87-1> (2.8 g, 15.9 mmol) to obtain the title compound 4 g (yield: 70%).

$^1$H-NMR (CDCl$_3$) δ: 8.79 (s, 1H), 8.51 (s, 1H), 8.40 (t, 1H), 7.75 (bs, 1H), 7.43-7.39 (m, 3H), 4.96 (bs, 1H), 4.32 (t, 2H), 3.41 (q, 2H), 2.31 (p, 2H), 1.45 (s, 9H).

<87-3> [7-(3-amino-propoxy)-6-nitro-quinazolin-4-yl]-(4-bromo-2-fluoro-phenyl)-amine The procedure of Example <1-9> was repeated except for using the compound of <87-2> (3 g, 5.6 mmol) to obtain the title compound 2.4 g (yield: 98%).

¹H-NMR (CDCl₃+MeOD) δ: 9.01 (s, 1H), 8.51 (s, 1H), 7.54 (t, 1H), 7.43-7.30 (m, 3H), 4.37 (t, 2H), 2.97 (t, 2H), 2.09 (p, 2H).

<87-4> N-{3-[4-(4-bromo-2-fluoro-phenylamino)-6-nitro-quinazolin-7-yloxy]-propyl}-propionylamide The procedure of Example <1-10> was repeated except for using the compound of <87-3> (370 mg, 0.85 mmol) and propionyl chloride (86 mg, 0.93 mmol) to obtain the title compound 250 mg (yield: 60%).
¹H-NMR (CDCl₃+MeOD) δ: 8.85 (s, 1H), 8.58 (s, 1H), 7.76-7.69 (m, 1H), 7.34-7.24 (m, 3H), 4.27 (t, 2H), 3.48-3.39 (m, 2H), 2.22 (t, 2H), 2.10-1.98 (m, 2H), 1.09 (t, 3H).

<87-5> N-{3-[6-amino-4-(4-bromo-2-fluoro-phenylamino)-quinazolin-7-yloxy]-propyl}-propionylamide The procedure of Example <1-7> was repeated except for using the compound of <87-4> (200 mg, 0.41 mmol) to obtain the title compound 189 mg (yield: 99%).
¹H-NMR (CDCl₃+MeOD) δ: 8.48 (s, 1H), 8.32 (t, 1H), 7.33-7.30 (m, 2H), 7.08-7.00 (m, 2H), 6.72 (bs, 1H), 4.18 (t, 2H), 3.45 (t, 2H), 2.25-2.17 (m, 2H), 2.10-2.05 (m, 2H), 1.20-1.11 (m, 3H).

<87-6> N-[4-(4-bromo-2-fluoro-phenylamino)-7-(3-propionylamino-propoxy)-quinazolin-6-yl]-acrylamide The procedure of Example <29-5> was repeated except for using the compound of <87-5> (189 mg, 0.41 mmol) to obtain the title compound 34 mg (yield: 16%).
¹H-NMR (CDCl₃) δ: 9.20 (s, 1H), 9.02 (s, 1H), 8.66 (s, 1H), 8.37 (t, 1H), 7.51 (s, 1H), 7.36-7.33 (m, 2H), 6.82-6.73 (m, 1H), 6.55-6.50 (m, 1H), 5.85-5.79 (m, 1H), 5.66 (m, 1H), 4.27 (t, 2H), 3.55 (q, 2H), 2.25 (q, 2H), 2.12-2.03 (m, 2H), 1.17 (t, 3H).

Example 88

Preparation of N-[7-(1-acetyl-pyrrolidin-3-yloxy)-4-(4-bromo-2-fluoro-phenylamino)-quinazolin-6-yl]-acrylamide <88-1> 3-hydroxy-pyrrolidine-1-carboxylic acid t-butylester The procedure of Example <1-1> was repeated except for using pyrrolidinol (1.6 g, 18.36 mmol) to obtain the title compound 3.2 g (yield: 93%).
¹H NMR (CDCl₃) δ: 4.13 (s, 1H), 2.05-1.94 (m, 4H), 1.47 (s, 9H).

<88-2> 3-[4-(4-bromo-2-fluoro-phenylamino)-6-nitro-quinazolin-7-yloxy]-pyrrolidine-1-carboxylic acid t-butylester The procedure of Example <1-6> was repeated except for using the compound of Example <1-5> (300 mg, 0.79 mmol) and the compound of <88-1> (442 mg, 2.36 mmol) to obtain the title compound 210 mg (yield: 49%).
¹H NMR (CDCl₃) δ: 9.21 (s, 1H), 8.87 (d, 1H), 8.57 (s, 1H), 7.68 (d, 1H), 7.29-7.21 (m, 2H), 5.10 (s, 1H), 4.35 (s, 2H), 3.68-3.45 (m, 4H), 3.28 (d, 2H), 1.39 (s, 9H).

<88-3> (4-bromo-2-fluoro-phenyl)-[6-nitro-7-(pyrrolidin-3-yloxy)-quinazolin-4-yl]-amine The procedure of Example <1-9> was repeated except for using the compound of <88-2> (210 mg, 0.38 mmol) to obtain the title compound 154 mg (yield: 90%).
¹H NMR (CDCl₃) δ: 8.72 (s, 1H), 8.59 (s, 1H), 8.14 (t, 1H), 7.37-7.34 (m, 3H), 5.09 (s, 1H), 3.35-3.22 (m, 2H), 3.11 (d, 1H), 2.98 (s, 1H), 2.25-2.16 (m, 1H), 2.13-2.02 (m, 1H).

<88-4> 1-{3-[4-(4-bromo-2-fluoro-phenylamino)-6-nitro-quinazolin-7-yloxy]-pyrrolidin-1-yl}-ethanone The procedure of Example <1-10> was repeated except for using the compound of <88-3> (154 mg, 0.34 mmol) to obtain the title compound 148 mg (yield: 88%).
¹H NMR (CDCl₃) δ: 8.73 (s, 1H), 8.50 (s, 1H), 8.26 (t, 1H), 7.99 (s, 1H), 7.41 (s, 1H), 7.37 (s, 2H), 5.20 (t, 1H), 4.04 (d, 1H), 3.88-3.68 (m, 4H), 2.52-2.32 (m, 1H), 2.17 (s, 3H).

<88-5> 1-{3-[6-amino-4-(4-bromo-2-fluoro-phenylamino)-quinazolin-7-yloxy]-pyrrolidin-1-yl}-ethanone The procedure of Example <1-7> was repeated except for using the compound of <88-4> (148 mg, 0.30 mmol) to obtain the title compound 90 mg (yield: 65%).
¹H NMR (CDCl₃) δ: 8.63 (s, 2H), 7.37-7.17 (m, 5H), 6.97 (d, 1H), 5.22 (d, 1H), 4.30 (s, 2H), 3.87-3.64 (m, 4H), 2.48-2.25 (m, 2H), 1.61 (s, 3H).

<88-6> N-[7-(1-acetyl-pyrrolidin-3-yloxy)-4-(4-bromo-2-fluoro-phenylamino)-quinazolin-6-yl]-acrylamide The procedure of Example <29-5> was repeated except for using the compound of <88-5> (90 mg, 0.20 mmol) to obtain the title compound 13 mg (yield: 13%).
¹H NMR (CDCl₃) δ: 9.16 (d, 1H), 8.65 (d, 1H), 8.29-8.26 (m, 1H), 8.02 (d, 1H), 7.72 (s, 1H), 7.34-7.31 (m, 2H), 7.22 (s, 1H), 6.50 (d, 1H), 6.35 (ab, 1H), 5.85 (dd, 1H), 5.18 (dd, 1H), 4.04 (dd, 1H), 3.90-3.66 (m, 4H), 2.46-2.38 (m, 2H), 2.13 (s, 3H).

Example 89

Preparation of N-[7-(1-acetyl-piperidin-3-yloxy)-4-(4-bromo-2-fluoro-phenylamino)-quinazolin-6-yl]-acrylamide <89-1> 3-hydroxy-piperidine-1-carboxylic acid t-butylester The procedure of Example <1-1> was repeated except for using piperidin-3-ol (5 g, 49.4 mmol) to obtain the title compound 8.2 g (yield: 83%).
¹H NMR (CDCl₃) δ: 3.86-3.80 (m, 3H), 3.06-2.97 (m, 2H), 1.87-1.81 (m, 2H), 1.69 (t, 2H), 1.49 (s, 9H).

<89-2> 3-[4-(4-bromo-2-fluoro-phenylamino)-6-nitro-quinazolin-7-yloxy]-piperidine-1-carboxylic acid t-butylester The procedure of Example <1-6> was repeated except for using the compound of Example <1-5> (1 g, 2.62 mmol) and the compound of <89-1> (1.58 g, 7.86 mmol) to obtain the title compound 1.3 g (yield: 88%).

¹H NMR (CDCl₃) δ: 8.76 (s, 1H), 8.47 (s, 1H), 8.38 (t, 1H), 7.63 (bs, 1H), 7.45-7.38 (m, 3H), 3.74-3.70 (m, 3H), 3.51 (m, 1H), 3.15-3.09 (m, 1H), 2.07-1.97 (m, 4H), 1.46 (s, 9H).

<89-3> 3-[6-amino-4-(4-bromo-2-fluoro-phenylamino)-quinazolin-7-yloxy]-piperidine-1-carboxylic acid t-butylester The procedure of Example <1-7> was repeated except for using the compound of <89-2> (1.3 mg, 2.3 mmol) to obtain the title compound 1.08 g (yield: 88%).
¹H NMR (CDCl₃) δ: 8.68-8.60 (m, 2H), 7.37-7.32 (m, 2H), 7.21 (m, 2H), 6.93 (s, 1H), 4.35 (bs, 2H), 3.91 (m, 1H), 3.74-3.71 (m, 2H), 3.15-3.09 (m, 2H), 1.88 (m, 2H), 1.79-1.71 (m, 2H), 1.46 (s, 9H).

<89-4> 3-[6-acryloylamino-4-(4-bromo-2-fluoro-phenylamino)-quinazolin-7-yloxy]-piperidine-1-carboxylic acid t-butylester The procedure of Example <29-5> was repeated except for using the compound of <89-3> (210 mg, 0.4 mmol) to obtain the title compound 57 mg (yield: 24%).
¹H NMR (CDCl₃) δ: 9.22 (s, 1H), 8.64 (s, 1H), 8.26 (t, 1H), 7.79 (bs, 1H), 7.38-7.28 (m, 3H), 6.51-6.46 (m, 2H), 5.85-5.81 (m, 1H), 4.64 (bs, 1H), 3.78-3.73 (m, 2H), 3.52 (m, 1H), 3.14-3.03 (m, 2H), 1.88-1.73 (m, 4H), 1.45 (s, 9H).

<89-5> N-[4-(4-bromo-2-fluoro-phenylamino)-7-(piperidin-3-yloxy)-quinazolin-6-yl]-acrylamide The procedure of Example <1-9> was repeated except for using the compound of <89-4> (57 mg, 0.1 mmol) to obtain the title compound 31 mg (yield: 64%).
¹H NMR (CDCl₃) δ: 9.13 (s, 1H), 8.60 (s, 1H), 8.24 (t, 1H), 7.69 (bs, 1H), 7.32-7.29 (m, 2H), 7.21 (s, 1H), 6.44-6.42 (m, 2H), 5.79-5.75 (m, 1H), 4.59 (bs, 1H), 3.08-3.03 (m, 3H), 2.09-2.83 (m, 2H), 1.99-1.86 (m, 4H).

<89-6> N-[7-(1-acetyl-piperidin-3-yloxy)-4-(4-bromo-2-fluoro-phenylamino)-quinazolin-6-yl]-acrylamide The procedure of Example <1-10> was repeated except for using the compound of <89-5> (31 mg, 0.06 mmol) to obtain the title compound 12 mg (yield: 38%).
¹H NMR (CDCl₃) δ: 9.20 (s, 1H), 8.72 (bs, 1H), 8.63 (s, 1H), 8.30 (t, 1H), 7.67 (bs, 1H), 7.36-7.31 (m, 2H), 7.20 (s, 1H), 6.84-6.79 (m, 1H), 6.55-6.49 (m, 2H), 5.85-5.81 (m, 1H), 4.86 (d, 1H), 4.71 (s, 1H), 3.86 (m, 1H), 3.31 (m, 1H), 3.10-3.06 (m, 1H), 2.47-2.45 (m, 1H), 2.23 (s, 3H), 1.71-1.66 (m, 3H).

Example 90

Preparation of N-{4-(4-bromo-2-fluoro-phenylamino)-7-[2-(thiazol-2-ylamino)-ethoxy]-quinazolin-6-yl}-acrylamide <90-1> N-carboxylic acid (thiazol)-2-yl-oxalamic acid ethylester 2-amino thiazole (3 g, 30 mmol) was diluted with pyridine (7.5 ml), chlorooxoacetate (4.5 g, 33 mmol) was added thereto for 20 min, and acetone (30 ml) was added thereto. The solution was stirred at room temperature for 30 min, ice water (20 ml) was added thereto, and the resulting solid was filtered under a reduced pressure and washed with water to obtain the title compound 4.85 g (yield: 81%).
¹H NMR (CDCl₃) δ: 11.30 (bs, 1H), 7.66 (d, 1H), 7.12 (d, 1H), 4.47 (q, 2H), 1.46 (t, 3H).

<90-2> 2-(thiazol-2-ylamino)-ethanol

Lithium aluminum hydride (1.5 g, 40.4 mmol) was diluted with THF (60 ml), and the compound of <90-1> (2.7 g, 13.5 mmol) diluted with THF (20 ml) was added thereto for 20 min. The solution was stirred at room temperature for 1.5 hours, and the reaction was terminated by adding 1N NaOH. The reacted solution was filtered under a reduced pressure by using celite and washed with ethylacetate. The separated organic layer extracted with ethyl acetate was dried over magnesium sulfate, filtered and distilled under a reduced pressure to obtain the title compound 1.8 g (yield: 92%).
¹H NMR (CDCl₃) δ: 7.10 (d, 1H), 6.49 (d, 1H), 5.71 (bs, 1H), 3.85 (t, 2H), 3.49 (t, 2H).

<90-3> (4-bromo-2-fluoro-phenyl)-{6-nitro-7-[2-(thiazol-2-ylamino)-ethoxy]-quinazolin-4-yl}-amine The procedure of Example <1-6> was repeated except for using the compound of Example <1-5> (300 mg, 0.79 mmol) and the compound of <90-2> (170 mg, 1.2 mmol) to obtain the title compound 100 mg (yield: 25%).
¹H NMR (CDCl₃) δ: 8.86 (s, 1H), 8.64 (s, 1H), 8.37 (t, 1H), 8.05 (s, 1H), 7.75 (bs, 1H), 7.44-7.39 (m, 3H), 7.15 (d, 1H), 6.68 (d, 1H), 4.23 (t, 2H), 4.05 (q, 2H).

<90-4> N⁴-(4-bromo-2-fluoro-phenyl)-7-[2-(thiazol-2-ylamino)-ethoxy]-quinazoline-4,6-diamine The procedure of Example <1-7> was repeated except for using the compound of <90-3> (30 mg, 0.06 mmol) to obtain the title compound 19 mg (yield: 66%).
¹H NMR (CDCl₃+MeOD) δ: 8.36 (s, 1H), 7.79 (t, 1H), 7.47 (s, 1H), 7.36-7.31 (m, 2H), 7.22 (s, 1H), 7.05-7.01 (m, 2H), 6.49 (d, 1H), 4.33 (t, 2H), 3.82 (t, 2H).

<90-5> N-{4-(4-bromo-2-fluoro-phenylamino)-7-[2-(thiazol-2-ylamino)-ethoxy]-quinazolin-6-yl}-acrylamide The procedure of Example <29-5> was repeated except for using the compound of <90-4> (19 mg, 0.04 mmol) to obtain the title compound 5 mg (yield: 24%).
¹H NMR (CDCl₃) δ: 8.66 (s, 1H), 8.32-8.30 (m, 1H), 7.94 (s, 1H), 7.48-7.26 (m, 4H), 7.09 (m, 1H), 6.49-6.25 (m, 2H), 5.79-5.74 (m, 1H), 4.35 (t, 2H), 3.87 (q, 2H).

Example 91

Preparation of N-[4-(4-bromo-2-fluoro-phenylamino)-7-(2-oxo-oxazolidin-5-ylmethoxy)-quinazolin-6-yl]-acrylamide <91-1> 5-[4-(4-bromo-2-fluoro-phenylamino)-6-nitro-quinazolin-7-yloxymethyl]-oxazolidin-2-one The procedure of Example <1-6> was repeated except for using the compound of Example <1-5> (1.0 g, 2.62 mmol) and oxazolidinone (922 mg, 7.87 mmol) to obtain the title compound 546 mg (yield: 44%).

¹H NMR (CDCl₃) δ: 10.24 (s, 1H), 9.20 (s, 1H), 8.55 (s, 1H), 7.67 (t, 2H), 7.30 (t, 3H), 4.98 (s, 1H), 4.57-4.43 (m 2H), 3.63 (t, 1H).

<91-2> 5-[6-amino-4-(4-bromo-2-fluoro-phenylamino)-quinazolin-7-yloxymethyl]-oxazolidin-2-one The procedure of Example <1-7> was repeated except for using the compound of <91-1> (546 mg, 1.14 mmol) to obtain the title compound 420 mg (yield: 82%).
¹H NMR (DMSO-d₆) δ: 9.23 (s, 1H), 8.22 (s, 1H), 7.94-7.52 (m, 3H), 7.41 (d, 1H), 7.33 (s, 1H), 7.13 (s, 1H), 5.33 (s, 2H), 5.01 (s, 1H), 4.31 (s, 2H), 3.67 (t, 1H), 3.43 (t, 1H).

<91-3> N-[4-(4-bromo-2-fluoro-phenylamino)-7-(2-oxo-oxazolidin-5-ylmethoxy)-quinazolin-6-yl]-acrylamide The procedure of Example <29-5> was repeated except for using the compound of <91-2> (120 mg, 0.27 mmol) to obtain the title compound 8.5 mg (yield: 6%).
¹H NMR (CDCl₃+CD₃OD) δ: 8.91 (s, 1H), 8.42 (s, 1H), 7.69 (t, 1H), 7.30 (s, 2H), 7.13 (s, 1H), 6.38 (d, 2H), 5.78 (t, 1H), 5.04 (s, 1H), 4.37-4.26 (m, 2H), 3.49-3.27 (m, 2H), 3.01 (s, 1H).

Example 92

Preparation of thiophene-2-carboxylic acid {2-[6-acryloylamino-4-(4-bromo-2-fluoro-phenylamino)-quinazolin-7-yloxy]-ethyl}-amide The procedure of Example <1-10> was repeated except for using the compound of Example <29-6> (50 mg, 0.11 mmol) and 2-thiophenecarbonylchloride (0.015 ml, 0.13 mmol) to obtain the title compound 15 mg (yield: 24%).
¹H NMR (CDCl₃) δ: 8.98 (s, 1H), 8.43 (s, 1H), 8.08 (t, 1H), 7.73 (t, 1H), 7.55 (d, 1H), 7.41 (d, 1H), 7.32-7.28 (m, 2H), 7.03-6.99 (m, 3H), 6.45 (ab, 1H), 5.83 (ab, 1H), 4.21 (t, 2H), 3.86 (q, 2H).

Example 93

Preparation of morpholine-4-carboxylic acid {2-[6-acryloylamino-4-(4-bromo-2-fluoro-phenylamino)-quinazolin-7-yloxy]-ethyl}-amide The procedure of Example <1-10> was repeated except for using the compound of Example <29-6> (50 mg, 0.11 mmol) and 2-morpholine carbonyl chloride (0.014 ml, 0.12 mmol) to obtain the title compound 13 mg (yield: 20%).
¹H NMR (CDCl₃) δ: 9.23 (s, 2H), 8.66 (s, 1H), 8.32 (t, 1H), 7.59 (d, 1H), 7.57-7.32 (m 2H), 7.17 (s, 1H), 6.83 (ab, 1H), 6.53 (dd, 1H), 5.79 (dd, 1H), 4.87 (t, 1H), 4.21 (t, 2H), 3.84 (q, 2H), 3.69 (t, 4H), 3.38 (t, 4H).

Example 94

Preparation of piperazine-1-carboxylic acid {2-[6-acryloylamino-4-(4-bromo-2-fluoro-phenylamino)-quinazolin-7-yloxy]-ethyl}-amide <94-1> piperazine-1-carboxylic acid t-butylester The procedure of Example <1-1> was repeated except for using piperazine (1.7 g, 19.7 mmol) to obtain the title compound 1.5 g (yield: 41%).
¹H NMR (CDCl₃) δ: 3.08 (t, 4H), 2.81 (t, 4H), 1.40 (s, 9H).

<94-2> 4-chlorocarbonyl-piperazine-1-carboxylic acid t-butylester

The compound of <94-1> (500 mg, 2.7 mmol) was diluted with dichloromethane (1.35 ml), and pyridine (0.40 ml, 5.4 mmol) was added thereto. The reaction temperature was cooled to 0° C., triphosgene (319 mg, 1.1 mmol) diluted with dichloromethane (2.75 ml) and 0.1N HCl aqueous solution (2.7 ml) were sequentially added thereto. The solution was stirred at room temperature for 30 min, and the resulting residue was dried over magnesium sulfate, filtered and distilled under a reduced pressure to obtain the title compound 494 mg (yield: 74%).
¹H NMR (CDCl₃) δ: 3.89 (ab, 3H), 3.73-3.64 (m, 4H), 3.47-3.44 (m, 1H), 1.70 (s, 9H).

<94-3> 4-{2-[6-acryloylamino-4-(4-bromo-2-fluoro-phenylamino)-quinazolin-7-yloxy]-ethylcarbamoyl}-piperazine-1-carboxylic acid t-butylester The procedure of Example <1-10> was repeated except for using the compound of Example <29-6> (50 mg, 0.11 mmol) and the compound of <94-2> (33.4 mg, 0.134 mmol) to obtain the title compound 25 mg (yield: 34%).
¹H NMR (CDCl₃) δ: 9.23 (s, 1H), 9.22 (s, 1H), 8.65 (s, 1H), 8.33 (t, 1H), 7.71 (d, 1H), 7.54-7.36 (m, 1H), 7.36-7.33 (m, 2H), 7.14 (s, 1H), 6.84 (dd, 1H), 6.53 (ab, 1H), 5.82 (ab, 1H), 4.19 (t, 2H), 3.83 (q, 2H), 3.42 (t, 4H), 3.22 (t, 4H).

<94-4> piperazine-1-carboxylic acid {2-[6-acryloylamino-4-(4-bromo-2-fluoro-phenylamino)-quinazolin-7-yloxy]-ethyl}-amide The procedure of Example <1-9> was repeated except for using the compound of <94-3> (24 mg, 0.04 mmol) to obtain the title compound 20 mg (yield: 98%).
¹H NMR (CDCl₃) δ: 9.29 (s, 1H), 9.24 (s, 1H), 8.66 (s, 1H), 8.36 (t, 1H), 7.72 (m, 1H), 7.55-7.52 (m, 1H), 7.38-7.34 (m, 2H), 7.16 (s, 1H), 6.88-6.82 (m, 1H), 6.50 (dd, 1H), 5.81 (dd 1H), 4.20 (t, 2H), 3.83 (q, 2H), 3.39 (t, 4H), 2.86 (t, 4H).

Example 95

Preparation of 4-acetyl-piperazine-1-carboxylic acid {2-[6-acryloylamino-4-(4-bromo-2-fluoro-phenylamino)-quinazolin-7-yloxy]-ethyl}-amide The procedure of Example <1-10> was repeated except for using the compound of Example 94 (17 mg, 0.03 mmol) to obtain the title compound 4.2 mg (yield: 23%).
¹H NMR (CDCl₃) δ: 9.17 (s, 2H), 8.60 (s, 1H), 8.30 (t, 1H), 7.31-7.28 (m, 2H), 7.10 (s, 1H), 6.78 (dd, 1H), 6.49 (d, 1H), 5.06 (t, 1H), 4.16 (t, 2H), 3.79 (d, 2H), 3.59 (d, 2H), 3.46 (d, 4H), 3.33 (t, 2H), 2.05 (s, 3H), 1.98 (d, 1H).

Example 96

Preparation of 4-methyl-piperazine-1-carboxylic acid {2-[6-acryloylamino-4-(4-bromo-2-fluoro-phenylamino)-quinazolin-7-yloxy]-ethyl}-amide The procedure of Example 58 was repeated except for using the compound of Example 94 (30 mg, 0.05 mmol) to obtain the title compound 12 mg (yield: 39%).

¹H NMR (CDCl₃+CD₃OD) δ: 9.29 (s, 1H), 8.45 (s, 1H), 7.77 (t, 1H), 7.33 (d, 1H), 7.30 (s, 1H), 7.05 (s, 1H), 6.76 (ab, 1H), +6.45 (dd, 1H), 6.18 (s, 1H), 5.77 (dd, 1H), 4.13 (t, 2H), 3.66 (t, 2H), 2.31 (s, 4H), 2.24 (s, 4H), 1.16 (s, 3H).

Example 97

Preparation of pyrrolidine-2-carboxylic acid {2-[6-acryloylamino-4-(4-bromo-2-fluoro-phenylamino)-quinazolin-7-yloxy]-ethyl}-amide <97-1> 2-{2-[6-acryloylamino-4-(4-bromo-2-fluoro-phenylamino)-quinazolin-7-yloxy]-ethylcarbamoyl}-pyrrolidine-1-carboxylic acid t-butylester The procedure of Example 44 was repeated except for using the compound of Example <29-6> (500 mg, 1.12 mmol) and pyrrolidine-1,2-dicarboxylic acid 1-t-butylester (482 mg, 2.24 mmol) to obtain the title compound 470 mg (yield: 65%).
¹H NMR (CDCl₃) δ: 9.25 (s, 1H), 9.14 (s, 1H), 8.68 (s, 1H), 8.39 (t, 1H), 7.71 (s, 1H), 7.38 (d, 1H), 7.34 (s, 1H), 7.16 (s, 1H), 6.88 (ab, 1H), 6.56 (dd, 1H), 5.85 (dd, 1H), 4.50 (s, 1H), 4.33 (s, 1H), 3.84 (br s, 2H), 3.37 (br s, 2H), 1.89 (s, 2H), 1.80 (s, 2H), 1.26 (s, 9H).

<97-2> pyrrolidine-2-carboxylic acid {2-[6-acryloylamino-4-(4-bromo-2-fluoro-phenylamino)-quinazolin-7-yloxy]-ethyl}-amide The procedure of Example <1-9> was repeated except for using the compound of <97-1> (470 mg, 0.73 mmol) to obtain the title compound 390 mg (yield: 98%).
¹H NMR (CDCl₃) δ: 9.28 (s, 1H), 9.11 (s, 1H), 8.69 (s, 1H), 8.39 (t, 1H), 8.23 (t, 1H), 7.62 (s, 1H), 7.38 (d, 1H), 7.36 (s, 1H), 7.17 (s, 1H), 6.96 (ab, 1H), 6.56 (dd, 1H), 5.87 (dd, 1H), 4.23 (m, 1H), 4.05 (t, 1H), 3.92-3.77 (m, 3H), 3.06-3.03 (m, 1H), 2.88-2.85 (m, 1H), 2.17 (m, 1H), 1.72-1.54 (m, 1H).

Example 98

Preparation of 1-methyl-pyrrolidine-2-carboxylic acid {2-[6-acryloylamino-4-(4-bromo-2-fluoro-phenylamino)-quinazolin-7-yloxy]-ethyl}-amide The procedure of Example <74-3> was repeated except for using the compound of Example 97 (30 mg, 0.006 mmol) to obtain the title compound 16 mg (yield: 52%).
¹H NMR (CDCl₃) δ: 9.23 (s, 1H), 9.01 (s, 1H), 8.64 (s, 1H), 8.32 (t, 1H), 7.93 (s, 1H), 7.35 (d, 1H), 7.32 (s, 1H), 7.16 (s, 1H), 6.89 (ab, 1H), 6.53 (dd, 1H), 5.83 (dd, 1H), 4.22-4.17 (m, 2H), 3.92-3.92 (m, 1H), 3.74-3.30 (m, 1H), 3.10 (t, 1H), 3.01 (s, 1H), 2.35 (s, 3H), 1.85 (s, 2H), 1.25 (s, 2H).

Example 99

Preparation of 1H-pyrrole-2-carboxylic acid {2-[6-acryloylamino-4-(4-bromo-2-fluoro-phenylamino)-quinazolin-7-yloxy]-ethyl}-amide The procedure of Example 44 was repeated except for using the compound of Example <20-6> (50 mg, 0.11 mmol) and pyrrole-2-carboxylic acid (25 mg, 0.22 mmol) to obtain the title compound 25 mg (yield: 33%).
¹H NMR (DMSO-d₆) δ: 11.5 (s, 1H), 9.78 (s, 1H), 9.42 (s, 1H), 9.09 (s, 1H), 8.39-8.32 (m, 2H), 7.63 (d, 1H), 7.47 (s, 2H), 7.32 (s, 1H), 6.89 (s, 2H), 6.80 (s, 1H), 6.35 (d, 1H), 6.10 (s, 1H), 5.87 (d, 1H), 4.57 (s, 2H), 3.76 (s, 2H).

Example 100

Preparation of 1-methyl-pyrrolidine-2-carboxylic acid {2-[6-acryloylamino-4-(4-bromo-2-fluoro-phenylamino)-quinazolin-7-yloxy]-ethyl}-amide The procedure of Example 44 was repeated except for using the compound of Example <29-6> (30 mg, 0.07 mmol) and 1-methyl-pyrrolidine-2-carboxylic acid (17 mg, 0.13 mmol) to obtain the title compound 23 mg (yield: 61%).
¹H NMR (CDCl₃) δ: 9.24 (s, 1H), 9.00 (s, 1H), 8.65 (s, 1H), 8.31 (t, 1H), 7.83 (t, 1H), 7.64 (s, 1H), 7.35 (d, 1H), 7.32 (s, 1H), 7.16 (s, 1H), 6.89 (ab, 1H), 6.54 (dd, 1H), 5.84 (dd, 1H), 4.24-4.19 (m, 2H), 3.95-3.92 (m, 1H), 3.74 (m, 1H), 3.07 (t, 1H), 2.98-2.93 (m 1H), 2.32 (s, 3H), 1.85 (s, 2H), 1.26 (s, 2H).

Example 101

Preparation of N-{4-(4-bromo-2-fluoro-phenylamino)-7-[2-(2-piperidin-1-yl-acetylamino)-ethoxy]-quinazolin-6-yl}-acrylamide <101-1> N-[7-[2-(2-bromo-acetylamino)-ethoxy]-4-(4-bromo-2-fluoro-phenylamino)-quinazolin-6-yl]-acrylamide The procedure of Example 2 was repeated except for using the compound of Example <29-6> (8.5 g, 19.04 mmol) and bromoacetic acid (7.9 g, 57.14 mmol) to obtain the title compound 6.9 g (yield: 64%).
¹H NMR (CDCl₃) δ: 8.75 (s, 1H), 8.57 (s, 1H), 8.30 (t, 1H), 7.79 (bs, 1H), 7.37-7.34 (m, 2H), 7.25 (s, 1H), 6.76-6.70 (m, 1H), 6.53-6.47 (m, 1H), 5.85-5.81 (m, 1H), 5.12 (bs, 1H), 4.27 (t, 2H), 3.65 (q, 2H), 1.58-1.55 (m, 2H).

<101-2> N-{4-(4-bromo-2-fluoro-phenylamino)-7-[2-(2-piperidin-1-yl-acetylamino)-ethoxy]-quinazolin-6-yl}-acrylamide The procedure of Example 55 was repeated except for using the compound of <101-1> (150 mg, 0.26 mmol) and piperidine (27 mg, 0.32 mmol) to obtain the title compound 45 mg (yield: 30%).
¹H NMR (CDCl₃+CD₃OD) δ: 9.06 (s, 1H), 8.48 (s, 1H), 7.74 (t, 1H), 7.38 (t, 2H), 7.14 (s, 1H), 6.88-6.79 (m, 1H), 6.54-6.49 (m, 1H), 5.90-5.86 (m, 1H), 4.28 (t, 2H), 3.86 (q, 2H), 3.02 (s, 2H), 2.43 (m, 4H), 1.56-1.55 (m, 4H), 1.44-1.42 (m, 2H).

Example 102

Preparation of N-(4-(4-bromo-2-fluoro-phenylamino)-7-{2-[2-(4-methyl-piperazin-1-yl)-acetylamino]-ethoxy}-quinazolin-6-yl)-acrylamide The procedure of Example 55 was repeated except for using the compound of Example <101-1> (150 mg, 0.26 mmol) and 4-methylpiperazine (32 mg, 0.32 mmol) to obtain the title compound 21 mg (yield: 14%).
¹H NMR (CDCl₃) δ: 9.23 (s, 1H), 8.97 (bs, 1H), 8.64 (s, 1H), 8.29 (t, 1H), 7.67-7.65 (m, 2H), 7.65-7.32 (m, 2H), 7.16 (s, 1H), 6.85-6.79 (m, 1H), 6.56-6.50 (m, 1H), 5.85-5.82 (m, 1H), 4.22 (t, 2H), 3.86 (q, 2H), 3.08 (s, 2H), 2.56 (m, 4H), 2.45 (m, 4H), 2.28 (s, 3H).

Example 103

Preparation of N-{4-(4-bromo-2-fluoro-phenylamino)-7-[2-(2-morpholin-4-yl-acetylamino)-ethoxy]-quinazolin-6-yl}-acrylamide The procedure of Example 55 was repeated except for using the compound of Example <101-1> (150 mg, 0.26 mmol) and morpholine (28 mg, 0.32 mmol) to obtain the title compound 25 mg (yield: 17%).

$^1$H NMR (CDCl$_3$) δ: 9.23 (s, 1H), 8.97 (s, 1H), 8.66 (s, 1H), 8.30 (t, 1H), 7.68-7.61 (m, 2H), 7.36-7.33 (m, 3H), 7.17 (s, 1H), 6.89-6.80 (m, 1H), 6.57-6.51 (m, 1H), 5.87-5.83 (m, 1H), 4.24 (t, 2H), 3.88 (q, 2H), 3.71 (t, 4H), 3.09 (s, 2H), 2.53 (t, 4H).

Example 104

Preparation of N-{4-(4-bromo-2-fluoro-phenylamino)-7-[2-(3-piperidin-1-yl-propionylamino)-ethoxy]-quinazolin-6-yl}-acrylamide The procedure of Example 44 was repeated except for using the compound of Example <29-6> (50 mg, 0.11 mmol) and 1-piperidine propionic acid (21 mg, 0.13 mmol) to obtain the title compound 36 mg (yield: 56%).

$^1$H NMR (CDCl$_3$) δ: 9.25 (t, 1H), 9.22 (s, 1H), 9.03 (s, 1H), 8.64 (s, 1H), 8.31 (t, 1H), 7.61 (s, 1H), 7.35-7.30 (m, 1H), 7.14 (s, 1H), 6.86 (ab, 1H), 6.51 (dd, 1H), 5.81 (dd, 1H), 4.18 (t, 2H), 3.79 (q, 2H), 2.55 (t, 2H), 2.41 (t, 6H), 1.50 (t, 4H).

Example 105

Preparation of 1-acetyl-pyrrolidine-2-carboxylic acid {2-[6-acryloylamino-4-(4-bromo-2-fluoro-phenylamino)-quinazolin-7-yloxy]-ethyl}-amide The procedure of Example <1-10> was repeated except for using the compound of Example 97 (60 mg, 0.11 mmol) to obtain the title compound 63 mg (yield: 97%).

$^1$H NMR (CDCl$_3$) δ: 9.12 (s, 1H), 9.00 (s, 1H), 8.58 (s, 1H), 8.15-8.09 (m, 2H), 7.98 (s, 1H), 7.29 (s, 1H), 7.26 (s, 1H), 7.07 (s, 1H), 6.87 (ab, 1H), 6.51 (dd, 1H), 5.80 (dd, 1H), 4.59 (dd, 1H), 4.15 (s, 2H), 3.75-3.65 (m, 2H), 3.54 (t, 1H), 3.45 (q, 2H), 2.40 (s, 1H), 1.90 (t, 1H).

Example 106

Preparation of 1-propionyl-pyrrolidine-2-carboxylic acid {2-[6-acryloylamino-4-(4-bromo-2-fluoro-phenylamino)-quinazolin-7-yloxy]-ethyl}-amide The procedure of Example <1-10> was repeated except for using the compound of Example 97 (50 mg, 0.09 mmol) and propionic acid (6.7 mg, 0.09 mmol) to obtain the title compound 45 mg (yield: 82%).

$^1$H NMR (CDCl$_3$) δ: 9.16 (s, 1H), 9.04 (s, 1H), 8.62 (s, 1H), 8.22 (t, 1H), 8.10 (t, 1H), 7.33-7.28 (m, 3H), 7.12 (s, 1H), 6.88 (ab, 1H), 6.53 (dd, 1H), 5.82 (dd, 1H), 4.62 (dd, 1H), 4.19-3.80 (m, 2H), 3.79 (br s, 1H), 3.69 (br s, 1H), 3.49-3.38 (m, 2H), 2.48-2.43 (m, 1H), 2.27 (q, 2H), 2.04-1.98 (m, 2H), 1.25 (s, 2H), 1.02 (t, 3H).

Example 107

Preparation of N-{4-(4-bromo-2-fluoro-phenylamino)-7-[2-(2-pyrrolidin-1-yl-acetylamino)-ethoxy]-quinazolin-6-yl}-acrylamide <107-1> N-{2-[4-(4-bromo-2-fluoro-phenylamino)-6-nitro-quinazolin-7-yloxy]-ethyl}-2-pyrrolidin-1-yl-acetamide The procedure of Example 55 was repeated except for using the compound of Example <101-1> (100 mg, 0.18 mmol) and pyrrolidine (0.018 ml, 0.22 mmol) to obtain the title compound 97 mg (yield: 98%), $^1$H NMR (CDCl$_3$) δ: 8.79 (s, 1H), 8.50 (s, 1H), 8.40 (t, 1H), 7.77 (s, 1H), 7.56 (s, 1H), 7.41 (t, 2H), 7.38 (d, 1H), 4.34 (t, 2H), 3.82 (q, 2H), 3.20 (s, 2H), 2.61 (s, 4H), 1.82 (s, 4H).

<107-2> N-{2-[6-amino-4-(4-bromo-2-fluoro-phenylamino)-quinazolin-7-yloxy]-ethyl}-2-pyrrolidin-1-yl-acetamide The procedure of Example <1-7> was repeated except for using the compound of <107-1> (106 mg, 0.20 mmol) to obtain the title compound 95 mg (yield: 94%).

$^1$H NMR (CDCl$_3$) δ: 8.53 (t, 2H), 7.60 (s, 1H), 7.31-7.26 (m, 4H), 7.13 (s, 1H), 6.91 (s, 1H), 4.22 (t, 2H), 3.79 (q, 2H), 3.19 (s, 2H), 2.58 (s, 4H), 1.76 (s, 4H).

<107-3> N-{4-(4-bromo-2-fluoro-phenylamino)-7-[2-(2-pyrrolidin-1-yl-acetylamino)-ethoxy]-quinazolin-6-yl}-acrylamide The procedure of Example <1-10> was repeated except for using the compound of <107-2> (95 mg, 0.19 mmol) to obtain the title compound 27.7 mg (yield: 26%).

$^1$H NMR (CDCl$_3$) δ: 9.25 (s, 1H), 8.99 (s, 1H), 8.67 (s, 1H), 8.36 (t, 1H), 7.66 (t, 1H), 7.58 (s, 1H), 7.37-7.34 (m, 2H), 7.17 (s, 1H), 6.87 (dd, 1H), 6.54 (dd, 1H), 5.84 (dd, 1H), 4.24 (t, 2H), 3.87 (q, 2H), 3.23 (s, 2H), 2.59 (s, 4H), 1.79 (s, 4H).

Example 108

Preparation of N-{4-(4-bromo-2-fluoro-phenylamino)-7-[2-(2-2,5-dihydro-pyrrol-1-yl-acetylamino)-ethoxy]-quinazolin-6-yl}-acrylamide <108-1> N-{2-[4-(4-bromo-2-fluoro-phenylamino)-6-nitro-quinazolin-7-yloxy]-ethyl}-2-(2,5-dihydro-pyrrol-1-yl)-acetamide The procedure of Example 55 was repeated except for using the compound of Example <101-1> (100 mg, 0.18 mmol) and 3-pyrroline (0.017 ml, 0.22 mmol) to obtain the title compound 76 mg (yield: 78%).

$^1$H NMR (CDCl$_3$) δ: 8.72 (s, 2H), 8.01 (s, 4H), 7.74 (t, 1H), 7.36 (d, 1H), 5.75 (s, 2H), 4.33 (t, 2H), 3.80 (q, 2H), 3.59 (s, 4H), 3.35 (s, 2H).

<108-2> N-{2-[4-(4-bromo-2-fluoro-phenylamino)-6-nitro-quinazolin-7-yloxy]-ethyl}-2-(2,5-dihydro-pyrrol-1-yl)-acetamide The procedure of Example <1-7> was repeated except for using the compound of <108-1> (76 mg, 0.14 mmol) to obtain the title compound 65 mg (yield: 91%).

¹H NMR (CDCl₃) δ: 8.57 (s, 1H), 7.56 (t, 1H), 7.32 (s, 1H), 7.29 (d, 1H), 7.14 (s, 1H), 6.90 (s, 1H), 5.73 (s, 2H), 4.23 (t, 2H), 3.81 (q, 2H), 3.56 (s, 4H), 3.36 (s, 2H).

<108-3> N-{4-(4-bromo-2-fluoro-phenylamino)-7-[2-(2-2,5-dihydro-pyrrol-1-yl-acetylamino)-ethoxy]-quinazolin-6-yl}-acrylamide The procedure of Example <29-5> was repeated except for using the compound of <108-2> (65 mg, 0.13 mmol) to obtain the title compound 16 mg (yield: 22%).
¹H NMR (CDCl₃) δ: 9.23 (s, 1H), 8.98 (s, 1H), 8.66 (s, 1H), 8.32 (t, 1H), 7.71-7.66 (m, 2H), 7.37-7.34 (m, 1H), 7.33 (d, 1H), 7.17 (s, 1H), 6.90-6.81 (m, 1H), 6.53 (dd, 1H), 5.83 (dd, 1H), 5.75 (s, 1H), 4.23 (t, 2H), 3.87 (q, 2H), 3.56 (s, 4H), 3.40 (s, 2H).

Example 109

Preparation of N-[4-(4-bromo-2-fluoro-phenylamino)-7-(4,5-dihydro-oxazol-2-ylmethoxy)-quinazolin-6-yl]-acrylamide <109-1> (4,5-dihydro-oxazol-2-yl)-methanol Glycolic acid (1.9 g, 25 mmol) and 2-aminoethanol (1.5 ml, 25 mmol) were diluted with xylene (30 ml), and the solution was refluxed and stirred by using Dean-Stark-trap for 6 hours. The reaction temperature was cooled to room temperature, the solution was filtered under a reduced pressure to remove the solvent, and the impure residue was subjected to column chromatography to obtain the title compound 2.5 g (yield: 99%).
¹H NMR (MeOD, 300 MHz) δ: 3.97 (s, 2H), 3.62 (t, 2H), 3.37 (t, 2H).

<109-2> (4-bromo-2-fluoro-phenyl)-[7-(4,5-dihydro-oxazol-2-ylmethoxy)-6-nitro-quinazolin-4-yl]-amine The procedure of Example <1-6> was repeated except for using the compound of Example <1-5> (590 mg, 1.42 mmol) and the compound of <109-1> (430 mg, 4.25 mmol) to obtain the title compound 452 mg (yield: 69%).
¹H NMR (DMSO-d₆, 300 MHz) δ: 9.38 (brs, 1H), 8.29 (s, 1H), 8.00 (s, 1H), 7.64 (d, J=9.7 Hz, 1H), 7.45 (s, 1H), 6.99 (s, 1H), 3.70 (t, 2H), 3.44 (t, 2H), 3.29 (s, 2H).

<109-3> N⁴-(4-bromo-2-fluoro-phenyl)-7-(4,5-dihydro-oxazol-2-ylmethoxy)-quinazoline-4,6-diamine The procedure of Example <1-7> was repeated except for using the compound of <109-2> (200 mg, 0.43 mmol) to obtain the title compound 118 mg (yield: 63%).
¹H NMR (DMSO-d₆, 300 MHz) δ: 8.86 (brs, 1H), 8.14 (s, 1H), 7.63 (t, 1H), 7.56 (d, 1H), 7.39 (d, 1H), 7.19 (s, 1H), 6.60 (s, 1H), 3.68 (t, 2H), 3.29 (s, 2H), 3.28 (t, 2H).

<109-4> N-[4-(4-bromo-2-fluoro-phenylamino)-7-(4,5-dihydro-oxazol-2-ylmethoxy)-quinazolin-6-yl]-acrylamide The procedure of Example <29-5> was repeated except for using the compound of <109-3> (50 mg, 0.12 mmol) to obtain the title compound 10 mg (yield: 17%).
¹H NMR (MeOD, 300 MHz) δ: 8.28 (s, 1H), 8.20 (s, 1H), 7.57 (t, 1H), 7.43 (d, 1H), 7.38 (d, 1H), 6.85 (s, 1H), 6.53 (d, 1H), 6.41 (dd, 1H), 5.84 (d, 1H), 3.82 (t, 2H), 3.41 (t, 2H), 3.29 (s, 2H).

Example 110

Preparation of N-[7-[2-(2-azetidin-1-yl-acetylamino)-ethoxy]-4-(4-bromo-2-fluoro-phenylamino)-quinazolin-6-yl]-acrylamide <110-1> 2-azetidin-1-yl-N-{2-[4-(4-bromo-2-fluoro-phenylamino)-6-nitro-quinazolin-7-yloxy]-ethyl}-acetamide The procedure of Example 55 was repeated except for using the compound of Example <101-1> (80 mg, 0.15 mmol) and azetidine (0.012 ml, 0.18 mmol) to obtain the title compound 76 mg (yield: 99%).
¹H NMR (CDCl₃) δ: 8.79 (s, 1H), 8.63 (s, 1H), 7.88 (d, 1H), 7.35 (d, 1H), 7.31 (s, 2H), 4.27 (t, 2H), 3.73 (t, 2H), 3.29 (t, 4H), 3.09 (s, 2H), 2.11-2.04 (m, 2H).

<110-2> N-{2-[6-amino-4-(4-bromo-2-fluoro-phenylamino)-quinazolin-7-yloxy]-ethyl}-2-azetidin-1-yl-acetamide The procedure of Example <1-7> was repeated except for using the compound of <110-1> (76 mg, 0.15 mmol) to obtain the title compound 70 mg (yield: 97%).
¹H NMR (CDCl₃) δ: 8.57 (s, 2H), 7.47 (t, 1H), 7.32 (s, 1H), 7.29 (s, 1H), 7.13 (s, 1H), 6.91 (s, 1H), 4.19 (t, 2H), 3.78 (q, 2H), 3.29 (t, 4H), 3.14 (s, 2H), 2.05 (m 2H).

<110-3> N-[7-[2-(2-azetidin-1-yl-acetylamino)-ethoxy]-4-(4-bromo-2-fluoro-phenylamino)-quinazolin-6-yl]-acrylamide The procedure of Example <29-5> was repeated except for using the compound of <110-2> (70 mg, 0.14 mmol) to obtain the title compound 7 mg (yield: 9%).
¹H NMR (CDCl₃) δ: 9.18 (s, 1H), 8.86 (s, 1H), 8.65 (s, 1H), 8.31 (t, 1H), 7.82 (s, 1H), 7.36-7.32 (m, 1H), 7.15 (s, 1H), 6.83-6.77 (m, 1H), 6.56 (d, 2H), 6.36 (d, 1H), 5.84-5.78 (m, 2H), 4.20 (t, 2H), 4.07 (s, 1H), 3.77 (s, 2H), 3.63 (t 2H), 3.48 (t, 2H).

Example 111

Preparation of N-[7-(2-acetylamino-ethoxy)-4-(3-chloro-4-fluoro-phenylamino)-quinazolin-6-yl]-acrylamide <111-1> {2-[4-(3-chloro-4-fluoro-phenylamino)-6-nitro-quinazolin-7-yloxy]-ethyl}-carbamic acid t-butylester The procedure of Example <1-5> was repeated except for using the compound of Example <1-4> (1.2 g, 5.24 mmol) and 4-chloro-2-fluoro-aniline (763 mg, 5.24 mmol) to obtain (3-chloro-4-fluoro-phenyl)-(7-fluoro-6-nitro-quinazolin-4-yl)-amine 1.5 g (yield: 85%), and then the procedure of Example <1-6> was repeated without any purification to obtain the title compound 1 g (yield: 70%).
¹H NMR (DMSO-d₆) δ: 10.15 (s, 1H), 9.19 (s, 1H), 8.97 (s, 1H), 8.66 (s, 1H), 8.16-8.13 (m, 1H), 7.81-7.76 (m, 1H), 7.48 (s, 1H), 6.94 (t, 1H), 4.30 (t, 2H), 3.35 (q, 2H), 1.36 (s, 9H).

<111-2> [7-(2-amino-ethoxy)-6-nitro-quinazolin-4-yl]-(3-chloro-4-fluoro-phenyl)-amine The procedure of Example <1-9> was repeated except for using the compound of <111-1> (1 g, 2.09 mmol) to obtain the title compound 270 mg (yield: 34%).
$^1$H NMR (DMSO-$d_6$) δ: 9.22 (s, 1H), 8.66 (s, 1H), 8.16-8.13 (m, 1H), 7.81-7.76 (m, 1H), 7.49-7.43 (m, 2H), 4.26 (t, 2H), 3.32 (q, 2H).

<111-3> N-{2-[4-(3-chloro-4-fluoro-phenylamino)-6-nitro-quinazolin-7-yloxy]-ethyl}-acetamide The procedure of Example <1-10> was repeated except for using the compound of <111-2> (250 mg, 0.66 mmol) to obtain the title compound 250 mg (yield: 98%).
$^1$H NMR (DMSO-$d_6$) δ: 10.15 (s, 1H), 9.20 (s, 1H), 8.66 (s, 1H), 8.16-8.13 (m, 1H), 8.06 (t, 1H), 7.81-7.78 (m, 1H), 7.49-7.42 (m, 2H), 4.31 (t, 2H), 3.45 (q, 2H), 1.81 (s, 3H).

<111-4> N-{2-[6-amino-4-(3-chloro-4-fluoro-phenylamino)-quinazolin-7-yloxy]-ethyl}-acetamide The procedure of Example <1-7> was repeated except for using the compound of <111-3> (250 mg, 0.66 mmol) to obtain the title compound 70 mg (yield: 30%).
$^1$H NMR (DMSO-$d_6$) δ: 9.83 (bs, 1H), 8.45 (s, 1H), 8.25 (t, 1H), 8.12-8.09 (m, 1H), 7.76-7.71 (m, 1H), 7.44-7.38 (m, 2H), 7.06 (s, 1H), 5.68 (bs, 2H), 4.09 (t, 2H), 3.52 (q, 2H), 1.84 (s, 3H).

<111-5> N-[7-(2-acetylamino-ethoxy)-4-(3-chloro-4-fluoro-phenylamino)-quinazolin-6-yl]-acrylamide The procedure of Example <29-5> was repeated except for using the compound of <111-4> (70 mg, 0.18 mmol) to obtain the title compound III mg (yield: 14%).
$^1$H NMR (DMSO-$d_6$) δ: 9.78 (bs, 1H), 9.29 (s, 1H), 8.93 (s, 1H), 8.39 (s, 1H), 8.09 (t, 1H), 7.96-7.93 (m, 1H), 7.64-7.61 (m, 1H), 7.27 (t, 1H), 7.12 (s, 1H), 6.73-6.64 (m, 1H), 6.24-6.18 (m, 1H), 5.74-5.70 (m, 1H), 4.07 (t, 2H), 3.42 (q, 2H), 1.74 (s, 3H).

Example 112

Preparation of N-[7-(2-acetylamino-ethoxy)-4-(4-chloro-2-fluoro-phenylamino)-quinazolin-6-yl]-acrylamide <112-1> (4-chloro-2-fluoro-phenyl)-(7-fluoro-6-nitro-quinazolin-4-yl)-amine The procedure of Example <1-5> was repeated except for using the compound of Example <1-4> (3 g, 11.3 mmol) and 4-chloro-2-fluoro-aniline (1.97 g, 13.6 mmol) to obtain the title compound 3 g (yield: 79%).
$^1$H NMR (DMSO-$d_6$) δ: 8.60 (bs, 1H), 8.32 (s, 1H), 7.86-7.77 (m, 2H), 7.62-7.57 (m, 2H), 7.39-7.37 (m, 1H).

<112-2> {2-[4-(4-chloro-2-fluoro-phenylamino)-6-nitro-quinazolin-7-yloxy]-ethyl}-carbamic acid t-butylester The procedure of Example <1-6> was repeated except for using the compound of <112-1> (2 g, 5.94 mmol) to obtain the title compound 450 mg (yield: 16%).
$^1$H NMR (CDCl$_3$) δ: 8.77 (s, 1H), 8.56 (s, 1H), 8.37 (t, 1H), 7.69 (bs, 1H), 7.40 (s, 1H), 7.28-7.21 (m, 2H), 5.13 (bs, 1H), 4.29 (t, 2H), 3.70 (q, 2H), 1.45 (s, 9H).

<112-3> [7-(2-amino-ethoxy)-6-nitro-quinazolin-4-yl]-(4-chloro-2-fluoro-phenyl)-amine The procedure of Example <1-9> was repeated except for using the compound of <112-2> (450 mg, 0.94 mmol) to obtain the title compound 355 mg (yield: 99%).
$^1$H NMR (CDCl$_3$+MeOD) δ: 8.86 (s, 1H), 8.64 (s, 1H), 7.87 (t, 1H), 7.35 (s, 1H), 7.26-7.21 (m, 2H), 4.30 (t, 2H), 3.40 (q, 2H).

<112-4> N-{2-[4-(4-chloro-2-fluoro-phenylamino)-6-nitro-quinazolin-7-yloxy]-ethyl}-acetamide The procedure of Example <1-10> was repeated except for using the compound of <112-3> (355 mg, 0.94 mmol) to obtain the title compound 300 mg (yield: 75%).
$^1$H NMR (CDCl$_3$+MeOD) δ: 8.95 (s, 1H), 8.60 (s, 1H), 7.73 (t, 1H), 7.35 (s, 1H), 7.25-7.22 (m, 2H), 7.15 (bs, 1H), 4.33 (t, 2H), 3.74 (q, 2H), 2.03 (s, 3H).

<112-5> N-{2-[6-amino-4-(4-chloro-2-fluoro-phenylamino)-quinazolin-7-yloxy]-ethyl}-acetamide The procedure of Example <1-7> was repeated except for using the compound of <112-4> (150 mg, 0.36 mmol) to obtain the title compound 115 mg (yield: 82%).
$^1$H NMR (CDCl$_3$+MeOD) δ: 9.17 (bs, 1H), 8.22-8.20 (m, 2H), 7.60 (t, 1H), 7.49-7.45 (m, 1H), 7.29-7.27 (m, 2H), 7.02 (s, 1H), 5.49 (bs, 2H), 4.08 (t, 2H), 3.51 (q, 2H), 1.85 (s, 3H).

<112-6> N-[7-(2-acetylamino-ethoxy)-4-(4-chloro-2-fluoro-phenylamino)-quinazolin-6-yl]-acrylamide The procedure of Example <29-5> was repeated except for using the compound of <112-5> (32 mg, 0.35 mmol) to obtain the title compound 8 mg (yield: 6%).
$^1$H NMR (DMSO-$d_6$) δ: 9.59 (bs, 1H), 9.18 (s, 1H), 8.86 (s, 1H), 8.17 (s, 1H), 8.02 (t, 1H), 7.34-7.28 (m, 2H), 7.11-7.03 (m, 2H), 6.66-6.57 (m, 1H), 6.16-6.10 (m, 1H), 5.66-5.62 (m, 1H), 4.00 (t, 2H), 3.34 (q, 2H), 1.67 (s, 3H).

Example 113

Preparation of N-[7-(2-acetylamino-ethoxy)-4-(4-chloro-2-chloro-phenylamino)-quinazolin-6-yl]-acrylamide <113-1> (4-chloro-2-chloro-phenyl)-(7-fluoro-6-nitro-quinazolin-4-yl)-amine The procedure of Example <1-6> was repeated except for using the compound of Example <1-4> (1 g, 3.8 mmol) and 4-chloro-2-chloro-aniline (674 mg, 4.1 mmol) to obtain the title compound 1.1 g (yield: 82%).
$^1$H NMR (DMSO-$d_6$) δ: 9.36 (bs, 1H), 8.56 (d, 1H), 8.38 (bs, 1H), 8.20 (s, 1H), 7.73-7.60 (m, 2H), 7.25 (s, 1H).

<113-2> {2-[4-(4-chloro-2-chloro-phenylamino)-6-nitro-quinazolin-7-yloxy]-ethyl}-carbamic acid t-butylester The procedure of Example <1-6> was repeated except for using the compound of <113-1> (1.1 g, 3.11 mmol) to obtain the title compound 570 mg (yield: 37%).

¹H NMR (CDCl₃) δ: 8.80 (s, 1H), 8.60 (d, 1H), 8.49 (s, 1H), 7.89 (bs, 1H), 7.51 (s, 1H), 7.42 (s, 1H), 7.39-7.35 (m, 1H), 5.10 (bs, 1H), 4.31 (t, 2H), 3.67 (q, 2H), 1.46 (s, 9H).

<113-3> [7-(2-amino-ethoxy)-6-nitro-quinazolin-4-yl]-(4-chloro-2-chloro-phenyl)-amine The procedure of Example <1-9> was repeated except for using the compound of <113-2> (570 mg, 1.15 mmol) to obtain the title compound 380 mg (yield: 83%).
¹H NMR (CDCl₃+MeOD) δ: 8.88 (s, 1H), 8.62 (s, 1H), 7.84 (t, 1H), 7.55 (s, 1H), 7.30-7.27 (m, 2H), 4.33 (t, 2H), 3.73 (q, 2H).

<113-4> N-{2-[4-(4-chloro-2-chloro-phenylamino)-6-nitro-quinazolin-7-yloxy]-ethyl}-acetamide The procedure of Example <1-10> was repeated except for using the compound of <113-3> (380 mg, 0.96 mmol) to obtain the title compound 161 mg (yield: 38%).
¹H NMR (CDCl₃+MeOD) δ: 8.80 (s, 1H), 8.59 (d, 1H), 8.51 (s, 1H), 7.93 (bs, 1H), 7.51 (s, 1H), 7.42 (s, 1H), 7.39-7.35 (m, 1H), 6.12 (bs, 1H), 4.33 (t, 2H), 3.79 (q, 2H), 2.05 (s, 3H).

<113-5> N-{2-[6-amino-4-(4-chloro-2-chloro-phenylamino)-quinazolin-7-yloxy]-ethyl}-acetamide The procedure of Example <1-7> was repeated except for using the compound of <113-4> (160 mg, 0.37 mmol) to obtain the title compound 120 mg (yield: 80%).
¹H NMR (CDCl₃+MeOD) δ: 8.48-8.45 (m, 2H), 7.48 (s, 1H), 7.32 (s, 1H), 7.09-7.07 (m, 2H), 4.23 (t, 2H), 3.74 (q, 2H), 2.01 (s, 3H).

<113-6> N-[7-(2-acetylamino-ethoxy)-4-(4-chloro-2-chloro-phenylamino)-quinazolin-6-yl]-acrylamide The procedure of Example <29-5> was repeated except for using the compound of <113-5> (100 mg, 0.24 mmol) to obtain the title compound 30 mg (yield: 26%).
¹H NMR (DMSO-d₆) δ: 9.16 (s, 1H), 8.54 (s, 1H), 8.32-8.29 (m, 1H), 8.14-8.11 (m, 1H), 7.78 (bs, 1H), 7.52-7.49 (m, 1H), 7.38-7.31 (m, 2H), 7.17-7.13 (m, 1H), 6.81-6.76 (m, 1H), 6.55-6.49 (m, 1H), 5.89-5.86 (m, 1H), 4.22 (t, 2H), 3.75 (q, 2H), 2.03 (s, 3H).

Example 114

Preparation of N-[7-(2-acetylamino-ethoxy)-4-(4-bromo-2-trifluoromethyl-phenylamino)-quinazolin-6-yl]-acrylamide <114-1> (4-chloro-2-trifluoromethyl-phenyl)-(7-fluoro-6-nitro-quinazolin-4-yl)-amine The procedure of Example <1-5> was repeated except for using the compound of Example <1-4> (1 g, 3.8 mmol) and 4-chloro-2-trifluoromethyl-aniline (1.0 g, 4.16 mmol) to obtain the title compound 850 mg (yield: 52%).
¹H NMR (CDCl₃) δ: 8.22 (s, 1H), 7.85 (d, 1H), 7.16 (s, 1H), 6.88 (s, 1H), 6.82 (d, 1H), 6.55 (d, 2H).

<114-2> {2-[4-(4-chloro-2-trifluoromethyl-phenylamino)-6-nitro-quinazolin-7-yloxy]-ethyl}-carbamic acid t-butylester The procedure of Example <1-6> was repeated except for using the compound of <114-1> (850 mg, 1.97 mmol) to obtain the title compound 490 mg (yield: 43%).
¹H NMR (CDCl₃) δ: 8.72 (s, 1H), 8.47 (bs, 1H), 8.06 (d, 1H), 7.87 (d, 1H), 7.78 (dd, 2H), 7.41 (s, 1H), 5.11 (bs, 1H), 4.30 (t, 2H), 3.66 (q, 2H), 1.45 (s, 9H).

<114-3> [7-(2-amino-ethoxy)-6-nitro-quinazolin-4-yl]-(4-chloro-2-trifluoromethyl-phenyl)-amine The procedure of Example <1-9> was repeated except for using the compound of <114-2> (490 mg, 0.85 mmol) to obtain the title compound 381 mg (yield: 95%).
¹H NMR (CDCl₃+MeOD) δ: 8.55 (s, 1H), 7.95 (s, 1H), 7.86 (s, 1H), 7.70 (d, 1H), 7.35 (s, 1H), 7.27 (s, 1H), 4.14 (t, 2H), 3.81 (q, 2H).

<114-4> N-{2-[4-(4-chloro-2-trifluoromethyl-phenylamino)-6-nitro-quinazolin-7-yloxy]-ethyl}-acetamide The procedure of Example <1-10> was repeated except for using the compound of <114-3> (540 mg, 1.14 mmol) to obtain the title compound 335 mg (yield: 57%).
¹H NMR (CDCl₃) δ: 8.67 (bs, 1H), 8.53 (s, 1H), 8.00 (s, 1H), 7.86 (s, 1H), 7.77 (d, 1H), 7.39 (s, 1H), 7.28 (s, 1H), 6.17 (t, 1H), 4.32 (t, 2H), 3.79 (q, 2H), 2.04 (s, 3H).

<114-5> N-{2-[6-amino-4-(4-chloro-2-trifluoromethyl-phenylamino)-quinazolin-7-yloxy]-ethyl}-acetamide The procedure of Example <1-7> was repeated except for using the compound of <114-4> (335 mg, 0.65 mmol) to obtain the title compound 170 mg (yield: 53%).
¹H NMR (CDCl₃+MeOD) δ: 8.47 (s, 1H), 8.24 (d, 1H), 7.82 (s, 1H), 7.75 (d, 1H), 7.12 (s, 1H), 6.93 (s, 1H), 4.24 (t, 2H), 3.76 (q, 2H), 2.02 (s, 3H).

<114-6> N-[7-(2-acetylamino-ethoxy)-4-(4-bromo-2-trifluoromethyl-phenylamino)-quinazolin-6-yl]-acrylamide The procedure of Example <29-5> was repeated except for using the compound of <114-5> (150 mg, 0.31 mmol) to obtain the title compound 40 mg (yield: 24%).
¹H NMR (CDCl₃) δ: 9.23 (s, 1H), 8.90 (s, 1H), 8.63 (s, 1H), 8.24 (d, 1H), 7.82 (d, 1H), 7.75-7.66 (m, 2H), 7.16 (s, 1H), 6.87-6.78 (m, 1H), 6.58-6.51 (m, 1H), 5.93 (t, 1H), 5.86-5.82 (m, 1H), 4.21 (t, 2H), 3.83 (q, 2H), 2.08 (s, 3H).

Example 115

Preparation of N-[7-(2-acetylamino-ethoxy)-4-(4-bromo-2-chloro-phenylamino)-quinazolin-6-yl]-acrylamide <115-1> (4-bromo-2-chloro-phenyl)-(7-fluoro-6-nitro-quinazolin-4-yl)-amine The procedure of Example <1-5> was repeated except for using the compound of Example <1-4> (1 g, 3.8 mmol) and 4-bromo-2-chloro-aniline (860 g, 4.16 mmol) to obtain the title compound 1.0 g (yield: 66%).

<115-2> {2-[4-(4-bromo-2-chloro-phenylamino)-6-nitro-quinazolin-7-yloxy]-ethyl}-carbamic acid t-butylester The procedure of Example <1-6> was repeated except for using the compound of <115-1> (1.0 g, 2.51 mmol) to obtain the title compound 760 mg (yield: 56%).
$^1$H NMR (CDCl$_3$) δ: 8.81 (s, 1H), 8.56 (d, 1H), 8.49 (s, 1H), 7.90 (bs, 1H), 7.66 (d, 1H), 7.52 (dd, 1H), 7.43 (s, 1H), 5.11 (bs, 1H), 4.31 (t, 2H), 3.69 (q, 2H), 1.47 (s, 9H).

<115-3> [7-(2-amino-ethoxy)-6-nitro-quinazolin-4-yl]-(4-bromo-2-chloro-phenyl

The procedure of Example <1-9> was repeated except for using the compound of <115-2> (760 mg, 1.41 mmol) to obtain the title compound 618 mg (yield: 99%).
$^1$H NMR (CDCl$_3$+MeOD) δ: 8.82 (s, 1H), 8.51-8.48 (m, 2H), 8.00 (bs, 1H), 7.53 (d, 1H), 7.50 (dd, 1H), 7.39 (s, 1H), 4.31 (t, 2H), 3.85 (q, 2H).

<115-4> N-{2-[4-(4-bromo-2-chloro-phenylamino)-6-nitro-quinazolin-7-yloxy]-ethyl}-acetamide The procedure of Example <1-10> was repeated except for using the compound of <115-3> (630 mg, 1.43 mmol) to obtain the title compound 630 mg (yield: 91%).
$^1$H NMR (CDCl$_3$) δ: 8.80 (s, 1H), 8.57-8.51 (m, 2H), 7.98 (bs, 1H), 7.66 (d, 1H), 7.51 (dd, 1H), 7.43 (s, 1H), 6.15 (bs, 1H), 4.33 (t, 2H), 3.80 (q, 2H), 2.05 (s, 3H).

<115-5> N-{2-[6-amino-4-(4-bromo-2-chloro-phenylamino)-quinazolin-7-yloxy]-ethyl}-acetamide The procedure of Example <1-7> was repeated except for using the compound of <115-4> (595 mg, 1.23 mmol) to obtain the title compound 250 mg (yield: 45%).
$^1$H NMR (CDCl$_3$+MeOD) δ: 8.49-8.44 (m, 2H), 7.61 (s, 1H), 7.49-7.45 (m, 1H), 7.36 (s, 1H), 7.07 (d, 2H), 4.23 (t, 2H), 3.74 (q, 2H), 2.01 (s, 3H).

<115-6> N-[7-(2-acetylamino-ethoxy)-4-(4-bromo-2-chloro-phenylamino)-quinazolin-6-yl]-acrylamide The procedure of Example <29-5> was repeated except for using the compound of <115-5> (150 mg, 0.33 mmol) to obtain the title compound 26 mg (yield: 15%).
$^1$H NMR (CDCl$_3$) δ: 9.31 (s, 1H), 8.91 (bs, 1H), 8.68 (s, 1H), 8.63 (d, 1H), 7.95 (bs, 1H), 7.61 (d, 1H), 7.46 (d, 1H), 7.16 (s, 1H), 6.88-6.79 (m, 1H), 6.57-6.52 (m, 1H), 5.92 (t, 1H), 5.86-5.82 (m, 1H), 4.21 (t, 2H), 3.83 (q, 2H), 2.08 (s, 3H).

Example 116

Preparation of N-{4-(4-chloro-2-fluoro-phenylamino)-7-[2-(2-dimethylamino-acetylamino)-ethoxy]-quinazolin-6-yl}-acrylamide <116-1> {2-[6-amino-4-(4-chloro-2-fluoro-phenylamino)-quinazolin-7-yloxy]-ethyl}-carbamic acid t-butylester The procedure of Example <1-7> was repeated except for using the compound of <112-2> (5.7 g, 11.93 mmol) to obtain the title compound 4.24 g (yield: 79%).
$^1$H NMR (CDCl$_3$) δ: 8.69-8.60 (m, 2H), 7.20-7.15 (m, 4H), 6.91 (s, 1H), 4.94 (bs, 1H), 4.40 (bs, 2H), 4.21 (t, 2H), 3.72-3.66 (m, 2H), 1.46 (s, 9H).

<116-2> {2-[6-acryloylamino-4-(4-chloro-2-fluoro-phenylamino)-quinazolin-7-yloxy]-ethyl}-carbamic acid t-butylester The procedure of Example <29-5> was repeated except for using the compound of <116-1> (4.24 g, 9.47 mmol) to obtain the title compound 2.51 g (yield: 53%).
$^1$H NMR (DMSO-d$_6$) δ: 9.76 (s, 1H), 9.44 (s, 1H), 9.05 (s, 1H), 8.36 (s, 1H), 7.54-7.49 (m, 2H), 7.31-7.24 (m, 3H), 6.74-6.68 (m, 1H), 6.37-6.30 (m, 1H), 5.87-5.83 (m, 1H), 4.17 (t, 2H), 2.94 (q, 2H), 1.37 (s, 9H).

<116-3> N-[7-(2-amino-ethoxy)-4-(4-chloro-2-fluoro-phenylamino)-quinazolin-6-yl]-acrylamide The procedure of Example <1-9> was repeated except for using the compound of <116-2> (2.5 g, 5 mmol) to obtain the title compound 1.65 g (yield: 82%).
$^1$H NMR (DMSO-d$_6$) δ: 8.95 (s, 1H), 8.36 (s, 1H), 7.51-7.40 (m, 2H), 7.30 (d, 1H), 7.25 (s, 1H), 6.87-6.78 (m, 1H), 6.33-6.27 (m, 1H), 5.82-5.78 (m, 1H), 4.18 (t, 2H), 3.02 (q, 2H).

<116-4> N-{4-(4-chloro-2-fluoro-phenylamino)-7-[2-(2-dimethylamino-acetylamino)-ethoxy]-quinazolin-6-yl}-acrylamide The procedure of Example 44 was repeated except for using the compound of <116-3> (600 mg, 1.5 mmol) and N,N-dimethyl glycine (231 mg, 2.24 mmol) to obtain the title compound 250 mg (yield: 34%).
$^1$H NMR (DMSO-d$_6$) δ: 9.77 (s, 1H), 9.39 (s, 1H), 9.06 (s, 1H), 8.35 (s, 1H), 8.23 (t, 1H), 7.50-7.47 (m, 2H), 7.31 (d, 1H), 7.22 (s, 1H), 6.88-6.79 (m, 1H), 6.36-6.30 (m, 1H), 5.86-5.82 (m, 1H), 4.21 (t, 2H), 3.54 (q, 2H), 2.89 (s, 2H), 2.12 (s, 6H).

Example 117

Preparation of N-[4-(3-chloro-2-fluoro-phenylamino)-7-{2-[2-(dimethylamino)-acetamido]-ethoxy}quinazolin-6-yl]-acrylamide <117-1> N-(3-chloro-2-fluorophenyl)-7-fluoro-6-nitroquinazoline-4-amine The procedure of Example <1-5> was repeated except for using the compound of Example <1-4> (500 mg, 1.89 mmol) and 3-chloro-2-fluoro-aniline (264 μl, 2.46 mmol) to obtain the title compound 497 mg (yield: 68%)
$^1$H NMR (300 MHz, DMSO-d$_6$) 9.87 (d, 1H), 8.88 (s, 1H), 8.02 (d, 1H), 7.62 (t, 1H), 7.55 (t, 1H), 7.37 (t, 1H).

<117-2> t-butyl 2-[4-(3-chloro-2-fluoro-phenylamino)-6-nitroquinazolin-7-yloxy]-ethylcarbamate The procedure of Example <1-6> was repeated except for using the compound of <117-1> (420 mg, 1.08 mmol) to obtain the title compound 295 mg (yield: 57%)
$^1$H NMR (300 MHz, DMSO-d$_6$) 10.15 (s, 1H), 9.14 (s, 1H), 8.51 (s, 1H), 7.57-7.52 (m, 1H), 7.48 (s, 1H), 7.42-7.35 (m, 1H), 7.18-7.15 (m, 1H), 6.96-6.94 (m, 1H), 4.29 (t, 2H), 3.35 (q, 2H), 1.36 (s, 9H).

<117-3> 7-(2-aminoethoxy)-N-(3-chloro-2-fluo-rophenyl)-6-nitroquinazoline-4-amine The procedure of Example <1-9> was repeated except for using the compound of <117-2> (280 mg, 0.59 mmol) to obtain the title compound 223 mg (yield: 99%).
$^1$H NMR (300 MHz, DMSO-$d_6$) 9.15 (s, 1H), 8.52 (s, 1H), 7.52-7.47 (m, 3H), 7.26 (t, J=7.5 Hz, 1H), 4.28 (t, J=5.4 Hz, 2H), 3.31 (brs, 1H), 2.98 (q, J=5.4 Hz, 2H).

<117-4> N-{2-[4-(3-chloro-2-fluoro-phenylamino)-6-nitroquinazolin-7-yloxy]-ethyl}-2-(dimethy-lamino)-acetamide The procedure of Example <116-4> was repeated except for using the compound of <117-3> (210 mg, 0.56 mmol) to obtain the title compound 200 mg (yield: 77%).
$^1$H NMR (300 MHz, CDCl$_3$) 8.78 (s, 1H), 8.71 (s, 1H), 8.23 (brs, 1H), 8.19 (t, J=8.1 Hz, 1H), 7.82 (brs, 1H), 7.41 (s, 1H), 7.30-7.16 (m, 2H), 4.35 (t, 2H), 3.82 (q, 2H), 2.99 (s, 2H), 2.32 (s, 6H).

<117-5> N-{2-[6-amino-4-(3-chloro-2-fluoro-pheny-lamino)-quinazolin-7-yloxy]-ethyl}-2-(dimethy-lamino)-acetamide The procedure of Example <1-7> was repeated except for using the compound of <117-4> (184 mg, 0.40 mmol) to obtain the title compound 165 mg (yield: 95%).
$^1$H NMR (300 MHz, MeOD) 8.23 (brs, 1H), 7.63 (t, 1H), 7.32 (t, 1H), 7.29 (s, 1H), 7.18 (t, 1H), 7.05 (s, 1H), 4.24 (t, 2H), 3.76 (t, 2H), 3.04 (s, 2H), 2.30 (s, 6H).

<117-6> N-[4-(3-chloro-2-fluoro-phenylamino)-7-{2-[2-(dimethylamino)-acetamido]-ethoxy}-quinazo-lin-6-yl]-acrylamide The procedure of Example <29-5> was repeated except for using the compound of <117-5> (130 mg, 0.30 mmol) to obtain the title compound 35 mg (yield: 24%)
$^1$H NMR (300 MHz, DMSO-$d_6$) 9.88 (s, 1H), 9.38 (s, 1H), 9.12 (s, 1H), 8.41 (s, 1H), 8.22 (t, 1H), 7.51-7.44 (m, 2H), 7.28-7.24 (m, 2H), 6.87 (dd, 1H), 6.37 (d, 1H), 5.87 (d, 1H), 4.26 (t, J=5.4 Hz, 2H), 3.64 (t, 2H), 2.93 (s, 2H), 2.17 (s, 6H).

Example 118

Preparation of N-[7-(2-acetylamino-ethoxy)-4-(2,3,4-trifluoro-phenylamino)-quinazolin-6-yl]-acryla-mide <118-1> (2,3,4-trifluoro-phenyl)-(7-fluoro-6-nitro-quinazolin-4-yl)-amine The procedure of Example <1-5> was repeated except for using the compound of Example <1-4> (1 g, 3.8 mmol) and 2,3,4-trifluoro-aniline (611 mg, 4.16 mmol) to obtain the title compound 1.14 g (yield: 80%).
$^1$H NMR (CDCl$_3$) δ: 9.48 (bs, 1H), 8.74 (d, 1H), 8.27 (s, 1H), 7.79 (d, 1H), 7.45-7.37 (m, 2H).

<118-2> {2-[4-(2,3,4-trifluoro-phenylamino)-6-ni-tro-quinazolin-7-yloxy]-ethyl)}-carbamic acid t-bu-tylester The procedure of Example <1-6> was repeated except for using the compound of <118-1> (700 mg, 2.07 mmol) to obtain the title compound 250 mg (yield: 26%).

$^1$H NMR (CDCl$_3$) δ: 8.91 (s, 1H), 8.63 (s, 1H), 7.49-7.47 (m, 1H), 7.36 (s, 1H), 7.09-7.05 (m, 1H), 5.40 (bs, 1H), 4.30 (t, 2H), 3.65 (q, 2H), 1.46 (s, 9H).

<118-3> [7-(2-amino-ethoxy)-6-nitro-quinazolin-4-yl]-(2,3,4-trifluoro-phenyl)-amine The procedure of Example <1-9> was repeated except for using the compound of <118-2> (250 mg, 0.52 mmol) to obtain the title compound 185 mg (yield: 93%).
$^1$H NMR (CDCl$_3$+MeOD) δ: 8.73 (s, 1H), 8.10 (s, 1H), 7.43 (s, 1H), 7.10 (t, 1H), 6.21-6.18 (m, 1H), 4.35 (t, 2H), 3.86 (q, 2H).

<118-4> N-{2-[4-(2,3,4-trifluoro-phenylamino)-6-nitro-quinazolin-7-yloxy]-ethyl}-acetamide The procedure of Example <1-10> was repeated except for using the compound of <118-3> (185 mg, 0.49 mmol) to obtain the title compound 189 mg (yield: 92%).
$^1$H NMR (CDCl$_3$) δ: 8.73 (s, 1H), 8.05 (s, 1H), 7.41 (s, 1H), 7.06 (t, 1H), 6.25-6.23 (m, 1H), 4.32 (t, 2H), 3.79 (q, 2H), 2.05 (s, 3H).

<118-5> N-{2-[6-amino-4-(2,3,4-trifluoro-pheny-lamino)-quinazolin-7-yloxy]-ethyl}-acetamide The procedure of Example <1-7> was repeated except for using the compound of <118-4> (250 mg, 0.59 mmol) to obtain the title compound 96 mg (yield: 40%).
$^1$H NMR (CDCl$_3$+MeOD) δ: 8.39 (s, 1H), 7.68-7.63 (m, 1H), 7.22 (s, 1H), 7.09-7.00 (m, 2H), 4.23 (t, 2H), 3.73 (t, 2H), 2.01 (s, 3H).

<118-6> N-[7-(2-acetylamino-ethoxy)-4-(2,3,4-trif-luoro-phenylamino)-quinazolin-6-yl]-acrylamide The procedure of Example <29-5> was repeated except for using the compound of <118-5> (95 mg, 0.24 mmol) to obtain the title compound 30 mg (yield: 27%).
$^1$H NMR (CDCl$_3$) δ: 9.21 (s, 1H), 8.95 (s, 1H), 8.61 (s, 1H), 7.86 (bs, 1H), 7.53 (bs, 1H), 7.13 (s, 1H), 7.02-7.00 (m, 1H), 6.89-6.80 (m, 1H), 6.55-6.49 (m, 1H), 6.12 (m, 1H), 5.85-5.82 (m, 1H), 4.05 (t, 2H), 3.95 (q, 2H), 2.08 (s, 3H).

Example 119

Preparation of N-[7-(2-acetylamino-ethoxy)-4-(4-bromo-2,5-difluoro-phenylamino)-quinazolin-6-yl]-acrylamide <119-1> (4-bromo-2,5-difluoro-phenyl)-(7-fluoro-6-nitro-quinazolin-4-yl)-amine The procedure of Example <1-5> was repeated except for using the compound of Example <1-4> (1 g, 3.8 mmol) and 4-bromo-2,5-difluoro-aniline (866 mg, 4.16 mmol) to obtain the title compound 1.2 g (yield: 79%).
$^1$H NMR (CDCl$_3$) δ: 9.31 (bs, 1H), 8.56 (d, 1H), 8.13 (s, 1H), 7.72-7.52 (m, 3H).

<119-2> {2-[4-(4-bromo-2,5-difluoro-phenylamino)-6-nitro-quinazolin-7-yloxy]-ethyl}-carbamic acid t-butylester The procedure of Example <1-6> was repeated except for using the compound of <119-1> (1.2 g, 3.0 mmol) to obtain the title compound 720 mg (yield: 44%).

¹H NMR (CDCl₃) δ: 8.80 (s, 1H), 8.72 (s, 1H), 8.12-8.06 (m, 1H), 7.45-7.38 (m, 2H), 4.30 (t, 2H), 3.65 (q, 2H), 1.46 (s, 9H).

<119-3> [7-(2-amino-ethoxy)-6-nitro-quinazolin-4-yl]-(4-bromo-2,5-difluoro-phenyl)-amine The procedure of Example <1-9> was repeated except for using the compound of <119-2> (720 mg, 1.33 mmol) to obtain the title compound 500 mg (yield: 85%).
¹H NMR (CDCl₃+MeOD) δ: 8.95 (s, 1H), 8.50 (s, 1H), 7.81 (t, 1H), 7.46-7.43 (m, 1H), 7.38 (s, 1H), 4.06 (t, 2H), 3.61 (t, 2H).

<119-4> N-{2-[4-(4-bromo-2,5-difluoro-phenylamino)-6-nitro-quinazolin-7-yloxy]-ethyl}-acetamide The procedure of Example <1-10> was repeated except for using the compound of <119-3> (500 mg, 1.13 mmol) to obtain the title compound 380 mg (yield: 69%).
¹H NMR (CDCl₃) δ: 8.93 (s, 1H), 8.68 (s, 1H), 7.90 (t, 1H), 7.46-7.43 (m, 1H), 7.41 (s, 1H), 4.33 (t, 2H), 3.73 (t, 2H), 2.03 (s, 3H).

<119-5> N-{2-[6-amino-4-(4-bromo-2,5-difluoro-phenylamino)-quinazolin-7-yloxy]-ethyl}-acetamide The procedure of Example <1-7> was repeated except for using the compound of <119-4> (380 mg, 0.79 mmol) to obtain the title compound 280 mg (yield: 78%).
¹H NMR (CDCl₃+MeOD) δ: 8.51 (s, 1H), 8.42 (t, 1H), 7.41-7.38 (m, 1H), 7.10 (d, 2H), 4.23 (t, 2H), 3.73 (q, 2H), 2.01 (s, 3H).

<119-6> N-[7-(2-acetylamino-ethoxy)-4-(4-bromo-2,5-difluoro-phenylamino)-quinazolin-6-yl]-acrylamide The procedure of Example <29-5> was repeated except for using the compound of <119-5> (120 mg, 0.26 mmol) to obtain the title compound 40 mg (yield: 29%).
¹H NMR (CDCl₃+MeOD) δ: 9.10 (s, 1H), 8.57 (s, 1H), 8.21 (bs, 1H), 8.04 (t, 1H), 7.88 (m, 1H), 7.45-7.43 (m, 2H), 7.15 (s, 1H), 6.84-6.75 (m, 1H), 6.55-6.49 (m, 1H), 5.90 (5.86 (m, 1H), 4.22 (t, 2H), 3.73 (q, 2H), 2.03 (s, 3H).

Example 120

Preparation of N-[7-(2-acetylamino-ethoxy)-4-(4-bromo-2,6-difluoro-phenylamino)-quinazolin-6-yl]-acrylamide <120-1> (4-bromo-2,5-difluoro-phenyl)-(7-fluoro-6-nitro-quinazolin-4-yl)-amine The procedure of Example <1-5> was repeated except for using the compound of Example <1-4> (1 g, 3.8 mmol) and 4-bromo-2,6-difluoro-aniline (866 mg, 4.16 mmol) to obtain the title compound 1.28 g (yield: 84%).
¹H NMR (DMSO-d₆) δ: 8.74 (d, 1H), 8.30 (s, 1H), 7.79 (d, 1H), 7.36 (s, 2H).

<120-2> {2-[4-(4-bromo-2,6-difluoro-phenylamino)-6-nitro-quinazolin-7-yloxy]-ethyl}-carbamic acid t-butylester The procedure of Example <1-6> was repeated except for using the compound of <120-1> (1.0 g, 2.5 mmol) to obtain the title compound 810 mg (yield: 60%).
¹H NMR (CDCl₃) δ: 8.69 (s, 2H), 7.41-7.38 (m, 2H), 7.23 (s, 1H), 5.13 (t, 1H), 4.28 (t, 2H), 3.65 (q, 2H), 1.46 (s, 9H).

<120-3> [7-(2-amino-ethoxy)-6-nitro-quinazolin-4-yl]-(4-bromo-2,6-difluoro-phenyl)-amine The procedure of Example <1-9> was repeated except for using the compound of <120-2> (810 mg, 1.49 mmol) to obtain the title compound 655 mg (yield: 99%).
¹H NMR (DMSO-d₆) δ: 9.18 (s, 1H), 8.51 (s, 1H), 7.63 (d, 2H), 7.55 (s, 1H), 4.51 (t, 2H), 3.31 (q, 2H).

<120-4> N-{2-[4-(4-bromo-2,6-difluoro-phenylamino)-6-nitro-quinazolin-7-yloxy]-ethyl}-acetamide The procedure of Example <1-10> was repeated except for using the compound of <120-3> (940 mg, 2.13 mmol) to obtain the title compound 170 mg (yield: 25%).
¹H NMR (CDCl₃+MeOD) δ: 8.99 (s, 1H), 8.58 (s, 1H), 7.35 (s, 1H), 7.25 (d, 2H), 4.32 (t, 2H), 3.75 (t, 2H), 2.03 (s, 3H).

<120-5> N-{2-[6-amino-4-(4-bromo-2,6-difluoro-phenylamino)-quinazolin-7-yloxy]-ethyl}-acetamide The procedure of Example <1-7> was repeated except for using the compound of <120-4> (170 mg, 0.35 mmol) to obtain the title compound 150 mg (yield: 94%).
¹H NMR (CDCl₃+MeOD) δ: 8.39 (s, 1H), 7.23-7.18 (m, 3H), 7.08 (s, 1H), 4.22 (t, 2H), 3.73 (q, 2H), 2.01 (s, 3H).

<120-6> N-[7-(2-acetylamino-ethoxy)-4-(4-bromo-2,6-difluoro-phenylamino)-quinazolin-6-yl]-acrylamide The procedure of Example <29-5> was repeated except for using the compound of <120-5> (150 mg, 0.33 mmol) to obtain the title compound 39 mg (yield: 23%).
¹H NMR (CDCl₃+MeOD) δ: 9.05 (s, 1H), 8.47 (s, 1H), 7.38 (t, 1H), 7.24 (d, 2H), 7.11 (s, 1H), 6.85-6.76 (m, 1H), 6.54-6.48 (m, 1H), 5.88-5.85 (m, 1H), 4.21 (t, 2H), 3.76 (q, 2H), 2.03 (s, 3H).

Example 121

Preparation of N-[7-(2-acetylamino-ethoxy)-4-(4,5-dichloro-2-fluoro-phenylamino)-quinazolin-6-yl]-acrylamide The procedure of Example <1-10> was repeated except for using the compound of Example <136-6> (150 mg, 0.35 mmol) to obtain the title compound 21 mg (yield: 12%).
¹H NMR (CDCl₃+MeOD) δ: 9.05 (s, 1H), 8.57 (s, 1H), 8.23 (d, 1H), 7.40 (t, 1H), 7.35 (s, 1H), 7.13 (s, 1H), 6.85 (m, 1H), 6.55-6.49 (m, 1H), 5.89 (m, 1H), 4.21 (t, 2H), 3.75 (d, 2H), 2.03 (s, 3H).

Example 122

Preparation of N-[7-(2-acetylamino-ethoxy)-4-(2,4,5-trichloro-phenylamino)-quinazolin-6-yl]-acrylamide <122-1> (2,4,5-trichloro-phenyl)-(7-fluoro-6-nitro-quinazolin-4-yl)-amine The procedure of Example <1-5> was repeated except for using the compound of Example <1-4> (1 g, 3.8 mmol) and 2,4,5-trichloro-aniline (818 mg, 4.16 mmol) to obtain the title compound 1.27 g (yield: 86%).
$^1$H NMR (DMSO-$d_6$) δ: 8.74 (d, 1H), 8.37 (s, 1H), 7.98 (s, 1H), 7.78 (d, 2H).

<122-2> {2-[4-(2,4,5-trichloro-phenylamino)-6-nitro-quinazolin-7-yloxy]-ethyl}-carbamic acid t-butylester The procedure of Example <1-6> was repeated except for using the compound of <122-1> (1.0 g, 2.58 mmol) to obtain the title compound 660 mg (yield: 48%).
$^1$H NMR (CDCl$_3$) δ: 9.00 (s, 1H), 8.86 (s, 1H), 8.46 (s, 1H), 7.91 (bs, 1H), 7.59 (s, 1H), 7.44 (s, 1H), 4.31 (t, 2H), 3.68 (q, 2H), 1.46 (s, 9H).

<122-3> [7-(2-amino-ethoxy)-6-nitro-quinazolin-4-yl]-(2,4,5-trichloro-phenyl)-amine The procedure of Example <1-9> was repeated except for using the compound of <122-2> (660 mg, 1.24 mmol) to obtain the title compound 425 mg (yield: 80%).
$^1$H NMR (DMSO-$d_6$) δ: 9.10 (s, 1H), 8.71-8.69 (m, 1H), 7.59 (s, 1H), 7.41 (s, 1H), 4.48 (t, 2H), 3.80 (q, 2H).

<122-4> N-{2-[4-(2,4,5-trichloro-phenylamino)-6-nitro-quinazolin-7-yloxy]-ethyl}-acetamide The procedure of Example <1-10> was repeated except for using the compound of <122-3> (770 mg, 1.8 mmol) to obtain the title compound 625 mg (yield: 74%).
$^1$H NMR (CDCl$_3$+MeOD) δ: 8.81 (s, 1H), 8.71-8.69 (m, 1H), 8.31 (bs, 1H), 7.62 (s, 1H), 7.38 (s, 1H), 6.89 (bs, 1H), 4.33 (t, 2H), 3.75 (q, 2H), 2.03 (s, 3H).

<122-5> N-{2-[6-amino-4-(2,4,5-trichloro-phenylamino)-quinazolin-7-yloxy]-ethyl}-acetamide The procedure of Example <1-7> was repeated except for using the compound of <122-4> (625 mg, 1.32 mmol) to obtain the title compound 200 mg (yield: 34%).
$^1$H NMR (CDCl$_3$+MeOD) δ: 9.00 (s, 1H), 8.58 (s, 1H), 7.55 (s, 1H), 7.11 (s, 1H), 6.97 (s, 1H), 4.24 (t, 2H), 3.75 (q, 2H), 2.02 (s, 3H).

<122-6> N-[7-(2-acetylamino-ethoxy)-4-(2,4,5-trichloro-phenylamino)-quinazolin-6-yl]-acrylamide The procedure of Example <29-5> was repeated except for using the compound of <122-5> (150 mg, 0.34 mmol) to obtain the title compound 41 mg (yield: 24%).
$^1$H NMR (CDCl$_3$+MeOD) δ: 9.18 (s, 1H), 8.60 (d, 2H), 7.60 (s, 1H), 7.15 (s, 1H), 6.85 (m, 1H), 6.55 (m, 1H), 5.89-5.85 (m, 1H), 4.22 (t, 2H), 3.77 (q, 2H), 2.03 (s, 3H).

Example 123

Preparation of N-[4-(4-bromo-2,6-difluorophenylamino)-7-{2-[2-(dimethylamino)-acetamido]-ethoxy}-quinazolin-6-yl]-acrylamide <123-1> N-(4-bromo-2,6-difluorophenyl)-7-fluoro-6-nitroquinazoline-4-amine The procedure of Example <1-5> was repeated except for using the compound of Example <1-4> (500 mg, 1.89 mmol) and 4-bromo-2,6-difluoroaniline (393 mg, 1.89 mmol) to obtain the title compound 600 mg (yield: 71%)
$^1$H NMR (300 MHz, DMSO-$d_6$) 9.60 (s, 1H), 8.85 (s, 1H), 9.60 (d, 1H), 7.68 (d, 2H).

<123-2> t-butyl 2-(4-(4-bromo-2,6-difluorophenylamino)-6-nitroquinazolin-7-yloxy)-ethylcarbamate The procedure of Example <1-6> was repeated except for using the compound of <123-1> (600 mg, 1.33 mmol) to obtain the title compound 282 mg (yield: 39%).
$^1$H NMR (300 MHz, CDCl$_3$) 8.90 (s, 1H), 8.66 (s, 1H), 7.35 (s, 1H), 7.24 (d, 2H), 4.25 (t, 2H), 3.28 (q, 2H), 1.45 (s, 9H).

<123-3> 7-(2-aminoethoxy)-N-(4-bromo-2,6-difluorophenyl)-6-nitroquinazoline-4-amine The procedure of Example <1-9> was repeated except for using the compound of <123-2> (280 mg, 0.52 mmol) to obtain the title compound 145 mg (yield: 63%)
$^1$H NMR (300 MHz, DMSO-$d_6$) 9.00 (s, 1H), 8.46 (s, 1H), 7.42 (s, 1H), 7.39 (d, 2H), 4.34 (t, 2H), 3.13 (t, 2H).

<123-4> N-{2-[4-(4-bromo-2,6-difluorophenylamino)-6-nitroquinazolin-7-yloxy]-ethyl}-2-(dimethylamino)-acetamide The procedure of Example 44 was repeated except for using the compound of <123-3> (135 mg, 0.31 mmol) to obtain the title compound 148 mg (yield: 91%)
$^1$H NMR (300 MHz, CDCl$_3$) 8.80 (s, 1H), 8.68 (s, 1H), 8.06 (brs, 1H), 7.83 (brs, 1H), 7.38 (s, 1H), 7.25 (d, 2H), 4.33 (t, 2H), 3.82 (q, 2H), 2.99 (s, 2H), 2.30 (s, 6H).

<123-5> N-{2-[6-amino-4-(4-bromo-2,6-difluorophenylamino)-quinazolin-7-yloxy]-ethyl}-2-(dimethylamino)-acetamide The procedure of Example <1-7> was repeated except for using the compound of <123-4> (140 mg, 0.27 mmol) to obtain the title compound 100 mg (yield: 75%).
$^1$H NMR (300 MHz, MeOD) 8.36 (s, 1H), 7.37 (d, 2H), 7.33 (s, 1H), 7.09 (s, 1H), 4.28 (t, 2H), 3.79 (t, 2H), 3.07 (s, 2H), 2.32 (s, 6H).

<123-6> N-[4-(4-bromo-2,6-difluorophenylamino)-7-{2-[2-(dimethylamino)-acetamido]-ethoxy}-quinazolin-6-yl)-acrylamide The procedure of Example <29-5> was repeated except for using the compound of <123-5> (90 mg, 0.18 mmol) to obtain the title compound 20 mg (yield: 20%)
$^1$H NMR (300 MHz, DMSO-$d_6$) 9.70 (s, 1H), 8.35 (s, 1H), 7.38 (d, 2H), 7.22 (s, 1H), 6.81 (dd, 1H), 6.48 (d, 1H), 5.87 (d, 1H), 4.32 (t, J=5.4 Hz, 2H), 3.80 (t, 2H), 3.08 (s, 2H), 2.31 (s, 6H).

Example 124

Preparation of N-{4-(4-bromo-2,3-difluoro-phenylamino)-7-[2-(2-dimethylamino-acetylamino)-ethoxy]-quinazolin-6-yl}-acrylamide <124-1> 4-bromo-2,3-difluoro-phenylamine 2,3-difluoro-phenylamine (13.45 g, 104.2 mmol) was diluted with acetic acid (180 ml), bromine (2.6 ml) diluted with acetic acid (5 ml) was slowly added thereto at 0° C., and the solution was stirred for 5 hours. The resulting solution was distilled under a reduced pressure to remove the solvent, basified by adding 50% sodium hydroxide solution (250 ml), and extracted with dichloromethane (200 ml) twice. The separated organic layer was dried over magnesium sulfate, filtered and distilled under a reduced pressure to obtain the title compound 6.46 g (yield: 30%).

$^1$H NMR (CDCl$_3$) δ: 7.08-7.02 (m, 1H), 6.49-6.42 (m, 1H), 3.72 (bs, 2H).

<124-2> (4-bromo-2,3-difluoro-phenyl)-(7-fluoro-6-nitro-quinazolin-4-yl)-amine

The procedure of Example <1-5> was repeated except for using the compound of Example <1-4> (8.2 g, 31.08 mmol) and the compound of <124-1> (6.46 g, 31.08 mmol) to obtain the title compound 8.82 g (yield: 63%).

$^1$H NMR (DMSO) δ: 9.49 (s, 1H), 8.63 (s, 1H), 7.66 (s, 1H), 7.66-7.60 (m, 1H), 7.37-7.31 (m, 1H).

<124-3> {2-[4-(4-bromo-2,3-difluoro-phenylamino)-6-nitro-quinazolin-7-oxy]-ethyl}-carbamic acid t-butylester The procedure of Example <1-6> was repeated except for using the compound of <124-2> (4.5 g, 9.96 mmol) to obtain the title compound 3.50 g (yield: 65%).

$^1$H NMR (DMSO) δ: 9.04 (s, 1H), 8.44 (s, 1H), 7.56-7.50 (m, 1H), 7.41 (s, 1H), 7.33-7.27 (m, 1H), 6.93 (bs, aH), 4.28 (t, 2H), 3.34 (t, 2H), 1.35 (s. 9H).

<124-4> [7-(2-amino-ethoxy)-6-nitro-quinazolin-4-yl]-(4-bromo-2,3-difluoro-phenyl)-amide The procedure of Example <1-9> was repeated except for using the compound of <124-3> (2.0 g, 3.70 mmol) to obtain the title compound 1.59 g (yield: 98%).

$^1$H NMR (DMSO) δ: 9.08 (s, 1H), 8.46 (s, 1H), 7.57-7.51 (m, 1H), 7.41 (s, 1H), 7.33-7.27 (m, 1H), 4.27 (t, 2H), 3.33 (bs, 2H), 2.98 (t, 2H).

<124-5> N-{2-[4-(4-bromo-2,3-difluoro-phenylamino)-6-nitro-quinazoline-7-oxy]-ethyl}-2-dimethylamino-acetamide The procedure of Example <12-1> was repeated except for using the compound of <124-4> (135 mg, 0.31 mmol) to obtain the title compound 105 mg (yield: 65%).

$^1$H NMR (CDCl$_3$) δ: 8.78 (s, 1H), 8.71 (s, 1H), 8.31 (bs, 1H), 7.98-7.92 (m, 1H), 7.83-7.79 (m, 1H), 7.42-7.37 (m, 2H), 4.34 (t, 2H), 3.81 (dd, 2H), 2.98 (s, 2H), 2.30 (s, 6H).

<124-6> N-{2-[6-amino-4-(4-bromo-2,3-difluoro-phenylamino)-quinazolin-7-oxy]-ethyl}-2-dimethylamino-acetamide The procedure of Example <1-7> was repeated except for using the compound of <124-5> (105 mg, 0.199 mmol) to obtain the title compound 95.4 mg (yield: 96%).

$^1$H NMR (DMSO) δ: 9.38 (s, 1H), 8.23 (s, 1H), 7.55-7.57 (m, 1H), 7.38-7.39 (m, 1H), 7.24 (s, 1H), 7.04 (s, 1H), 5.55 (bs, 2H), 4.12 (t, 2H), 3.52 (t, 2H), 2.89 (s, 2H), 2.50 (s, 6H).

<124-7> N-{4-(4-bromo-2,3-difluoro-phenylamino)-7-[2-(2-dimethylamino-acetylamino)-ethoxy]-quinazolin-6-yl}-acrylamide The procedure of Example <29-5> was repeated except for using the compound of <124-6> (95.4 mg, 0.192 mmol) to obtain the title compound 83.2 mg (yield: 79%).

$^1$H NMR (CDCl$_3$) δ: 9.20 (s, 1H), 8.98 (s, 1H), 8.61 (s, 1H), 7.96-7.90 (m, 1H), 7.78-7.73 (m, 1H), 7.18 (s, 1H), 6.88-6.79 (m, 1H), 5.81 (d, 1H), 4.22 (t, 2H), 3.85 (t, 2H), 3.03 (s, 2H), 2.27 (s, 6H), 2.03 (s, 2H).

Example 125

Preparation of N-{4-(4-bromo-2,3-difluoro-phenylamino)-7-[2-(3-diethylamino-propionylamino)-ethoxy]-quinazolin-6-yl}-acrylamide <125-1> N-{2-[4-(4-bromo-2,3-difluoro-phenylamino)-6-nitro-quinazolin-7-oxy]-ethyl}-3-diethylamino-propionylamide The procedure of Example 44 was repeated except for using the compound of Example <124-4> (35 mg, 0.306 mmol) and 3-diethylamino-propionic acid (111 mg, 0.61 mmol) to obtain the title compound 98 mg (yield: 78%).

$^1$H NMR (DMSO) δ: 9.22 (s, 1H), 8.79 (s, 1H), 8.56 (s, 1H), 8.16-8.11 (m, 1H), 7.39 (s, 1H), 7.38-7.35 (m, 1H), 4.33 (t, 2H), 3.80 (t, 2H), 2.69 (t, 2H), 2.56 (dd, 4H), 2.40 (s, 2H), 1.02 (t, 6H).

<125-2> N-{2-[6-amino-4-(4-bromo-2,3-difluoro-phenylamino)-quinazolin-7-oxy]-ethyl}-3-diethylamino-propionylamide The procedure of Example <1-7> was repeated except for using the compound of <125-1> (98.9 mg, 0.176 mmol) to obtain the title compound 93.3 mg (yield: 97%).

$^1$H NMR (CDCl$_3$) δ: 9.06 (s, 1H), 8.53 (s, 1H), 8.37-8.34 (m, 1H), 7.29-7.26 (m, 1H), 7.15 (s, 1H), 6.83 (s, 1H), 4.35 (bs, 2H), 4.15 (t, 2H), 3.67 (t, 2H), 2.69 (t, 2H), 2.51 (t, 2H), 2.44 (dd, 4H), 2.34 (t, 2H), 0.92 (t, 6H).

<125-3> N-{4-(4-bromo-2,3-difluoro-phenylamino)-7-[2-(3-diethylamino-propionylamino)-ethoxy]-quinazolin-6-yl}-acrylamide The procedure of Example <29-5> was repeated except for using the compound of <125-2> (93.3 mg, 0.168 mmol) to obtain the title compound 50 mg (yield: 50%).

$^1$H NMR (CDCl$_3$) δ: 9.29 (s, 1H), 9.10 (s, 1H), 8.11 (s, 1H), 8.11-8.09 (m, 1H), 7.76-7.74 (m, 1H), 7.39-7.36 (m, 1H), 7.18 (s, 1H), 6.91-6.86 (m, 1H), 5.87 (d, 1H), 4.21 (t, 2H), 3.80 (t, 2H), 2.66 (t, 2H), 2.57 (dd, 2H), 2.43 (t, 4H), 2.05 (d, 2H), 0.88 (t, 6H).

Example 126

Preparation of N-{4-(4-bromo-2,3-difluoro-phenylamino)-7-[2-(3-piperidin-1-yl-propionylamino)-ethoxy]-quinazolin-6-yl}-acrylamide <126-1> N-{2-[4-(4-bromo-2,3-difluoro-phenylamino)-6-nitro-quinazolin-7-oxy]-ethyl}-3-piperidin-1-yl-propionylamide The procedure of Example 44 was repeated except for using the compound of Example <124-4> (135 mg, 0.306 mmol) and 3-piperidin-1-yl-propionic acid (96.4 mg, 0.613 mmol) to obtain the title compound 133 mg (yield: 75%).
¹H NMR (CDCl₃) δ: 9.05 (s, 1H), 8.75 (s, 1H), 8.64 (s, 1H), 8.16-8.13 (m, 1H), 7.39 (s, 1H), 7.39-7.36 (m, 1H), 4.33 (t, 2H), 3.76 (t, 2H), 2.63-2.59 (m, 2H), 2.04-2.02 (m, 2H), 1.72-1.68 (m, 2H), 1.59-1.54 (m, 6H), 1.46-1.33 (m, 2H).

<126-2> N-{2-[6-amino-4-(4-bromo-2,3-difluoro-phenylamino)-quinazolin-7-oxy]-ethyl}-3-piperidin-1-yl-propionylamide The procedure of Example <1-7> was repeated except for using the compound of <126-1> (134 mg, 0.231 mmol) to obtain the title compound 114 mg (yield: 89%).
¹H NMR (CDCl₃) δ: 9.12 (s, 1H), 8.61 (s, 1H), 8.47-8.45 (m, 1H), 7.38-7.33 (m, 1H), 7.18 (s, 1H), 6.91 (s, 1H), 4.26 (bs, 1H), 4.24 (t, 2H), 3.88 (t, 2H), 2.61 (t, 2H), 2.04 (t, 2H), 1.63-1.61 (m, 2H), 1.52-1.47 (m, 6H), 1.42-1.41 (m, 2H).

<126-3> N-{4-(4-bromo-2,3-difluoro-phenylamino)-7-[2-(3-piperidin-1-yl-propionylamino)-ethoxy]-quinazolin-6-yl}-acrylamide The procedure of Example <29-5> was repeated except for using the compound of <126-2> (114 mg, 0.207 mmol) to obtain the title compound 79 mg (yield: 64%).
¹H NMR (CDCl₃) δ: 9.22 (s, 1H), 9.04 (s, 1H), 8.61 (s, 1H), 7.94 (bs, 2H), 7.13 (s, 1H), 6.90-6.81 (m, 1H), 6.53-6.48 (m, 1H), 5.81 (d, 1H), 4.18 (t, 2H), 3.79 (t, 2H), 2.54 (t, 2H), 2.16 (t, 2H), 1.52-1.45 (m, 8H), 1.44-1.25 (m, 2H).

Example 127

Preparation of N-{2-[6-acryloylamino-4-(4-bromo-2,3-difluoro-phenylamino)-quinazolin-7-oxy]-ethyl}-4-dimethylamino-butylamide <127-1> N-{2-[4-(4-bromo-2,3-difluoro-phenylamino)-6-nitro-quinazolin-7-oxy]-ethyl}-4-dimethylamino-butylamide The procedure of Example 44 was repeated except for using the compound of Example <124-4> (135 mg, 0.306 mmol) and 4-dimethylamino-butyric acid (102 mg, 0.613 mmol) to obtain the title compound 25 mg (yield: 20%).
¹H NMR (CDCl₃) δ: 8.75 (s, 1H), 8.70 (s, 1H), 7.95-7.97 (m, 1H), 7.40-7.35 (m, 3H), 4.40 (t, 2H), 3.93 (t, 2H), 2.02 (t, 2H), 1.44 (s, 2H), 1.34-1.30 (m, 2H), 1.25 (s, 6H).

<127-2> N-{2-[6-amino-4-(4-bromo-2,3-difluoro-phenylamino)-quinazolin-7-oxy]-ethyl}-4-dimethylamino-butylamide The procedure of Example <1-7> was repeated except for using the compound of <127-1> (25 mg, 0.045 mmol) to obtain the title compound 20 mg (yield: 81%).
¹H NMR (CDCl₃) δ: 8.59 (s, 1H), 7.36 (s, 1H), 7.28-7.25 (m, 2H), 7.13 (s, 1H), 4.89 (bs, 2H), 4.29 (t, 2H), 3.90 (t, 2H), 2.05 (t, 2H), 1.49-1.43 (m, 4H), 1.27 (s, 6H).

<127-3> N-{2-[6-acryloylamino-4-(4-bromo-2,3-difluoro-phenylamino)-quinazolin-7-oxy]-ethyl}-4-dimethylamino-butylamide The procedure of Example <29-5> was repeated except for using the compound of <127-2> (20 mg, 0.036 mmol) to obtain the title compound 14 mg (yield: 67%).
¹H NMR (CDCl₃) δ: 9.14 (s, 1H), 9.10 (s, 1H), 8.70 (s, 2H), 7.45 (m, 1H), 4.48 (t, 2H), 3.88 (t, 2H), 3.21-3.19 (m, 2H), 2.70-2.69 (m, 2H), 2.02 (s, 2H), 2.01-1.98 (m, 2H), 1.19 (s, 6H).

Example 128

Preparation of N-[7-(2-acetylamino-ethoxy)-4-(6-chloro-pyridin-3-ylamino)-quinazolin-6-yl]-acrylamide <128-1> (6-chloro-pyridin-3-yl)-(7-fluoro-6-nitro-quinazolin-4-yl)-amine The procedure of Example <1-5> was repeated except for using the compound of Example <1-4> (1.5 g, 6.59 mmol) and 5-amino-2-chloro-pyridine (0.93 g, 7.25 mmol) to obtain the title compound 1.3 g (yield: 61%).
¹H NMR (DMSO) δ: 10.65 (s, 1H), 9.58 (d, 1H), 8.83 (s, 1H), 8.74 (s, 1H), 8.34 (d, 1H), 7.88 (d, 1H), 7.59 (d, 1H).

<128-2> {2-[4-(6-chloro-pyridin-3-ylamino)-6-nitro-quinazolin-7-yloxy]-ethyl}-carbamic acid t-butylester The procedure of Example <1-6> was repeated except for using the compound of <128-1> (1.0 g, 3.13 mmol) and (2-hydroxy-ethyl)-carbamic acid t-butylester (1.0 g, 6.26 mmol) to obtain the title compound 1.1 g (yield: 76%).
¹H NMR (DMSO) δ: 10.23 (s, 1H), 9.15 (s, 1H), 8.77 (s, 1H), 8.62 (s, 1H), 8.29 (d, 1H), 7.51 (d, 1H), 7.46 (s, 1H), 6.91 (br s, 1H), 4.26 (t, 2H), 3.31 (q, 2H), 1.36 (s, 9H).

<128-3> [7-(2-amino-ethoxy)-6-nitro-quinazolin-4-yl]-(6-chloro-pyridin-3-yl)-amine The procedure of Example <1-9> was repeated except for using the compound of <128-2> (1.1 g, 2.39 mmol) to obtain the title compound 720 mg (yield: 85%).
¹H NMR (DMSO) δ: 9.21 (s, 1H), 8.81 (s, 1H), 8.65 (s, 1H), 8.36-8.32 (m, 1H), 7.55 (d, 1H), 7.48 (s, 1H), 4.32 (s, 2H), 4.25 (t, 2H), 3.76 (q, 2H), 3.31 (s, 2H), 2.95 (s, 2H).

<128-4> N-{2-[4-(6-chloro-pyridin-3-ylamino)-6-nitro-quinazolin-7-yloxy]-ethyl}-acetamide The procedure of Example <1-10> was repeated except for using the compound of <128-3> (500 mg, 1.39 mmol) to obtain the title compound 340 mg (yield: 61%).
¹H NMR (CDCl₃+CD₃OD) δ: 9.02 (s, 1H), 8.63 (d, 3H), 8.49-8.43 (m, 2H), 7.40-7.28 (m, 3H), 4.29 (t, 2H), 3.67 (q, 2H), 2.00 (s, 3H).

<128-5> N-{2-[6-amino-4-(6-chloro-pyridin-3-ylamino)-quinazolin-7-yloxy]-ethyl}-acetamide The procedure of Example <1-7> was repeated except for using the compound of <128-4> (340 mg, 0.84 mmol) to obtain the title compound 300 mg (yield: 95%).
¹H NMR (CDCl₃+CD₃OD) δ: 8.74 (s, 1H), 8.43 (s, 2H), 7.39 (d, 2H), 7.09 (s, 1H), 4.25 (t, 2H), 3.74 (q, 2H), 2.03 (s, 3H).

<128-6> N-[7-(2-acetylamino-ethoxy)-4-(6-chloro-pyridin-3-ylamino)-quinazolin-6-yl]-acrylamide The procedure of Example <29-5> was repeated except for using the compound of <128-5> (300 mg, 0.80 mmol) to obtain the title compound 54 mg (yield: 16%).

¹H NMR (CDCl₃+CD₃OD) δ: 9.00 (s, 1H), 8.82 (d, 1H), 8.53 (s, 1H), 8.35 (dd, 1H), 7.40 (d, 1H), 7.14 (s, 1H), 6.79 (q, 1H), 6.51 (dd, 1H), 5.88 (dd, 1H), 4.23 (t, 2H), 4.07 (s, 1H), 3.75 (q, 2H), 2.01 (s, 3H).

Example 129

Preparation of N-[7-(2-acetylamino-ethoxy)-4-(4-chloro-2-fluoro-5-methoxy-phenylamino)-quinazolin-6-yl]-acrylamide <129-1> (4-chloro-2-fluoro-5-methoxy-phenyl)-(7-fluoro-6-nitro-quinazolin-4-yl)-amine The procedure of Example <1-5> was repeated except for using the compound of Example <1-4> (1.5 g, 5.7 mmol) and 4-chloro-2-fluoro-5-methoxy-aniline (1.0 g, 6.25 mmol) to obtain the title compound 1.03 g (yield: 49%).
¹H NMR (DMSO-d₆) δ: 8.74 (s, 1H), 8.31 (s, 1H), 7.87-7.81 (m, 1H), 7.58 (d, 1H), 7.32 (d, 1H).

<129-2> {2-[4-(4-chloro-2-fluoro-5-methoxy-phenylamino)-6-nitro-quinazolin-7-yloxy]-ethyl}-carbamic acid t-butylester The procedure of Example <1-6> was repeated except for using the compound of <129-1> (1.0 g, 2.72 mmol) to obtain the title compound 497 mg (yield: 36%).
¹H NMR (CDCl₃) δ: 8.80 (s, 1H), 8.54 (s, 1H), 8.33 (s, 1H), 7.71 (bs, 1H), 7.40 (s, 1H), 7.28-7.22 (m, 2H), 4.29 (t, 2H), 3.96 (s, 3H), 3.29 (q, 2H), 1.45 (s, 9H).

<129-3> [7-(2-amino-ethoxy)-6-nitro-quinazolin-4-yl]-(4-chloro-2-fluoro-5-methoxy-phenyl)-amine The procedure of Example <1-9> was repeated except for using the compound of <129-2> (497 mg, 0.98 mmol) to obtain the title compound 399 mg (yield: 99%).
¹H NMR (DMSO-d₆) δ: 9.07 (s, 1H), 8.71 (s, 1H), 7.52 (s, 1H), 7.36 (s, 1H), 4.51 (t, 2H), 3.89 (s, 3H), 3.83 (q, 2H).

<129-4> N-{2-[4-(4-chloro-2-fluoro-5-methoxy-phenylamino)-6-nitro-quinazolin-7-yloxy]-ethyl}-acetamide The procedure of Example <1-10> was repeated except for using the compound of <129-3> (399 mg, 0.98 mmol) to obtain the title compound 250 mg (yield: 56%).
¹H NMR (CDCl₃+MeOD) δ: 8.94 (s, 1H), 8.61 (s, 1H), 7.48 (d, 1H), 7.32 (s, 1H), 7.23 (s, 1H), 4.32 (t, 2H), 3.91 (s, 3H), 3.72 (q, 2H), 2.03 (s, 3H).

<129-5> N-{2-[6-amino-4-(4-chloro-2-fluoro-5-methoxy-phenylamino)-quinazolin-7-yloxy]-ethyl}-acetamide The procedure of Example <1-7> was repeated except for using the compound of <129-4> (250 mg, 0.55 mmol) to obtain the title compound 140 mg (yield: 60%).
¹H NMR (CDCl₃+MeOD) δ: 8.50 (s, 1H), 8.20 (d, 1H), 7.25 (d, 1H), 7.09 (d, 2H), 4.22 (t, 2H), 3.95 (s, 3H), 3.73 (q, 2H), 2.01 (s, 3H).

<129-6> N-[7-(2-acetylamino-ethoxy)-4-(4-chloro-2-fluoro-5-methoxy-phenylamino)-quinazolin-6-yl]-acrylamide The procedure of Example <29-5> was repeated except for using the compound of <129-5> (140 mg, 0.33 mmol) to obtain the title compound 20 mg (yield: 13%).

¹H NMR (DMSO-d₆) δ: 9.87 (s, 1H), 9.38 (s, 1H), 9.09 (s, 1H), 8.39 (s, 1H), 8.23 (t, 1H), 7.50 (d, 1H), 7.30-7.25 (m, 2H), 6.88-6.79 (m, 1H), 6.38-6.32 (m, 1H), 5.88-5.84 (m, 1H), 4.22 (t, 2H), 3.83 (s, 3H), 3.56 (q, 2H), 1.93 (s, 3H).

Example 130

Preparation of N-{7-(2-acetylamino-ethoxy)-4-[3-chloro-4-(pyridin-3-ylmethoxy)-phenylamino]-quinazolin-6-yl}-acrylamide <130-1> 7-(2-amino-ethoxy)-6-nitro-quinazolin-4-yl]-[3-chloro-4-(pyridin-3-ylmethoxy)-phenyl]-amine The procedure of Example <1-9> was repeated except for using {2-[4-(4-chloro-2-fluoro-5-methoxy-phenylamino)-6-nitro-quinazolin-7-yloxy]-ethyl}-carbamic acid t-butylester (800 mg, 1.73 mmol, see International Patent Publications WO WO2006/071079) to obtain the title compound 690 mg (yield: 85%).
¹H NMR (DMSO-d₆) δ: 9.46 (s, 1H), 8.58 (t, 1H), 8.49 (s, 1H), 7.98-7.83 (m, 3H), 7.68 (d, 1H), 7.56 (d, 1H), 7.37-7.33 (m, 1H), 7.26-7.23 (m, 1H), 6.99 (s, 1H), 5.27 (s, 2H), 3.69 (q, 2H), 3.43 (q, 2H), 3.29 (s, 2H).

<130-2> N-(2-{4-[3-chloro-4-(pyridin-3-ylmethoxy)-phenylamino]-6-nitro-quinazolin-7-yloxy}-ethyl)-acetamide The procedure of Example <1-10> was repeated except for using the compound of <130-1> (500 mg, 1.07 mmol) to obtain the title compound 170 mg (yield: 31%).
¹H NMR (CDCl₃+MeOD) δ: 8.97 (s, 1H), 8.60-8.54 (m, 2H), 7.89-7.79 (m, 2H), 7.71 (d, 1H), 7.55-7.52 (m, 1H), 7.32-7.28 (m, 2H), 7.03 (d, 1H), 4.30 (t, 2H), 3.72 (q, 2H), 3.61 (s, 2H), 2.05 (s, 3H).

<130-3> N-(2-{6-amino-4-[3-chloro-4-(pyridin-3-ylmethoxy)-phenylamino]-quinazolin-7-yloxy}-ethyl)-acetylamide The procedure of Example <1-7> was repeated except for using the compound of <130-2> (170 mg, 0.33 mmol) to obtain the title compound 26 mg (yield: 16%).
¹H NMR (CDCl₃+MeOD) δ: 8.55 (d, 1H), 8.37 (s, 1H), 7.85-7.78 (m, 1H), 7.71 (d, 1H), 7.53 (dd, 1H), 7.34-7.32 (m, 2H), 7.03 (d, 1H), 5.27 (bs, 2H), 4.20 (t, 2H), 3.70 (q, 2H), 3.38 (s, 2H), 2.01 (s, 3H).

<130-4> N-{7-(2-acetylamino-ethoxy)-4-[3-chloro-4-(pyridin-3-ylmethoxy)-phenylamino]-quinazolin-6-yl}-acrylamide The procedure of Example <29-5> was repeated except for using the compound of <130-3> (25 mg, 0.05 mmol) to obtain the title compound 7 mg (yield: 25%).
¹H NMR (DMSO-d₆) δ: 8.93 (s, 1H), 8.49 (m, 2H), 7.83-7.49 (m, 4H), 7.21-7.14 (m, 2H), 6.97 (d, 1H), 6.76-6.74 (m, 1H), 6.48-6.42 (m, 1H), 5.81-5.78 (m, 1H), 4.14 (t, 2H), 3.67 (q, 2H), 3.56 (s, 2H), 1.95 (s, 3H).

Example 131

Preparation of 5-[7-(2-acetylamino-ethoxy)-6-acryloylamino-quinazolin-4-ylamino]-2-bromo-4-fluoro-N-methoxy-benzamide <131-1> 5-amino-2,4-difluoro-N-methyl-benzamide 5-amino-2,4-difluoro-benzoic acid (6 g, 34.6 mmol), 1-(3-dimethylaminopropyl)-3-ethylcarbodiimide hydrochloride (13.3 g, 69.3 mmol) and 1-hydroxybenzotriazole (9.3 g, 69.3 mmol) was stirred in THF (100 ml). Diisopropylethylamine (7.2 ml, 41.5 mmol) and methylhydroxyamine hydrochloride (4.3 g, 51.9 mmol) were added thereto, and the solution was stirred for 5 hours. The resulting solution was extracted with ethylacetate and washed with salt solution. The resulting residue was recrystallized with diethylether to obtain the title compound 5 g (yield: 71%).
$^1$H NMR (CD$_3$OD) δ: 87.18-7.12 (m, 1H), 6.93 (t, 1H), 3.79 (s, 3H).

<131-2> 2,4-difluoro-5-(7-fluoro-6-nitro-quinazolin-4-ylamino)-N-methyl-benzamide The procedure of Example <1-5> was repeated except for using the compound of <131-1> (765 mg, 3.78 mmol) and the compound of Example <1-4> (1 g, 3.78 mmol) to obtain the title compound 1.38 g (yield: 92%).
$^1$H-NMR (DMSO-d$_6$) δ: 11.65 (s, 1H), 10.61 (bs, 1H), 9.49 (d, 1H), 8.60 (s, 1H), 7.90-7.75 (m, 2H), 7.55 (t, 1H), 3.70 (s, 3H).

<131-3> {5-[7-(2-acetylamino-ethoxy)-6-nitro-quinazolin-4-ylamino]-2,4-difluoro-N-methyl-benzamide The procedure of Example <1-6> was repeated except for using the compound of <131-2> (600 mg, 1.52 mmol) and N-(2-hydroxy-ethyl)-acetamide (421 μl, 4.57 mmol) to obtain the title compound 170 mg (yield: 23%).
$^1$H-NMR (DMSO-d$_6$) δ: 11.77 (s, 1H), 10.36 (s, 1H), 9.25 (s, 1H), 8.65 (s, 1H), 8.20 (t, 1H), 7.91-7.86 (m, 2H), 7.66 (t, 1H), 4.44 (t, 2H), 3.82 (s, 3H), 3.59 (q, 2H), 2.09 (s, 3H).

<131-4> 5-[7-(2-acetylamino-ethoxy)-6-amino-quinazolin-4-ylamino]-2,4-difluoro-N-methyl-benzamide The procedure of Example <1-7> was repeated except for using the compound of <131-3> (340 mg, 0.35 mmol) to obtain the title compound 140 mg (yield: 87%).
$^1$H-NMR (DMSO-d$_6$) δ: 11.60 (s, 1H), 9.27 (s, 1H), 8.19 (s, 2H), 7.73 (t, 1H), 7.57-7.50 (m, 1H), 7.45 (s, 1H), 7.26 (s, 1H), 4.75 (bs, 2H), 4.09 (t, 2H), 3.51 (q, 2H), 1.85 (s, 3H).

<131-5> 5-[7-(2-acetylamino-ethoxy)-6-acryloylamino-quinazolin-4-ylamino]-2-bromo-4-fluoro-N-methoxy-benzamide The procedure of Example <1-8> was repeated except for using the compound of <131-4> (100 mg, 0.22 mmol) to obtain the title compound 27 mg (yield: 25%).
$^1$H-NMR (DMSO-d$_6$) δ: 11.57 (s, 1H), 9.42 (s, 1H), 8.09 (s, 1H), 7.76 (s, 1H), 7.65-7.61 (m, 2H), 7.42 (t, 1H), 6.85-6.79 (m, 1H), 6.31-6.25 (m, 1H), 5.81-5.77 (m, 1H), 4.06 (t, 2H), 3.39 (q, 2H), 1.90 (s, 3H).

Example 132

Preparation of N-[7-(2-acetylamino-ethoxy)-4-(2,4-dichloro-5-methoxy-phenylamino)-quinazolin-6-yl]-acrylamide <132-1> (2,4-dichloro-5-methoxy-phenyl)-(7-fluoro-6-nitro-quinazolin-4-yl)-amine The procedure of Example <1-5> was repeated except for using the compound of Example <1-4> (1.15 g, 4.37 mmol) and 2,4-dichloro-5-methoxy-aniline (1.0 g, 4.80 mmol) to obtain the title compound 1.6 g (yield: 95%).
$^1$H NMR (DMSO-d$_6$) δ: 8.74 (d, 1H), 8.56 (s, 1H), 7.83 (d, 1H), 7.33 (s, 1H), 6.52 (s, 1H), 3.83 (s, 3H).

<132-2> {2-[4-(2,4-dichloro-5-methoxy-phenylamino)-6-nitro-quinazolin-7-yloxy]-ethyl}-carbamic acid t-butylester The procedure of Example <1-6> was repeated except for using the compound of <132-1> (1.0 g, 2.60 mmol) to obtain the title compound (430 mg, yield 31%).
$^1$H NMR (CDCl$_3$) δ: 8.83 (s, 1H), 8.54 (s, 1H), 8.49 (s, 1H), 7.99 (bs, 1H), 7.48 (s, 1H), 7.42 (s, 1H), 5.12 (bs, 1H), 4.31 (t, 2H), 3.99 (s, 3H), 3.67 (q, 2H), 1.46 (s, 9H).

<132-3> [7-(2-amino-ethoxy)-6-nitro-quinazolin-4-yl]-(2,4-dichloro-5-methoxy-phenyl)-amine The procedure of Example <1-9> was repeated except for using the compound of <132-2> (430 mg, 0.82 mmol) to obtain the title compound (350 mg, yield 99%).
$^1$H NMR (CDCl$_3$+MeOD) δ: 8.91 (s, 1H), 8.60 (s, 1H), 7.55-7.52 (m, 2H), 7.37 (s, 1H), 4.31 (t, 2H), 3.94 (s, 3H), 3.36 (q, 2H).

<132-4> N-{2-[4-(2,4-dichloro-5-methoxy-phenylamino)-6-nitro-quinazolin-7-yloxy]-ethyl}-acetamide The procedure of Example <1-10> was repeated except for using the compound of <132-3> (350 mg, 0.82 mmol) to obtain the title compound (300 mg, yield 78%).
$^1$H NMR (CDCl$_3$+MeOD) δ: 8.82 (s, 1H), 8.67 (s, 1H), 7.75 (s, 1H), 7.51 (s, 1H), 7.38 (s, 1H), 7.10 (bs, 1H), 4.34 (t, 2H), 3.95 (s, 3H), 3.74 (q, 2H), 2.03 (s, 3H).

<132-5> N-{2-[6-amino-4-(2,4-dichloro-5-methoxy-phenylamino)-quinazolin-7-yloxy]-ethyl}-acetamide The procedure of Example <1-7> was repeated except for using the compound of <132-4> (295 mg, 0.63 mmol) to obtain the title compound (260 mg, yield 94%).
$^1$H NMR (CDCl$_3$+MeOD) δ: 8.59 (s, 1H), 8.55 (s, 1H), 7.44 (s, 1H), 7.11 (s, 1H), 7.02 (s, 1H), 4.24 (t, 2H), 3.99 (s, 1H), 3.74 (q, 2H), 2.02 (s, 3H).

<132-6> N-[7-(2-acetylamino-ethoxy)-4-(2,4-dichloro-5-methoxy-phenylamino)-quinazolin-6-yl]-acrylamide The procedure of Example <29-5> was repeated except for using the compound of <132-5> (120 mg, 0.27 mmol) to obtain the title compound (30 mg, yield 22%).

¹H NMR (DMSO-d₆) δ: 9.73 (s, 1H), 9.36 (s, 1H), 9.08 (s, 1H), 8.35 (s, 1H), 8.22 (s, 1H), 7.64 (s, 1H), 7.23 (s, 1H), 7.02 (s, 1H), 6.82 (dd, 1H), 6.28 (d, 1H), 5.84 (d, 1H), 4.20 (t, 2H), 3.83 (s, 3H), 3.54 (q, 2H), 1.95 (s, 3H).

Example 133

Preparation of N-[7-(2-acetylamino-ethoxy)-4-(4-bromo-5-chloro-2-fluoro-phenylamino)-quinazolin-6-yl]-acrylamide <133-1> 4-bromo-5-chloro-2-fluoro-phenylamine The procedure of Example <124-1> was repeated except for using 5-chloro-2-fluoro-phenylamine (3.0 g, 20.6 mmol) to obtain the title compound (4.8 g, yield 97%).
¹H NMR (CDCl₃) δ: 7.31-7.20 (m, 1H), 6.88 (d, 1H), 3.80 (1s, 2H).

<133-2> (4-bromo-5-chloro-2-fluoro-phenyl)-(7-fluoro-6-nitro-quinazolin-4-yl)-amine The procedure of Example <1-5> was repeated except for using the compound of Example <1-4> (4.9 g, 21.44 mmol) and the compound of <133-1> (4.8 g, 21.44 mmol) to obtain the title compound 5.7 g (yield: 64%).
¹H NMR (DMSO-d₆) δ: 10.67 (s, 1H), 9.48 (s, 1H), 8.63 (s, 1H), 7.95-7.87 (m, 4H).

<133-3> {2-[4-(4-bromo-5-chloro-2-fluoro-phenylamino)-6-nitro-quinazolin-7-yloxy]-ethyl}-carbamic acid t-butylester The procedure of Example <1-6> was repeated except for using the compound of <133-2> (3.0 g, 7.22 mmol) and (2-hydroxy-ethyl)-carbamic acid t-butylester (3.5 g, 21.66 mmol) to obtain the title compound 2.7 g (yield: 67%).
¹H NMR (CDCl₃) δ: 8.90 (s, 1H), 8.78 (s, 1H), 8.59 (s, 1H), 8.04 (s, 2H), 7.87 (s, 1H), 7.53-7.48 (m, 1H), 7.44 (s, 1H), 4.32 (t, 2H), 3.69 (q, 2H), 1.48 (s, 9H).

<133-4> {2-[6-amino-4-(4-bromo-5-chloro-2-fluoro-phenylamino)-quinazolin-7-yloxy]-ethyl}-carbamic acid t-butylester The procedure of Example <1-7> was repeated except for using the compound of <133-3> (1.7 g, 3.05 mmol) to obtain the title compound 1.4 g (yield: 85%).
¹H NMR (CDCl₃) δ: 9.08 (t, 1H), 8.66 (s, 1H), 7.43 (d, 2H), 7.17 (s, 1H), 6.90 (d, 2H), 4.95 (s, 1H), 4.44 (s, 2H), 4.24 (t, 2H), 3.69 (q, 2H), 1.48 (s, 9H).

<133-5> {2-[6-acryloylamino-4-(4-bromo-5-chloro-2-fluoro-phenylamino)-quinazolin-7-yloxy]-ethyl}-carbamic acid t-butylester The procedure of Example <1-8> was repeated except for using the compound of <133-4> (1.4 g, 2.60 mmol) to obtain the title compound 380 mg (yield: 25%).
¹H NMR (CDCl₃+CD₃OD) δ: 9.06 (s, 1H), 8.50 (s, 1H), 8.08 (d, 1H), 7.64 (d, 2H), 7.55 (d, 1H), 7.18 (s, 1H), 6.91-6.80 (m, 1H), 6.15 (d, 1H), 5.87 (d, 1H), 4.34 (s, 1H), 4.25 (t, 2H), 3.63 (t, 2H), 1.46 (s, 9H).

<133-6> N-[7-(2-amino-ethoxy)-4-(4-bromo-5-chloro-2-fluoro-phenylamino)-quinazolin-6-yl]-acrylamide The procedure of Example <1-9> was repeated except for using the compound of <133-5> (380 mg, 0.65 mmol) to obtain the title compound 300 mg (yield: 95%).
¹H NMR (CDCl₃+CD₃OD) δ: 9.06 (s, 1H), 8.50 (s, 1H), 8.08 (d, 1H), 7.64 (d, 2H), 7.55 (d, 1H), 7.18 (s, 1H), 6.91-6.80 (m, 1H), 6.15 (d, 1H), 5.87 (d, 1H), 4.34 (s, 1H), 4.25 (t, 2H), 3.63 (t, 2H).

<133-7> N-[7-(2-acetylamino-ethoxy)-4-(4-bromo-5-chloro-2-fluoro-phenylamino)-quinazolin-6-yl]-acrylamide The procedure of Example <1-10> was repeated except for using the compound of <133-6> (63 mg, 0.13 mmol) to obtain the title compound 8.9 mg (yield: 13%).
¹H NMR (CDCl₃+CD₃OD) δ: 9.06 (s, 1H), 8.50 (s, 1H), 8.08 (d, 1H), 7.64 (d, 2H), 7.55 (d, 1H), 7.18 (s, 1H), 6.91-6.80 (m, 1H), 6.51 (d, 1H), 5.87 (d, 1H), 4.24 (t, 2H), 3.63 (t, 2H), 1.46 (s, 9H).

Example 134

Preparation of N-[4-(4-bromo-5-chloro-2-fluoro-phenylamino)-7-(2-propionylamino-ethoxy)-quinazolin-6-yl]-acrylamide The procedure of Example <1-9> was repeated except for using the compound of Example <133-6> (53 mg, 0.11 mmol) and propionyl chloride (0.01, ml 0.12 mmol) to obtain the title compound 26 mg (yield: 44%).
¹H NMR (CDCl₃+CD₃OD) δ: 9.03 (s, 1H), 8.56 (s, 1H), 8.29 (t, 1H), 7.44 (d, 1H), 7.09 (s, 1H), 6.91-6.80 (m, 2H), 6.49 (d, 1H), 5.82 (d, 1H), 4.17 (t, 2H), 3.74 (s, 2H), 2.21 (q, 2H), 1.12 (t, 3H).

Example 135

Preparation of N-{4-(4-bromo-5-chloro-2-fluoro-phenylamino)-7-[2-(2-dimethylamino-acetylamino)-ethoxy]-quinazolin-6-yl}-acrylamide The procedure of Example <25-1> was repeated except for using the compound of Example <133-6> (150 mg, 0.31 mmol) to obtain the title compound 109 mg (yield: 61%).
¹H NMR (DMSO-d₆) δ: 9.30 (s, 1H), 9.06 (s, 1H), 8.44-8.21 (m, 2H), 7.84-7.76 (m, 2H), 7.16-7.06 (m, 1H), 6.88-6.78 (m, 1H), 6.35-6.29 (m, 1H), 5.84-5.81 (m, 1H), 4.20 (t, 2H), 3.60 (q, 2H), 2.89 (s, 2H), 2.13 (s, 6H).

Example 136

Preparation of N-[4-(4,5-dichloro-2-fluoro-phenylamino)-7-(2-dimethylamino-ethoxy)-quinazolin-6-yl]-acrylamide <136-1> 4,5-dichloro-2-fluoro-phenylamine The procedure of Example <65-2> was repeated except for using 1,2-dichloro-4-fluoro-5-nitro-benzene (15 g, 7.14 mmol) to obtain the title compound 12.9 g (yield: 99%).
¹H NMR (CDCl₃+MeOD) δ: 7.10 (d, 1H), 6.95 (d, 1H).

<136-2> (4,5-dichloro-2-fluoro-phenyl)-(7-fluoro-6-nitro-quinazolin-4-yl)-amine

The procedure of Example <1-5> was repeated except for using the compound of Example <1-4> (19 g, 72 mmol) and the compound of <136-1> (13 g, 72 mmol) to obtain the title compound 23 g (yield: 86%).
$^1$H NMR (DMSO-$d_6$) δ: 9.45 (d, 1H), 8.60 (s, 1H), 7.89-7.77 (m, 3H).

<136-3> {2-[4-(4,5-dichloro-2-fluoro-phenylamino)-6-nitro-quinazolin-7-yloxy]-ethyl}-carbamic acid t-butylester The procedure of Example <1-6> was repeated except for using the compound of <136-2> (23 g, 62 mmol) and (2-hydroxy-ethyl)-carbamic acid t-butylester (30 g, 186 mmol) to obtain the title compound 20 g (yield: 63%).
$^1$H NMR (CDCl$_3$+MeOD) δ: 8.81 (s, 1H), 8.67 (s, 1H), 8.18 (d, 1H), 7.33-7.29 (m, 2H), 5.36 (bs, 1H), 4.26 (t, 3H), 3.61 (q, 2H), 1.42 (s, 9H).

<136-4> {2-[6-amino-4-(4,5-dichloro-2-fluoro-phenylamino)-quinazolin-7-yloxy]-ethyl}-carbamic acid t-butylester The procedure of Example <1-7> was repeated except for using the compound of <136-3> (20 g, 39 mmol) to obtain the title compound 17.7 g (yield: 94%).
$^1$H NMR (CDCl$_3$+MeOD) δ: 8.82 (d, 1H), 8.55 (s, 1H), 7.28 (s, 1H), 7.09 (s, 1H), 6.94 (s, 1H), 4.17 (t, 2H), 3.62 (m, 2H), 1.44 (s, 9H).

<136-5> {2-[6-acryloylamino-4-(4,5-dichloro-2-fluoro-phenylamino)-quinazolin-7-yloxy]-ethyl}-carbamic acid t-butylester The procedure of Example <29-5> was repeated except for using the compound of <136-4> (17.7 g, 36.7 mmol) to obtain the title compound 6.7 g (yield: 34%).
$^1$H NMR (DMSO-$d_6$) δ: 9.87 (bs, 1H), 9.45 (s, 1H), 9.08 (s, 1H), 8.43 (bs, 1H), 7.84 (bs, 1H), 7.78 (d, 1H), 7.26 (m, 2H), 6.80-6.71 (m, 1H), 6.39-6.33 (m, 1H), 5.87 (d, 1H), 4.20 (m, 2H), 3.45 (d, 2H), 1.39 (s, 9H).

<136-6> N-[7-(2-amino-ethoxy)-4-(4,5-dichloro-2-fluoro-phenylamino)-quinazolin-6-yl]-acrylamide The procedure of Example <1-9> was repeated except for using the compound of <136-5> (6.7 g, 12.5 mmol) to obtain the title compound 5.4 g (yield: 99%).
$^1$H NMR (DMSO-$d_6$) δ: 9.05 (s, 1H), 8.33 (s, 1H), 7.86 (d, 1H), 7.71 (d, 1H), 7.21 (s, 1H), 6.80-6.71 (m, 1H), 6.34-6.28 (m, 1H), 5.83-5.75 (m, 1H), 4.14 (m, 3H), 2.96 (m, 2H).

<136-7> N-[4-(4,5-dichloro-2-fluoro-phenylamino)-7-(2-dimethylamino-ethoxy)-quinazolin-6-yl]-acrylamide The procedure of Example <74-3> was repeated except for using the compound of <136-6> (50 mg, 0.11 mmol) to obtain the title compound 29 mg (yield: 57%).
$^1$H NMR (CDCl$_3$) δ: 9.31 (s, 1H), 9.16 (s, 1H), 8.69-8.64 (m, 2H), 7.72 (s, 1H), 7.29-7.23 (m, 2H), 6.53-6.40 (m, 2H), 5.84-5.80 (m, 1H), 4.29 (t, 2H), 2.97 (t, 2H), 2.40 (s, 6H).

Example 137

Preparation of N-[4-(4,5-dichloro-2-fluoro-phenylamino)-7-(2-propionylamino-ethoxy)-quinazolin-6-yl]-acrylamide The procedure of Example <1-10> was repeated except for using the compound of Example <136-6> (50 mg, 0.11 mmol) and propionyl chloride (13 mg, 0.14 mmol) to obtain the title compound 20 mg (yield: 37%).
$^1$H NMR (CDCl$_3$+MeOD) δ: 9.05 (s, 1H), 8.52 (s, 1H), 8.12 (s, 1H), 7.37 (d, 1H), 7.15 (s, 1H), 6.92-6.83 (m, 1H), 6.55-6.49 (m, 1H), 5.91-5.87 (m, 1H), 4.24 (t, 2H), 3.76 (t, 2H), 2.28 (q, 2H), 1.64 (t, 3H).

Example 138

Preparation of N-{4-(4,5-dichloro-2-fluoro-phenylamino)-7-[2-(2-methoxy-acetylamino)-ethoxy]-quinazolin-6-yl}-acrylamide The procedure of Example <1-10> was repeated except for using the compound of Example <136-6> (50 mg, 0.11 mmol) and methoxyacetyl chloride (20 μl, 0.221 mmol) to obtain the title compound 28 mg (yield: 50%).
$^1$H NMR (CDCl$_3$+MeOD) δ: 9.07 (s, 1H), 8.99 (s, 1H), 8.60 (s, 1H), 8.34 (d, 1H), 7.31-7.20 (m, 2H), 7.12 (s, 1H), 6.82-6.73 (m, 1H), 6.53-6.48 (m, 1H), 5.85-5.81 (m, 1H), 4.23 (t, 2H), 3.94 (s, 2H), 3.84 (m, 2H), 3.41 (s, 3H).

Example 139

Preparation of N-{4-(4,5-dichloro-2-fluoro-phenylamino)-7-[2-(2-methanesulfonyl-acetylamino)-ethoxy]-quinazolin-6-yl}-acrylamide The procedure of Example 44 was repeated except for using the compound of Example <136-6> (50 mg, 0.11 mmol) and methylsulfonyl acetic acid (30 mg, 0.220 mmol) to obtain the title compound 18 mg (29%).
$^1$H NMR (DMSO-$d_6$) δ: 9.87 (bs, 1H), 9.05 (s, 1H), 8.44 (s, 1H), 7.86-7.80 (m, 2H), 7.30 (s, 1H), 6.73 (m, 1H), 6.37-6.31 (m, 1H), 5.83 (m, 1H), 4.66-4.58 (m, 2H), 4.36 (s, 2H), 3.83-3.73 (m, 2H), 3.12 (s, 3H).

Example 140

Preparation of N-{4-(4,5-dichloro-2-fluoro-phenylamino)-7-[2-(2-dimethylamino-acetylamino)-ethoxy]-quinazolin-6-yl}-acrylamide The procedure of Example <25-1> was repeated except for using the compound of Example <136-6> (150 mg, 0.31 mmol) to obtain the title compound 109 mg (yield: 61%).
$^1$H NMR (DMSO-$d_6$) δ: 9.30 (s, 1H), 9.06 (s, 1H), 8.30-8.21 (m, 2H), 7.84-7.81 (m, 2H), 7.16 (m, 1H), 6.88-6.78 (m, 1H), 6.35-6.29 (m, 1H), 5.84-5.81 (m, 1H), 4.12 (t, 2H), 3.76 (q, 2H), 2.89 (s, 2H), 2.13 (s, 3H).

Example 141

Preparation of N-[7-(2-acetylamino-ethoxy)-4-(4-bromo-3-chloro-2-fluoro-phenylamino)-quinazolin-6-yl]-acrylamide <141-1> 4-bromo-3-chloro-2-fluoro-phenylamine The procedure of Example <124-1> was repeated except for using 3-chloro-2-fluoroaniline (1.0 g, 6.87 mmol) to obtain the title compound 900 mg (yield: 58%).

¹H NMR (CDCl₃) δ: 7.18-7.15 (m, 1H), 6.68-6.55 (m, 1H), 3.84 (s, 2H).

<141-2> (4-bromo-3-chloro-2-fluoro-phenyl)-(7-fluoro-6-nitro-quinazolin-4-yl)-amine The procedure of Example <1-5> was repeated except for using the compound of Example <1-4> (913 mg, 4.0 mmol) and the compound of <141-1> (900 mg, 4.0 mmol) to obtain the title compound 665 mg (yield: 40%).
¹H NMR (DMSO-d₆) δ: 10.77 (s, 1H), 9.56 (s, 1H), 8.61 (s, 1H), 7.84 (d, 1H), 7.71 (d, 1H), 7.48 (s, 1H).

<141-3> {2-[4-(4-bromo-3-chloro-2-fluoro-phenylamino)-6-nitro-quinazolin-7-yloxy]-ethyl}-carbamic acid t-butylester The procedure of Example <30-2> was repeated except for using the compound of <141-2> (665 mg, 1.6 mmol) to obtain the title compound 470 mg (yield: 53%).
¹H NMR (CDCl₃) δ: 8.76 (s, 1H), 8.67 (s, 1H), 8.17 (t, 1H), 8.09 (s, 1H), 8.02 (s, 1H), 7.50 (dd, 1H), 7.40 (s, 1H), 5.11 (s, 1H), 4.29 (t, 2H), 3.66 (q, 2H), 1.45 (s, 9H).

<141-4> {2-[6-amino-4-(4-bromo-3-chloro-2-fluoro-phenylamino)-quinazolin-7-yloxy]-ethyl}-carbamic acid t-butylester The procedure of Example <1-7> was repeated except for using the compound of <141-3> (470 mg, 0.84 mmol) to obtain the title compound 400 mg (yield: 90%).
¹H NMR (CDCl₃+CD₃OD) δ: 8.40 (s, 1H), 7.91 (t, 1H), 7.49 (dd, 1H), 7.22 (s, 1H), 7.07 (s, 1H), 6.21 (br t, 1H), 4.22 (t, 2H), 3.91 (s, 2H), 3.64 (q, 2H), 1.47 (s, 9H).

<141-5> {2-[6-acryloylamino-4-(4-bromo-3-chloro-2-fluoro-phenylamino)-quinazolin-7-yloxy]-ethyl}-carbamic acid t-butylester The procedure of Example <25-1> was repeated except for using the compound of <141-4> (400 mg, 0.76 mmol) to obtain the title compound 66 mg (yield: 15%).
¹H NMR (CDCl₃+CD₃OD) δ: 9.00 (s, 1H), 8.47 (s, 1H), 7.69 (t, 1H), 7.43 (dd, 1H), 7.03 (s, 1H), 6.75-6.66 (m, 1H), 6.47 (dd, 1H), 5.81 (dd, 2H), 4.06 (t, 2H), 3.59 (q, 2H) 1.39 (s, 9H).

<141-6> N-[7-(2-amino-ethoxy)-4-(4-bromo-3-chloro-2-fluoro-phenylamino)-quinazolin-6-yl]-acrylamide The procedure of Example <1-9> was repeated except for using the compound of <141-5> (66 mg, 0.11 mmol) to obtain the title compound 45 mg (yield: 82%).
¹H NMR (CDCl₃+CD₃OD) δ: 8.98 (s, 1H), 8.47 (s, 1H), 7.66 (t, 1H), 7.43 (d, 1H), 7.16 (s, 1H), 6.66-6.44 (m, 2H), 5.82 (dd, 1H), 4.22 (t, 2H), 3.22 (t, 2H).

<141-7> N-[7-(2-acetylamino-ethoxy)-4-(4-bromo-3-chloro-2-fluoro-phenylamino)-quinazolin-6-yl]-acrylamide The procedure of Example <1-10> was repeated except for using the compound of <141-6> (20 mg, 0.04 mmol) to obtain the title compound 12 mg (yield: 56%).

¹H NMR (CDCl₃+CD₃OD) δ: 8.95 (s, 1H), 8.43 (s, 1H), 7.64 (t, 1H), 7.40 (dd, 1H), 7.03 (s, 1H), 6.75-6.67 (m, 1H), 6.43 (d, 1H), 5.79 (d, 1H), 4.12 (t, 2H), 3.65 (t, 2H), 1.94 (s, 3H).

Example 142

Preparation of N-[4-(4-bromo-3-chloro-2-fluoro-phenylamino)-7-(2-propionylamino-ethoxy)-quinazolin-6-yl]-acrylamide The procedure of Example 106 was repeated except for using the compound of Example <141-6> (20 mg, 0.04 mmol) to obtain the title compound 16 mg (yield: 70%).
¹H NMR (CDCl₃+CD₃OD) δ: 8.95 (s, 1H), 8.41 (s, 1H), 7.61 (t, 1H), 7.40 (d, 1H), 7.02 (s, 1H), 6.82-6.73 (m, 1H), 6.42 (d, 1H), 5.77 (d, 1H), 4.10 (t, 2H), 3.27 (s, 6H), 2.17 (q, 2H), 1.05 (t, 3H).

Example 143

Preparation of N-{4-(4-bromo-3-chloro-2-fluoro-phenylamino)-7-[2-(2-dimethylamino-acetylamino)-ethoxy]-quinazolin-6-yl}-acrylamide The procedure of Example <25-1> was repeated except for using the compound of Example <141-6> (400 mg, 0.83 mmol) to obtain the title compound 191 mg (yield: 41%).
¹H NMR (CDCl₃+CD₃OD) δ: 8.89 (s, 1H), 8.36 (s, 1H), 7.59-7.33 (m, 1H), 7.32 (dd, 1H), 7.17 (s, 1H), 6.97 (s, 1H), 6.70-6.61 (m, 1H), 6.35 (dd, 1H), 5.70 (dd, 1H), 4.09 (t, 2H), 3.67 (q, 2H), 2.85 (s, 1H), 2.11 (s, 6H).

Example 144

Preparation of N-{4-(4-bromo-3-chloro-2-fluoro-phenylamino)-7-[2-(3-diethylamino-propionylamino)-ethoxy]-quinazolin-6-yl}-acrylamide The procedure of Example 44 was repeated except for using the compound of Example <141-6> (150 mg, 0.31 mmol) and 3-diethylamino propionic acid hydrochloride (67 mg, 0.37 mmol) to obtain the title compound 40 mg (yield: 22%).
¹H NMR (CDCl₃) δ: 9.33 (t, 1H), 9.23 (s, 1H), 9.08 (s, 1H), 8.97 (s, 1H), 8.23 (t, 1H), 7.70 (s, 1H), 7.42 (d, 1H), 7.14 (s, 1H), 6.88 (dd, 1H), 6.53 (d, 1H), 5.82 (d, 1H), 4.18 (t, 2H), 3.78 (q, 2H), 3.37-3.30 (m, 1H), 2.80 (t, 1H), 2.66 (t, 2H), 2.59-2.48 (m, 6H), 2.42 (t, 2H), 1.19-0.97 (m, 7H).

Example 145

Preparation of N-{4-(4-bromo-3-chloro-2-fluoro-phenylamino)-7-[2-(3-hydroxy-propionylamino)-ethoxy]-quinazolin-6-yl}-acrylamide The procedure of Example 44 was repeated except for using the compound of Example <141-6> (60 mg, 0.12 mmol) and 3-hydroxypropionic acid (1.0 ml, 0.24 mmol) to obtain the title compound 2.0 mg (yield: 3%).
¹H NMR (CDCl₃+CD₃OD) δ: 9.41 (s, 1H), 8.52 (s, 1H), 7.71 (t, 1H), 7.36 (d, 1H), 6.84 (s, 1H), 6.75 (dd, 1H), 6.51 (d, 1H), 5.88 (d, 1H), 4.29 (t, 2H), 3.86 (t, 2H), 3.31 (s, s 2H).

Example 146

Preparation of N-{4-(4-bromo-3-chloro-2-fluoro-phenylamino)-7-[2-(2-methoxy-acetylamino)-ethoxy]-quinazolin-6-yl}-acrylamide The procedure of Example 138 was repeated except for using the compound of Example <141-6> (70 mg, 0.146 mmol) to obtain the title compound 10 mg (yield: 13%).

$^1$H NMR (300 MHz, DMSO-d$_6$) δ: 10.4 (br, 1H), 9.12 (s, 1H), 8.53 (s, 1H), 8.08 (t, 1H), 7.71 (d, 1H), 7.50 (s, 2H), 6.87 (m, 1H), 6.58 (d, 1H), 5.83 (d, 1H), 4.35 (t, 2H), 3.53-3.46 (m, 5H), 3.19 (s, 3H).

Example 147

Preparation of N-{4-(4-bromo-3-chloro-2-fluoro-phenylamino)-7-[2-(3-piperidin-1-yl-propiony-lamino)-ethoxy]-quinazolin-6-yl}-acrylamide The procedure of Example 44 was repeated except for using the compound of Example <141-6> (700 mg, 1.46 mmol) and 3-piperidin-1-yl-propionic acid (367 mg, 2.19 mmol) to obtain the title compound 60 mg (yield: 7%).

$^1$H NMR (300 MHz, CDCl$_3$) δ: 9.29 (t, 1H), 9.23 (s, 1H), 9.06 (s, 1H), 8.23 (t, 2H), 7.79 (br, 1H), 7.46 (dd, 1H), 7.16 (s, 1H), 6.92-6.83 (m, 1H), 6.56 (d, 1H), 5.85 (d, 1H), 4.21 (t, 2H), 3.78 (m, 2H), 2.55 (m, 2H), 2.35 (m, 2H), 1.46 (m, 6H).

Example 148

Preparation of N-{2-[6-acryloylamino-4-(4-bromo-3-chloro-2-fluoro-phenylamino)-quinazolin-7-yloxy]-ethyl}-4-dimethylamino-butylamide The procedure of Example 44 was repeated except for using the compound of Example <141-6> (700 mg, 1.46 mmol) and 4-dimethylamino-butyric acid (367 mg, 2.19 mmol) to obtain the title compound 87 mg (yield: 10%).

$^1$H NMR (300 MHz, CDCl$_3$) δ: 9.22 (s, 1H), 9.07 (s, 1H), 8.63 (s, 1H), 8.20 (t, 1H), 7.79 (br, 1H), 7.65 (t, 1H), 7.44 (dd, 1H), 7.13 (s, 1H), 6.93 (m, 1H), 6.55 (d, 1H), 5.84 (d, 1H), 4.20 (t, 2H), 3.78 (q, 2H), 3.13 (m, 2H), 2.33 (m, 2H), 2.15 (s, 6H), 1.80 (p, 2H).

Example 149

Preparation of N-{4-(4-bromo-3-chloro-2-fluoro-phenylamino)-7-[2-(2-hydroxy-acetylamino)-ethoxy]-quinazolin-6-yl}-acrylamide The procedure of Example 44 was repeated except for using the compound of Example <141-6> (700 mg, 1.46 mmol) and hydroxyacetic acid (167 mg, 2.19 mmol) to obtain the title compound 77 mg (yield: 10%).

$^1$H NMR (300 MHz, CD$_3$OD) δ: 9.07 (s, 1H), 8.46 (s, 1H), 7.57 (s, 2H), 7.19 (s, 1H), 6.85-6.76 (m, 1H), 6.50 (d, 1H), 5.88 (d, 1H), 4.30 (t, 2H), 4.22 (s, 2H), 3.82 (m, 2H).

Example 150

Preparation of N-{4-(4-bromo-3-chloro-2-fluoro-phenylamino)-7-[2-(3-methoxy-propionylamino)-ethoxy]-quinazolin-6-yl}-acrylamide The procedure of Example 44 was repeated except for using the compound of Example <141-6> (90 mg, 0.187 mmol) and 3-methoxy-propionic acid (19 mg, 0.281 mmol) to obtain the title compound 25 mg (yield: 19%).

$^1$H NMR (300 MHz, CDCl$_3$) δ: 9.21 (s, 1H), 8.98 (s, 1H), 8.64 (s, 1H), 8.23 (t, 1H), 7.8 (br, 1H), 7.45 (m, 1H), 7.15 (s, 1H), 6.90 (m, 1H), 6.57 (d, 1H), 5.86 (d, 1H), 4.23 (t, 2H), 3.82 (m, 2H), 3.63 (t, 2H), 3.35 (s, 3H), 2.53 (t, 2H).

Example 151

Preparation of N-{4-(4-bromo-3-chloro-2-fluoro-phenylamino)-7-[2-(2-diethylamino-acetylamino)-ethoxy]-quinazolin-6-yl}-acrylamide <151-1> 2-bromo-N-{2-[4-(4-bromo-3-chloro-2-fluoro-phenylamino)-6-nitro-quinazolin-7-yloxy]-ethyl}-acetamide The procedure of Example <1-9> was repeated except for using the compound of Example <141-3> (1.6 g, 2.9 mmol) to obtain [7-(2-amino-ethoxy)-6-nitro-quinazolin-4-yl]-(4-bromo-3-chloro-2-fluoro-phenyl)-amine, and then the procedure of Example 44 was repeated except for using bromoacetic acid (456 mg, 3.28 mmol) without any purification to obtain the title compound 800 mg (yield: 67%).

$^1$H NMR (300 MHz, DMSO-d$_6$) δ: 9.23 (s, 1H), 8.99 (s, 1H), 8.58 (s, 1H), 8.19 (t, 1H), 7.73 (d, 1H), 7.54 (m, 2H), 4.37 (t, 2H), 4.09 (s, 2H), 3.54 (t, 2H).

<151-2> N-{2-[4-(4-bromo-3-chloro-2-fluoro-phenylamino)-6-nitro-quinazolin-7-yloxy]-ethyl}-2-diethylamino-acetylamino The procedure of Example 55 was repeated except for using the compound of <151-1> (400 mg, 0.693 mmol) and diethylamine (0.108 ml, 1.04 mmol) to obtain the title compound 190 mg (yield: 48%).

$^1$H NMR (300 MHz, CDCl$_3$) δ: 8.76 (s, 1H), 8.62 (m, 2H), 8.23 (t, 1H), 8.03 (s, 1H), 7.51 (m, 1H), 7.41 (s, 1H), 4.32 (t, 2H), 3.82 (m, 2H), 3.08 (s, 2H), 2.60 (m, 4H), 1.01 (m, 6H).

<151-3> N-{2-[6-amino-4-(4-bromo-3-chloro-2-fluoro-phenylamino)-quinazolin-7-yloxy]-ethyl}-2-diethylamino-acetylamino The procedure of Example <1-7> was repeated except for using the compound of <151-2> (190 mg, 0.343 mmol) to obtain the title compound 108 mg (yield: 99%).

$^1$H NMR (300 MHz, CDCl$_3$) δ: 8.76 (s, 1H), 8.62 (m, 2H), 8.23 (t, 1H), 8.03 (s, 1H), 7.51 (m, 1H), 7.41 (s, 1H), 4.32 (t, 2H), 3.82 (m, 2H), 3.08 (s, 2H), 2.60 (m, 4H), 1.01 (m, 6H).

<151-4> N-{4-(4-bromo-3-chloro-2-fluoro-phenylamino)-7-[2-(2-diethylamino-acetylamino)-ethoxy]-quinazolin-6-yl}-acrylamide The procedure of Example <29-5> was repeated except for using the compound of <151-3> (108 mg, 0.200 mmol) to obtain the title compound 25 mg (yield: 21%).

$^1$H NMR (300 MHz, CDCl$_3$) δ: 9.22 (s, 1H), 8.64 (s, 1H), 8.22 (t, 1H), 7.9 (t, 1H), 7.8 (br, 1H), 7.46 (dd, 1H), 7.16 (s, 1H), 6.90 (m, 1H), 6.57 (d, 1H), 5.86 (d, 1H), 4.23 (t, 2H), 3.84 (m, 2H), 3.08 (s, 2H), 2.55 (m, 4H), 0.95 (m, 6H).

Example 152

Preparation of N-{4-(4-bromo-3-chloro-phenylamino)-7-[2-(2-dimethylamino-acetylamino)-ethoxy]-quinazolin-6-yl-acrylamide <152-1> (4-bromo-3-chloro-phenyl)-(7-fluoro-6-nitro-quinazolin-4-yl)-amine The procedure of Example <1-5> was repeated except for using the compound of Example <1-4> (639 mg, 2.42 mmol) and 4-bromo-3-chloro-phenylamine (500 mg, 2.42 mmol) to obtain the title compound 658 mg (yield: 68%).
$^1$H NMR (DMSO-d$_6$) δ: 9.78 (d, 1H), 8.85 (s, 1H), 8.27 (s, 1H), 7.93 (d, 1H), 7.85-7.87 (m, 3H).

<152-2> {2-[4-(4-bromo-3-chloro-phenylamino)-6-nitro-quinazolin-7-oxy]-ethyl}-carbamic acid t-butylester The procedure of Example <67-2> was repeated except for using the compound of <152-1> (658 mg, 1.65 mmol) to obtain the title compound 782 mg (yield: 86%).
$^1$H NMR (DMSO-d$_6$) δ: 9.23 (s, 1H), 8.72 (s, 1H), 8.28 (s, 1H), 7.80 (s, 2H), 7.52 (s, 1H), 6.98 (bs, 1H), 4.33 (t, 2H), 3.39 (t, 2H), 1.38 (s, 9H).

<152-3> 7-(2-amino-ethoxy)-6-nitro-quinazolin-4-yl]-(4-bromo-3-chloro-phenyl)-amine The procedure of Example <1-9> was repeated except for using the compound of <152-2> (781 mg, 1.41 mmol) to obtain the title compound 517 mg (yield: 81%).
$^1$H NMR (DMSO-d$_6$) δ: 9.47 (s, 1H), 8.69 (d, 1H), 8.08 (d, 1H), 7.72-7.65 (m, 1H), 7.63-7.59 (m, 1H), 7.47 (s, 1H), 4.26 (t, 2H), 2.95 (s, 2H).

<152-4> N-{2-[4-(4-bromo-3-chloro-phenylamino)-6-nitro-quinazolin-7-oxy]-ethyl}-2-dimethylamino-acetylamino The procedure of Example 44 was repeated except for using the compound of <152-3> (135 mg, 0.298 mmol) to obtain the title compound 97 mg (yield: 62%).
$^1$H NMR (DMSO-d$_6$) δ: 10.22 (s, 1H), 9.27 (s, 1H), 8.76 (s, 1H), 8.32 (s, 1H), 8.01 (m, 1H), 7.96 (s, 2H), 7.59 (s, 1H), 4.43 (t, 2H), 3.58 (t, 2H), 3.28 (s, 2H), 2.53 (s, 6H).

<152-5> N-2-[6-amino-4-(4-bromo-3-chloro-phenylamino)-quinazolin-7-oxy]-ethyl-2-dimethylamino-acetylamino The procedure of Example <1-7> was repeated except for using the compound of <152-4> (97 mg, 0.184 mmol) to obtain the title compound 92 mg (yield: 91%).
$^1$H NMR (DMSO-d$_6$) δ: 9.40 (s, 1H), 8.36 (s, 1H), 8.28 (s, 1H), 8.14 (m, 1H), 8.78 (d, 1H), 7.66 (d, 1H), 7.33 (s, 1H), 7.03 (s, 1H), 5.49 (bs, 2H), 4.10 (t, 2H), 3.56 (t, 2H), 2.86 (s, 2H), 2.15 (s, 6H).

<152-6> N-{4-(4-bromo-3-chloro-phenylamino)-7-[2-(2-dimethylamino-acetylamino)-ethoxy]-quinazolin-6-yl-acrylamide The procedure of Example <29-5> was repeated except for using the compound of <152-5> (92 mg, 0.187 mmol) to obtain the title compound 10 mg (yield: 10%).
$^1$H NMR (CD$_3$OD) δ: 9.00 (s, 1H), 8.45 (s, 1H), 8.26 (s, 1H), 8.12 (s, 1H), 7.67 (d, 2H), 7.23 (s, 1H), 6.86 (s, 2H), 6.50 (d, 2H), 5.88 (d, 1H), 4.25 (t, 2H), 3.82 (t, 2H), 3.31 (s, 2H), 2.51 (s, 6H).

Example 153

Preparation of N-{4-(4-bromo-2-fluoro-phenylamino)-7-[2-(2-dimethylamino-acetylamino-propoxy]-quinazolin-6-yl-acrylamide The procedure of Example 44 was repeated except for using the compound of Example <81-5> (100 mg, 0.219 mmol) to obtain the title compound 38 mg (yield: 32%).
$^1$H NMR (CDCl$_3$) δ: 9.21 (s, 1H), 8.98 (s, 1H), 8.63 (s, 1H), 8.27 (t, 1H), 7.35-7.31 (m, 3H), 7.13 (s, 1H), 6.86 (dd, 1H), 6.53 (d, 1H), 4.25-4.21 (m, 1H), 3.89-3.82 (m, 1H), 3.00 (dd, 2H), 2.24 (s, 6H), 2.01 (s, 2H), 1.34 (d, 3H).

Example 154

Preparation of N-{4-(4-bromo-2-fluoro-phenylamino)-7-[2-(2-dimethylamino-acetylamino)-2-methyl-propoxy]-quinazolin-6-yl}-acrylamide <154-1> {2-[4-(4-bromo-2-fluoro-phenylamino)-6-nitro-quinazolin-7-yloxy]-1,1-dimethyl-ethyl}-carbamic acid t-butylester The procedure of Example <30-2> was repeated except for using the compound of Example <1-5> (5 g, 12.0 mmol) to obtain the title compound 4 g (yield: 61%).
$^1$H NMR (300 MHz, DMSO-d$_6$) δ: 9.15 (s, 1H), 8.50 (s, 1H), 7.70 (m, 1H), 4.32 (s, 2H), 1.28 (m, 9H), 1.17 (s, 6H).

<154-2> [7-(2-amino-2-methyl-propoxy)-6-nitro-quinazolin-4-yl]-(4-bromo-2-fluoro-phenyl)-amine The procedure of Example <1-9> was repeated except for using the compound of <154-1> (4 g, 7.26 mmol) to obtain the title compound 1.2 g (yield: 45%).
$^1$H NMR (300 MHz, DMSO-d$_6$) δ: 9.02 (s, 1H), 8.32 (s, 1H), 7.49 (t, 1H), 7.41-7.13 (m, 2H), 7.05 (s, 1H) 3.96 (s, 2H), 1.13 (s, 6H).

<154-3> N-{2-[4-(4-bromo-2-fluoro-phenylamino)-6-nitro-quinazolin-7-yloxy]-1,1-dimethyl-ethyl}-2-dimethylamino-acetamide The procedure of Example <74-3> was repeated except for using the compound of <154-2> (500 mg, 1.11 mmol) to obtain the title compound 360 mg (yield: 61%).
$^1$H NMR (300 MHz, CDCl$_3$) δ: 10.45 (br, 1H), 9.16 (s, 1H), 8.56 (s, 1H), 7.71 (d, 1H), 7.54-7.45 (m, 3H), 7.33 (s, 1H), 4.43 (s, 2H), 2.77 (s, 2H), 2.16 (s, 6H), 1.40 (d, 3H).

<154-4> N-{4-(4-bromo-2-fluoro-phenylamino)-7-[2-(2-dimethylamino-acetylamino)-2-methyl-propoxy]-quinazolin-6-yl}-acrylamide The procedure of Example <65-5> was repeated except for using the compound of <154-3> (360 mg, 0.289 mmol) to obtain the title compound 140 mg (yield: 38%).
$^1$H NMR (300 MHz, CDCl$_3$) δ: 10.45 (br, 1H), 9.16 (s, 1H), 8.56 (s, 1H), 7.71 (d, 1H), 7.54-7.45 (m, 3H), 7.33 (s, 1H), 4.43 (s, 2H), 2.77 (s, 2H), 2.16 (s, 6H), 1.40 (d, 3H).

Example 155

Preparation of N-{4-(4-bromo-2-fluoro-phenylamino)-7-[2-(3-diethylamino-propionylamino)-propoxy]-quinazolin-6-yl}-acrylamide <155-1> N-{2-[4-(4-bromo-2-fluoro-phenylamino)-6-nitro-quinazolin-7-yloxy]-1-methyl-ethyl}-3-diethylamino-propionamide The procedure of Example <125-1> was repeated except for using the compound of Example <1-5> (314 mg, 0.667 mmol) to obtain the title compound 130 mg (yield: 61%).
$^1$H NMR (300 MHz, DMSO-$d_6$) δ: 9.24 (d, 1H), 8.71 (s, 1H), 8.61 (s, 1H), 8.18 (t, 1H), 7.52 (dd, 1H), 7.38 (s, 1H), 4.48 (m, 1H), 4.23 (m, 2H), 2.68 (t, 2H), 2.56 (q, 4H), 2.35 (t, 2H), 1.34 (d, 3H), 1.04 (t, 6H).

<155-2> N-{4-(4-bromo-2-fluoro-phenylamino)-7-[2-(3-diethylamino-propionylamino)-propoxy]-quinazolin-6-yl}-acrylamide The procedure of Example <65-5> was repeated except for using the compound of <155-1> (130 mg, 0.217 mmol) to obtain the title compound 100 mg (yield: 29%).
$^1$H NMR (300 MHz, CDCl$_3$) δ: 9.24 (m, 2H), 9.10 (s, 1H), 8.66 (s, 1H), 8.27 (t, 1H), 7.70 (s, 1H), 7.47 (dd, 1H), 7.14 (s, 1H), 6.91 (m, 1H), 6.55 (m, 1H), 5.84 (m, 1H), 4.60 (m, 1H), 4.20 (dd, 1H), 3.75 (m, 1H), 2.55 (t, 2H), 2.41 (q, 4H), 1.34 (d, 3H), 0.98 (t, 6H).

Example 156

Preparation of N-{4-(4-bromo-2-fluoro-phenylamino)-7-[2-(2-dimethylamino-acetylamino)-3-methyl-buthoxy]-quinazolin-6-yl}-acrylamide <156-1> N-{2-[4-(4-bromo-2-fluoro-phenylamino)-6-nitro-quinazolin-7-yloxy]-1-methyl-ethyl}-3-diethylamino-propionamide The procedure of Example <65-5> was repeated except for using the compound of Example <1-5> (2 g, 4.81 mmol) to obtain the title compound 411 mg (yield: 41%).
$^1$H NMR (300 MHz, DMSO-$d_6$) δ: 8.84 (s, 1H), 8.61 (s, 1H), 8.45 (t, 1H), 7.70 (s, 1H), 7.47-7.44 (m, 4H), 4.75 (m, 1H), 4.40 (m, 1H), 4.32 (m, 1H), 2.12 (m, 1H), 1.51 (s, 9H), 1.04 (t, 6H).

<156-2> [7-(2-amino-3-methyl-buthoxy)-6-nitro-quinazolin-4-yl]-(4-bromo-2-fluoro-phenyl)-amine The procedure of Example <1-7> was repeated except for using the compound of <156-1> (1.1 g, 1.95 mmol) to obtain the title compound 800 mg (yield: 89%).
$^1$H NMR (300 MHz, CD$_3$OD) δ: 9.00 (s, 1H), 8.49 (s, 1H), 7.59 (t, 1H), 7.48 (dd, 1H), 7.43-7.39 (m, 2H), 4.42-4.26 (m, 1H), 4.21-4.17 (m, 1H), 3.05 (m, 1H), 1.90 (m, 1H), 1.04 (d, 6H).

<156-3> N-{1-[4-(4-bromo-2-fluoro-phenylamino)-6-nitro-quinazolin-7-yloxymethyl]-2-methyl-propyl}-2-dimethylamino-acetamide The procedure of Example 10 was repeated except for using the compound of <156-2> (400 mg, 0.862 mmol) to obtain the title compound 473 mg (yield: 99%).
$^1$H NMR (300 MHz, CDCl$_3$) δ: 8.78 (s, 1H), 8.54 (s, 1H), 8.34 (t, 1H), 7.80 (m, 1H), 7.58 (d, 1H), 7.40-7.33 (m, 3H), 4.35-4.28 (m, 2H), 4.15 (m, 1H), 2.99 (s, 2H), 2.32 (s, 6H), 2.05 (m, 1H), 0.98 (d, 6H).

<156-4> N-{4-(4-bromo-2-fluoro-phenylamino)-7-[2-(2-dimethylamino-acetylamino)-3-methyl-buthoxy]-quinazolin-6-yl}-acrylamide The procedure of Example <65-5> was repeated except for using the compound of <156-3> (500 mg, 0.910 mmol) to obtain the title compound 89 mg (yield: 16%).
$^1$H NMR (300 MHz, CDCl$_3$) δ: 9.21 (s, 1H), 8.96 (s, 1H), 8.64 (s, 1H), 8.27 (t, 1H), 7.70 (br, 1H), 7.45 (d, 1H), 7.42-7.33 (m, 2H), 7.16 (s, 1H), 6.80 (m, 1), 6.55 (d, 1H), 5.83 (m, 1H), 4.36-4.32 (m, 2H), 3.96 (m, 1H), 3.80 (m, 1H), 3.09 (m, 2H), 2.27 (s, 6H), 1.07 (m, 6H).

Example 157

Preparation of N-{4-(4-bromo-3-chloro-2-fluoro-phenylamino)-7-[2-(2-dimethylamino-acetylamino)-propoxy]-quinazolin-6-yl-acrylamide <157-1> 2-[4-(4-bromo-3-chloro-2-fluoro-phenylamino)-6-nitro-quinazolin-7-oxy]-1-methyl-ethyl-carbamic acid t-butylester The procedure of Example <81-2> was repeated except for using the compound of Example <141-2> (800 mg, 1.925 mmol) to obtain the title compound 765 mg (yield: 70%).
$^1$H NMR (300 MHz, DMSO-$d_6$) δ: 10.33 (s, 1H), 9.15 (s, 1H), 8.57 (s, 1H), 7.71 (d, 1H), 6.90 (d, 1H), 4.55 (t, 2H), 4.18 (m, 1H), 1.16 (d, 3H), 0.98 (d, 9H).

<157-2> [7-(2-amino-propoxy)-6-nitro-quinazolin-4-yl]-(4-bromo-3-chloro-2-fluoro-phenyl)-amine The procedure of Example <1-9> was repeated except for using the compound of <157-1> (765 mg, 1.34 mmol) to obtain the title compound 520 mg (yield: 82%).
$^1$H NMR (300 MHz, DMSO-$d_6$) δ: 9.15 (s, 1H), 8.52 (s, 1H), 7.69 (d, 1H), 7.48 (d, 2H), 4.82-4.80 (m, 1H), 4.23 (dd, 2H), 1.24 (d, 3H).

<157-3> N-{2-[4-(4-bromo-3-chloro-2-fluoro-phenylamino)-6-nitro-quinazolin-7-oxy]-1-methyl-ethyl}-2-dimethylamino-acetylamino The procedure of Example 44 was repeated except for using the compound of <157-2> (150 mg, 0.318 mmol) to obtain the title compound 107 mg (yield: 60%).
$^1$H NMR (300 MHz, DMSO-$d_6$) δ: 8.80 (s, 1H), 8.58 (s, 1H), 8.31 (t, 1H), 7.75 (s, 1H), 7.52 (t, 2H), 4.52-4.50 (m, 1H), 4.16 (t, 2H), 2.98 (s, 2H), 2.31 (s, 6H), 1.30 (d, 3H).

<157-4> N-2-[6-amino-4-(4-bromo-3-chloro-2-fluoro-phenylamino)-quinazolin-7-oxy]-1-methyl-ethyl-2-dimethylamino-acetamide The procedure of Example <1-7> was repeated except for using the compound of <157-3> (107 mg, 0.193 mmol) to obtain the title compound 50 mg (yield: 49%).
$^1$H NMR (300 MHz, CDCl$_3$) δ: 8.66 (s, 1H), 7.48-7.43 (m, 2H), 7.17 (s, 1H), 6.88 (s, 1H), 4.62-4.56 (m, 1H), 4.11 (dd, 2H), 2.99 (s, 2H), 2.28 (s, 6H), 1.36 (d, 3H).

<157-5> N-{4-(4-bromo-3-chloro-2-fluoro-phenylamino)-7-[2-(2-dimethylamino-acetylamino)-propoxy]-quinazolin-6-yl-acrylamide The procedure of Example <29-5> was repeated except for using the compound of <157-4> (50 mg, 0.095 mmol) to obtain the title compound 20 mg (yield: 36%).
$^1$H NMR (300 MHz, CDCl$_3$) δ: 9.22 (s, 1H), 8.99 (s, 1H), 8.64 (s, 1H), 8.23 (t, 1H), 7.73 (bs, 1H), 7.44 (dd, 1H), 7.14 (s, 1H), 6.86 (dd, 1H), 6.53 (d, 1H), 5.83 (d, 1H), 4.69-4.66 (m, 1H), 4.24 (dd, 1H), 3.86 (t, 1H), 2.97 dd, 2H), 2.25 (s, 6H), 1.35 (d, 3H).

Example 158

Preparation of (S)—N-4-(4-bromo-3-chloro-2-fluoro-phenylamino)-7-[2-(2-dimethylamino-acetylamino)-propoxy]-quinazolin-6-yl-acrylamide <158-1> (S)-{2-[4-(4-bromo-3-chloro-2-fluoro-phenylamino)-6-nitro-quinazolin-7-oxy]-1-methyl-ethyl-carbamic acid t-butylester The procedure of Example <1-6> was repeated except for using the compound of Example <1-5> (1 g, 2.62 mmol) and (S)-(2-hydroxy-1-methyl-ethyl)-carbamic acid t-butylester (1.38 g, 7.86 mmol) to obtain the title compound 1.09 g (yield: 71%).
$^1$H NMR (300 MHz, DMSO-d$_6$) δ: 10.58 (s, 1H), 9.95 (s, 1H), 9.13 (d, 1H), 8.96-8.92 (m, 3H), 8.36-8.33 (m, 1H), 5.64 (m, 2H), 5.39-5.28 (m, 1H), 2.83 (s, 9H), 2.61 (d, 3H).

<158-2> (S)-[7-(2-amino-propoxy)-6-nitro-quinazolin-4-yl]-(4-bromo-2-fluoro-phenyl)-amine The procedure of Example <1-9> was repeated except for using the compound of <158-1> (400 mg, 0.745 mmol) to obtain the title compound 311 mg (yield: 95%).
$^1$H NMR (300 MHz, DMSO-d$_6$) δ: 10.19 (s, 1H), 9.53 (s, 1H), 8.70 (d, 2H), 8.54-8.51 (m, 2H), 8.47 (s, 1H), 5.12 (t, 2H), 3.56 (m, 1H), 2.14 (d, 3H).

<158-3> (S)—N-2-[4-(4-bromo-2-fluoro-phenylamino)-6-nitro-quinazolin-7-oxy]-1-methyl-ethyl-2-dimethylamino-acetylamino The procedure of Example 44 was repeated except for using the compound of <158-2> (311 mg, 0.712 mmol) to obtain the title compound 110 mg (yield: 30%).
$^1$H NMR (300 MHz, DMSO-d$_6$) δ: 10.19 (s, 1H), 9.53 (s, 1H), 8.70 (d, 2H), 8.54-8.51 (m, 2H), 8.47 (s, 1H), 5.12 (t, 2H), 3.56 (m, 1H), 2.14 (d, 3H).

<158-4> (S)—N-2-[6-amino-4-(4-bromo-3-chloro-2-fluoro-phenylamino)-quinazolin-7-oxy]-1-methyl-ethyl-2-dimethylamino-acetamide The procedure of Example <1-7> was repeated except for using the compound of <158-3> (110 mg, 0.210 mmol) to obtain the title compound 40 mg (yield: 39%).
$^1$H NMR (300 MHz, CDCl$_3$) δ: 8.61 (s, 1H), 7.37-7.33 (m, 2H), 7.03 (s, 1H), 6.91 (s, 1H), 4.63-4.53 (m, 1H), 4.21-4.02 (dd, 2H), 3.00 (s, 2H), 7.03 (s, 1H), 2.26 (s, 6H), 1.38 (d, 3H).

<158-5> (S)—N-4-(4-bromo-3-chloro-2-fluoro-phenylamino)-7-[2-(2-dimethylamino-acetylamino)-propoxy]-quinazolin-6-yl-acrylamide The procedure of Example <29-5> was repeated except for using the compound of <158-4> (40 mg, 0.018 mmol) to obtain the title compound 9 mg (yield: 20%).
$^1$H NMR (300 MHz, CDCl$_3$) δ: 9.21 (s, 1H), 8.98 (s, 1H), 8.63 (s, 1H), 8.27 (t, 1H), 7.35-7.31 (m, 3H), 7.13 (s, 1H), 6.86 (dd, 1H), 6.53 (d, 1H), 4.25-4.21 (m, 1H), 3.89-3.82 (m, 1H), 3.00 (dd, 2H), 2.24 (s, 6H), 2.01 (s, 2H), 1.34 (d, 3H).

Example 159

Preparation of (R)—N-{4-(4-bromo-3-chloro-2-fluoro-phenylamino)-7-[2-(2-dimethylamino-acetylamino)-propoxy]-quinazolin-6-yl-acrylamide <159-1> (R)-2-[4-(4-bromo-2-fluoro-phenylamino)-6-nitro-quinazolin-7-oxy]-1-methyl-ethyl-carbamic acid t-butylester The procedure of Example <1-6> was repeated except for using the compound of Example <1-5> (1 g, 2.62 mmol) and (R)-(2-hydroxy-1-methyl-ethyl)-carbamic acid t-butylester (1.38 g, 7.86 mmol) to obtain the title compound 1.02 g (yield: 70%).
$^1$H NMR (300 MHz, DMSO-d$_6$) δ: 10.58 (s, 1H), 9.95 (s, 1H), 9.13 (d, 1H), 8.96-8.92 (m, 3H), 8.36-8.33 (m, 1H), 5.64 (m, 2H), 5.39-5.28 (m, 1H), 2.83 (s, 9H), 2.61 (d, 3H).

<159-2> (R)-[7-(2-amino-propoxy)-6-nitro-quinazolin-4-yl]-(4-bromo-2-fluoro-phenyl)-amine The procedure of Example <1-9> was repeated except for using the compound of <159-1> (400 mg, 0.745 mmol) to obtain the title compound 344 mg (yield: 99%).
$^1$H NMR (300 MHz, DMSO-d$_6$) δ: 10.19 (s, 1H), 9.53 (s, 1H), 8.70 (d, 2H), 8.54-8.51 (m, 2H), 8.47 (s, 1H), 5.12 (t, 2H), 3.56 (m, 1H), 2.14 (d, 3H).

<159-3> (S)—N-{2-[4-(4-bromo-2-fluoro-phenylamino)-6-nitro-quinazolin-7-oxy]-1-methyl-ethyl}-2-dimethylamino-acetamide The procedure of Example 44 was repeated except for using the compound of <159-2> (344 mg, 0.788 mmol) to obtain the title compound 156 mg (yield: 38%).
$^1$H NMR (300 MHz, CDCl$_3$) δ: 8.79 (s, 1H), 8.51 (s, 1H), 8.38 (t, 1H), 7.60 (s, 1H), 7.47 (m, 1H), 7.42-7.39 (m, 2H), 7.37 (s, 1H), 4.52-4.48 (m, 1H), 4.30-4.21 (m, 2H), 2.95 (s, 2H), 2.28 (s, 6H), 1.40 (d, 3H).

<159-4> (R)—N-2-[6-amino-4-(4-bromo-2-fluoro-phenylamino)-quinazolin-7-oxy]-1-methyl-ethyl-2-dimethylamino-acetamide The procedure of Example <1-7> was repeated except for using the compound of <159-3> (150 mg, 0.287 mmol) to obtain the title compound 57 mg (yield: 40%).
$^1$H NMR (300 MHz, CDCl$_3$) δ: 8.61 (s, 1H), 7.37-7.33 (m, 2H), 7.03 (s, 1H), 6.91 (s, 1H), 4.63-4.53 (m, 1H), 4.21-4.02 (dd, 2H), 3.00 (s, 2H), 7.03 (s, 1H), 2.26 (s, 6H), 1.38 (d, 3H).

<159-5> (R)—N-{4-(4-bromo-3-chloro-2-fluoro-phenylamino)-7-[2-(2-dimethylamino-acetylamino)-propoxy]-quinazolin-6-yl-acrylamide The procedure of Example <29-5> was repeated except for using the compound of <159-4> (57 mg, 0.116 mmol) to obtain the title compound 4.5 mg (yield: 7%).
$^1$H NMR (300 MHz, CDCl$_3$) δ: 9.21 (s, 1H), 8.98 (s, 1H), 8.63 (s, 1H), 8.27 (t, 1H), 7.35-7.31 (m, 3H), 7.13 (s, 1H), 6.86 (dd, 1H), 6.53 (d, 1H), 4.25-4.21 (m, 1H), 3.89-3.82 (m, 1H), 3.00 (dd, 2H), 2.24 (s, 6H), 2.01 (s, 2H), 1.34 (d, 3H).

Example 160

Preparation of N-{4-(4-bromo-2-fluoro-phenylamino)-7-[2-(2-dimethylamino-acetylamino)-butoxy]-quinazolin-6-yl}-acrylamide <160-1> {1-[4-(4-bromo-2-fluoro-phenylamino)-6-nitro-quinazolin-7-yloxymethyl]-propyl}-carbamic acid t-butylester The procedure of Example <1-6> was repeated except for using the compound of Example <1-5> (2 g, 4.81 mmol) and (1-hydroxymethyl-2-methyl-propyl)-carbamic acid t-butylester (2.73 g, 14.4 mmol) to obtain the title compound 2.6 g (yield: 99%).
$^1$H NMR (300 MHz, DMSO-d$_6$) δ: 10.58 (s, 1H), 9.95 (s, 1H), 9.13 (d, 1H), 8.96-8.92 (m, 3H), 8.36-8.33 (m, 1H), 5.64 (m, 2H), 5.39-5.28 (m, 1H), 2.83 (s, 9H), 2.61 (d, 3H).

<160-2> [7-(2-amino-buthoxy)-6-nitro-quinazolin-4-yl]-(4-bromo-2-fluoro-phenyl)-amine The procedure of Example <1-9> was repeated except for using the compound of <160-1> (2.7 g, 4.91 mmol) to obtain the title compound 2.2 g (yield: 99%).
$^1$H NMR (300 MHz, DMSO-d$_6$) δ: 10.19 (s, 1H), 9.53 (s, 1H), 8.70 (d, 2H), 8.54-8.51 (m, 2H), 8.47 (s, 1H), 5.12 (t, 2H), 3.56 (m, 1H), 2.14 (d, 3H).

<160-3> N-{1-[4-(4-bromo-2-fluoro-phenylamino)-6-nitro-quinazolin-7-yloxymethyl]-propyl}-2-dimethylamino-acetamide The procedure of Example 44 was repeated except for using the compound of <160-2> (500 mg, 1.11 mmol) to obtain the title compound 360 mg (yield: 44%).
$^1$H NMR (300 MHz, CDCl$_3$) δ: 8.77 (s, 1H), 8.54 (s, 1H), 8.37 (t, 1H), 7.72 (s, 1H), 7.49 (d, 1H), 7.46-7.37 (m, 3H), 4.28 (s, 3H), 2.97 (s, 2H), 2.29 (s, 6H), 1.67 (m, 2H), 1.10 (t, 3H).

<160-4> N-{1-[6-amino-4-(4-bromo-2-fluoro-phenylamino)-quinazolin-7-yloxymethyl]-propyl}-2-dimethylamino-acetamide The procedure of Example <65-5> was repeated except for using the compound of <160-3> (260 mg, 0.486 mmol) to obtain the title compound 92 mg (yield: 35%).
$^1$H NMR (300 MHz, CDCl$_3$) δ: 9.23 (s, 1H), 8.99 (s, 1H), 8.65 (s, 1H), 8.33 (t, 1H), 7.60 (s, 1H), 7.37-7.33 (m, 2H), 7.15 (s, 1H), 6.80 (m, 1), 6.55 (d, 1H), 5.83 (m, 1H), 4.30 (m, 1H), 4.26 (m, 1H), 3.96 (1H), 2.98 (q, 2H), 2.27 (s, 6H), 1.60 (m, 2H), 1.10 (t, 3H).

Example 161

Preparation of N-{4-(4-bromo-2-fluoro-phenylamino)-7-[2-(2-dimethylamino-3-methoxy-propionylamino)-ethoxy]-quinazolin-6-yl}-acrylamide <161-1> (1-{2-[4-(4-bromo-2-fluoro-phenylamino)-6-nitro-quinazolin-7-yloxy]-ethylcarbamoyl}-2-methoxy-ethyl)-carbamic acid t-butylester The procedure of Example 44 was repeated except for using the compound of Example <18-3> (1.54 g, 3.65 mmol) and 2-t-buthoxycarbonylamino-3-methoxy-propionic acid (1.2 g, 5.47 mmol) to obtain the title compound 1.5 g (yield: 68%).
$^1$H NMR (300 MHz, CDCl$_3$) δ: 8.77 (s, 1H), 8.56 (s, 1H), 8.32 (t, 1H), 7.80 (s, 1H), 7.41-7.37 (m, 2H), 7.10 (t, 1H), 4.31 (m, 2H), 3.83-3.79 (m, 4H), 3.48 (m, 1H), 3.33 (s, 3H), 1.42 (s, 9H).

<161-2> 2-amino-N-{2-[4-(4-bromo-2-fluoro-phenylamino)-6-nitro-quinazolin-7-yloxy]-ethyl}-3-methoxy-propionamide The procedure of Example <1-9> was repeated except for using the compound of <161-1> (1.5 g, 2.41 mmol) to obtain the title compound 1.3 g (yield: 99%).
$^1$H NMR (300 MHz, CD$_3$OD) δ: 8.05 (s, 1H), 8.47 (d, 1H), 7.55 (t, 1H), 7.52 (d, 1H), 7.44-7.37 (m, 2H), 4.38 (m, 2H), 4.10 (m, 2H), 3.70 (m, 2H), 3.54 (m, 1H), 3.33 (s, 3H).

<161-3> N-{2-[4-(4-bromo-2-fluoro-phenylamino)-6-nitro-quinazolin-7-yloxy]-ethyl}-2-dimethylamino-3-methoxy-propionamide The procedure of Example <74-3> was repeated except for using the compound of <161-2> (1.3 g, 2.48 mmol) to obtain the title compound 600 mg (yield: 44%).
$^1$H NMR (300 MHz, CDCl$_3$) δ: 8.78 (s, 1H), 8.51 (s, 1H), 8.37 (t, 2H), 7.82 (t, 1H), 7.60 (s, 1H), 7.42-7.37 (m, 3H), 4.38 (m, 2H), 3.81-3.66 (m, 4H), 3.37 (s, 3H), 3.09 (m, 1H), 2.37 (s, 6H).

<161-4> N-{4-(4-bromo-2-fluoro-phenylamino)-7-[2-(2-dimethylamino-3-methoxy-propionylamino)-ethoxy]-quinazolin-6-yl}-acrylamide The procedure of Example <65-5> was repeated except for using the compound of <161-3> (250 mg, 0.353 mmol) to obtain the title compound 23 mg (yield: 91%).
$^1$H NMR (300 MHz, CDCl$_3$) δ: 9.57 (s, 1H), 9.02 (s, 1H), 8.66 (s, 1H), 8.34 (t, 1H), 7.76 (t, 1H) 7.57 (s, 1H), 7.37-7.23 (m, 2H), 7.16 (s, 1H), 6.87 (m, 1), 6.56 (d, 1H), 5.86 (m, 1H), 4.25 (m, 2H), 3.76 (m, 4H), 3.14 (s, 3H), 2.99 (m, 1H), 2.32 (s, 6H).

Example 162

Preparation of N-{4-(4-bromo-2-fluoro-phenylamino)-7-[2-(2-dimethylamino-3-hydroxy-propionylamino)-ethoxy]-quinazolin-6-yl}-acrylamide <162-1> N-{2-[4-(4-bromo-2-fluoro-phenylamino)-6-nitro-quinazolin-7-yloxy]-ethyl}-2-dimethylamino-3-hydroxy-propionamide The procedure of Example <67-2> was repeated except for using the compound of Example <161-3> (350 mg, 0.635 mmol) to obtain the title compound 318 mg (yield: 96%).

¹H NMR (300 MHz, CDCl₃) δ: 8.78 (s, 1H), 8.52 (s, 1H), 8.35 (t, 1H), 7.91 (t, 1H), 7.64 (br, 1H), 7.43-7.36 (m, 3H), 4.37 (m, 2H), 3.82 (m, 4H), 3.14 (m, 1H), 2.38 (s, 6H).

<162-2> N-{4-(4-bromo-2-fluoro-phenylamino)-7-[2-(2-dimethylamino-3-hydroxy-propionylamino)-ethoxy]-quinazolin-6-yl}-acrylamide The procedure of Example <65-5> was repeated except for using the compound of <162-1> (318 mg, 0.611 mmol) to obtain the title compound 23 mg (yield: 8.4%).

¹H NMR (300 MHz, CDCl₃) δ: 9.21 (s, 1H), 8.87 (s, 1H), 8.65 (s, 1H), 8.35 (t, 1H), 7.86 (t, 1H), 7.63 (s, 2H), 7.37-7.32 (m, 2H), 7.19 (s, 1H), 6.73 (m, 1), 6.56 (d, 1H), 5.89 (m, 1H), 4.27 (m, 2H), 3.97-3.85 (m, 4H), 3.12 (m, 1H), 2.30 (s, 6H).

Example 163

Preparation of (S)—N-4-(4-bromo-3-chloro-2-fluoro-phenylamino)-7-[2-(2-dimethylamino-acetylamino)-propoxy]-quinazolin-6-yl-acrylamide <163-1> (S)-2-[4-(4-bromo-3-chloro-2-fluoro-phenylamino)-6-nitro-quinazolin-7-oxy]-1-methyl-ethyl-carbamic acid t-butylester The procedure of Example <158-1> was repeated except for using the compound of Example <141-2> (500 mg, 1.20 mmol) to obtain the title compound 600 mg (yield: 87%).

¹H NMR (300 MHz, DMSO-d₆) δ: 10.33 (s, 1H), 9.15 (s, 1H), 8.57 (s, 1H), 7.71 (d, 1H), 6.90 (d, 1H), 4.55 (t, 2H), 4.18 (m, 1H), 1.16 (d, 3H), 0.98 (d, 9H).

<163-2> (S)-[7-(2-amino-propoxy)-6-nitro-quinazolin-4-yl]-(4-bromo-3-chloro 2-fluoro-phenyl)-amine The procedure of Example <1-9> was repeated except for using the compound of <163-1> (600 mg, 1.05 mmol) to obtain the title compound 271 mg (yield: 55%).

¹H NMR (300 MHz, DMSO-d₆) δ: 9.15 (s, 1H), 8.52 (s, 1H), 7.69 (d, 1H), 7.48 (d, 2H), 4.82-4.80 (m, 1H), 4.23 (dd, 2H), 1.24 (d, 3H).

<163-3> (S)—N-{2-[4-(4-bromo-3-chloro-2-fluoro-phenylamino)-6-nitro-quinazolin-7-oxy]-1-methyl-ethyl}-2-dimethylamino-acetylamino The procedure of Example 44 was repeated except for using the compound of <163-2> (271 mg, 0.575 mmol) to obtain the title compound 209 mg (yield: 65%).

¹H NMR (300 MHz, CDCl₃) δ: 8.80 (s, 1H), 8.58 (s, 1H), 8.31 (t, 1H), 7.75 (s, 1H), 7.52 (t, 2H), 4.52-4.50 (m, 1H), 4.16 (t, 2H), 2.98 (s, 2H), 2.31 (s, 6H), 1.30 (d, 3H).

<163-4> (S)—N-{2-[6-amino-4-(4-bromo-3-chloro-2-fluoro-phenylamino)-quinazolin-7-oxy]-1-methyl-ethyl}-2-dimethylamino-acetylamino The procedure of Example <1-7> was repeated except for using the compound of <163-3> (209 mg, 0.376 mmol) to obtain the title compound 145 mg (yield: 73%).

¹H NMR (300 MHz, CDCl₃) δ: 8.66 (s, 1H), 7.48-7.43 (m, 2H), 7.17 (s, 1H), 6.88 (s, 1H), 4.62-4.56 (m, 1H), 4.11 (dd, 2H), 2.99 (s, 2H), 2.28 (s, 6H), 1.36 (d, 3H).

<163-5> (S)—N-4-(4-bromo-3-chloro-2-fluoro-phenylamino)-7-[2-(2-dimethylamino-acetylamino)-propoxy]-quinazolin-6-yl-acrylamide The procedure of Example <29-5> was repeated except for using the compound of <163-4> (145 mg, 0.25 mmol) to obtain the title compound 53 mg (yield: 33%).

¹H NMR (300 MHz, CDCl₃) δ: 9.22 (s, 1H), 8.99 (s, 1H), 8.64 (s, 1H), 8.23 (t, 1H), 7.73 (bs, 1H), 7.44 (dd, 1H), 7.14 (s, 1H), 6.86 (dd, 1H), 6.53 (d, 1H), 5.83 (d, 1H), 4.69-4.66 (m, 1H), 4.24 (dd, 1H), 3.86 (t, 1H), 2.97 (dd, 2H), 2.25 (s, 6H), 1.35 (d, 3H).

Example 164

Preparation of (R)—N-4-(4-bromo-3-chloro-2-fluoro-phenylamino)-7-[2-(2-dimethylamino-acetylamino)-propoxy]-quinazolin-6-yl-acrylamide <164-1> (R)-2-[4-(4-bromo-3-chloro-2-fluoro-phenylamino)-6-nitro-quinazolin-7-oxy]-1-methyl-ethyl-carbamic acid t-butylester The procedure of Example <159-1> was repeated except for using the compound of Example <141-2> (500 mg, 1.20 mmol) to obtain the title compound 531 mg (yield: 77%).

¹H NMR (300 MHz, DMSO-d₆) δ: 10.33 (s, 1H), 9.15 (s, 1H), 8.57 (s, 1H), 7.71 (d, 1H), 6.90 (d, 1H), 4.55 (t, 2H), 4.18 (m, 1H), 1.16 (d, 3H), 0.98 (d, 9H).

<164-2> (S)-[7-(2-amino-propoxy)-6-nitro-quinazolin-4-yl]-(4-bromo-3-chloro-2-fluoro-phenyl)-amine The procedure of Example <1-9> was repeated except for using the compound of <164-1> (531 mg, 0.930 mmol) to obtain the title compound 236 mg (yield: 54%).

¹H NMR (300 MHz, DMSO-d₆) δ: 9.15 (s, 1H), 8.52 (s, 1H), 7.69 (d, 1H), 7.48 (d, 2H), 4.82-4.80 (m, 1H), 4.23 (dd, 2H), 1.24 (d, 3H).

<164-3> (R)—N-{2-[4-(4-bromo-3-chloro-2-fluoro-phenylamino)-6-nitro-quinazolin-7-oxy]-1-methyl-ethyl}-2-dimethylamino-acetamide The procedure of Example 44 was repeated except for using the compound of <164-2> (236 mg, 0.501 mmol) to obtain the title compound 160 mg (yield: 21%).

¹H NMR (300 MHz, CDCl₃) δ: 8.80 (s, 1H), 8.58 (s, 1H), 8.31 (t, 1H), 7.75 (s, 1H), 7.52 (t, 2H), 4.52-4.50 (m, 1H), 4.16 (t, 2H), 2.98 (s, 2H), 2.31 (s, 6H), 1.30 (d, 3H).

<164-4> (R)—N-{2-[6-amino-4-(4-bromo-3-chloro-2-fluoro-phenylamino)-quinazolin-7-oxy]-1-methyl-ethyl}-2-dimethylamino-acetamide The procedure of Example <1-7> was repeated except for using the compound of <164-3> (184 mg, 0.331 mmol) to obtain the title compound 161 mg (yield: 92%).

¹H NMR (300 MHz, CDCl₃) δ: 8.66 (s, 1H), 7.48-7.43 (m, 2H), 7.17 (s, 1H), 6.88 (s, 1H), 4.62-4.56 (m, 1H), 4.11 (dd, 2H), 2.99 (s, 2H), 2.28 (s, 6H), 1.36 (d, 3H).

<164-5> (R)—N-4-(4-bromo-3-chloro-2-fluoro-phenylamino)-7-[2-(2-dimethylamino-acetylamino)-propoxy]-quinazolin-6-yl-acrylamide The procedure of Example <29-5> was repeated except for using the compound of <164-4> (162 mg, 0.308 mmol) to obtain the title compound 65 mg (yield: 37%).

$^1$H NMR (300 MHz, CDCl$_3$) δ: 9.22 (s, 1H), 8.99 (s, 1H), 8.64 (s, 1H), 8.23 (t, 1H), 7.73 (bs, 1H), 7.44 (dd, 1H), 7.14 (s, 1H), 6.86 (dd, 1H), 6.53 (d, 1H), 5.83 (d, 1H), 4.69-4.66 (m, 1H), 4.24 (dd, 1H), 3.86 (t, 1H), 2.97 (dd, 2H), 2.25 (s, 6H), 1.35 (d, 3H).

Example 165

Preparation of {2-[6-acryloylamino-4-(4-bromo-3-chloro-2-fluoro-phenylamino)-quinazolin-7-yloxy]-ethyl}-carbamic acid methylester The procedure of Example 63 was repeated except for using the compound of Example <141-6> (100 mg, 0.208 mmol) to obtain the title compound 12 mg (yield: 11%).

$^1$H NMR (300 MHz, CDCl$_3$) δ: 9.25 (s, 1H), 9.03 (s, 1H), 8.67 (s, 1H), 8.28 (t, 1H), 7.73 (s, 1H), 7.44 (d, 2H), 7.17 (s, 1H), 6.80 (m, 1), 6.56 (d, 1H), 5.86 (m, 1H), 4.22 (m, 2H), 3.79 (m, 2H), 3.67 (s, 3H).

Example 166

Preparation of N-{4-(4-chloro-2,5-dimethoxy-phenylamino)-7-[2-(2-dimethylamino-acetylamino)-ethoxy]-quinazolin-6-yl}-acrylamide <166-1> (4-chloro-2,5-dimethoxy-phenyl)-(7-fluoro-6-nitro-quinazolin-4-yl)-amine The procedure of Example <1-5> was repeated except for using the compound of Example <1-4> (2 g, 7.57 mmol) and 4-chloro-2,5-dimethoxy-phenylamine (1.42 g, 7.57 mmol) to obtain the title compound 2.86 g (yield: 99%).

$^1$H NMR (300 MHz, DMSO-d$_6$) δ: 10.32 (s, 1H), 9.56 (d, 1H), 8.55 (s, 1H), 7.78 (d, 1H), 7.24 (d, 2H), 3.78 (s, 3H), 3.73 (s, 3H).

<166-2> {2-[4-(4-chloro-2,5-dimethoxy-phenylamino)-6-nitro-quinazolin-7-oxy]-ethyl}-carbamic acid t-butylester The procedure of Example <18-2> was repeated except for using the compound of <166-1> (1 g, 2.64 mmol) to obtain the title compound 400 mg (yield: 32%)

$^1$H NMR (300 MHz, DMSO-d$_6$) δ: 8.86 (s, 1H), 8.67 (d, 2H), 8.23 (s, 1H), 8.02 (t, 1H), 7.12 (s, 1H), 7.00 (s, 1H), 4.43 (t, 2H), 3.99 (s, 3H), 3.96 (s, 3H), 3.67 (q, 2H), 2.13 (s, 3H).

<166-3> [7-(2-amino-ethoxy)-6-nitro-quinazolin-4-yl]-(4-chloro-2,5-dimethoxy-phenyl)-amine The procedure of Example <1-9> was repeated except for using the compound of <166-2> (270 mg, 0.518 mmol) to obtain the title compound 132 mg (yield: 61%)

$^1$H NMR (300 MHz, DMSO-d$_6$) δ: 9.18 (s, 1H), 8.47 (s, 1H), 7.43 (s, 1H), 7.32 (s, 1H), 7.23 (s, 1H), 4.24 (t, 2H), 3.71 (d, 6H), 2.94 (t, 2H).

<166-4> N-{2-[4-(4-chloro-2,5-dimethoxy-phenylamino)-6-nitro-quinazolin-7-oxy]-ethyl-2-dimethylamino-acetamide The procedure of Example 44 was repeated except for using the compound of <166-3> (132 mg, 0.314 mmol) to obtain the title compound 108 mg (yield: 70%)

$^1$H NMR (300 MHz, CDCl$_3$) δ: 8.83 (s, 1H), 8.67 (s, 1H), 8.46 (s, 1H), 8.20 (s, 1H), 7.70 (bs, 1H), 7.41 (s, 1H), 7.02 (s, 1H), 4.36 (t, 2H), 3.99 (d, 6H), 3.84 (t, 2H), 3.01 (s, 2H) 2.33 (s, 6H).

<166-5> N-{2-[6-amino-4-(4-chloro-2,5-dimethoxy-phenylamino)-quinazolin-7-oxy]-ethyl-2-dimethylamino-acetamide The procedure of Example <1-7> was repeated except for using the compound of <166-4> (108 mg, 0.220 mmol) to obtain the title compound 95 mg (yield: 90%)

$^1$H NMR (300 MHz, CDCl$_3$) δ: 8.83 (s, 1H), 8.67 (s, 1H), 8.46 (s, 1H), 8.20 (s, 1H), 7.70 (bs, 1H), 7.41 (s, 1H), 7.02 (s, 1H), 4.36 (t, 2H), 3.99 (d, 6H), 3.84 (t, 2H), 3.01 (s, 2H) 2.33 (s, 6H).

<166-6> N-{4-(4-chloro-2,5-dimethoxy-phenylamino)-7-[2-(2-dimethylamino-acetylamino)-ethoxy]-quinazolin-6-yl}-acrylamide The procedure of Example <29-5> was repeated except for using the compound of <166-4> (95 mg, 0.200 mmol) to obtain the title compound 39 mg (yield: 37%)

$^1$H NMR (300 MHz, CDCl$_3$) δ: 9.28 (s, 1H), 8.94 (s, 1H), 8.72 (s, 1H), 8.66 (s, 1H), 8.21 (bs, 1H), 7.21 (bs, 1H), 7.18 (s, 1H), 7.00 (s, 2H), 6.91-6.82 (m, 1H), 6.55 (d, 1H), 5.86 (d, 2H), 4.25 (t, 2H), 3.99 (d, 6H), 3.88 (t, 2H), 3.04 (s, 2H), 2.29 (s, 6H).

Example 167

Preparation of N-{4-(4-bromo-2-fluoro-phenylamino)-7-[2-(2-diethylamino-acetylamino)-ethoxy]-quinazolin-6-yl}-acrylamide <167-1> 2-bromo-N-{2-[4-(4-bromo-2-fluoro-phenylamino)-6-nitro-quinazolin-7-yloxy]-ethyl}-acetamide The procedure of Example 44 was repeated except for using the compound of Example <18-3> (900 mg, 2.13 mmol) and bromoacetic acid (355 mg, 2.56 mmol) to obtain the title compound 745 mg (yield: 64%).

$^1$H NMR (300 MHz, CDCl$_3$+CD$_3$OD) δ: 8.97 (s, 1H), 8.51 (s, 1H), 7.59 (t, 1H), 7.31-7.26 (m, 3H), 4.54-4.26 (m, 2H), 3.76-3.70 (m, 2H), 3.09-3.02 (m, 2H).

<167-2> N-{2-[4-(4-bromo-2-fluoro-phenylamino)-6-nitro-quinazolin-7-yloxy]-ethyl}-2-diethylamino-acetamide Diethylamine (0.16 ml, 1.55 mmol) and potassium carbonate (267 mg, 1.93 mmol) were diluted with dimethylformamide (40 ml), and the compound of <167-1> (700 mg, 1.29 mmol) was added thereto. The solution was refluxed at 90° C.

for 3 hours, slowly cooled to room temperature, and the reaction was terminated with saturated sodium bicarbonate aqueous solution (40 ml). The resulting solution was extracted with ethylacetate (100 ml) and washed with distilled water (100 ml) 4 times. The separated organic layer was dried over magnesium sulfate, filtered and distilled under a reduced pressure, and subjected to column chromatography to obtain the title compound 240 mg (yield: 35%).

$^1$H NMR (300 MHz, CDCl$_3$) δ: 8.81 (s, 1H), 8.75 (s, 1H), 8.51 (s, 1H), 7.38 (t, 4H), 4.33 (t, 2H), 3.82 (q, 2H), 2.57 (q, 4H), 1.02 (t, 5H).

<167-3> N-{2-[6-amino-4-(4-bromo-2-fluoro-phenylamino)-quinazolin-7-yloxy]-ethyl}-2-diethylamino-acetamide The procedure of Example <1-7> was repeated except for using the compound of <167-2> (240 mg, 0.45 mmol) and bromoacetic acid (355 mg, 2.56 mmol) to obtain the title compound 223 mg (yield: 99%).

$^1$H NMR (300 MHz, DMSO-d$_6$) δ: 8.62 (s, 1H), 8.56 (t, 2H), 7.88 (t, 1H), 7.45-7.35 (m, 4H), 7.18 (s, 1H), 7.02 (s, 1H), 4.68 (s, 2H), 4.26 (t, 2H), 3.85 (q, 2H), 2.59 (q, 4H), 0.91 (t, 6H).

<167-4> N-{4-(4-bromo-2-fluoro-phenylamino)-7-[2-(2-diethylamino-acetylamino)-ethoxy]-quinazolin-6-yl}-acrylamide The procedure of Example <29-5> was repeated except for using the compound of <167-3> (240 mg, 0.45 mmol) and bromoacetic acid (355 mg, 2.56 mmol) to obtain the title compound 39 mg (yield: 16%).

$^1$H NMR (300 MHz, CDCl$_3$) δ: 9.22 (s, 1H), 9.00 (s, 1H), 8.63 (s, 1H), 8.27 (t, 1H), 7.92 (t, 1H), 7.66 (s, 1H), 7.33-7.28 (m, 3H), 7.13 (s, 1H), 6.91-6.83 (m, 1H), 6.52 (d, 1H), 5.83 (d, 1H), 4.19 (t, 2H), 3.84 (q, 2H), 3.27 (t, 2H), 3.08 (s, 2H), 2.53 (q, 4H), 0.96 (t, 6H).

Example 168

Preparation of N-{4-(4-bromo-3-chloro-2-fluoro-phenylamino)-7-[2-(3-ethyl-ureido)-ethoxy]-quinazolin-6-yl}-acrylamide The procedure of Example <23-1> was repeated except for using the compound of Example <141-6> (80 mg, 0.166 mmol) to obtain the title compound 21 mg (yield: 23%)

$^1$H NMR (300 MHz, CDCl$_3$) δ: 9.91 (s, 1H), 9.63 (s, 1H), 9.16 (s, 1H), 8.41 (s, 1H), 7.68 (d, 1H), 7.48 (t, 1H), 7.24 (s, 1H), 6.91-6.82 (m, 1H), 6.38 (d, 1H), 6.22 (t, 1H), 4.18 (m, 2H), 3.53 (m, 2H), 3.08 (q, 2H), 0.98 (t, 3H).

Example 169

Preparation of N-{4-(4-bromo-3-chloro-2-fluoro-phenylamino)-7-[2-(3-propyl-ureido)-ethoxy]-quinazolin-6-yl}-acrylamide The procedure of Example 34 was repeated except for using the compound of Example <141-6> (80 mg, 0.166 mmol) to obtain the title compound 30 mg (yield: 32%).

$^1$H NMR (CD$_3$OD) δ: 9.91 (s, 1H), 9.63 (s, 1H), 9.16 (s, 1H), 8.41 (s, 1H), 7.68 (d, 1H), 7.48 (t, 1H), 7.24 (s, 1H), 6.91-6.82 (m, 1H), 6.38 (d, 1H), 6.22 (t, 1H), 4.26 (t, 2H), 3.71 (t, 2H), 3.13 (t, 2H), 1.49 (m, 2H), 0.90 (t, 3H).

Example 170

Preparation of N-{4-(4-bromo-3-chloro-2-fluoro-phenylamino)-7-[2-(3-ethyl-thioureido)-ethoxy]-quinazolin-6-yl}-acrylamide The procedure of Example 36 was repeated except for using the compound of Example <141-6> (80 mg, 0.166 mmol) to obtain the title compound 28 mg (yield: 30%).

$^1$H NMR (CD$_3$OD) δ: 9.91 (s, 1H), 9.63 (s, 1H), 9.16 (s, 1H), 8.41 (s, 1H), 7.68 (d, 1H), 7.48 (t, 1H), 7.24 (s, 1H), 6.91-6.82 (m, 1H), 6.38 (d, 1H), 5.45 (dd, 1H), 4.19 (s, 2H), 4.09 (s, 2H), 3.33 (s, 2H), 1.13 (t, 3H).

Example 171

Preparation of 4-[6-acryloylamino-4-(4-bromo-2-fluoro-phenylamino)-quinazolin-7-yloxymethyl]-piperidine-1-carboxylic acid ethylamide The procedure of Example <26-1> was repeated except for using the compound of Example <1-9> (100 mg, 0.20 mmol) to obtain the title compound 4.2 mg (yield: 37%)

$^1$H NMR (300 MHz, CDCl$_3$) δ: 9.17 (s, 1H), 8.68 (s, 1H), 8.35 (t, 1H), 8.11 (t, 1H), 7.66 (s, 1H), 7.38-7.34 (m, sH), 6.54-6.30 (m, 1H), 5.91-5.87 (m, 1H), 4.93 (bs, 1H), 4.43 (s, 1H), 4.13 (d, 2H), 4.05 (d, 2H), 3.32 (q, 2H), 2.87 (t, 2H), 2.13 (m, 1H), 1.89 (d, 2H), 1.51-1.46 (m, 2H), 1.17 (t, 3H).

Example 172

Preparation of N-[7-(2-acetylamino-ethoxy)-4-(4-chloro-2,5-dimethoxy-phenylamino)-quinazolin-6-yl]-acrylamide <172-1> N-{2-[4-(4-chloro-2,5-dimethoxy-phenylamino)-6-nitro-quinazolin-7-yloxy]-ethyl}-acetamide The procedure of Example <1-10> was repeated except for using the compound of Example <166-3> (1 g, 2.64 mmol) to obtain the title compound 400 mg (yield: 32%)

$^1$H NMR (300 MHz, CDCl$_3$) δ: 8.86 (s, 1H), 8.67 (d, 2H), 8.23 (s, 1H), 8.02 (t, 1H), 7.12 (s, 1H), 7.00 (s, 1H), 4.43 (t, 2H), 3.99 (s, 3H), 3.96 (s, 3H), 3.67 (q, 2H), 2.13 (s, 3H).

<172-2> N-{2-[6-amino-4-(4-chloro-2,5-dimethoxy-phenylamino)-quinazolin-7-yloxy]-ethyl}-acetamide The procedure of Example <1-7> was repeated except for using the compound of <172-1> (150 mg, 0.25 mmol) to obtain the title compound 127 mg (yield: 85%)

$^1$H NMR (300 MHz, CDCl$_3$) δ: 8.78 (s, 1H), 8.63 (s, 1H), 7.81 (s, 1H), 7.01 (s, 1H), 6.95 (s, 2H), 4.45 (t, 2H), 3.97 (s, 3H), 3.95 (s, 3H), 3.70 (s, 2H), 3.54 (d, 2H), 2.12 (s, 3H).

<172-3> N-[7-(2-acetylamino-ethoxy)-4-(4-chloro-2,5-dimethoxy-phenylamino)-quinazolin-6-yl]-acrylamide The procedure of Example <29-5> was repeated except for using the compound of <172-2> (120 mg, 0.23 mmol) to obtain the title compound 18 mg (yield: 25%)

$^1$H NMR (300 MHz, CDCl$_3$) δ: 9.28 (s, 1H), 8.94 (s, 1H), 8.72 (s, 1H), 8.66 (s, 1H), 8.21 (bs, 1H), 7.21 (bs, 1H), 7.18 (s,

1H), 7.00 (s, 2H), 6.91-6.82 (m, 1H), 6.55 (d, 1H), 5.86 (d, 2H), 4.25 (t, 2H), 3.99 (d, 6H), 3.88 (t, 2H), 2.06 (s, 6H).

Example 173

Preparation of N-[7-[2-(2-amino-propionylamino)-ethoxy]-4-(4-bromo-2-fluoro-phenylamino)-quinazolin-6-yl]-acrylamide <173-1> (1-{2-[6-acryloylamino-4-(4-bromo-2-fluoro-phenylamino)-quinazolin-7-yloxy]-ethylcarbamoyl}-ethyl)-carbamic acid t-butylester The procedure of Example <12-1> was repeated except for using the compound of Example <29-6> (150 mg, 0.31 mmol) and 2-t-buthoxycarbonylaminopropionic acid (70 mg, 0.37 mmol) to obtain the title compound 109 mg (yield: 58%).

$^1$H NMR (300 MHz, CDCl$_3$+CD$_3$OD) δ: 9.12 (s, 1H), 8.53 (s, 1H), 7.95 (t, 1H), 7.82 (t, 1H), 7.42 (t, 3H), 7.15 (s, 1H), 6.90-6.81 (m, 1H), 6.55 (d, 1H), 5.91 (d, 1H), 5.74 (s, 1H), 4.26 (t, 2H), 4.13 (t, 1H), 3.80 (q, 2H), 1.39 (s, 9H).

<173-2> N-[7-[2-(2-amino-propionylamino)-ethoxy]-4-(4-bromo-2-fluoro-phenylamino)-quinazolin-6-yl]-acrylamide The procedure of Example <1-9> was repeated except for using the compound of <173-1> (109 mg, 0.18 mmol) to obtain the title compound 93 mg (yield: 99%).

$^1$H NMR (300 MHz, CDCl$_3$) δ: 9.25 (s, 1H), 9.07 (s, 1H), 8.67 (s, 1H), 8.36 (t, 1H), 8.02 (t, 1H), 7.57 (s, 1H), 7.39 (d, 1H), 7.34 (s, 1H), 7.16 (s, 1H), 6.97-6.88 (m, 1H), 6.55 (d, 1H), 5.85 (d, 1H), 4.23 (t, 2H), 3.94-3.61 (m, 4H), 3.59 (q, 2H), 1.36 (d, 4H), 1.26 (s, 9H).

Preparation of Formulation for Oral Administration and Injection

The Representative Preparation Examples for administration of inventive compound of formula (I) or a pharmaceutically acceptable salt thereof (hereinafter, "compound X") are as follows:

Preparation Example 1

Tablet

TABLE 1

| Ingredient | Amount (mg/tablet) |
| --- | --- |
| Compound X | 50 |
| Lactose Ph. Eur | 223.75 |
| Sodium Croscarmellose | 6.0 |
| Corn Starch | 15.0 |
| Polyvinylpyrrolidine paste (5% w/v paste) | 2.25 |
| Magnesium Stearate | 3.0 |

Preparation Example 2

Injection Formulation

TABLE 2

| Ingredient | Amount (1 mg/ml) |
| --- | --- |
| Compound X | 0.1% w/v |
| Sodium Phosphate BP | 2.26% w/v |
| Citric Acid | 0.38% w/v |
| Polyethylene Glycol 400 | 3.5% w/v | pH was controlled to 7.6 by using 0.1 N HCl, and the volume was adjusted to 100% by injectable water The formulations of Preparation Examples 1 and 2 may be prepared in accordance with any of the conventional methods in the pharmaceutical field. Further, the tablet may be coated with for example, cellulose acetate phthalate in accordance with any of the conventional methods.

Test of Cancer Cell Growth Inhibition

Test Example 1

Inhibitory Effect on Growth of Human Umbilical Vein Endothelial Cell (HUVEC)

HUVECs (Young Science, Inc) were suspended in a culture medium, EBM-2 (Endothelial Basic Media, Cambrex) supplemented with 2% bovine serum (Cambrex) and auxiliary additives for HUVEC culture (e.g., EGF, VEGF, FGF, etc., Cambrex), inoculated into a culture flask coated with 1% gelatin, and incubated in an incubator at 37° C. under 5% CO$_2$ and 100% humidity.

100 μl of 5% bovine serum medium containing 10 ng/ml of vascular endothelial growth factor (VEGF) and auxiliary additives, while excluding other growth factors was added to each well of a 96-well plate. The test compounds obtained in Examples 1 to 173 (100 mM) were diluted to 10 μM, added to the first well and diluted three times. DMSO (Dimethylsulfoxide) was used to dissolve the test compounds, and the final concentration of DMSO was less than 1%. PTK787 (Novartis, Control 1) selectively inhibiting VEGFR1, VEGFR2 and VEGFR3, and ZD6474 (AstraZeneca, Control 2) selectively inhibiting VEGFR2 and EGFR1 were used as control compounds at a concentration of 10 μM.

The HUVECs cultured in the culture flask were separated from the flask by using Trypsin-EDTA (Ethylene Diamine Tetra Acetic acid, Gibco) solution, and the separated cells were diluted with EBM-2 (including 5% bovine serum) to a concentration of 0.5×10$^5$ to 1.0×10$^5$ cells/ml. 100 μl of the diluted cell solution was added to each well of the 96-well plate, which was incubated in an incubator for 96 hours.

Then, 20 μl of MTS (methanethiosulfonate, Promega) solution was added to each well of the plate, and the plate was incubated in an incubator for 4 hours to induce discoloration. After 4 hours, the pellets were dissolved by way of a thorough shaking, and the absorbance at 490 nm was determined. IC$_{50}$ was obtained by calculating the range of growth of 50% of cells untreated with the test compounds. The calculation of IC$_{50}$ and the analysis of results were carried out by using Microsoft Excel, and the results are shown in Table 3.

Test Example 2

Inhibitory Effect on Growth of Diverse Cancer Cell Lines

A skin cancer cell line, A431 (ATCC: CRL-1555), a breast cancer cell line, SK-Br3 (ATCC: HTB-30), and a colon and rectal cancer cell line, SW-620 (ATCC: CCL-227) were used to test the degrees of cancer cell growth inhibition using a culture medium, DEME (Dulbecco's Modified Eagle's Medium, JBI) including 4.5 g/l of glucose and 1.5 g/l of sodium bicarbonate and supplemented with 10% FBS (fetal bovine serum, JBI).

The cancer cell lines stored in a liquid nitrogen tank were each quickly thawed at 37° C., and centrifuged to remove the medium. The resulting cell pellet was mixed with a culture medium, incubated in a culture flask at 37° C. under 5% $CO_2$ for 2 to 3 days, and the medium was removed. The remaining cells were washed with DPBS (Dulbecco's Phosphate Buffered Saline, JBI) and separated from the flask by using Trypsin-EDTA solution, and the separated cells were diluted with a culture medium to a concentration of $1.0 \times 10^6$ cells/ml in case of A431 and SW-620, and $2.0 \times 10^6$ cells/ml in case of SK-Br3. 100 µl of the diluted cell solution was added to each well of a 96-well plate, which was incubated at 37° C. under 5% $CO_2$ for 1 day.

The test compounds obtained in Examples 1 to 173 were each dissolved in 99.5% DMSO to a concentration of 25 mM. In case that the test compound was not soluble in DMSO, a small amount of 1% HCl was added thereto and treated in a 40° C. water bath for 30 mins until complete dissolution was attained. The test compound solution was diluted with a culture medium to a final concentration of 10 µM, and then diluted 10 times serially to $10^{-4}$. The final concentration of DMSO was less than 1%, and the control compounds of Test Example 1 were used at a concentration of 0.0001 to 10 µM.

The medium was removed from each well of the 96-well microplate, 100 µl of a diluted test compound solution was added to each well holding cultured cells, and the microplate was incubated at 37° C. under 5% $CO_2$ for 72 hours. After removing the medium from the plate, 50 µl of 10% trichloroacetic acid was added to each well, and the plate was kept at 37° C. for 1 hour to fix the cells to the bottom of the plate. 10% trichloroacetic acid was removed from each well, the plate was dried, 100 µl of an SRB (Sulforhodamine-B, Sigma) dye solution was added thereto, and reacted for 10 mins. The SRB dye solution was prepared by dissolving SRB in 1% acetic acid to a concentration of 0.4%. After removing the dye solution, the plate was washed with water, and dried. When the dye solution was not removed by water, 1% acetic acid was used.

150 µl of 10 mM trisma base (Sigma) was added to each well, and the absorbance at 570 nm was determined with a microplate reader (Molecular device). $IC_{50}$, the concentration at which 50% inhibition occurred, was evaluated by regarding the difference between the final concentration of cells and the initial concentration of the cells incubated in a well untreated with the test compound as 100%. The calculation of $IC_{50}$ and the analysis of results were carried out by using Microsoft Excel, and the results are shown in Table 3.

Test Example 3

VEGFR2 (KDR) Enzyme Assay

VEGFR2 (KDR, Proquinase) enzyme assay (auto-phosphorylation assay) was carried out by using Tyrosine Kinase Assay Kit Green (Panvera). The entire assay was conducted in accordance with VEGFR PTK inhibitor cellular activity test S.O.P.

A typical kinase inhibition reaction requires a protein tyrosine kinase, a suitable buffer solution system, a peptide substrate and ATP. In the present VEGFR tyrosine kinase assay, a buffer solution system containing 20 mM HEPES (pH 7.4), 5 mM $MgCl_2$ and 2 mM $MnCl_2$; 50 µM $Na_3VO_4$; 200 ng/10 µl VEGFR (Proquinase); 5 µM ATP; and 10 ng/ml poly(Glu, Tyr) (4:1, Sigma) as a substrate were used.

First, 10 µl of VEGFR was added to each well of a 96-well plate, 10 µl of the test compounds diluted as described in Test Example 2 (Examples 1 to 173) was added to each well, and the plate was incubated at room temperature for 10 min. The compounds of Test Example 1 were used as control compounds at a concentration of 0.0001 to 10 µM. After 10 min, 10 µl of poly(Glu, Tyr) as a substrate was added to each well, and 10 µl of ATP was added thereto to initiate kinase reaction. The plate was incubated at room temperature for 1 hour, and 10 µl of 100 mM EDTA was added to each well to terminate the kinase reaction.

The added EDTA was mixed for 5 min. Thereafter, 10 µl of 10× anti-phosphotyrosine antibody (Panvera), 10 µl of 10×PTK Green Tracer (Panvera) and 30 µl of FP dilution buffer (Panvera) were added thereto, and the plate was incubated in a dark room at room temperature for 30 min. Then, fluorescence polarization value of each well was measured with VICTOR III fluorescence meter (Victor) at 488 nm (excitation filter) and 535 nm (emission filter), and $IC_{50}$ was calculated from the measured values. $IC_{50}$, the concentration at which 50% inhibition occurred, was determined by regarding the difference between mP (milliPolarization) value measured in a well untreated with the test compound as a maximum value and the value when the cell growth was inhibited 100% as a minimum value (0%). The calculation of $IC_{50}$ and the analysis of results were carried out by using Microsoft Excel, and the results are shown in Table 3.

Test Example 4

EGFR1 (HER-1) Enzyme Assay

EGFR1 (HER-1) enzyme assay was carried out by using Tyrosine Kinase Assay Kit Green. The entire assay was conducted in accordance with EGFR PTK inhibitor cellular activity test S.O.P., and the kinase inhibition reaction was carried out by repeating the procedure of Test Example 3 except for using 50 ng/10 µl EGFR (Proquinase) instead of VEGFR and using 100 µM ATP. The results are shown in Table 3.

TABLE 3

| Example | HUVEC | KDR | HER-1 | A431 | SK-Br3 | SW-620 |
|---|---|---|---|---|---|---|
| 1 | 0.085 | 0.131 | 0.003 | 0.048 | 0.283 | 3.058 |
| 2 | 0.096 | 0.250 | 0.047 | 0.082 | 0.240 | 4.578 |
| 3 | 0.090 | 0.108 | 0.026 | 0.048 | 0.216 | 6.308 |
| 4 | 0.087 | 0.136 | 0.015 | 0.025 | 0.147 | 5.675 |
| 5 | 0.034 | 0.203 | 0.003 | 0.037 | 0.241 | 2.347 |
| 6 | 0.450 | 0.500 | 0.056 | 0.168 | 1.346 | 8.456 |
| 7 | 0.099 | 0.250 | 0.026 | 0.038 | 0.067 | 9.567 |
| 8 | 0.098 | 0.148 | 0.013 | 0.020 | 0.149 | 2.527 |
| 9 | 0.048 | 0.045 | 0.036 | 0.051 | 0.266 | 2.585 |
| 10 | 0.049 | 0.055 | 0.006 | 0.008 | 0.330 | 2.755 |
| 11 | 0.041 | 0.050 | 0.014 | 0.059 | 0.456 | 5.678 |
| 12 | 0.156 | 0.347 | 0.002 | 0.017 | 0.157 | 2.504 |
| 13 | 0.079 | 0.157 | 0.004 | 0.028 | 0.045 | 10 |
| 14 | 0.286 | 0.591 | 0.059 | 0.097 | 0.057 | 10 |
| 15 | 0.150 | 0.330 | 0.068 | 0.118 | 0.734 | 9.569 |
| 16 | 0.102 | 0.208 | 0.011 | 0.018 | 0.228 | 10 |
| 17 | 0.087 | 0.154 | 0.003 | 0.011 | 0.064 | 2.025 |
| 18 | 0.052 | 0.096 | 0.002 | 0.015 | 0.137 | 8.066 |
| 19 | 0.350 | 0.450 | 0.009 | 0.039 | 0.813 | 10 |
| 20 | 0.682 | 0.545 | 0.010 | 0.045 | 1.096 | 10 |
| 21 | 0.951 | 0.513 | 0.008 | 0.020 | 0.036 | 7.897 |
| 22 | 0.961 | 0.523 | 0.005 | 0.045 | 0.092 | 9.780 |
| 23 | 0.099 | 0.250 | 0.002 | 0.015 | 0.038 | 8.100 |

TABLE 3-continued

| Example | HUVEC | KDR | HER-1 | A431 | SK-Br3 | SW-620 |
|---|---|---|---|---|---|---|
| 24 | 0.090 | 0.250 | 0.004 | 0.040 | 0.075 | 7.600 |
| 25 | 0.786 | 0.584 | 0.002 | 0.016 | 0.021 | 5.792 |
| 26 | 0.087 | 0.250 | 0.005 | 0.049 | 0.080 | 10 |
| 27 | 0.096 | 0.250 | 0.003 | 0.030 | 0.050 | 9.560 |
| 28 | 0.977 | 0.500 | 0.023 | 0.076 | 0.233 | 9.679 |
| 29 | 0.951 | 0.545 | 0.004 | 0.046 | 0.145 | 10 |
| 30 | 0.964 | 0.513 | 0.096 | 0.127 | 0.581 | 4.527 |
| 31 | 0.686 | 0.523 | 0.090 | 0.093 | 0.055 | 2.533 |
| 32 | 0.350 | 0.259 | 0.025 | 0.031 | 0.198 | 4.546 |
| 33 | 0.390 | 0.369 | 0.025 | 0.034 | 0.167 | 10 |
| 34 | 0.678 | 0.458 | 0.026 | 0.035 | 0.067 | 2.545 |
| 35 | 0.951 | 0.457 | 0.098 | 0.090 | 0.225 | 9.561 |
| 36 | 0.389 | 0.354 | 0.091 | 0.089 | 0.043 | 0.722 |
| 37 | 0.682 | 0.895 | 0.036 | 0.031 | 0.065 | 4.538 |
| 38 | 0.367 | 0.324 | 0.020 | 0.021 | 0.245 | 2.576 |
| 39 | 0.325 | 0.264 | 0.029 | 0.028 | 0.176 | 4.521 |
| 40 | 0.268 | 0.155 | 0.019 | 0.013 | 0.166 | 10 |
| 41 | 0.221 | 0.134 | 0.035 | 0.046 | 0.053 | 7.856 |
| 42 | 0.786 | 0.687 | 0.059 | 0.063 | 0.142 | 9.565 |
| 43 | 0.987 | 0.785 | 0.109 | 0.104 | 4.342 | 3.674 |
| 44 | 0.265 | 0.161 | 0.014 | 0.016 | 0.098 | 2.321 |
| 45 | 0.350 | 0.325 | 0.032 | 0.037 | 0.234 | 10 |
| 46 | 0.656 | 0.635 | 0.039 | 0.035 | 0.198 | 7.521 |
| 47 | 0.269 | 0.209 | 0.024 | 0.027 | 0.067 | 9.567 |
| 48 | 0.697 | 0.698 | 0.128 | 0.114 | 0.070 | 10 |
| 49 | 0.964 | 0.854 | 0.069 | 0.062 | 0.243 | 4.594 |
| 50 | 0.101 | 0.066 | 0.019 | 0.015 | 0.071 | 9.569 |
| 51 | 0.987 | 0.954 | 0.032 | 0.033 | 0.194 | 10 |
| 52 | 0.350 | 0.354 | 0.036 | 0.037 | 0.084 | 10 |
| 53 | 0.964 | 0.875 | 0.016 | 0.012 | 0.223 | 4.764 |
| 54 | 0.568 | 0.423 | 0.045 | 0.059 | 0.456 | 10 |
| 55 | 0.359 | 0.471 | 0.589 | 0.426 | 0.437 | 4.535 |
| 56 | 0.691 | 0.654 | 0.198 | 0.153 | 0.128 | 10 |
| 57 | 0.379 | 0.235 | 0.089 | 0.091 | 0.781 | 9.566 |
| 58 | 0.945 | 0.954 | 0.125 | 0.116 | 0.395 | 5.512 |
| 59 | 0.204 | 0.198 | 0.044 | 0.045 | 0.111 | 10 |
| 60 | 0.689 | 0.685 | 0.136 | 0.125 | 0.939 | 9.567 |
| 61 | 0.384 | 0.354 | 0.009 | 0.006 | 0.059 | 10 |
| 62 | 0.697 | 0.749 | 0.258 | 0.246 | 0.369 | 0.724 |
| 63 | 0.102 | 0.084 | 0.158 | 0.140 | 0.198 | 10 |
| 64 | 0.298 | 0.231 | 0.070 | 0.072 | 0.360 | 4.594 |
| 65 | 0.964 | 0.954 | 0.652 | 0.596 | 0.694 | 10 |
| 66 | 0.238 | 0.125 | 0.021 | 0.011 | 0.103 | 10 |
| 67 | 0.351 | 0.215 | 0.089 | 0.073 | 0.983 | 2.215 |
| 68 | 0.682 | 0.687 | 0.156 | 0.265 | 0.564 | 0.725 |
| 69 | 0.954 | 0.985 | 0.246 | 0.238 | 0.654 | 10 |
| 70 | 0.365 | 0.279 | 0.956 | 0.973 | 10 | 9.568 |
| 71 | 0.286 | 0.251 | 0.098 | 0.100 | 4.4047 | 2.978 |
| 72 | 0.106 | 0.084 | 0.102 | 0.125 | 5.407 | 10 |
| 73 | 0.634 | 0.668 | 0.256 | 0.365 | 0.589 | 10 |
| 74 | 0.358 | 0.372 | 0.251 | 0.321 | 0.658 | 0.726 |
| 75 | 0.690 | 0.658 | 0.325 | 0.452 | 0.658 | 2.658 |
| 76 | 10 | 10 | 1.02 | 2.884 | 6.337 | 10 |
| 77 | 0.350 | 0.365 | 0.866 | 0.951 | 7.798 | 10 |
| 78 | 10 | 10 | 0.389 | 0.396 | 1.206 | 10 |
| 79 | 0.723 | 1.432 | 0.078 | 0.084 | 0.313 | 10 |
| 80 | 0.109 | 0.077 | 0.036 | 0.041 | 0.211 | 10 |
| 81 | 0.205 | 0.041 | 0.154 | 0.365 | 0.896 | 2.504 |
| 82 | 0.205 | 0.158 | 0.029 | 0.035 | 0.060 | 10 |
| 83 | 0.106 | 0.071 | 0.098 | 0.113 | 0.933 | 2.871 |
| 84 | 0.113 | 0.094 | 0.026 | 0.034 | 0.071 | 10 |
| 85 | 0.964 | 0.784 | 0.029 | 0.038 | 0.178 | 2.761 |
| 86 | 0.118 | 0.098 | 0.069 | 0.071 | 0.208 | 0.722 |
| 87 | 0.692 | 0.698 | 0.040 | 0.044 | 0.288 | 10 |
| 88 | 10 | 10 | 0.094 | 0.099 | 0.297 | 0.723 |
| 89 | 10 | 10 | 0.128 | 0.368 | 0.965 | 10 |
| 90 | 0.589 | 0.477 | 0.295 | 0.310 | 1.279 | 10 |
| 91 | 0.696 | 0.587 | 0.017 | 0.015 | 0.335 | 2.790 |
| 92 | 0.258 | 0.129 | 0.047 | 0.057 | 0.437 | 0.729 |
| 93 | 0.269 | 0.197 | 0.036 | 0.046 | 0.053 | 10 |
| 94 | 0.694 | 0.698 | 0.698 | 0.739 | 2.561 | 2.321 |
| 95 | 0.786 | 0.782 | 0.076 | 0.086 | 0.236 | 10 |
| 96 | 0.352 | 0.358 | 0.013 | 0.021 | 0.239 | 10 |
| 97 | 0.867 | 0.658 | 1.954 | 2.384 | 10 | 2.743 |
| 98 | 0.966 | 0.965 | 0.069 | 0.078 | 0.179 | 9.567 |
| 99 | 0.989 | 0.997 | 0.368 | 0.408 | 3.307 | 10 |
| 100 | 0.897 | 0.995 | 0.024 | 0.025 | 0.101 | 10 |
| 101 | 0.964 | 0.857 | 0.007 | 0.008 | 0.076 | 2.921 |
| 102 | 0.682 | 0.654 | 0.012 | 0.015 | 0.112 | 0.727 |
| 103 | 0.932 | 0.782 | 0.032 | 0.035 | 0.399 | 3.674 |
| 104 | 0.855 | 0.945 | 0.014 | 0.016 | 0.093 | 5.258 |
| 105 | 0.654 | 0.654 | 0.025 | 0.030 | 0.100 | 6.704 |
| 106 | 0.951 | 0.853 | 0.196 | 0.264 | 0.311 | 2.802 |
| 107 | 0.289 | 0.200 | 0.045 | 0.048 | 0.119 | 3.594 |
| 108 | 0.497 | 0.486 | 0.032 | 0.041 | 0.103 | 2.954 |
| 109 | 0.486 | 0.478 | 0.125 | 0.147 | 0.572 | 10 |
| 110 | 0.956 | 0.951 | 0.987 | 1.023 | 1.365 | 4.594 |
| 111 | 10 | 10 | 0.012 | 0.009 | 0.026 | 8.534 |
| 112 | 0.189 | 0.114 | 0.018 | 0.019 | 0.100 | 9.560 |
| 113 | 0.369 | 0.268 | 0.049 | 0.058 | 0.289 | 2.205 |
| 114 | 10 | 10 | 0.456 | 0.468 | 0.897 | 10 |
| 115 | 0.934 | 0.854 | 0.042 | 0.045 | 0.897 | 10 |
| 116 | 0.951 | 0.758 | 0.419 | 0.437 | 0.253 | 2.965 |
| 117 | 0.998 | 0.945 | 0.924 | 1.235 | 1.258 | 10 |
| 118 | 0.681 | 0.489 | 0.014 | 0.015 | 0.079 | 0.725 |
| 119 | 0.921 | 0.782 | 0.012 | 0.014 | 0.178 | 2.890 |
| 120 | 0.269 | 0.127 | 0.022 | 0.026 | 0.186 | 10 |
| 121 | 0.383 | 0.153 | 0.005 | 0.007 | 0.022 | 10 |
| 122 | 0.913 | 0.789 | 0.876 | 1.032 | 1.025 | 2.321 |
| 123 | 0.328 | 0.268 | 0.175 | 0.181 | 0.126 | 10 |
| 124 | 0.268 | 0.136 | 0.018 | 0.019 | 0.060 | 2.682 |
| 125 | 0.657 | 0.218 | 0.019 | 0.022 | 0.242 | 2.976 |
| 126 | 0.286 | 0.140 | 0.894 | 1.254 | 1.368 | 7.534 |
| 127 | 0.676 | 0.958 | 0.568 | 0.698 | 1.023 | 6.514 |
| 128 | 0.945 | 0.823 | 0.065 | 0.068 | 0.095 | 10 |
| 129 | 0.350 | 0.357 | 0.080 | 0.082 | 0.106 | 0.721 |
| 130 | 0.964 | 0.853 | 0.796 | 0.789 | 0.987 | 5.534 |
| 131 | 0.965 | 0.756 | 10 | 10 | 10 | 10 |
| 132 | 10 | 10 | 0.042 | 0.047 | 0.036 | 2.704 |
| 133 | 0.429 | 0.419 | 0.015 | 0.017 | 0.064 | 2.319 |
| 134 | 1.063 | 0.172 | 0.013 | 0.018 | 0.062 | 9.589 |
| 135 | 1.307 | 0.784 | 0.009 | 0.011 | 0.042 | 2.430 |
| 136 | 0.923 | 0.856 | 0.321 | 0.343 | 0.181 | 2.937 |
| 137 | 0.951 | 0.954 | 0.004 | 0.005 | 0.040 | 9.576 |
| 138 | 0.845 | 0.823 | 0.020 | 0.021 | 0.039 | 0.721 |
| 139 | 0.682 | 0.657 | 0.040 | 0.048 | 0.109 | 2.832 |
| 140 | 0.756 | 0.751 | 0.009 | 0.008 | 0.057 | 9.545 |
| 141 | 0.066 | 0.056 | 0.013 | 0.012 | 0.037 | 10 |
| 142 | 0.132 | 0.106 | 0.014 | 0.015 | 0.045 | 10 |
| 143 | 0.239 | 0.087 | 0.019 | 0.011 | 0.007 | 2.812 |
| 144 | 0.154 | 0.054 | 0.007 | 0.006 | 0.012 | 0.721 |
| 145 | 0.116 | 0.088 | 0.041 | 0.045 | 0.058 | 2.632 |
| 146 | 0.365 | 0.257 | 0.213 | 0.203 | 0.097 | 2.793 |
| 147 | 0.167 | 0.079 | 0.012 | 0.040 | 0.125 | 9.534 |
| 148 | 0.348 | 0.206 | 0.028 | 0.030 | 0.040 | 2.321 |
| 149 | 0.204 | 0.147 | 0.016 | 0.015 | 0.041 | 9.565 |
| 150 | 0.358 | 0.278 | 0.021 | 0.022 | 0.242 | 9.534 |
| 151 | 0.351 | 0.309 | 0.058 | 0.068 | 0.153 | 9.521 |
| 152 | 10 | 10 | 0.075 | 0.099 | 0.647 | 10 |
| 153 | 0.521 | 0.433 | 0.172 | 0.160 | 0.207 | 9.566 |
| 154 | 10 | 10 | 0.222 | 0.248 | 0.240 | 9.127 |
| 155 | 0.314 | 0.249 | 0.024 | 0.035 | 0.110 | 9.547 |
| 156 | 10 | 10 | 0.149 | 0.196 | 0.462 | 3.274 |
| 157 | 0.752 | 0.687 | 0.088 | 0.095 | 0.165 | 8.358 |
| 158 | 10 | 10 | 0.0231 | 0.259 | 0.381 | 5.146 |
| 159 | 0.423 | 0.419 | 0.286 | 0.254 | 0.162 | 6.654 |
| 160 | 0.867 | 0.984 | 0.023 | 0.055 | 0.096 | 6.547 |
| 161 | 1.234 | 1.117 | 0.057 | 0.095 | 0.118 | 10 |
| 162 | 0.882 | 0.797 | 0.126 | 0.154 | 0.141 | 10 |
| 163 | 0.735 | 0.722 | 0.012 | 0.018 | 0.045 | 10 |
| 164 | 0.754 | 0.713 | 0.014 | 0.019 | 0.036 | 8.974 |
| 165 | 0.189 | 0.079 | 0.098 | 0.137 | 0.198 | 9.765 |
| 166 | 10 | 10 | 0.014 | 0.030 | 0.027 | 5.647 |
| 167 | 0.108 | 0.462 | 0.026 | 0.042 | 0.103 | 10 |
| 168 | 0.117 | 0.038 | 0.008 | 0.012 | 0.032 | 10 |
| 169 | 0.233 | 0.128 | 0.026 | 0.035 | 0.067 | 9.100 |
| 170 | 0.287 | 0.189 | 0.068 | 0.089 | 0.043 | 8.246 |
| 171 | 0.150 | 0.136 | 0.020 | 0.025 | 0.147 | 10 |
| 172 | 0.125 | 0.090 | 0.087 | 0.091 | 3.298 | 10 |
| 173 | 0.213 | 0.165 | 0.018 | 0.038 | 0.504 | 10 |
| Control 1 | 0.040 | 0.032 | 5 | 10 | 10 | 10 |
| Control 2 | 0.070 | 0.032 | 5 | 0.028 | 2.6 | 4.5 |

Unit: μM

As shown in Table 3, the inventive compound of formula (I) effectively inhibited the growth of A431 having overexpressed EGFR1 (HER-1) and SK-Br3 having overexpressed EGFR2 (HER-2) at a low drug concentration, while the compound did not inhibit the growth of SW-620 not having overexpressed EGFR and EGFR2. Further, the inventive compound of formula (I) also showed an excellent inhibitory effect on VEGFR-2 (KDR), which is an importance factor for inducing angiogenesis. Therefore, the compounds of formula (I) of the present invention can be used for treating diseases including cancer by effectively inhibiting the activity of a tyrosine kinase.

What is claimed is:

1. A compound selected from the group consisting of:
N-[7-(1-acetyl-piperidin-4-ylmethoxy)-4-(4-bromo-2-fluoro-phenylamino)-quinazolin-6-yl]-acrylamide;
N-{4-(4-bromo-2-fluoro-phenylamino)-7-[1-(2,2,2-trifluoro-acetyl)-piperidin-4-ylmethoxy]-quinazolin-6-yl}-acrylamide;
N-{4-(4-bromo-2-fluoro-phenylamino)-7-[1-(2-methanesulfonyl-acetyl)-piperidin-4-ylmethoxy]-quinazolin-6-yl}-acrylamide;
4-[6-acryloylamino-4-(4-bromo-2-fluoro-phenylamino)-quinazolin-7-yloxymethyl]piperidin-1-carboxylic acid amide;
N-[7-(1-acryloyl-piperidin-4-ylmethoxy)-4-(4-bromo-2-fluoro-phenylamino)-quinazolin-6-yl]-acrylamide;
N-[4-(4-bromo-2-fluoro-phenylamino)-7-(pyridin-4-ylmethoxy)-quinazolin-6-yl]-acrylamide;
N-[7-(1-acetyl-piperidin-4-ylmethoxy)-4-(2,3,4-trifluoro-phenylamino)-quinazolin-6-yl]-acrylamide;
N-[7-(1-acetyl-piperidin-4-ylmethoxy)-4-(4-bromo-2,6-difluoro-phenylamino)-quinazolin-6-yl]-acrylamide;
4-[6-acryloylamino-4-(4-bromo-2-fluoro-phenylamino)-quinazolin-7-yloxymethyl]-piperidin-1-carboxylic acid propylamide;
N-{4-(4-bromo-2-fluoro-phenylamino)-7-[1-(2-dimethylamino-acetyl)-piperidin-4-ylmethoxy]-quinazolin-6-yl}-acrylamide;
4-[6-acryloylamino-4-(4-bromo-2-fluoro-phenylamino)-quinazolin-7-yloxymethyl]-piperidin-1-carboxylic acid 1-butylamide;
N-{4-(4-bromo-2-fluoro-phenylamino)-7-[3-(2-dimethylamino-acetylamino)-propoxy]-quinazolin-6-yl}-acrylamide;
N-[7-(3-acetylamino-propoxy)-4-(4-bromo-2-fluoro-phenylamino)-quinazolin-6-yl]-acrylamide;
N-{4-(4-bromo-2-fluoro-phenylamino)-7-[3-(2,2,2-trifluoro-acetylamino)-propoxy]-quinazolin-6-yl}-acrylamide;
N-{4-(4-bromo-2-fluoro-phenylamino)-7-[3-(2-methanesulfonyl-acetylamino)-propoxy]-quinazolin-6-yl}-acrylamide;
N-[4-(4-bromo-2-fluoro-phenylamino)-7-[3-(3-ethyl-ureido)-propoxy]-quinazolin-6-yl]-acrylamide;
N-[4-(4-bromo-2-fluoro-phenylamino)-7-(3-methylamino-propoxy)-quinazolin-6-yl]-acrylamide;
N-[7-(2-acetylamino-ethoxy)-4-(4-bromo-2-fluoro-phenylamino)-quinazolin-6-yl]-acrylamide;
N-[4-(4-bromo-2-fluoro-phenylamino)-7-(2-dimethylamino-ethoxy)-quinazolin-6-yl]-acrylamide;
N-[7-(4-acetylamino-butoxy)-4-(4-bromo-2-fluoro-phenylamino)-quinazolin-6-yl]-acrylamide,
Cyclopropane carboxylic acid {2-[6-acrylamino-4-(4-bromo-2-fluoro-phenylamino)-quinazolin-7-yloxy]-ethyl}-amide;
N-{4-(4-bromo-2-fluoro-phenylamino)-7-[2-(2,2-difluoro-acetylamino)-ethoxy]-quinazolin-6-yl}-acrylamide;
N-{4-(4-bromo-2-fluoro-phenylamino)-7-[2-(3-ethyl-ureido)-ethoxy]-quinazolin-6-yl}-acrylamide;
N-[4-(4-bromo-2-fluoro-phenylamino)-7-(2-ureido-ethoxy)-quinazolin-6-yl]-acrylamide;
N-[4-(4-bromo-2-fluoro-phenylamino)-7-[2-(2-dimethylamino-acetylamino)-ethoxy]-quinazolin-6-yl]-acrylamide;
N-{2-[6-acryloylamino-4-(4-bromo-2-fluoro-phenylamino)-quinazolin-7-yloxy]-ethyl}-acrylamide;
N-[4-(4-bromo-2-fluoro-phenylamino)-7-(2-propionylamino-ethoxy)-quinazolin-6-yl]-acrylamide;
N-[4-(4-bromo-2-fluoro-phenylamino)-7-[2-(2,2,2-trifluoro-acetylamino)-ethoxy]-quinazolin-6-yl]-acrylamide;
N-[7-(2-amino-ethoxy)-4-(4-bromo-2-fluoro-phenylamino)-quinazolin-6-yl]-acrylamide;
N-[4-(4-bromo-2-fluoro-phenylamino)-7-(2-methylamino-ethoxy)-quinazolin-6-yl]-acrylamide;
N-[4-(4-bromo-2-fluoro-phenylamino)-7-but-3-enyloxy-quinazolin-6-yl]-acrylamide;
N-[4-(4-bromo-2-fluoro-phenylamino)-7-(2-methoxy-ethoxy)-quinazolin-6-yl]-acrylamide;
N-[4-(4-bromo-2-fluoro-phenylamino)-7-(2-methanesulfonylamino-ethoxy)-quinazolin-6-yl]-acrylamide;
N-{4-(4-bromo-2-fluoro-phenylamino)-7-[2-(3-propyl-ureido)-ethoxy]-quinazolin-6-yl}-acrylamide;
N-{4-(4-bromo-2-fluoro-phenylamino)-7-[2-(3-methyl-thioureido)-ethoxy]-quinazolin-6-yl}-acrylamide;
N-{4-(4-bromo-2-fluoro-phenylamino)-7-[2-(3-ethyl-thioureido)-ethoxy]-quinazolin-6-yl}-acrylamide;
N-{4-(4-bromo-2-fluoro-phenylamino)-7-[2-(3-isopropyl-ureido)-ethoxy]-quinazolin-6-yl}acrylamide;
N-{4-(4-bromo-2-fluoro-phenylamino)-7-[2-(3-sec-butyl-ureido)-ethoxy]-quinazolin-6-yl}-acrylamide;
N-{4-(4-bromo-2-fluoro-phenylamino)-7-[2-(3-vinyl-ureido)-ethoxy]-quinazolin-6-yl}-acrylamide;
N-[7-[2-(3-allyl-ureido)-ethoxy]-4-(4-bromo-2-fluoro-phenylamino)-quinazolin-6-yl]-acrylamide;
Morpholine-4-carboxylic acid {2-[6-acryloylamino-4-(4-bromo-3-chloro-2-fluoro-phenylamino)-quinazolin-7-yloxy]-ethyl}-amide;
N-[7-[2-(acetyl-methyl-amino)-ethoxy]-4-(4-bromo-2-fluoro-phenylamino)-quinazolin-6-yl]-acrylamide;
N-{4-(4-bromo-2-fluoro-phenylamino)-7-[2-(2-methoxy-acetylamino)-ethoxy]-quinazolin-6-yl}-acrylamide;
N-{4-(4-bromo-2-fluoro-phenylamino)-7-[2-(2-hydroxy-acetylamino)-ethoxy]-quinazolin-6-yl}-acrylamide;
N-{4-(4-bromo-2-fluoro-phenylamino)-7-[2-(2-methylsulfanyl-acetylamino)-ethoxy]-quinazolin-6-yl}-acrylamide;
N-{4-(4-bromo-2-fluoro-phenylamino)-7-[2-(2-methanesulfonyl-acetylamino)-ethoxy]-quinazolin-6-yl}-acrylamide;
N-[4-(4-bromo-2-fluoro-phenylamino)-7-(2-isobutyrylamino-ethoxy)-quinazolin-6-yl]-acrylamide;
N-{2-[6-acryloylamino-4-(4-bromo-2-fluoro-phenylamino)-quinazolin-7-yloxy]-ethyl}-2-methyl-acrylamide;
But-2-enoic acid {2-[6-acryloylamino-4-(4-bromo-2-fluoro-phenylamino)-quinazolin-7-yloxy]-ethyl}-amide;
N-{2-[6-acryloylamino-4-(4-bromo-2-fluoro-phenylamino)-quinazolin-7-yloxy]-ethyl}-butylamide;
Pent-2-enoic acid {2-[6-acryloylamino-4-(4-bromo-2-fluoro-phenylamino)-quinazolin-7-yloxy]-ethyl}-amide;

4-dimethylamino-but-2-enoic acid {2-[6-acryloylamino-4-(4-bromo-2-fluoro-phenylamino)-quinazolin-7-yloxy]-ethyl}-amide;
N-{4-(4-bromo-3-chloro-2-fluoro-phenylamino)-7-[2-(3-t-butyl-ureido)-ethoxy]-quinazolin-6-yl}-acrylamide;
N-{4-(4-bromo-2-fluoro-phenylamino)-7-[2-(2-oxo-propylamino)-ethoxy]-quinazolin-6-yl}-acrylamide;
N-(4-(4-bromo-2-fluoro-phenylamino)-7-{2-[2-(ethyl-methyl-amino)-acetylamino]-ethoxy}-quinazolin-6-yl)-acrylamide;
N-[7-[2-(2-amino-acetylamino)-ethoxy]-4-(4-bromo-2-fluoro-phenylamino)-quinazolin-6-yl]-acrylamide;
N-{4-(4-bromo-2-fluoro-phenylamino)-7-[2-(2-dimethylamino-propionylamino)-ethoxy]-quinazolin-6-yl}-acrylamide;
N-{4-(4-bromo-2-fluoro-phenylamino)-7-[2-(3-diethylamino-propionylamino)-ethoxy]-quinazolin-6-yl}-acrylamide;
N-{4-(4-bromo-2-fluoro-phenylamino)-7-[2-(2-methylamino-acetylamino)-ethoxy-quinazolin-6-yl]-acrylamide;
N-{4-(4-bromo-2-fluoro-phenylamino)-7-[2-(3-dimethylamino-propionylamino)-ethoxy]-quinazolin-6-yl}-acrylamide;
N-[7-[2-(3-amino-propionylamino)-ethoxy]-4-(4-bromo-2-fluoro-phenylamino)-quinazolin-6-yl]-acrylamide;
{2-[6-acryloylamino-4-(4-bromo-2-fluoro-phenylamino)-quinazolin-7-yloxy]-ethyl}-carbamic acid methylester;
N-{4-(4-bromo-2-fluoro-phenylamino)-7-[2-(3-methoxy-propionylamino)-ethoxy]-quinazolin-6-yl}-acrylamide;
N-{4-(4-bromo-2-fluoro-phenylamino)-7-[(2-diethylamino-ethylcarbamoyl)-methoxy]-quinazolin-6-yl}-acrylamide;
N-{2-[6-acryloylamino-4-(4-bromo-2-fluoro-phenylamino)-quinazolin-7-yloxy]-ethyl}-4-dimethylamino-butylamide;
N-{4-(4-bromo-2-fluoro-phenylamino)-7-[2-(3-hydroxy-propionylamino)-ethoxy]-quinazolin-6-yl}-acrylamide;
N-[4-(2,4-difluorophenylamino)-7-{2-[2-(dimethylamino)-acetylamino]-ethoxy}-quinazolin-6-yl]-acrylamide;
N-{2-[6-acryloylamino-4-(4-bromo-2-fluoro-phenylamino)-quinazolin-7-yloxy]-ethyl}-malonic acid ethylester;
{2-[6-acryloylamino-4-(4-bromo-2-fluoro-phenylamino)-quinazolin-7-yloxy]-ethyl}-oxalamic acid ethylester;
{2-[6-acryloylamino-4-(4-bromo-2-fluoro-phenylamino)-quinazolin-7-yloxy]-ethyl}-oxalamic acid;
N-{4-(4-bromo-2-fluoro-phenylamino)-7-[2-(2-methoxy-imino-acetylamino)-ethoxy]-quinazolin-6-yl}-acrylamide;
N-{4-(4-bromo-2-fluoro-phenylamino)-7-[2-(3-dimethylamino-2-methyl-propionylamino)-ethoxy]-quinazolin-6-yl}-acrylamide;
N-{2-[6-acryloylamino-4-(4-bromo-2-fluoro-phenylamino)-quinazolin-7-yloxy]-ethyl}-3-dimethylamino-butylamide;
N-[7-(2-acetylamino-ethoxy)-4-(4-bromo-2-fluoro-phenylamino)-quinazolin-6-yl]-2-methyl-acrylamide;
Propionic acid [7-(2-acetylamino-ethoxy)-4-(4-bromo-2-fluoro-phenylamino)-quinazolin-6-yl]-amide;
N-[7-(2-acetylamino-ethoxy)-4-(4-bromo-2-fluoro-phenylamino)-quinazolin-6-yl]-N-methyl-acrylamide;
N-4-(4-bromo-3-fluoro-phenylamino)-7-[2-(2-dimethylamino-acetylamino)-ethoxy]-quinazolin-6-yl-acrylamide;
N-[7-(2-acetylamino-1-methyl-ethoxy)-4-(4-bromo-2-fluoro-phenylamino)-quinazolin-6-yl]-acrylamide;
N-[7-(2-acetylamino-propoxy)-4-(4-bromo-2-fluoro-phenylamino)-quinazolin-6-yl]-acrylamide;
(R)—N—F-(2-acetylamino-propoxy)-4-(4-bromo-2-fluoro-phenylamino)-quinazolin-6-yl]-acrylamide;
(S)—N-[7-(2-acetylamino-propoxy)-4-(4-bromo-2-fluoro-phenylamino)-quinazolin-6-yl]-acrylamide;
N-[4-(4-bromo-2-fluoro-phenylamino)-7-(2-propionylamino-propoxy)-quinazolin-6-yl]-acrylamide;
N-{4-(4-bromo-2-fluoro-phenylamino)-7-[2-(3-propyl-ureido)-propoxy]-quinazolin-6-yl}-acrylamide;
N-[7-(2-acetylamino-butoxy)-4-(4-bromo-2-fluoro-phenylamino)-quinazolin-6-yl]-acrylamide;
N-[4-(4-bromo-2-fluoro-phenylamino)-7-(3-propionylamino-propoxy)-quinazolin-6-yl]-acrylamide;
N-[7-(1-acetyl-pyrrolidin-3-yloxy)-4-(4-bromo-2-fluoro-phenylamino)-quinazolin-6-yl]-acrylamide;
N-[7-(1-acetyl-piperidin-3-yloxy)-4-(4-bromo-2-fluoro-phenylamino)-quinazolin-6-yl]-acrylamide;
N-{4-(4-bromo-2-fluoro-phenylamino)-7-[2-(thiazol-2-ylamino)-ethoxy]-quinazolin-6-yl}-acrylamide;
N-[4-(4-bromo-2-fluoro-phenylamino)-7-(2-oxo-oxazolidin-5-ylmethoxy)-quinazolin-6-yl]-acrylamide;
Thiophene-2-carboxylic acid {2-[6-acryloylamino-4-(4-bromo-2-fluoro-phenylamino)-quinazolin-7-yloxy]-ethyl}-amide;
Morpholine-4-carboxylic acid {2-[6-acryloylamino-4-(4-bromo-2-fluoro-phenylamino)-quinazolin-7-yloxy]-ethyl}-amide;
Piperazine-1-carboxylic acid {2-[6-acryloylamino-4-(4-bromo-2-fluoro-phenylamino)-quinazolin-7-yloxy]-ethyl}-amide;
4-acetyl-piperazine-1-carboxylic acid {2-[6-acryloylamino-4-(4-bromo-2-fluoro-phenylamino)-quinazolin-7-yloxy]-ethyl)-amide;
4-methyl-piperazine-1-carboxylic acid {2-[6-acryloylamino-4-(4-bromo-2-fluoro-phenylamino)-quinazolin-7-yloxy]-ethyl}amide;
Pyrrolidine-2-carboxylic acid {2-[6-acryloylamino-4-(4-bromo-2-fluoro-phenylamino)-quinazolin-7-yloxy]-ethyl}-amide;
1-methyl-pyrrolidine-2-carboxylic acid (2-[6-acryloylamino-4-(4-bromo-2-fluoro-phenylamino)-quinazolin-7-yloxy]-ethyl}-amide;
1H-pyrrole-2-carboxylic acid {2-[6-acryloylamino-4-(4-bromo-2-fluoro-phenylamino)-quinazolin-7-yloxy]-ethyl}-amide;
N-{4-(4-bromo-2-fluoro-phenylamino)-7-[2-(2-piperidin-1-yl-acetylamino)-ethoxy]-quinazolin-6-yl}-acrylamide;
N-(4-(4-bromo-2-fluoro-phenylamino)-7-{2-[2-(4-methyl-piperazin-1-yl)-acetylamino]-ethoxy}-quinazolin-6-yl)-acrylamide;
N-{4-(4-bromo-2-fluoro-phenylamino)-7-[2-(2-morpholin-4-yl-acetylamino)-ethoxy]-quinazolin-6-yl}-acrylamide;
N-{4-(4-bromo-2-fluoro-phenylamino)-7-[2-(3-piperidin-1-yl-propionylamino)-ethoxy]-quinazolin-6-yl}-acrylamide;
1-acetyl-pyrrolidine-2-carboxylic acid {2-[6-acryloylamino-4-(4-bromo-2-fluoro-phenylamino)-quinazolin-7-yloxy]-ethyl}-amide;

1-propionyl-pyrrolidine-2-carboxylic acid {2-[6-acryloylamino-4-(4-bromo-2-fluoro-phenylamino)-quinazolin-7-yloxy]-ethyl}-amide;

N-{4-(4-bromo-2-fluoro-phenylamino)-7-[2-(2-pyrrolidin-1-yl-acetylamino)-ethoxy]-quinazolin-6-yl}-acrylamide;

N-{4-(4-bromo-2-fluoro-phenylamino)-7-[2-(2-2,5-dihydro-pyrrol-1-yl-acetylamino)-ethoxy]-quinazolin-6-yl}-acrylamide;

N-[4-(4-bromo-2-fluoro-phenylamino)-7-(4,5-dihydro-oxazol-2-ylmethoxy)-quinazolin-6-yl]-acrylamide;

N-[7-[2-(2-azetidin-1-yl-acetylamino)-ethoxy]-4-(4-bromo-2-fluoro-phenylamino)-quinazolin-6-yl]-acrylamide;

N-[7-(2-acetylamino-ethoxy)-4-(3-chloro-4-fluoro-phenylamino)-quinazolin-6-yl]-acrylamide;

N-[7-(2-acetylamino-ethoxy)-4-(4-chloro-2-fluoro-phenylamino)-quinazolin-6-yl]-acrylamide;

N-[7-(2-acetylamino-ethoxy)-4-(4-chloro-2-chloro-phenylamino)-quinazolin-6-yl]-acrylamide;

N-[7-(2-acetylamino-ethoxy)-4-(4-bromo-2-trifluoromethyl-phenylamino)-quinazolin-6-yl]-acrylamide;

N-[7-(2-acetylamino-ethoxy)-4-(4-bromo-2-chloro-phenylamino)-quinazolin-6-yl]-acrylamide;

N-{4-(4-chloro-2-fluoro-phenylamino)-7-[2-(2-dimethylamino-acetylamino)-ethoxy]-quinazolin-6-yl}-acrylamide;

N-[4-(3-chloro-2-fluoro-phenylamino)-7-{2-[2-(dimethylamino)-acetamido]-ethoxy}quinazolin-6-yl]-acrylamide;

N-[7-(2-acetylamino-ethoxy)-4-(2,3,4-trifluoro-phenylamino)-quinazolin-6-yl]-acrylamide;

N-[7-(2-acetylamino-ethoxy)-4-(4-bromo-2,5-difluoro-phenylamino)-quinazolin-6-yl]-acrylamide;

N-[7-(2-acetylamino-ethoxy)-4-(4-bromo-2,6-difluoro-phenylamino)-quinazolin-6-yl]-acrylamide;

N-[7-(2-acetylamino-ethoxy)-4-(4,5-dichloro-2-fluoro-phenylamino)-quinazolin-6-yl]-acrylamide;

N-[7-(2-acetylamino-ethoxy)-4-(2,4,5-trichloro-phenylamino)-quinazolin-6-yl]-acrylamide;

N-[4-(4-bromo-2,6-difluorophenylamino)-7-{2-[2-(dimethylamino)-acetamido]-ethoxy}-quinazolin-6-yl]-acrylamide;

N-{4-(4-bromo-2,3-difluoro-phenylamino)-7-[2-(2-dimethylamino-acetylamino)-ethoxy]-quinazolin-6-yl}-acrylamide;

N-{4-(4-bromo-2,3-difluoro-phenylamino)-7-[2-(3-diethylamino-propionylamino)-ethoxy]-quinazolin-6-yl}-acrylamide;

N-{4-(4-bromo-2,3-difluoro-phenylamino)-7-[2-(3-piperidin-1-yl-propionylamino)-ethoxy]-quinazolin-6-yl}-acrylamide;

N-{2-[6-acryloylamino-4-(4-bromo-2,3-difluoro-phenylamino)-quinazolin-7-oxy]-ethyl}-4-dimethylamino-butylamide;

N-[7-(2-acetylamino-ethoxy)-4-(6-chloro-pyridin-3-ylamino)-quinazolin-6-yl]-acrylamide;

N-[7-(2-acetylamino-ethoxy)-4-(4-chloro-2-fluoro-5-methoxy-phenylamino)-quinazolin-6-yl]-acrylamide;

N-{7-(2-acetylamino-ethoxy)-4-[3-chloro-4-(pyridin-3-ylmethoxy)-phenylamino]-quinazolin-6-yl}-acrylamide;

5-[7-(2-acetylamino-ethoxy)-6-acryloylamino-quinazolin-4-ylamino]-2-bromo-4-fluoro-N-methoxy-benzamide;

N-[7-(2-acetylamino-ethoxy)-4-(2,4-dichloro-5-methoxy-phenylamino)-quinazolin-6-yl]-acrylamide;

N-[7-(2-acetylamino-ethoxy)-4-(4-bromo-5-chloro-2-fluoro-phenylamino)-quinazolin-6-yl]-acrylamide;

N-[4-(4-bromo-5-chloro-2-fluoro-phenylamino)-7-(2-propionylamino-ethoxy)-quinazolin-6-yl]-acrylamide;

N-{4-(4-bromo-5-chloro-2-fluoro-phenylamino)-7-[2-(2-dimethylamino-acetylamino)-ethoxy]-quinazolin-6-yl}-acrylamide;

N-[4-(4,5-dichloro-2-fluoro-phenylamino)-7-(2-dimethylamino-ethoxy)-quinazolin-6-yl]-acrylamide;

N-[4-(4,5-dichloro-2-fluoro-phenylamino)-7-(2-propionylamino-ethoxy)-quinazolin-6-yl]-acrylamide;

N-{4-(4,5-dichloro-2-fluoro-phenylamino)-7-[2-(2-methoxy-acetylamino)-ethoxy]-quinazolin-6-yl}-acrylamide;

N-{4-(4,5-dichloro-2-fluoro-phenylamino)-7-[2-(2-methanesulfonyl-acetylamino)-ethoxy]-quinazolin-6-yl}-acrylamide;

N-{4-(4,5-dichloro-2-fluoro-phenylamino)-7-[2-(2-dimethylamino-acetylamino)-ethoxy]-quinazolin-6-yl}-acrylamide;

N-[7-(2-acetylamino-ethoxy)-4-(4-bromo-3-chloro-2-fluoro-phenylamino)-quinazolin-6-yl]-acrylamide;

N-[4-(4-bromo-3-chloro-2-fluoro-phenylamino)-7-(2-propionylamino-ethoxy)-quinazolin-6-yl]-acrylamide;

N-{4-(4-bromo-3-chloro-2-fluoro-phenylamino)-7-[2-(2-dimethylamino-acetylamino)-ethoxy]-quinazolin-6-yl}-acrylamide;

N-{4-(4-bromo-3-chloro-2-fluoro-phenylamino)-7-[2-(3-diethylamino-propionylamino)-ethoxy]-quinazolin-6-yl}-acrylamide;

N-{4-(4-bromo-3-chloro-2-fluoro-phenylamino)-7-[2-(3-hydroxy-propionylamino)-ethoxy]-quinazolin-6-yl}-acrylamide;

N-{4-(4-bromo-3-chloro-2-fluoro-phenylamino)-7-[2-(2-methoxy-acetylamino)-ethoxy]-quinazolin-6-yl}-acrylamide;

N-{4-(4-bromo-3-chloro-2-fluoro-phenylamino)-7-[2-(3-piperidin-1-yl-propionylamino)-ethoxy]-quinazolin-6-yl}-acrylamide;

N-{2-[6-acryloylamino-4-(4-bromo-3-chloro-2-fluoro-phenylamino)-quinazolin-7-yloxy]-ethyl}-4-dimethylamino-butylamide;

N-{4-(4-bromo-3-chloro-2-fluoro-phenylamino)-7-[2-(2-hydroxy-acetylamino)-ethoxy]-quinazolin-6-yl}-acrylamide;

N-{4-(4-bromo-3-chloro-2-fluoro-phenylamino)-7-[2-(3-methoxy-propionylamino)-ethoxy]-quinazolin-6-yl}-acrylamide;

N-{4-(4-bromo-3-chloro-2-fluoro-phenylamino)-7-[2-(2-diethylamino-acetylamino)-ethoxy]-quinazolin-6-yl}-acrylamide;

N-{4-(4-bromo-3-chloro-phenylamino)-7-[2-(2-dimethylamino-acetylamino)-ethoxy]-quinazolin-6-yl}-acrylamide;

N-{4-(4-bromo-2-fluoro-phenylamino)-7-[2-(2-dimethylamino-acetylamino-propoxy]-quinazolin-6-yl}-acrylamide;

N-{4-(4-bromo-2-fluoro-phenylamino)-7-[2-(2-dimethylamino-acetylamino)-2-methyl-propoxy]-quinazolin-6-yl}-acrylamide;

N-{4-(4-bromo-2-fluoro-phenylamino)-7-[2-(3-diethylamino-propionylamino)-propoxy]-quinazolin-6-yl}-acrylamide;

N-{4-(4-bromo-2-fluoro-phenylamino)-7-[2-(2-dimethylamino-acetylamino)-3-methylbutoxy]-quinazolin-6-yl}-acrylamide;

N-{4-(4-bromo-3-chloro-2-fluoro-phenylamino)-7-[2-(2-dimethylamino-acetylamino)-propoxy]-quinazolin-6-yl-acrylamide;

(S)—N-4-(4-bromo-3-chloro-2-fluoro-phenylamino)-7-[2-(2-dimethylamino-acetylamino)-propoxy]-quinazolin-6-yl-acrylamide;

(R)—N-{4-(4-bromo-3-chloro-2-fluoro-phenylamino)-7-[2-(2-dimethylamino-acetylamino)-propoxy]-quinazolin-6-yl-acrylamide;

N-{4-(4-bromo-2-fluoro-phenylamino)-7-[2-(2-dimethylamino-acetylamino)-butoxy]-quinazolin-6-yl}-acrylamide;

N-{4-(4-bromo-2-fluoro-phenylamino)-7-[2-(2-dimethylamino-3-methoxy-propionylamino)-ethoxy]-quinazolin-6-yl}-acrylamide;

N-{4-(4-bromo-2-fluoro-phenylamino)-7-[2-(2-dimethylamino-3-hydroxy-propionylamino)-ethoxy]-quinazolin-6-yl}-acrylamide;

(S)—N-4-(4-bromo-3-chloro-2-fluoro-phenylamino)-7-[2-(2-dimethylamino-acetylamino)-propoxyl-quinazolin-6-yl-acrylamide;

(R)—N-4-(4-bromo-3-chloro-2-fluoro-phenylamino)-7-[2-(2-dimethylamino-acetylamino)-propoxy]-quinazolin-6-yl-acrylamide;

{2-[6-acryloylamino-4-(4-bromo-3-chloro-2-fluoro-phenylamino)-quinazolin-7-yloxy]-ethyl}-carbamic acid methylester;

N-{4-(4-chloro-2,5-dimethoxy-phenylamino)-7-[2-(2-dimethylamino-acetylamino)-ethoxy]-quinazolin-6-yl}-acrylamide;

N-{4-(4-bromo-2-fluoro-phenylamino)-7-[2-(2-diethylamino-acetylamino)-ethoxy]-quinazolin-6-yl}-acrylamide;

N-{4-(4-bromo-3-chloro-2-fluoro-phenylamino)-7-[2-(3-ethyl-ureido)-ethoxy]-quinazolin-6-yl}-acrylamide;

N-{4-(4-bromo-3-chloro-2-fluoro-phenylamino)-7-[2-(3-propyl-ureido)-ethoxy]-quinazolin-6-yl}-acrylamide;

N-{4-(4-bromo-3-chloro-2-fluoro-phenylamino)-7-[2-(3-ethyl-thioureido)-ethoxy]-quinazolin-6-yl}-acrylamide;

4-[6-acryloylamino-4-(4-bromo-2-fluoro-phenylamino)-quinazolin-7-yloxymethyl]-piperidine-1-carboxylic acid ethylamide;

N-[7-(2-acetylamino-ethoxy)-4-(4-chloro-2,5-dimethoxy-phenylamino)-quinazolin-6-yl]-acrylamide; and N-[7-[2-(2-amino-propionylamino)-ethoxy]-4-(4-bromo-2-fluoro-phenylamino)-quinazolin-6-yl]-acrylamide, or a pharmaceutically acceptable salt thereof.

2. A pharmaceutical composition comprising a compound selected from the group defined in claim 1 or the pharmaceutically acceptable salt thereof as an active ingredient and a carrier or excipient.

3. The composition of claim 2, wherein the pharmaceutically acceptable salt is a salt of an acid selected from the group consisting of hydrochloric acid, sulfuric acid, phosphoric acid, nitric acid, malonic acid, succinic acid, citric acid, glutaric acid, acetic acid, maloic acid, formic acid, fumaric acid, tartaric acid, maleic acid, benzoic acid, methanesulfonic acid, benzenesulfonic acid and toluenesulfonic acid.

* * * * *